(12) United States Patent
Alitalo et al.

(10) Patent No.: US 8,025,886 B2
(45) Date of Patent: Sep. 27, 2011

(54) MODIFIED VEGF-A WITH IMPROVED ANGIOGENIC PROPERTIES

(75) Inventors: Kari Alitalo, Helsinki (FI); Tuomas Tammela, Helsinki (FI); Salla Keskitalo, Helsinki (FI); Katri Pajusola, Helsinki (FI); Markku M. Jeltsch, Helsinki (FI); Seppo Yla-Herttuala, Helsinki (FI); Terhi Karpanen, Helsinki (FI); Ulf Eriksson, Stockholm (SE); Marko J. T. Uutela, Helsinki (FI)

(73) Assignee: Vegenics Pty Ltd, Toorak, Victoria (AU)

( * ) Notice: Subject to any disclaimer, the term of this patent is extended or adjusted under 35 U.S.C. 154(b) by 1184 days.

(21) Appl. No.: 11/505,100

(22) Filed: Aug. 15, 2006

(65) Prior Publication Data
US 2007/0142282 A1    Jun. 21, 2007

Related U.S. Application Data

(60) Provisional application No. 60/708,226, filed on Aug. 15, 2005.

(51) Int. Cl.
| A61K 39/385 | (2006.01) |
| A61K 39/00 | (2006.01) |
| A61K 38/24 | (2006.01) |
| A61F 13/00 | (2006.01) |
| A61B 17/10 | (2006.01) |
| C12N 5/00 | (2006.01) |
| C12N 15/00 | (2006.01) |
| C12P 21/06 | (2006.01) |
| C07H 21/04 | (2006.01) |
| C07K 1/00 | (2006.01) |

(52) U.S. Cl. ............. 424/195.11; 424/192.1; 424/198.1; 424/422; 424/449; 606/139; 435/325; 435/320.1; 435/69.1; 536/23.4; 536/23.5; 530/350; 530/399

(58) Field of Classification Search ........................ None
See application file for complete search history.

(56) References Cited

U.S. PATENT DOCUMENTS

| 5,607,918 | A | 3/1997 | Eriksson et al. |
| 5,776,755 | A | 7/1998 | Alitalo et al. |
| 5,840,693 | A | 11/1998 | Eriksson et al. |
| 5,919,899 | A | 7/1999 | Persico et al. |
| 6,221,839 | B1 | 4/2001 | Alitalo et al. |
| 6,235,713 | B1 | 5/2001 | Achen et al. |
| 6,245,530 | B1 | 6/2001 | Alitalo et al. |
| 6,361,946 | B1 | 3/2002 | Alitalo et al. |
| 6,403,088 | B1 | 6/2002 | Alitalo et al. |
| 6,645,933 | B1 | 11/2003 | Alitalo et al. |
| 6,689,580 | B1 | 2/2004 | Achen et al. |
| 6,730,658 | B1 | 5/2004 | Alitalo et al. |
| 6,965,010 | B2 | 11/2005 | Alitalo et al. |
| 7,148,037 | B2 | 12/2006 | Eriksson et al. |
| 7,309,604 | B2 | 12/2007 | Alitalo et al. |

| 2002/0127222 | A1 | 9/2002 | Achen et al. |
| 2002/0151680 | A1 | 10/2002 | Alitalo et al. |
| 2002/0164687 | A1 | 11/2002 | Eriksson et al. |
| 2003/0027751 | A1 | 2/2003 | Kovesdi et al. |
| 2003/0064053 | A1 | 4/2003 | Liu et al. |
| 2003/0113324 | A1 | 6/2003 | Alitalo et al. |
| 2003/0113870 | A1 | 6/2003 | Ferrara et al. |
| 2003/0166523 | A1 | 9/2003 | Achen et al. |
| 2003/0211994 | A1 | 11/2003 | Li et al. |
| 2004/0214766 | A1 | 10/2004 | Alitalo et al. |
| 2005/0032697 | A1 | 2/2005 | Alitalo et al. |
| 2005/0043235 | A1 | 2/2005 | Alitalo et al. |
| 2005/0267024 | A1 | 12/2005 | Alitalo et al. |
| 2008/0058263 | A1 | 3/2008 | Alitalo et al. |

FOREIGN PATENT DOCUMENTS

| WO | WO 96/26736 | 9/1996 |
| WO | WO 97/05250 | 2/1997 |
| WO | WO 97/12972 | 4/1997 |
| WO | WO 98/01973 | 1/1998 |
| WO | WO 98/02543 | 1/1998 |
| WO | WO 98/07832 | 2/1998 |
| WO | WO 98/33917 | 8/1998 |
| WO | WO 00/21560 | 10/1999 |
| WO | WO 00/18212 | 4/2000 |
| WO | WO 00/24412 | 5/2000 |
| WO | WO 00/25805 | 5/2000 |
| WO | WO 00/27879 | 5/2000 |
| WO | WO 01/62942 | 8/2001 |
| WO | WO 02/060950 | 8/2002 |
| WO | WO 2005/011722 | 2/2005 |
| WO | WO 2005/016963 | 2/2005 |

OTHER PUBLICATIONS

International preliminary Report on Patentability from the International Bureau of WIPO for PCT/US2006/032012, dated Feb. 20, 2008.
U.S. Appl. No. 12/422,048, Alitalo et al.
AASE et al., Expression analysis of PDGF-C in adult and developing mouse tissues, Mech. Dev., 110:187-191, 2002.
Achen et al., Vascular endothelial growth factor D (VEGF-D) is a ligand for the tyrosine kinase VEGF receptor 2 (Flk1) and VEGF receptor 3 (Flt4), Proc. Natl. Acad. Sci. USA, 95:548-553, 1998.
Asahara et al., Local delivery of vascular endothelial growth factor accelerated reendothelialization and attenuates intimal hyperplasia in balloon-injured rat carotid artery, Circulation, 91:2793-2801, 1995.
Azzouz et al., VEGF delivery with retrogradely transported lentivector prolongs survival in a mouse ALS model, Nature, 429:413-417, 2004.
Baluk et al., Pathogenesis of persistent lymphatic vessel hyperplasia in chronic airway inflammation, J. Clin. Invest., 115(2):247-257, 2005.

(Continued)

Primary Examiner — Shulamith H Shafer
(74) Attorney, Agent, or Firm — Marshall, Gerstein & Borun LLP

(57) ABSTRACT

The present invention is directed to methods and compositions for making and using chimeric polypeptides that comprise a VEGFR-2 ligand. The chimeric molecules of the present invention retain VEGFR-2 binding activity and an enhanced angiogenic activity as compared to native VEGF-A.

48 Claims, 2 Drawing Sheets

OTHER PUBLICATIONS

Banai et al., Angiogenic-induced enhancement of collateral blood flow to ischemic myocardium by vascular endothelial growth factor in dogs, Circulation, 89(5):2183-2189, 1994.
Baron et al., The oligodendrocyte precursor mitogen PDGF stimulates proliferation by activation of $\alpha v\beta 3$ integrins, EMBO J., 21(8):1957-1966, 2002.
Bauters et al., Physiological assessment of augmented vascularity induced by VEGF in ischemic rabbit hindlimb, Am. J. Physiol., 267:H1263-1271, 1994.
Bauters et al., Recovery of disturbed endothelium-dependent flow in the collateral-perfused rabbit ischemic hindlimb after administration of vascular endothelial growth factor, Circulation, 91:2802-2809, 1995.
Bellomo et al., Mice lacking the vascular endothelial growth factor-B gene (VEGF-B) have smaller hearts, dysfunctional coronary vasculature, and impaired recovery from cardiac ischemia; Circ. Res., 86:E29-E35, 2000.
Betsholtz et al., Developmental roles of platelet-derived growth factors, Bioassays, 23:494-507, 2001.
Blacher et al., Improved quantification of angiogenesis in the rat aortic ring assay, Angiogenesis, 4:133-142, 2001.
Caldwell et al., Growth factors regulate the survival and fate of cells derived from human neurospheres, Nat. Biotechnol., 19:475-479, 2001.
Cao et al., Angiogenesis stimulated by PDGF-CC, a novel member in the PDGF family, involves activation of PDGFR-$\alpha\alpha$ and -$\alpha\beta$ receptors, FASEB J., 16:1575-1583, 2002.
Carmeliet et al., Abnormal blood vessel development and lethality in embryos lacking a single VEGF allele, Nature, 380:435-439, 1996.
Carmeliet, One cell, two fates, Nature, 408:43-45, 2000.
Cursiefen et al., Inhibition of hemangiogenesis and lymphangiogenesis after normal-risk corneal transplantation by neutralizing VEGF promotes graft survival, Invest. Ophthamol. Vis. Sci., 45(8):2666-2673, 2004.
De Marchis et al., Platelet-derived growth factor inhibits basic fibroblast growth factor angiogenic properties in vitro and in vivo through its a receptor, Blood, 99(6):2045-2053, 2002.
De Vries et al., The fms-like tyrosine kinase, a receptor for vascular endothelial growth factor, Science, 255:989-991, 1992.
Dumont et al., Cardiovascular failure in mouse embryos deficient in VEGF receptor-3, Science, 282:946-949, 1998.
Fairbrother et al., Solution structure of the heparin-binding domain of vascular endothelial growth factor, Structure, 6:637-648, 1998.
Ferrara, Molecular and biological properties of vascular endothelial growth factor, J. Mol. Med., 77:527-543, 1999.
Ferrell et al., Hereditary lymphedema: evidence for linkage and genetic heterogeneity, Hum. Mol. Genetics, 7(13):2073-2078, 1998.
Folkman et al., Angiogenesis, J. Biol. Chem., 267(16):10931-10934, 1992.
Forstreuter et al., Vascular endothelial growth factor induces chemotaxis and proliferation of microglial cells, J. Neuroimmunol., 132:93-98, 2002.
Gilbertson et al., Platelet-derived growth factor C (PDGF-C), a novel growth factor that binds to PDGF a and $\beta$ receptor, J. Biol. Chem., 276(6):27406-27414, 2001.
Hauser et al., A heparin-binding form of placenta growth factor (PLGF-2) is expressed in human umbilical vein endothelial cells and in placenta, Growth Factors, 9:259-268, 1993.
Heinzelmann et al., Heparin binding protein (CAP37) differentially modulates endotoxin-induced cytokine production, J. Surg. Investig., 2(6):457-466, 2001.
Heldin et al., Mechanism of action and in vivo role of platelet-derived growth factor, Physiol. Rev., 79(4):1283-1316, 1999.
Hellstrom et al., Lack of pericytes leads to endothelial hyperplasia and abnormal vascular morphogenesis, J. Cell. Biol., 153(3):543-553, 2001.
Hong et al., VEGF-A promotes tissue repair-associated lymphatic vessel formation via VEGFR-2 and the $\alpha\beta 1$ integrins, FASEB J., 10:1111-1113, 2004.
Isner et al., Myocardial gene therapy, Nature, 415:234-239, 2002.
Jeltsch et al., Hyperplasia of lymphatic vessels in VEGF-C transgenic mice, Science, 276:1423-1425, 1997.

Jeltsch et al., Vascular endothelial growth factor (VEGF)/VEGF-C mosaic molecules reveal specificity determinants and feature novel receptor binding patterns, J. Biol. Chem., 281:12187-12195, 2006.
Joukov et al., A novel vascular endothelial growth factor, VEGF-C, is a ligand for the Flt4 (VEGFR-3) and KDR (VEGFR-2) receptor tyrosine kinases, EMBO J., 15(2):290-298, 1996.
Joukov et al., Proteolytic processing regulates receptor specificity and activity of VEGF-C, EMBO J., 16(13):3898-3911, 1997.
Joukov et al., Vascular endothelial growth factors VEGF-B and VEGF-C, J. Cell Physiol., 173:211-215, 1997.
Karkkainen et al., A model for gene therapy of human hereditary lymphedema, Proc. Natl. Acad. Sci. USA, 98(22):12677-12682, 2001.
Karkkainen et al., Vascular endothelial growth factor C is required for sprouting of the first lymphatic vessels from embryonic veins, Nat Immunol, 5(1):74-80, 2004.
Karpanen et al., Functional interaction of VEGF-C and VEGF-D with neuropilin receptors, FASEB J., 20:1462-1472, 2006.
Keck et al., Disulfide structure of the heparin binding domain in vascular endothelial growth factor: characterization of post-translational modifications in VEGF, Arch. Biochem. Biophys., 344(1):103-113, 1997.
Krum et al., Angiogenic and astroglial responses to vascular endothelial growth factor administration in adult rat brain, Neuroscience, 110(4):589-604, 2002.
Kubo et al., Blockade of vascular endothelial growth factor receptor-3 signaling inhibits fibroblast growth factor-2-induced lymphangiogenesis in mouse cornea, Proc. Natl. Acad. Sci. USA, 99(13):8868-8873, 2002.
Li et al., Novel PDGF family members: PDGF-C and PDGF-D, Cytokine & Growth Factor Rev., 14:91-98, 2003.
Li et al., PDGF-C is a new protease-activated ligand for the PDGF a-receptor, Nat. Cell Biol., 2:302-309, 2000.
Maglione et al., Isolation of a human placenta cDNA coding for a protein related to the vascular permeability factor, Proc. Natl. Acad. Sci. USA, 88:9267-9271, 1991.
Maglione et al., Two alternative mRNAs coding for the angiogenic factor, placenta growth factor (PlGF), are transcribed from a single gene of chromosome 14, Oncogene, 8:925-931, 1993.
Makinen et al., Differential binding of vascular endothelial growth factor B splice and proteolytic isoforms to neuropilin-1, J. Biol. Chem., 274(30):21217-21222, 1999.
Makinen et al., Inhibition of lymphangiogenesis with resulting lymphedema in transgenic mice expressing soluble VEGF receptor-3, Nat. Med., 7(2):199-205, 2001.
Matthews et al., A receptor tyrosine kinase cDNA isolated from a population of enriched primitive hematopoietic cells and exhibiting close genetic linkage to c-kit, Proc. Natl. Acad. Sci. USA, 88:9026-9030, 1991.
Meyer et al., A novel vascular endothelial growth factor encoded by Orf virus, VEGF-E, mediates angiogenesis via signaling through VEGFR-2 (KDR) but not VEGFR-1 (FLT-1) receptor tyrosine kinases, EMBO J., 18(2):363-374, 1999.
Mulloy et al., Out of order complexity—protein structures that interact with heparin, Curr. Opin. Struct. Biol., 11(5):623-628, 2001.
Nagy et al., Vascular permeability factor/vascular endothelial growth factor induced lymphangiogenesis as well as angiogenesis, J. Exp. Med., 196(11):1497-1506, 2002.
Nelson et al., The 50- and 58-kdalton keratin classes as molecular markers for stratified squamous epithelia: cell culture studies, J. Cell. Biol., 97:244-251, 1983.
Neufeld et al., Vascular endothelial growth factor (VEGF) and its receptors, FASEB J., 13:9-22, 1999.
Niwa et al., Efficient selection for high-expression transfectants with a novel eukaryotic vector, Gene, 108(2):193-200, 1991.
Oh et al., VEGF and VEGF-C: specific induction of angiogenesis and lymphangiogenesis in the differentiated avian chorioallantoic membrane, Dev. Biol., 188:96-109, 1997.
Oloffson et al., Genomic organization of the mouse and human genes for vascular endothelial growth factor B (VEGF-B) and characterization of a second splice isoform, J. Biol. Chem., 271(32):19310-19317, 1996.

Oosthuyse et al., Deletion of the hypoxia-response element in the vascular endothelial growth factor promoter causes motor neuron degeneration, Nat. Genet., 28:131-138, 2001.

Ortega et al., Signal relays in the VEGF system, Fron. Biosci., 4:141-152, 1999.

Pajusola et al., Signaling properties of FLT4, a proteolytically processed receptor tyrosine kinase related to two VEGF receptors, Oncogene, 9:3545-3555, 1994.

Palumbo et al., Different effects of high and low shear stress on platelet-derived growth factor isoform release by endothelial cells, Arterioscler. Thromb. Vasc. Biol., 22:405-411, 2002.

Paterna et al., Influence of promoter and WHV post-transcriptional regulatory element of AAV-mediated transgene expression in the rat, Gene Ther., 7(15):1304-1311, 2000.

Peichev et al., Expression of VEGFR-2 and AC133 by circulating human CD34+ cells identifies a population of functional endothelial precursors, Blood, 95(3):952-958, 2000.

Petrova et al., Signaling via vascular endothelial growth factor receptors, Exp. Cell Res., 253:117-130, 1990.

Pietras et al., PDGF receptors as cancer drug targets, Cancer Cell, 3:439-443, 2003.

Poltorak et al., The VEGF splice variants: properties, receptors, and usage for the treatment of ischemic diseases, Herz, 25:126-129, 2000.

Pu et al., A persistent hindlimb ischemia model in the rabbit, J. Invest. Surgery, 7:49-60, 1994.

Rauvala et al., Heparin-binding proteins HB-GAM (pleiotrophin) and amphoterin in the regulation of cell motility, Matrix Biol., 19(5):377-387, 2000.

Rissanen et al., VEGF-D is the strongest angiogenic and lymphangiogenic effector among VEGFs delivered into skeletal muscle via adenoviruses, Circ. Res., 92(10):1098-1106, 2003.

Ruhrberg et al., Spatially restricted patterning cues provided by heparin-binding VEGF-A control blood vessel branching morphogenesis, Genes Dev., 16:2684-2698, 2002.

Saaristo et al., Adenoviral VEGF-C overexpression induces blood vessel enlargement, tortuosity, and leakiness but no sprouting angiogenesis in the skin or mucous membranes, FASEB J., 16:1041-1049, 2002.

Saaristo et al., Lymphangiogenic gene therapy with minimal blood vascular side effects, J. Exp. Med., 196(6):719-730, 2002.

Salven et al., VEGFR-3 and CD133 identify a population of CD34+ lymphatic/vascular endothelial precursor cells, Blood, 101(1):168-172, 2003.

Schoppmann et al., Tumor-associated macrophages express lymphatic endothelial growth factors and are related to peritumoral lymphangiogenesis, Am. J. Pathol., 161(3):947-956, 2002.

Schratzberger, Favorable effect of VEGF gene transfer on ischemic peripheral neuropathy, Nat. Med., 6:405-413, 2000.

Selke et al., Endothelial modulation of porcine coronary microcirculation perfused via immature collaterals, Am. J. Physiol., 262:H1669-1675, 1992.

Senger et al., Stimulation of endothelial cell migration by vascular permeability factor/vascular endothelial growth factor through cooperative mechanisms involving the αvβ3 integrin, osteopontin, and thrombin, Am. J. Pathol., 149(1):293-305, 1996.

Shand et al., Specific amino acid substitutions determine the differential contribution of the N- and C-terminal domains of insulin-like growth factor (IGF)-binding protein-5 in binding IGF-I, J. Biol. Chem., 278(20): 17859-17866, 2003.

Shin et al., The chemical synthesis and binding affinity to the EGF receptor of the EFG-like domain of heparin-binding EGF-like growth factor (HB-EGF), J. Pept Sci, 9(4):244-250, 2003.

Silverman et al., Vascular, glial and neuronal effects of vascular endothelial growth factor in mesenchphalic explant cultures, Neuroscience, 90:1529-1541, 1999.

Sondell et al., Postnatal expression of VEGF and its receptor flk-1 in peripheral ganglia, Neuroreport, 12(1):105-108, 2001.

Sondell et al., Vascular endothelial growth factor has neurotrophic activity and stimulates axonal outgrowth, enhancing cell survival and Schwann cell proliferation in the peripheral nervous system, J. Neurosci., 19(14):5731-5740, 1999.

Stacker et al., The vascular endothelial growth factor family: signaling for vascular development, Growth Factors, 17:1-11, 1999.

Takeshita et al., Therapeutic angiogenesis: a single intraarterial bolus of vascular endothelial growth factor augments revascularization in a rabbit ischemic hind limb model, J. Clin. Invest., 93(2):662-670, 1994.

Terman et al., Identification of the KDR tyrosine kinase as a receptor for vascular endothelial cell growth factor, Biochem. Biophys. Res. Comm., 187(3):1579-1586, 1992.

Thommen et al., PGDF-BB increases endothelial migration and cord movements during angiogenesis in vitro, J. Cell Biochem., 64:403-413, 1997.

Thuringer et al., Rapid transactivation of the vascular endothelial growth factor receptor KDR/Flk-1 by the bradykinin B2 receptor contributes to endothelial nitric-oxide synthase activation in cardiac capillary endothelial cells, J. Biol. Chem., 227:2028-2032, 2002.

Uutela et al., Chromosomal location, exon structure, and vascular expression patterns of the human PDGFC and PDGFD genes, Circulation, 103:2242-2247, 2001.

Vale et al., Therapeutic angiogenesis in critical limb and myocardial ischemia, J. Interv. Cardiol., 14(5):511-528, 2001.

Valtola et al., VEGFR-3 and its ligand VEGF-C are associated with angiogenesis in breast cancer, Am. J. Path., 154(5):1381-1390, 1999.

Vassar et al., Tissue-specific and differentiation-specific expression of a human K14 keratin gene in transgenic mice, Proc. Natl. Acad. Sci. USA, 86:1563-1567, 1989.

Vassar et al., Transgenic mice provide new insights into the role of TGF-α during epidermal development and differentiation, Genes Dev., 5:714-727, 1991.

Veikkola et al., Signaling via vascular endothelial growth factor receptor-3 is sufficient for lymphangiogenesis in transgenic mice, EMBO J., 6:1223-1231, 2001.

Yamashita et al., Flk1-positive cells derived from embryonic stem cells serve as vascular progenitors, Nature, 408:92-96, 2000.

Yasuda et al., Involvement of CD44 in induction of matrix metalloproteinases by a COOH-terminal heparin-binding fragment of fibronectin in human articular cartilage in culture, Arthritis Rheum., 48(5):1271-1280, 2003.

Yu et al., Both platelet-derived growth factor receptor ((PDGFR)-α and PDGFR-β promote murine fibroblast cell migration), Biochem. Biophys. Res. Comm., 282:697-700, 2001.

Zachary, Vascular endothelial growth factor, Intl. J. Biochem. Cell Bio., 30:1169-1174, 1998.

Achen et al., Monoclonal antibodies to vascular endothelial growth factor-D block its interactions with both VEGF receptor-2 and VEGF receptor-3, Eur. J. Biochem., 267:2505-2515, 2000.

Bergsten et al., PDGF-D is a specific, protease-activated ligand for the PDGF beta-receptor, Nature Cell Biol., 3:512-516, 2001.

GenBank accession No. Q9GZPO, Platelet-derived growth factor D precursor (PDGF D) (Iris-expressed growth factor) (Spinal cord-derived growth factor B) (SCDGF-B), sequence updated Mar. 1, 2001, annotation updated Jul. 10, 2007.

International Search Report (Partial), PCT/US2006/32012, European Patent Office, Apr. 25, 2007.

International Search Report, PCT/US2006/32012, European Patent Office, Jun. 12, 2007.

Tammela et al., Modulation of the biological activities of VEGF and VEGF-C by swapping of the silk and heparin-binding domains, Nature Biotechnology Symposium, Miami, Feb. 2006.

Written Opinion of the International Searching Authority, PCT/US2006/32012, European Patent Office, Jun. 12, 2007.

Zheng et al., Chimeric VEGF-E (NZ7) promotes angiogenesis via VEGFR-2 without significant enhancement of vascular permeability and inflammation, Arterioscler. Thromb. Vasc. Biol., 26(9):2019-2026, 2006.

SEQUENCE LISTING

<160> NUMBER OF SEQ ID NOS: 65

<210> SEQ ID NO 1
<211> LENGTH: 649
<212> TYPE: DNA
<213> ORGANISM: Homo sapiens
<220> FEATURE:
<221> NAME/KEY:
<223> OTHER INFORMATION: VEGF-A

<400> SEQUENCE: 1

```
tcgggcctcc gaaaccatga actttctgct gtcttgggtg cattggagcc ttgccttgct    60
gctctacctc caccatgcca agtggtccca ggctgcaccc atggcagaag gaggagggca   120
gaatcatcac gaagtggtga agttcatgga tgtctatcag cgcagctact gccatccaat   180
cgagaccctg gtggacatct tccaggagta ccctgatgag atcgagtaca tcttcaagcc   240
atcctgtgtg cccctgatgc gatgcggggg ctgctgcaat gacgagggcc tggagtgtgt   300
gcccactgag gagtccaaca tcaccatgca gattatgcgg atcaaacctc accaaggcca   360
gcacatagga gagatgagct tcctacagca acaaatgt gaatgcagac caaagaaaga   420
tagagcaaga caagaaaatc cctgtgggcc ttgctcagag cggagaaagc atttgtttgt   480
acaagatccg cagacgtgta aatgttcctg caaaaacaca gactcgcgtt gcaaggcgag   540
gcagcttgag ttaaacgaac gtacttgcag atgtgacaag ccgaggcggt gagccgggca   600
ggaggaagga gcctccctca gcgtttcggg aaccagatct ctcaccagg                649
```

<210> SEQ ID NO 2
<211> LENGTH: 191
<212> TYPE: PRT
<213> ORGANISM: Homo sapiens
<220> FEATURE:
<221> NAME/KEY:
<223> OTHER INFORMATION: VEGF-A

<400> SEQUENCE: 2

```
Met Asn Phe Leu Leu Ser Trp Val His Trp Ser Leu Ala Leu Leu Leu
 1               5                  10                  15
```

```
Tyr Leu His His Ala Lys Trp Ser Gln Ala Pro Met Ala Glu Gly
         20                  25                  30

Gly Gly Gln Asn His His Glu Val Val Lys Phe Met Asp Val Tyr Gln
             35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
65                   70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 3
<211> LENGTH: 232
<212> TYPE: PRT
<213> ORGANISM: Homo sapiens
<220> FEATURE:
<221> NAME/KEY:
<223> OTHER INFORMATION: VEGF206

<400> SEQUENCE: 3

Met Asn Phe Leu Leu Ser Trp Val His Trp Ser Leu Ala Leu Leu Leu
1               5                   10                  15

Tyr Leu His His Ala Lys Trp Ser Gln Ala Pro Met Ala Glu Gly
         20                  25                  30

Gly Gly Gln Asn His His Glu Val Val Lys Phe Met Asp Val Tyr Gln
             35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
65                   70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190
```

```
His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
            210                 215                 220

Cys Arg Cys Asp Lys Pro Arg Arg
225                 230

<210> SEQ ID NO 4
<211> LENGTH: 147
<212> TYPE: PRT
<213> ORGANISM: Homo sapiens
<220> FEATURE:
<221> NAME/KEY:
<223> OTHER INFORMATION: VEGF121

<400> SEQUENCE: 4

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Cys Asp Lys
    130                 135                 140

Pro Arg Arg
145

<210> SEQ ID NO 5
<211> LENGTH: 171
<212> TYPE: PRT
<213> ORGANISM: Homo sapiens
<220> FEATURE:
<221> NAME/KEY:
<223> OTHER INFORMATION: VEGF145

<400> SEQUENCE: 5

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95
```

-continued

```
Thr Glu Glu Ser Asn Ile Thr Met Gln Ile Met Arg Ile Lys Pro His
                100                 105                 110
Gln Gly Gln His Ile Gly Glu Met Ser Phe Leu Gln His Asn Lys Cys
            115                 120                 125
Glu Cys Arg Pro Lys Lys Asp Arg Ala Arg Gln Glu Lys Lys Ser Val
130                 135                 140
Arg Gly Lys Gly Lys Gly Gln Lys Arg Lys Arg Lys Lys Ser Arg Tyr
145                 150                 155                 160
Lys Ser Trp Ser Val Cys Asp Lys Pro Arg Arg
                165                 170

<210> SEQ ID NO 6
<211> LENGTH: 191
<212> TYPE: PRT
<213> ORGANISM: Homo sapiens

<400> SEQUENCE: 6

Met Asn Phe Leu Leu Ser Trp Val His Trp Ser Leu Ala Leu Leu Leu
1               5                   10                  15
Tyr Leu His His Ala Lys Trp Ser Gln Ala Ala Pro Met Ala Glu Gly
            20                  25                  30
Gly Gly Gln Asn His His Glu Val Val Lys Phe Met Asp Val Tyr Gln
        35                  40                  45
Arg Ser Tyr Cys His Pro Ile Glu Thr Leu Val Asp Ile Phe Gln Glu
    50                  55                  60
Tyr Pro Asp Glu Ile Glu Tyr Ile Phe Lys Pro Ser Cys Val Pro Leu
65                  70                  75                  80
Met Arg Cys Gly Gly Cys Cys Asn Asp Glu Gly Leu Glu Cys Val Pro
                85                  90                  95
Thr Glu Glu Ser Asn Ile Thr Met Gln Ile Met Arg Ile Lys Pro His
                100                 105                 110
Gln Gly Gln His Ile Gly Glu Met Ser Phe Leu Gln His Asn Lys Cys
            115                 120                 125
Glu Cys Arg Pro Lys Lys Asp Arg Ala Arg Gln Glu Asn Pro Cys Gly
130                 135                 140
Pro Cys Ser Glu Arg Arg Lys His Leu Phe Val Gln Asp Pro Gln Thr
145                 150                 155                 160
Cys Lys Cys Ser Cys Lys Asn Thr Asp Ser Arg Cys Lys Ala Arg Gln
                165                 170                 175
Leu Glu Leu Asn Glu Arg Thr Cys Arg Cys Asp Lys Pro Arg Arg
                180                 185                 190

<210> SEQ ID NO 7
<211> LENGTH: 215
<212> TYPE: PRT
<213> ORGANISM: Homo sapiens
<220> FEATURE:
<221> NAME/KEY:
<223> OTHER INFORMATION: VEGF189

<400> SEQUENCE: 7

Met Asn Phe Leu Leu Ser Trp Val His Trp Ser Leu Ala Leu Leu Leu
1               5                   10                  15
Tyr Leu His His Ala Lys Trp Ser Gln Ala Ala Pro Met Ala Glu Gly
            20                  25                  30
Gly Gly Gln Asn His His Glu Val Val Lys Phe Met Asp Val Tyr Gln
        35                  40                  45
Arg Ser Tyr Cys His Pro Ile Glu Thr Leu Val Asp Ile Phe Gln Glu
```

```
                50                  55                  60
Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Lys Lys Ser Val
            130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
            195                 200                 205

Arg Cys Asp Lys Pro Arg Arg
        210                 215

<210> SEQ ID NO 8
<211> LENGTH: 1645
<212> TYPE: DNA
<213> ORGANISM: Homo sapiens
<220> FEATURE:
<221> NAME/KEY:
<223> OTHER INFORMATION: PlGF

<400> SEQUENCE: 8
gggattcggg ccgcccagct acgggaggac ctggagtggc actgggcgcc cgacggacca      60
tccccgggac ccgcctgccc ctcggcgccc cgccccgccg ggccgctccc cgtcgggttc     120
cccagccaca gccttaccta cgggctcctg actccgcaag gcttccagaa gatgctcgaa     180
ccaccggccg gggcctcggg gcagcagtga gggaggcgtc cagccccca ctcagctctt      240 ctcctcctgt gccaggggct ccccggggga tgagcatggt ggttttccct cggagccccc     300
tggctcggga cgtctgagaa gatgccggtc atgaggctgt tcccttgctt cctgcagctc     360
ctggccgggc tggcgctgcc tgctgtgccc cccagcagt gggccttgtc tgctgggaac      420
ggctcgtcag aggtggaagt ggtacccttc caggaagtgt ggggccgcag ctactgccgg     480
gcgctggaga ggctggtgga cgtcgtgtcc gagtacccca gcgaggtgga gcacatgttc     540
agcccatcct gtgtctccct gctgcgctgc accggctgct gcggcgatga aatctgcac     600 tgtgtgccgg tggagacggc caatgtcacc atgcagctcc taaagatccg ttctggggac     660
cggccctcct acgtggagct gacgttctct cagcacgttc gctgcgaatg ccggcctctg     720
cgggagaaga tgaagccgga aggtgcggc gatgctgttc cccggaggta acccaccct       780 tggaggagag agaccccgca cccggctcgt gtatttatta ccgtcacact cttcagtgac     840
tcctgctggt acctgccctc tatttattag ccaactgttt cctgctgaa tgcctcgctc      900 ccttcaagac gaggggcagg gaaggacagg accctcagga attcagtgcc ttcaacaacg     960
tgagagaaag agagaagcca gccacagacc cctgggagct tccgctttga aagaagcaag    1020
acacgtggcc tcgtgagggg caagctaggc cccagaggcc ctgaggtct ccaggggcct     1080 gcagaaggaa agaaggggggc cctgctacct gttcttgggc ctcaggctct gcacagacaa   1140
```

```
gcagcccttg ctttcggagc tcctgtccaa agtagggatg cggattctgc tggggccgcc    1200
acggcctggt ggtgggaagg ccggcagcgg gcggagggga ttcagccact tccccctctt    1260
cttctgaaga tcagaacatt cagctctgga gaacagtggt tgcctggggg cttttgccac    1320
tccttgtccc ccgtgatctc ccctcacact ttgccatttg cttgtactgg gacattgttc    1380
tttccggccg aggtgccacc accctgcccc cactaagaga cacatacaga gtgggccccg    1440
ggctggagaa agagctgcct ggatgagaaa cagctcagcc agtggggatg aggtcaccag    1500
gggaggagcc tgtgcgtccc agctgaaggc agtggcaggg gagcaggttc cccaagggcc    1560
ctggcacccc cacaagctgt ccctgcaggg ccatctgact gccaagccag attctcttga    1620
ataaagtatt ctagtgtgga aacgc                                          1645
```

<210> SEQ ID NO 9
<211> LENGTH: 149
<212> TYPE: PRT
<213> ORGANISM: Homo sapiens
<220> FEATURE:
<221> NAME/KEY:
<223> OTHER INFORMATION: PlGF

<400> SEQUENCE: 9

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140

Ala Val Pro Arg Arg
145
```

<210> SEQ ID NO 10
<211> LENGTH: 755
<212> TYPE: DNA
<213> ORGANISM: Homo sapiens
<220> FEATURE:
<221> NAME/KEY:
<223> OTHER INFORMATION: VEGF-B

<400> SEQUENCE: 10

```
caccatgagc cctctgctcc gccgcctgct gctcgccgca ctcctgcagc tggccccgc      60 ccaggcccct gtctcccagc ctgatgcccc tggccaccag aggaaagtgg tgtcatggat    120
agatgtgtat actcgcgcta cctgccagcc ccgggaggtg gtggtgccct tgactgtgga    180
gctcatgggc accgtggcca aacagctggt gcccagctgc gtgactgtgc agcgctgtgg    240
tggctgctgc cctgacgatg gcctggagtg tgtgcccact gggcagcacc aagtccggat    300
```

```
gcagatcctc atgatccggt acccgagcag tcagctgggg gagatgtccc tggaagaaca    360
cagccagtgt gaatgcagac ctaaaaaaaa ggacagtgct gtgaagccag acagggctgc    420
cactccccac caccgtcccc agcccgttc tgttccgggc tgggactctg ccccggagc     480 accctcccca gctgacatca cccatcccac tccagcccca ggcccctctg cccacgctgc    540
acccagcacc accagcgccc tgaccccgg acctgccgcc gccgctgccg acgccgcagc    600
ttcctccgtt gccaagggcg gggcttagag ctcaacccag acacctgcag gtgccggaag    660
ctgcgaaggt gacacatggc ttttcagact cagcagggtg acttgcctca gaggctatat    720
cccagtgggg gaacaaagag gagcctggta aaaaa                              755
```

<210> SEQ ID NO 11
<211> LENGTH: 207
<212> TYPE: PRT
<213> ORGANISM: Homo sapiens
<220> FEATURE:
<221> NAME/KEY:
<223> OTHER INFORMATION: VEGF-B

<400> SEQUENCE: 11

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205
```

<210> SEQ ID NO 12
<211> LENGTH: 2076
<212> TYPE: DNA
<213> ORGANISM: Homo sapiens
<220> FEATURE:
<221> NAME/KEY:
<223> OTHER INFORMATION: VEGF-C

<400> SEQUENCE: 12

```
cggggaaggg gagggaggag ggggacgagg gctctggcgg gtttggaggg gctgaacatc    60
```

```
gcggggtgtt ctggtgtccc ccgccccgcc tctccaaaaa gctacaccga cgcggaccgc    120
ggcggcgtcc tccctcgccc tcgcttcacc tcgcgggctc cgaatgcggg gagctcggat    180
gtccggtttc ctgtgaggct tttacctgac acccgccgcc tttccccggc actggctggg    240
agggcgccct gcaaagttgg gaacgcggag ccccggaccc gctcccgccg cctccggctc    300 gcccagggg ggtcgccggg aggagcccgg gggagaggga ccaggagggg cccgcggcct    360
cgcaggggcg cccgcgcccc cacccctgcc ccgccagcg gaccggtccc caccccgg      420 tccttccacc atgcacttgc tgggcttctt ctctgtggcg tgttctctgc tcgccgctgc    480
gctgctcccg gtcctcgcg aggcgcccgc cgccgccgcc gccttcgagt ccggactcga    540
cctctcggac gcggagcccg acgcgggcga ggccacggct tatgcaagca agatctgga    600 ggagcagtta cggtctgtgt ccagtgtaga tgaactcatg actgtactct acccagaata    660
ttggaaaatg tacaagtgtc agctaaggaa aggaggctgg caacataaca gagaacaggc    720
caacctcaac tcaaggacag aagagactat aaaatttgct gcagcacatt ataatacaga    780
gatcttgaaa agtattgata tgagtggag aaagactcaa tgcatgccac gggaggtgtg    840
tatagatgtg gggaaggagt ttggagtcgc gacaaacacc ttctttaaac ctccatgtgt    900
gtccgtctac agatgtgggg gttgctgcaa tagtgagggg ctgcagtgca tgaacaccag    960
cacgagctac ctcagcaaga cgttatttga aattacagtg cctctctctc aaggccccaa    1020
accagtaaca atcagttttg ccaatcacac ttcctgccga tgcatgtcta aactggatgt    1080
ttacagacaa gttcattcca ttattagacg ttccctgcca gcaacactac acagtgtca    1140 ggcagcgaac aagacctgcc ccaccaatta catgtggaat aatcacatct gcagatgcct    1200
ggctcaggaa gattttatgt tttcctcgga tgctggagat gactcaacag atggattcca    1260
tgacatctgt ggaccaaaca aggagctgga tgaagagacc tgtcagtgtg tctgcagagc    1320
ggggcttcgg cctgccagct gtggacccca caagaactaa gacagaaact catgccagtg    1380
tgtctgtaaa acaaactct tccccagcca atgtggggcc aaccgagaat tgatgaaaa    1440 cacatgccag tgtgtatgta aagaacctg ccccagaaat caaccctaa atcctggaaa    1500 atgtgcctgt gaatgtacag aaagtccaca gaaatgcttg ttaaaaggaa agaagttcca    1560 ccaccaaaaca tgcagctgtt acagacggcc atgtacgaac cgccagaagg cttgtgagcc    1620
aggattttca tatagtgaag aagtgtgtcg ttgtgtccct tcatattgga aaagaccaca    1680
aatgagctaa gattgtactg tttttccagtt catcgatttt ctattatgga aaactgtgtt    1740
gccacagtag aactgtctgt gaacagagag acccttgtgg gtccatgcta acaaagacaa    1800
aagtctgtct ttcctgaacc atgtggataa ctttacagaa atggactgga gctcatctgc    1860
aaaaggcctc ttgtaaagac tggttttctg ccaatgacca aacagccaag atttttcctct    1920 tgtgatttct ttaaaagaat gactatataa ttttatttcca ctaaaaatat tgtttctgca    1980 ttcatttta tagcaacaac aattggtaaa actcactgtg atcaatattt tatatcatg     2040 caaaatatgt ttaaaataaa atgaaaattg tattat                              2076
```

<210> SEQ ID NO 13
<211> LENGTH: 419
<212> TYPE: PRT
<213> ORGANISM: Homo sapiens
<220> FEATURE:
<221> NAME/KEY:
<223> OTHER INFORMATION: VEGF-C

<400> SEQUENCE: 13

Met His Leu Leu Gly Phe Phe Ser Val Ala Cys Ser Leu Leu Ala Ala

```
              1               5              10              15
Ala Leu Leu Pro Gly Pro Arg Glu Ala Pro Ala Ala Ala Ala Ala Phe
                        20              25              30

Glu Ser Gly Leu Asp Leu Ser Asp Ala Glu Pro Asp Ala Gly Glu Ala
            35              40              45

Thr Ala Tyr Ala Ser Lys Asp Leu Glu Glu Gln Leu Arg Ser Val Ser
        50              55              60

Ser Val Asp Glu Leu Met Thr Val Leu Tyr Pro Glu Tyr Trp Lys Met
 65             70              75              80

Tyr Lys Cys Gln Leu Arg Lys Gly Gly Trp Gln His Asn Arg Glu Gln
                85              90              95

Ala Asn Leu Asn Ser Arg Thr Glu Thr Ile Lys Phe Ala Ala Ala
               100             105             110

His Tyr Asn Thr Glu Ile Leu Lys Ser Ile Asp Asn Glu Trp Arg Lys
            115             120             125

Thr Gln Cys Met Pro Arg Glu Val Cys Ile Asp Val Gly Lys Glu Phe
            130             135             140

Gly Val Ala Thr Asn Thr Phe Phe Lys Pro Pro Cys Val Ser Val Tyr
145             150             155             160

Arg Cys Gly Gly Cys Cys Asn Ser Glu Gly Leu Gln Cys Met Asn Thr
                165             170             175

Ser Thr Ser Tyr Leu Ser Lys Thr Leu Phe Glu Ile Thr Val Pro Leu
                180             185             190

Ser Gln Gly Pro Lys Pro Val Thr Ile Ser Phe Ala Asn His Thr Ser
                195             200             205

Cys Arg Cys Met Ser Lys Leu Asp Val Tyr Arg Gln Val His Ser Ile
210             215             220

Ile Arg Arg Ser Leu Pro Ala Thr Leu Pro Gln Cys Gln Ala Ala Asn
225             230             235             240

Lys Thr Cys Pro Thr Asn Tyr Met Trp Asn Asn His Ile Cys Arg Cys
                245             250             255

Leu Ala Gln Glu Asp Phe Met Phe Ser Ser Asp Ala Gly Asp Asp Ser
                260             265             270

Thr Asp Gly Phe His Asp Ile Cys Gly Pro Asn Lys Glu Leu Asp Glu
            275             280             285

Glu Thr Cys Gln Cys Val Cys Arg Ala Gly Leu Arg Pro Ala Ser Cys
            290             295             300

Gly Pro His Lys Glu Leu Asp Arg Asn Ser Cys Gln Cys Val Cys Lys
305             310             315             320

Asn Lys Leu Phe Pro Ser Gln Cys Gly Ala Asn Arg Glu Phe Asp Glu
                325             330             335

Asn Thr Cys Gln Cys Val Cys Lys Arg Thr Cys Pro Arg Asn Gln Pro
            340             345             350

Leu Asn Pro Gly Lys Cys Ala Cys Glu Cys Thr Glu Ser Pro Gln Lys
            355             360             365

Cys Leu Leu Lys Gly Lys Lys Phe His His Gly Thr Cys Ser Cys Tyr
        370             375             380

Arg Arg Pro Cys Thr Asn Arg Gln Lys Ala Cys Glu Pro Gly Phe Ser
385             390             395             400

Tyr Ser Glu Glu Val Cys Arg Cys Val Pro Ser Tyr Trp Lys Arg Pro
                405             410             415

Gln Met Ser
```

```
<210> SEQ ID NO 14
<211> LENGTH: 2128
<212> TYPE: DNA
<213> ORGANISM: Homo sapiens
<220> FEATURE:
<221> NAME/KEY:
<223> OTHER INFORMATION: VEGF-D

<400> SEQUENCE: 14
caagacttct ctgcattttc tgccaaaatc tgtgtcagat ttaagacaca tgcttctgca    60
agcttccatg aaggttgtgc aaaaaagttt caatccagag ttgggttcca gctttctgta   120
gctgtaagca ttggtggcca caccacctcc ttacaaagca actagaacct gcggcataca   180
ttggagagat tttttaatt ttctggacat gaagtaaatt tagagtgctt tctaatttca   240
ggtagaagac atgtccacct tctgattatt tttggagaac attttgattt ttttcatctc   300
tctctcccca cccctaagat tgtgcaaaaa aagcgtacct tgcctaattg aaataatttc   360
attggatttt gatcagaact gattatttgg ttttctgtgt gaagttttga ggtttcaaac   420
tttccttctg gagaatgcct tttgaaacaa ttttctctag ctgcctgatg tcaactgctt   480
agtaatcagt ggatattgaa atattcaaaa tgtacagaga gtgggtagtg gtgaatgttt   540
tcatgatgtt gtacgtccag ctggtgcagg gctccagtaa tgaacatgga ccagtgaagc   600
gatcatctca gtccacattg gaacgatctg aacagcagat cagggctgct tctagtttgg   660
aggaactact tcgaattact cactctgagg actggaagct gtggagatgc aggctgaggc   720
tcaaagtttt taccagtatg gactctcgct cagcatccca tcggtccact aggtttgcgg   780
caactttcta tgacattgaa acactaaaag ttatagatga agaatggcaa agaactcagt   840
gcagccctag agaaacgtgc gtggaggtgg ccagtgagct ggggaagagt accaacacat   900
tcttcaagcc cccttgtgtg aacgtgttcc gatgtggtgg ctgttgcaat gaagagagcc   960
ttatctgtat gaacaccagc acctcgtaca tttccaaaca gctctttgag atatcagtgc  1020
ctttgacatc agtacctgaa ttagtgcctg ttaaagttgc caatcataca ggttgtaagt  1080
gcttgccaac agcccccgc catccatact caattatcag aagatccatc cagatccctg  1140
aagaagatcg ctgttcccat tccaagaaac tctgtcctat tgacatgcta tgggatagca  1200
acaaatgtaa atgtgttttg caggaggaaa atccacttgc tggaacagaa gaccactctc  1260
atctccagga accagctctc tgtgggccac acatgatgtt tgacgaagat cgttgcgagt  1320
gtgtctgtaa aacaccatgt cccaaagatc taatccagca ccccaaaaac tgcagttgct  1380
ttgagtgcaa agaaagtctg gagacctgct gccagaagca caagctatttt cacccagaca  1440 cctgcagctg tgaggacaga tgccccttc ataccagacc atgtgcaagt ggcaaaacag  1500
catgtgcaaa gcattgccgc tttccaaagg agaaaagggc tgcccagggg ccccacagcc  1560
gaaagaatcc ttgattcagc gttccaagtt ccccatccct gtcatttta acagcatgct  1620 gctttgccaa gttgctgtca ctgttttttt cccaggtgtt aaaaaaaaaa tccattttac  1680
acagcaccac agtgaatcca gaccaacctt ccattcacac cagctaagga gtccctggtt  1740
cattgatgga tgtcttctag ctgcagatgc ctctgcgcac caaggaatgg agaggagggg  1800
acccatgtaa tccttttgtt tagttttgtt tttgtttttt ggtgaatgag aaaggtgtgc  1860
tggtcatgga atggcaggtg tcatatgact gattactcag agcagatgag gaaaactgta  1920
gtctctgagt cctttgctaa tcgcaactct tgtgaattat tctgattctt ttttatgcag  1980
aatttgattc gtatgatcag tactgacttt ctgattactg tccagcttat agtcttccag  2040
tttaatgaac taccatctga tgtttcatat ttaagtgtat ttaaagaaaa taacaccat   2100
```

-continued tattcaagcc aaaaaaaaaa aaaaaaa        2128

<210> SEQ ID NO 15
<211> LENGTH: 354
<212> TYPE: PRT
<213> ORGANISM: Homo sapiens
<220> FEATURE:
<221> NAME/KEY:
<223> OTHER INFORMATION: VEGF-D

<400> SEQUENCE: 15

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 16
<211> LENGTH: 2797
<212> TYPE: DNA
<213> ORGANISM: Homo sapiens
<220> FEATURE:
<221> NAME/KEY:
<223> OTHER INFORMATION: PDGF-A

<400> SEQUENCE: 16

| | | | | | |
|---|---|---|---|---|---|
| acgcgcgccc | tgcggagccc | gcccaactcc | ggcgagccgg | gcctgcgcct | actcctcctc | 60 |
| ctcctctccc | ggcggcggct | gcggcggagg | cgccgactcg | gccttgcgcc | cgccctcagg | 120 |
| cccgcgcggg | cggcgcagcg | aggccccggg | cggcgggtgg | tggctgccag | gcggctcggc | 180 |
| cgcgggcgct | gccggcccc | ggcgagcgga | gggcggagcg | cggcgccgga | gccgagggcg | 240 |
| cgccgcggag | ggggtgctgg | gccgcgctgt | gccggccgg | gcggcggctg | caagaggagg | 300 |
| ccggaggcga | gcgcggggcc | ggcggtgggc | gcgcagggcg | gctcgcagct | cgcagccggg | 360 |
| gccgggccag | gcgttcaggc | aggtgatcgg | tgtggcggcg | gcggcggcgg | cggccccaga | 420 |
| ctccctccgg | agttcttctt | ggggctgatg | tccgcaaata | tgcagaatta | ccggccgggt | 480 |
| cgctcctgaa | gccagcgcgg | ggagcgagcg | cggcggcggc | cagcaccggg | aacgcaccga | 540 |
| ggaagaagcc | cagcccccgc | cctccgcccc | ttccgtcccc | accccctacc | cggcggccca | 600 |
| ggaggctccc | cggctgcggc | gcgcactccc | tgtttctcct | cctcctggct | ggcgctgcct | 660 |
| gcctctccgc | actcactgct | cgccgggcgc | cgtccgccag | ctccgtgctc | ccgcgccac | 720 |
| cctcctccgg | gccgcgctcc | ctaagggatg | gtactgaatt | cgccgccac | aggagaccgg | 780 |
| ctggagcgcc | cgccccgcgc | ctcgcctctc | ctccgagcag | ccagcgcctc | gggacgcgat | 840 |
| gaggaccttg | gcttgcctgc | tgctcctcgg | ctgcggatac | ctcgcccatg | ttctggccga | 900 |
| ggaagccgag | atccccgcg | aggtgatcga | gaggctggcc | cgcagtcaga | tccacagcat | 960 |
| ccgggacctc | cagcgactcc | tggagataga | ctccgtaggg | agtgaggatt | ctttggacac | 1020 |
| cagcctgaga | gctcacgggg | tccacgccac | taagcatgtg | cccgagaagc | ggcccctgcc | 1080 |
| cattcggagg | aagagaagca | tcgaggaagc | tgtccccgct | gtctgcaaga | ccaggacggt | 1140 |
| catttacgag | attcctcgga | gtcaggtcga | ccccacgtcc | gccaacttcc | tgatctggcc | 1200 |
| cccgtgcgtg | gaggtgaaac | gctgcaccgg | ctgctgcaac | acgagcagtg | tcaagtgcca | 1260 |
| gccctcccgc | gtccaccacc | gcagcgtcaa | ggtggccaag | gtggaatacg | tcaggaagaa | 1320 |
| gccaaaatta | aaagaagtcc | aggtgaggtt | agaggagcat | ttggagtgcg | cctgcgcgac | 1380 |
| cacaagcctg | aatccggatt | atcgggaaga | ggacacggga | aggcctaggg | agtcaggtaa | 1440 |
| aaaacggaaa | agaaaaaggt | taaaacccac | ctaagatgtg | aggtgaggat | gagccgcagc | 1500 |
| cctttcctgg | gacatggatg | tacatggcgt | gttacattcc | tgaacctact | atgtacggtg | 1560 |
| ctttattgcc | agtgtgcggt | ctttgttctc | ctccgtgaaa | aactgtgtcc | gagaacactc | 1620 |
| gggagaacaa | agagacagtg | cacatttgtt | taatgtgaca | tcaaagcaag | tattgtagca | 1680 |
| ctcggtgaag | cagtaagaag | cttccttgtc | aaaaagagag | agagagagag | agagagagaa | 1740 |
| aacaaaacca | caaatgacaa | aaacaaaacg | gactcacaaa | aatatctaaa | ctcgatgaga | 1800 |
| tggagggtcg | ccccgtggga | tggaagtgca | gaggtctcag | cagactggat | ttctgtccgg | 1860 |
| gtggtcacag | gtgctttttt | gccgaggatg | cagagcctgc | tttgggaacg | actccagagg | 1920 |
| ggtgctggtg | ggctctgcag | ggcccgcagg | aagcaggaat | gtcttggaaa | ccgcacgcg | 1980 |
| aactttagaa | accacacctc | ctcgctgtag | tatttaagcc | catacagaaa | ccttcctgag | 2040 |

```
agccttaagt ggtttttttt tttgttttttg ttttgttttt ttttttttttg tttttttttt    2100 tttttttttt tttacacca taaagtgatt attaagcttc cttttactct ttggctagct       2160
tttttttttt tttttttttt tttttttttt aattatctct tggatgacat ttacaccgat      2220
aacacacagg ctgctgtaac tgtcaggaca gtgcgacggt attttttccta gcaagatgca     2280 aactaatgag atgtattaaa ataaacatgg tatacctacc tatgcatcat ttcctaaatg      2340
tttctggctt tgtgtttctc ccttaccctg ctttatttgt taatttaagc cattttgaaa      2400
gaactatgcg tcaaccaatc gtacgccgtc cctgcggcac ctgccccaga gcccgtttgt      2460
ggctgagtga caacttgttc cccgcagtgc acacctagaa tgctgtgttc ccacgcggca      2520
cgtgagatgc attgccgctt ctgtctgtgt tgttggtgtg ccctggtgcc gtggtggcgg      2580
tcactccctc tgctgccagt gtttggacag aacccaaatt ctttattttt ggtaagatat      2640
tgtgctttac ctgtattaac agaaatgtgt gtgtgtggtt tgttttttttg taaaggtgaa     2700 gtttgtatgt ttacctaata ttacctgttt tgtatacctg agagcctgct atgttcttct      2760
tttgttgatc caaaattaaa aaaaaaatac caccaac                               2797
```

<210> SEQ ID NO 17
<211> LENGTH: 211
<212> TYPE: PRT
<213> ORGANISM: Homo sapiens
<220> FEATURE:
<221> NAME/KEY:
<223> OTHER INFORMATION: PDGF-A

<400> SEQUENCE: 17

```
Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
        50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
            195                 200                 205

Lys Pro Thr
    210
```

<210> SEQ ID NO 18
<211> LENGTH: 3373
<212> TYPE: DNA
<213> ORGANISM: Homo sapiens
<220> FEATURE:
<221> NAME/KEY:
<223> OTHER INFORMATION: PDGF-B

<400> SEQUENCE: 18

| | | | | | |
|---|---|---|---|---|---|
| ggtggcaact | tctcctcctg | cggccgggag | cggcctgcct | gcctccctgc | gcacccgcag | 60 |
| cctcccccgc | tgcctcccta | gggctcccct | ccggccgcca | gcgcccattt | ttcattccct | 120 |
| agatagagat | actttgcgcg | cacacacata | catacgcgcg | caaaaaggaa | aaaaaaaaaa | 180 |
| aaaagcccac | cctccagcct | cgctgcaaag | agaaaaccgg | agcagccgca | gctcgcagct | 240 |
| cgcagctcgc | agcccgcagc | ccgcagagga | cgcccagagc | ggcgagcagg | cgggcagacg | 300 |
| gaccgacgga | ctcgcgccgc | gtccacctgt | cggccgggcc | cagccgagcg | cgcagcgggc | 360 |
| acgccgcgcg | cgcggagcag | ccgtgcccgc | gcccgggcc | cgccgccagg | cgcacacgc | 420 |
| tcccgccccc | ctacccggcc | cgggcgggag | tttgcacctc | tccctgcccg | ggtgctcgag | 480 |
| ctgccgttgc | aaagccaact | ttggaaaaag | ttttttgggg | gagacttggg | ccttgaggtg | 540 |
| cccagctccg | cgctttccga | ttttgggggc | ctttccagaa | aatgttgcaa | aaaagctaag | 600 |
| ccggcgggca | gaggaaaacg | cctgtagccg | gcgagtgaag | acgaaccatc | gactgccgtg | 660 |
| ttccttttcc | tcttggaggt | tggagtcccc | tgggcgcccc | cacacggcta | gacgcctcgg | 720 |
| ctggttcgcg | acgcagcccc | ccggccgtgg | atgctgcact | cgggctcggg | atccgcccag | 780 |
| gtagccggcc | tcggacccag | gtcctgcgcc | caggtcctcc | cctgccccc | agcgacggag | 840 |
| ccggggccgg | gggcggcggc | gccggggca | tgcgggtgag | ccgcggctgc | agaggcctga | 900 |
| gcgcctgatc | gccgcggacc | tgagccgagc | cccccccct | ccccagcccc | ccaccctggc | 960 |
| cgcggggggcg | gcgcgctcga | tctacgcgtc | cggggcccg | cggggccggg | ccggagtcg | 1020 |
| gcatgaatcg | ctgctgggcg | ctcttcctgt | ctctctgctg | ctacctgcgt | ctggtcagcg | 1080 |
| ccgaggggga | ccccattccc | gaggagcttt | atgagatgct | gagtgaccac | tcgatccgct | 1140 |
| cctttgatga | tctccaacgc | ctgctgcacg | gagaccccgg | agaggaagat | ggggccgagt | 1200 |
| tggacctgaa | catgacccgc | tcccactctg | gaggcgagct | ggagagcttg | gctcgtggaa | 1260 |
| gaaggagcct | gggttccctg | accattgctg | agccggccat | gatcgccgag | tgcaagacgc | 1320 |
| gcaccgaggt | gttcgagatc | tcccggcgcc | tcatagaccg | caccaacgcc | aacttcctgg | 1380 |
| tgtggccgcc | ctgtgtggag | gtgcagcgct | gctccggctg | ctgcaacaac | cgcaacgtgc | 1440 |
| agtgccgccc | cacccaggtg | cagctgcgac | ctgtccaggt | gagaaagatc | gagattgtgc | 1500 |
| ggaagaagcc | aatctttaag | aaggccacgg | tgacgctgga | agaccacctg | gcatgcaagt | 1560 |
| gtgagacagt | ggcagctgca | cggcctgtga | cccgaagccc | gggggttcc | caggagcagc | 1620 |
| gagccaaaac | gccccaaact | cgggtgacca | ttcggacggt | gcgagtccgc | cggccccca | 1680 |
| agggcaagca | ccggaaattc | aagcacacgc | atgacaagac | ggcactgaag | agacccttg | 1740 |
| gagcctaggg | gcatcggcag | gagagtgtgt | gggcagggtt | atttaatatg | gtatttgctg | 1800 |
| tattgccccc | atggggtcct | tggagtgata | atattgtttc | cctcgtccgt | ctgtctcgat | 1860 |
| gcctgattcg | gacggccaat | ggtgcttccc | ccacccctcc | acgtgtccgt | ccacccttcc | 1920 |
| atcagcgggt | ctcctcccag | cggcctccgg | tcttgcccag | cagctcaaag | aagaaaaaga | 1980 |
| aggactgaac | tccatcgcca | tcttcttccc | ttaactccaa | gaacttggga | taagagtgtg | 2040 |
| agagagactg | atggggtcgc | tctttggggg | aaacggggttc | cttcccctgc | acctggcctg | 2100 |

-continued

```
ggccacacct gagcgctgtg gactgtcctg aggagccctg aggacctctc agcatagcct      2160
gcctgatccc tgaaccnctg ccagctctg aggggaggca cctccaggca ggccaggctg      2220
cctcggactc catggctaag accacagacg ggcacacaga ctggagaaaa cccctcccac      2280
ggtgcccaaa caccagtcac ctcgtctccc tggtgcctct gtgcacagtg gcttcttttc      2340
gttttcgttt tgaagacgtg gactcctctt ggtgggtgtg ccagcacac caagtggctg      2400 ggtgccctct caggtgggtt agagatggag tttgctgttg aggtggtgta gatggtgacc      2460
tgggtatccc ctgcctcctg ccacccttc ctccccatac tccactctga ttcacctctt      2520
cctctggttc ctttcatctc tctacctcca ccctgcattt tcctcttgtc ctggcccttc      2580
agtctgctcc accaagggc tcttgaaccc cttattaagg ccccagatga ccccagtcac      2640
tcctctctag ggcagaagac tagaggccag ggcagcaagg gacctgctca tcatattcca      2700
acccagccac gactgccatg taaggttgtg cagggtgtgt actgcacaag gacattgtat      2760
gcagggagca ctgttcacat catagataaa gctgatttgt atatttatta tgacaatttc      2820
tggcagatgt aggtaaagag gaaaaggatc cttttcctaa ttcacacaaa gactccttgt      2880
ggactggctg tgcccctgat gcagcctgtg gctggagtgg ccaaatagga gggagactgt      2940
ggtaggggca gggaggcaac actgctgtcc acatgacctc catttcccaa agtcctctgc      3000
tccagcaact gcccttccag gtgggtgtgg acacctggg agaaggtctc caagggaggg      3060
tgcagccctc ttgcccgcac ccctccctgc ttgcacactt ccccatcttt gatccttctg      3120
agctccacct ctggtggctc ctcctaggaa accagctcgt gggctgggaa tggggagag      3180 aagggaaaag atccccaaga ccccctgggg tgggatctga gctcccacct cccttcccac      3240
ctactgcact ttccccccttc ccgccttcca aaacctgctt ccttcagttt gtaaagtcgg      3300
tgattatatt tttgggggct ttccttttat tttttaaatg taaaatttat ttatattccg      3360
tatttaaagt tgt                                                        3373
```

<210> SEQ ID NO 19
<211> LENGTH: 241
<212> TYPE: PRT
<213> ORGANISM: Homo sapiens

<400> SEQUENCE: 19

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
```

```
                145                 150                 155                 160
Lys Lys Pro Ile Phe Lys Lys Ala Thr Val Thr Leu Glu Asp His Leu
                    165                 170                 175

Ala Cys Lys Cys Glu Thr Val Ala Ala Ala Arg Pro Val Thr Arg Ser
                180                 185                 190

Pro Gly Gly Ser Gln Glu Gln Arg Ala Lys Thr Pro Gln Thr Arg Val
                    195                 200                 205

Thr Ile Arg Thr Val Arg Val Arg Pro Pro Lys Gly Lys His Arg
        210                 215                 220

Lys Phe Lys His Thr His Asp Lys Thr Ala Leu Lys Glu Thr Leu Gly
225                 230                 235                 240

Ala

<210> SEQ ID NO 20
<211> LENGTH: 3007
<212> TYPE: DNA
<213> ORGANISM: Homo sapiens
<220> FEATURE:
<221> NAME/KEY:
<223> OTHER INFORMATION: PDGF-C

<400> SEQUENCE: 20
gcccggagag ccgcatctat tggcagcttt gttattgatc agaaactgct cgccgccgac      60
ttggcttcca gtctggctgc gggcaaccct tgagttttcg cctctgtcct gtccccgaa     120
ctgacaggtg ctcccagcaa cttgctgggg acttctcgcc gctccccgc gtccccaccc     180
cctcattcct ccctcgcctt caccccccacc cccaccactt cgccacagct caggatttgt    240
ttaaaccttg ggaaactggt tcaggtccag gttttgcttt gatccttttc aaaaactgga    300
gacacagaag agggctctag gaaaaagttt tggatgggat tatgtggaaa ctaccctgcg    360
attctctgct gccagagcag gctcggcgct tccaccccag tgcagccttc ccctggcgt    420
ggtgaaagag actcgggagt cgctgcttcc aaagtgcccg ccgtgagtga gctctcaccc    480
cagtcagcca aatgagcctc ttcgggcttc tcctgctgac atctgccctg ccggccaga    540
gacagggac tcaggcggaa tccaacctga gtagtaaatt ccagtttcc agcaacaagg     600
aacagaacgg agtacaagat cctcagcatg agagaattat tactgtgtct actaatggaa    660
gtattcacag cccaaggttt cctcatactt atccaagaaa tacggtcttg gtatggagat    720
tagtagcagt agaggaaaat gtatggatac aacttacgtt tgatgaaaga tttgggcttg    780
aagacccaga agatgacata tgcaagtatg atttttgtaga agttgaggaa cccagtgatg    840
gaactatatt agggcgctgg tgtggttctg gtactgtacc aggaaaacag atttctaaag    900
gaaatcaaat taggataaga tttgtatctg atgaatattt tccttctgaa ccagggttct    960
gcatccacta caacattgtc atgccacaat tcacagaagc tgtgagtcct tcagtgctac   1020
cccttcagc tttgccactg acctgcttaa taatgctat aactgccttt agtaccttgg    1080
aagaccttat tcgatatctt gaaccagaga gatggcagtt ggacttagaa gatctatata   1140
ggccaacttg gcaacttctt ggcaaggctt tgttttttgg aagaaaatcc agagtggtgg   1200
atctgaacct tctaacagag gaggtaagat tatacagctg cacacctcgt aacttctcag   1260
tgtccataag ggaagaacta aagagaaccg ataccatttt ctggccaggt tgtctcctgg   1320
ttaaacgctg tggtgggaac tgtgcctgtt gtctccacaa ttgcaatgaa tgtcaatgtg   1380
tcccaagcaa agttactaaa aaataccacg aggtccttca gttgagacca aagaccggtg   1440
tcaggggatt gcacaaatca ctcaccgacg tggccctgga gcaccatgag gagtgtgact   1500
```

-continued

```
gtgtgtgcag agggagcaca ggaggatagc cgcatcacca ccagcagctc ttgcccagag    1560
ctgtgcagtg cagtggctga ttctattaga gaacgtatgc gttatctcca tccttaatct    1620
cagttgtttg cttcaaggac ctttcatctt caggatttac agtgcattct gaaagaggag    1680
acatcaaaca gaattaggag ttgtgcaaca gctcttttga gaggaggcct aaaggacagg    1740
agaaaaggtc ttcaatcgtg gaaagaaaat taaatgttgt attaaataga tcaccagcta    1800
gtttcagagt taccatgtac gtattccact agctgggttc tgtatttcag ttcttttcgat   1860 acggcttagg gtaatgtcag tacaggaaaa aaactgtgca agtgagcacc tgattccgtt    1920
gccttgctta actctaaagc tccatgtcct gggcctaaaa tcgtataaaa tctggatttt    1980
tttttttttt tttgctcata ttcacatatg taaaccagaa cattctatgt actacaaacc    2040
tggtttttaa aaaggaacta tgttgctatg aattaaactt gtgtcgtgct gataggacag    2100
actggatttt tcatatttct tattaaaatt tctgccattt agaagaagag aactacattc    2160
atggtttgga agagataaac ctgaaaagaa gagtggcctt atcttcactt tatcgataag    2220
tcagtttatt tgtttcattg tgtacatttt tatattctcc ttttgacatt ataactgttg    2280
gcttttctaa tcttgttaaa tatatctatt tttaccaaag gtatttaata ttcttttttta   2340 tgacaactta gatcaactat ttttagcttg gtaaattttt ctaaacacaa ttgttatagc    2400
cagaggaaca aagatgatat aaaatattgt tgctctgaca aaaatacatg tatttcattc    2460
tcgtatggtg ctagagttag attaatctgc attttaaaaa actgaattgg aatagaattg    2520
gtaagttgca aagactttt gaaataatt aaattatcat atcttccatt cctgttattg      2580
gagatgaaaa taaaaagcaa cttatgaaag tagacattca gatccagcca ttactaacct    2640
attccttttt tggggaaatc tgagcctagc tcagaaaaac ataaagcacc ttgaaaaga     2700 cttggcagct tcctgataaa gcgtgctgtg ctgtgcagta ggaacacatc ctatttattg    2760
tgatgttgtg gttttattat cttaaactct gttccataca cttgtataaa tacatggata    2820
tttttatgta cagaagtatg tctcttaacc agttcactta ttgtactctg gcaatttaaa    2880
agaaaatcag taaatatttt tgcttgtaaa atgcttaata tcgtgcctag gttatgtggt    2940
gactatttga atcaaaaatg tattgaatca tcaaataaaa gaatgtggct attttgggga    3000
gaaaatt                                                              3007
```

<210> SEQ ID NO 21
<211> LENGTH: 345
<212> TYPE: PRT
<213> ORGANISM: Homo sapiens
<220> FEATURE:
<221> NAME/KEY:
<223> OTHER INFORMATION: PDGF-C

<400> SEQUENCE: 21

```
Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
        50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95
```

```
Glu Asp Pro Glu Asp Asp Ile Cys Lys Tyr Asp Phe Val Glu Val Glu
                100                 105                 110
Glu Pro Ser Asp Gly Thr Ile Leu Gly Arg Trp Cys Gly Ser Gly Thr
            115                 120                 125
Val Pro Gly Lys Gln Ile Ser Lys Gly Asn Gln Ile Arg Ile Arg Phe
        130                 135                 140
Val Ser Asp Glu Tyr Phe Pro Ser Glu Pro Gly Phe Cys Ile His Tyr
145                 150                 155                 160
Asn Ile Val Met Pro Gln Phe Thr Glu Ala Val Ser Pro Ser Val Leu
                165                 170                 175
Pro Pro Ser Ala Leu Pro Leu Asp Leu Leu Asn Asn Ala Ile Thr Ala
            180                 185                 190
Phe Ser Thr Leu Glu Asp Leu Ile Arg Tyr Leu Glu Pro Glu Arg Trp
        195                 200                 205
Gln Leu Asp Leu Glu Asp Leu Tyr Arg Pro Thr Trp Gln Leu Leu Gly
    210                 215                 220
Lys Ala Phe Val Phe Gly Arg Lys Ser Arg Val Val Asp Leu Asn Leu
225                 230                 235                 240
Leu Thr Glu Glu Val Arg Leu Tyr Ser Cys Thr Pro Arg Asn Phe Ser
                245                 250                 255
Val Ser Ile Arg Glu Glu Leu Lys Arg Thr Asp Thr Ile Phe Trp Pro
            260                 265                 270
Gly Cys Leu Leu Val Lys Arg Cys Gly Gly Asn Cys Ala Cys Cys Leu
        275                 280                 285
His Asn Cys Asn Glu Cys Gln Cys Val Pro Ser Lys Val Thr Lys Lys
    290                 295                 300
Tyr His Glu Val Leu Gln Leu Arg Pro Lys Thr Gly Val Arg Gly Leu
305                 310                 315                 320
His Lys Ser Leu Thr Asp Val Ala Leu Glu His His Glu Glu Cys Asp
                325                 330                 335
Cys Val Cys Arg Gly Ser Thr Gly Gly
                340                 345

<210> SEQ ID NO 22
<211> LENGTH: 2253
<212> TYPE: DNA
<213> ORGANISM: Homo sapiens
<220> FEATURE:
<221> NAME/KEY:
<223> OTHER INFORMATION: PDGF-D

<400> SEQUENCE: 22
cgctcggaaa gttcagcatg caggaagttt ggggagagct cggcgattag cacagcgacc      60
cgggccagcg cagggcgagc gcaggcggcg agagcgcagg gcggcgcggc gtcggtcccg     120
ggagcagaac ccggcttttt cttggagcga cgctgtctct agtcgctgat cccaaatgca     180
ccggctcatc tttgtctaca ctctaatctg cgcaaacttt tgcagctgtc gggacacttc     240
tgcaaccccg cagagcgcat ccatcaaagc tttgcgcaac gccaacctca ggcgagatga     300
gagcaatcac ctcacagact gtaccgaaag agatgagacc atccaggtga aggaaacgg      360 ctacgtgcag agtcctagat tcccgaacag ctacccagg aacctgctcc tgacatggcg      420
gcttcactct caggagaata cacggataca gctagtgttt gacaatcagt ttggattaga     480
ggaagcagaa aatgatatct gtaggtatga ttttgtggaa gttgaagata tatccgaaac     540
cagtaccatt attagaggac gatggtgtgg acacaaggaa gttcctccaa ggataaaatc     600
```

-continued

```
aagaacgaac caaattaaaa tcacattcaa gtccgatgac tactttgtgg ctaaacctgg    660
attcaagatt tattattctt tgctggaaga tttccaaccc gcagcagctt cagagaccaa    720
ctgggaatct gtcacaagct ctatttcagg ggtatcctat aactctccat cagtaacgga    780
tcccactctg attgcggatg ctctggacaa aaaaattgca gaatttgata cagtggaaga    840
tctgctcaag tacttcaatc agagtcatg gcaagaagat cttgagaata tgtatctgga    900
caccctcgg tatcgaggca ggtcatacca tgaccgaaag tcaaaagttg acctggatag    960
gctcaatgat gatgccaagc gttacagttg cactcccagg aattactcgg tcaatataag   1020
agaagagctg aagttggcca atgtggtctt ctttccacgt tgcctcctcg tgcagcgctg   1080
tggaggaaat tgtggctgtg aactgtcaa ctggaggtcc tgcacatgca attcaggaa    1140
aaccgtgaaa aagtatcatg aggtattaca gtttgagcct ggccacatca agaggagggg   1200
tagagctaag accatggctc tagttgacat ccagttggat caccatgaac gatgcgattg   1260
tatctgcagc tcaagaccac ctcgataaga gaatgtgcac atccttacat taagcctgaa   1320
agaacctta gtttaaggag ggtgagataa gagacccttt tcctaccagc aaccaaactt   1380
actactagcc tgcaatgcaa tgaacacaag tggttgctga gtctcagcct tgctttgtta   1440
atgccatggc aagtagaaag gtatatcatc aacttctata cctaagaata taggattgca   1500
tttaataata gtgtttgagg ttatatatgc acaaacacac acagaaatat attcatgtct   1560
atgtgtatat agatcaaatg ttttttttgg tatatataac caggtacacc agagcttaca   1620
tatgtttgag ttagactctt aaaatccttt gccaaaataa gggatggtca atatatgaa    1680
acatgtcttt agaaaattta ggagataaat ttattttaa attttgaaac acaaaacaat   1740
tttgaatctt gctctcttaa agaaagcatc ttgtatatta aaaatcaaaa gatgaggctt   1800
tcttacatat acatcttagt tgattattaa aaaaggaaaa aggtttccag agaaaaggcc   1860
aataccctaag cattttttcc atgagaagca ctgcatactt acctatgtgg actgtaataa   1920
cctgtctcca aaaccatgcc ataataatat aagtgcttta gaaattaaat cattgtgttt   1980
tttatgcatt tgctgaggc atccttattc atttaacacc tatctcaaaa acttacttag   2040
aaggttttt attatagtcc tacaaaagac aatgtataag ctgtaacaga attttgaatt   2100
gttttctttt gcaaaacccc tccacaaaag caaatccttt caagaatggc atgggcattc   2160
tgtatgaacc tttccagatg gtgttcagtg aaagatgtgg gtagttgaga acttaaaaag   2220
tgaacattga aacatcgacg taactggaaa ccg                                2253
```

<210> SEQ ID NO 23
<211> LENGTH: 370
<212> TYPE: PRT
<213> ORGANISM: Homo sapiens
<220> FEATURE:
<221> NAME/KEY:
<223> OTHER INFORMATION: PDGF-D

<400> SEQUENCE: 23

```
Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
```

|     |     |     |     | 65  |     |     |     |     | 70  |     |     |     |     | 75  |     |     |     |     | 80  |
Trp | Arg | Leu | His | Ser | Gln | Glu | Asn | Thr | Arg | Ile | Gln | Leu | Val | Phe | Asp

Asn Gln Phe Gly Leu Glu Glu Ala Glu Asn Asp Ile Cys Arg Tyr Asp
              85                        90                        95

Phe Val Glu Val Glu Asp Ile Ser Glu Thr Ser Thr Ile Ile Arg Gly
            100                       105                      110

Arg Trp Cys Gly His Lys Glu Val Pro Pro Arg Ile Lys Ser Arg Thr
            130                       135                      140

Asn Gln Ile Lys Ile Thr Phe Lys Ser Asp Asp Tyr Phe Val Ala Lys
145                       150                       155                      160

Pro Gly Phe Lys Ile Tyr Tyr Ser Leu Leu Glu Asp Phe Gln Pro Ala
                          165                       170                      175

Ala Ala Ser Glu Thr Asn Trp Glu Ser Val Thr Ser Ser Ile Ser Gly
                180                       185                       190

Val Ser Tyr Asn Ser Pro Ser Val Thr Asp Pro Thr Leu Ile Ala Asp
            195                       200                       205

Ala Leu Asp Lys Lys Ile Ala Glu Phe Asp Thr Val Glu Asp Leu Leu
            210                       215                       220

Lys Tyr Phe Asn Pro Glu Ser Trp Gln Glu Asp Leu Glu Asn Met Tyr
225                       230                       235                      240

Leu Asp Thr Pro Arg Tyr Arg Gly Arg Ser Tyr His Asp Arg Lys Ser
                          245                       250                      255

Lys Val Asp Leu Asp Arg Leu Asn Asp Asp Ala Lys Arg Tyr Ser Cys
                260                       265                       270

Thr Pro Arg Asn Tyr Ser Val Asn Ile Arg Glu Glu Leu Lys Leu Ala
            275                       280                       285

Asn Val Val Phe Phe Pro Arg Cys Leu Leu Val Gln Arg Cys Gly Gly
            290                       295                       300

Asn Cys Gly Cys Gly Thr Val Asn Trp Arg Ser Cys Thr Cys Asn Ser
305                       310                       315                      320

Gly Lys Thr Val Lys Lys Tyr His Glu Val Leu Gln Phe Glu Pro Gly
                          325                       330                      335

His Ile Lys Arg Arg Gly Arg Ala Lys Thr Met Ala Leu Val Asp Ile
                340                       345                       350

Gln Leu Asp His His Glu Arg Cys Asp Cys Ile Cys Ser Ser Arg Pro
            355                       360                       365

Pro Arg
    370

<210> SEQ ID NO 24
<211> LENGTH: 1830
<212> TYPE: DNA
<213> ORGANISM: ORF virus
<220> FEATURE:
<221> NAME/KEY:
<223> OTHER INFORMATION: VEGF-E

<400> SEQUENCE: 24
cggccacgcg gccgcgaact gcgcgctcgc gcgcgtggcg accgcgctga cgcgccgcgt      60
gcccgcgagc cggcacggcc tcgcggaggg cggcacgccg ccgtggacgc tgctgctggc     120
ggtggccgcg gtggcggtgc tcggcgtggt ggcaatttcg ctgctgcgcc gcgcgctaag     180
aatacggttt agatactcaa agtctatcca gacacttaga gtgtaacttt gagtaaaaaa     240
tgtaaatact aacgccaaaa tttcgatagt tgttaagcaa tatataacat ttttaaaacg     300

-continued

```
tcatcaccag catgaagtta acagctacgt tacaagttgt tgttgcattg ttaatatgta    360
tgtataattt gccagaatgc gtgtctcaga gtaatgattc acctccttca accaatgact    420
ggatgcgtac actagacaaa agtggttgta aacctagaga tactgttgtt tatttgggag    480
aagaatatcc agaaagcact aacctacaat ataatccccg gtgcgtaact gttaaacgat    540
gcagtggttg ctgtaacggt gacggtcaaa tatgtacagc ggttgaaaca agaaatacaa    600
ctgtaacagt ttcagtaacc ggcgtgtcta gttcgtctgg tactaatagt ggtgtatcta    660
ctaaccttca agaataagt gttacagaac acacaaagtg cgattgtatt ggtagaacaa     720
cgacaacacc tacgaccact agggaaccta gacgataact aataacaaaa aatgtttatt    780
tttgtaaata cttaattatt acacacttta caataatctc aaaaataaat tgcgtgcccg    840
gacggctgca gctggtgacg ctgctgtgtc acacactgcg tattcgattc aagttcacta    900
acgccactaa actagttgtg cgtgtccgag tgttaaccgt acgtcaaact aacatcttac    960
ctgtccgtga caagaactaa aacttgaacc acatattttt aaagtatatt taacaaaatc   1020
actcacactc acacaatcat aaacaccaca accacaacca aacacgcatg agaattaata   1080
ttcttactta tccgtaacac tctatgctgt acatcaacgc atcagagcag tctgagtctg   1140
actaatggcg gcaaacggga acgcaggcgc gacataatca ctgagaatct ccgcagcaac   1200
cgctcaagga catctctagc gctaacggct gtttgtcatt cccccgtgtg ttcatctcac   1260
acgacattgt gaccgtcgca aagcacacat tcaaagtgcc gcatgtggaa gaattcaccg   1320
tcgagacaca caccataatt aaacaagatc agtgcataag agagattagc attctacagc   1380
acaccacgtg cgaatacgga cctcgtaatt gtttagacta gaacacctct ggtctaaaca   1440
acatgtccga tcttagaaca gagtttatga cgcatatgta actgtgttct ttatgtagaa   1500
gttatctttt atgtcactcc cttgtcttag atgagttata catgacatga tgtatgtgtc   1560
gcccgcggcg gcgcggggcg ctcggcggcc gggctgctgc gcgcggcggg cccgcggtgg   1620
cggcggctgg cgcggcgctg cggccgcggg cgcgcggcgg ggtagcggcc cgcccgcccg   1680
ggcgcccgcc gcagcccttg ccccggacca ggcgccacgg agcaaagtga aaaaggaccg   1740
cctagcagtc gagaccctcc cgccgcagcc gcgacacccc cacccgcct tccacccgcc    1800
agacgccaac accacagcca acaagcatgc                                    1830
```

<210> SEQ ID NO 25
<211> LENGTH: 148
<212> TYPE: PRT
<213> ORGANISM: ORF virus
<220> FEATURE:
<221> NAME/KEY:
<223> OTHER INFORMATION: VEGF-E

<400> SEQUENCE: 25

```
Met Lys Leu Thr Ala Thr Leu Gln Val Val Ala Leu Leu Ile Cys
1               5                  10                  15

Met Tyr Asn Leu Pro Glu Cys Val Ser Gln Ser Asn Asp Ser Pro
                20                  25                  30

Ser Thr Asn Asp Trp Met Arg Thr Leu Asp Lys Ser Gly Cys Lys Pro
                35                  40                  45

Arg Asp Thr Val Val Tyr Leu Gly Glu Glu Tyr Pro Glu Ser Thr Asn
    50                  55                  60

Leu Gln Tyr Asn Pro Arg Cys Val Thr Val Lys Arg Cys Ser Gly Cys
65                  70                  75                  80

Cys Asn Gly Asp Gly Gln Ile Cys Thr Ala Val Glu Thr Arg Asn Thr
                85                  90                  95
```

Thr Val Thr Val Ser Val Thr Gly Val Ser Ser Ser Gly Thr Asn
            100                 105                 110

Ser Gly Val Ser Thr Asn Leu Gln Arg Ile Ser Val Thr Glu His Thr
            115                 120                 125

Lys Cys Asp Cys Ile Gly Arg Thr Thr Thr Pro Thr Thr Thr Arg
    130                 135                 140

Glu Pro Arg Arg
145

<210> SEQ ID NO 26
<211> LENGTH: 1251
<212> TYPE: DNA
<213> ORGANISM: Homo sapiens
<220> FEATURE:
<221> NAME/KEY:
<223> OTHER INFORMATION: CAC

<400> SEQUENCE: 26

```
atggagacag acacactcct gctatgggta ctgctgctct gggttccagg ttccactggt      60
gacgcggccc aggatccgtt cgagtccgga ctcgacctct cggacgcgga gcccgacgcg     120
ggcgaggcca cggcttatgc aagcaaagat ctggaggagc agttacggtc tgtgtccagt     180
gtagatgaac tcatgactgt actctaccca gaatattgga aaatgtacaa gtgtcagcta     240
aggaaaggag gctggcaaca taacagagaa caggccaacc tcaactcaag gacagaagag     300
actataaaat ttgctgcagg gcagaatcat acgaagtgg tgaaattcat ggatgtctat     360
cagcgcagct actgccatcc gatcgagaca ctggtggaca tcttccagga atacctgat     420
gagatcgagt acatcttcaa gccatcctgc gtgcccctga tgagatgtgg gggttgctgc     480
aatgacgaag ggctggagtg cgttcccacc gaggagtcca acatcaccat gcagattatg     540
agaattaaac ctcaccaagg gcagcacatc ggagagatga gctttctcca gcataacaaa     600
tgtgaatgta gaccaaagaa agatgtttac agacaagttc attccattat tagacgttcc     660
ctgccagcaa cactaccaca gtgtcaggca gcgaacaaga cctgccccac caattacatg     720
tggaataatc acatctgcag atgcctggct caggaagatt ttatgttttc ctcggatgct     780
ggagatgact caacagatgg attccatgac atctgtggac caaacaagga gctggatgaa     840
gagacctgtc agtgtgtctg cagagcgggg cttcggcctg ccagctgtgg accccacaaa     900
gaactagaca gaaactcatg ccagtgtgtc tgtaaaaaca aactcttccc cagccaatgt     960
ggggccaacc gagaatttga tgaaaacaca tgccagtgtg tatgtaaaag aacctgcccc   1020
agaaatcaac ccctaaatcc tggaaaatgt gcctgtgaat gtacagaaag tccacagaaa    1080
tgcttgttaa aggaaagaa gttccaccac caaacatgca gctgttacag acggccatgt    1140
acgaaccgcc agaaggcttg tgagccagga ttttcatata gtgaagaagt gtgtcgttgt    1200
gtcccttcat attggaaaag accacaaatg agccatcacc atcaccatca c            1251
```

<210> SEQ ID NO 27
<211> LENGTH: 418
<212> TYPE: PRT
<213> ORGANISM: Homo sapiens
<220> FEATURE:
<221> NAME/KEY:
<223> OTHER INFORMATION: CAC

<400> SEQUENCE: 27

Met Glu Thr Asp Thr Leu Leu Leu Trp Val Leu Leu Leu Trp Val Pro
1               5                   10                  15

```
Gly Ser Thr Gly Asp Ala Ala Gln Asp Pro Phe Glu Ser Gly Leu Asp
            20                  25                  30

Leu Ser Asp Ala Glu Pro Asp Ala Gly Glu Ala Thr Ala Tyr Ala Ser
        35                  40                  45

Lys Asp Leu Glu Glu Gln Leu Arg Ser Val Ser Ser Val Asp Glu Leu
50                  55                  60

Met Thr Val Leu Tyr Pro Glu Tyr Trp Lys Met Tyr Lys Cys Gln Leu
65                  70                  75                  80

Arg Lys Gly Gly Trp Gln His Asn Arg Glu Gln Ala Asn Leu Asn Ser
                85                  90                  95

Arg Thr Glu Glu Thr Ile Lys Phe Ala Ala Gly Gln Asn His His Glu
                100                 105                 110

Val Val Lys Phe Met Asp Val Tyr Gln Arg Ser Tyr Cys His Pro Ile
            115                 120                 125

Glu Thr Leu Val Asp Ile Phe Gln Glu Tyr Pro Asp Glu Ile Glu Tyr
        130                 135                 140

Ile Phe Lys Pro Ser Cys Val Pro Leu Met Arg Cys Gly Gly Cys Cys
145                 150                 155                 160

Asn Asp Glu Gly Leu Glu Cys Val Pro Thr Glu Glu Ser Asn Ile Thr
                165                 170                 175

Met Gln Ile Met Arg Ile Lys Pro His Gln Gly Gln His Ile Gly Glu
                180                 185                 190

Met Ser Phe Leu Gln His Asn Lys Cys Glu Cys Arg Pro Lys Lys Asp
            195                 200                 205

Val Tyr Arg Gln Val His Ser Ile Ile Arg Arg Ser Leu Pro Ala Thr
        210                 215                 220

Leu Pro Gln Cys Gln Ala Ala Asn Lys Thr Cys Pro Thr Asn Tyr Met
225                 230                 235                 240

Trp Asn Asn His Ile Cys Arg Cys Leu Ala Gln Glu Asp Phe Met Phe
                245                 250                 255

Ser Ser Asp Ala Gly Asp Asp Ser Thr Asp Gly Phe His Asp Ile Cys
                260                 265                 270

Gly Pro Asn Lys Glu Leu Asp Glu Glu Thr Cys Gln Cys Val Cys Arg
            275                 280                 285

Ala Gly Leu Arg Pro Ala Ser Cys Gly Pro His Lys Glu Leu Asp Arg
        290                 295                 300

Asn Ser Cys Gln Cys Val Cys Lys Asn Lys Leu Phe Pro Ser Gln Cys
305                 310                 315                 320

Gly Ala Asn Arg Glu Phe Asp Glu Asn Thr Cys Gln Cys Val Cys Lys
                325                 330                 335

Arg Thr Cys Pro Arg Asn Gln Pro Leu Asn Pro Gly Lys Cys Ala Cys
                340                 345                 350

Glu Cys Thr Glu Ser Pro Gln Lys Cys Leu Leu Lys Gly Lys Lys Phe
            355                 360                 365

His His Gln Thr Cys Ser Cys Tyr Arg Arg Pro Cys Thr Asn Arg Gln
        370                 375                 380

Lys Ala Cys Glu Pro Gly Phe Ser Tyr Ser Glu Glu Val Cys Arg Cys
385                 390                 395                 400

Val Pro Ser Tyr Trp Lys Arg Pro Gln Met Ser His His His His
                405                 410                 415

His Lys

<210> SEQ ID NO 28
<211> LENGTH: 36
```

```
<212> TYPE: DNA
<213> ORGANISM: Artificial Sequence
<220> FEATURE:
<223> OTHER INFORMATION: Synthetic primer

<400> SEQUENCE: 28
gcggatccgt tcgagtccgg actcgacctc tcggac                              36

<210> SEQ ID NO 29
<211> LENGTH: 68
<212> TYPE: DNA
<213> ORGANISM: Artificial sequence
<220> FEATURE:
<223> OTHER INFORMATION: Synthetic primer

<400> SEQUENCE: 29
cttttagtgt tcaatgtca tagaaagttg cagcaaattt tatagtctct tctgtccttg     60
agttgagg                                                             68

<210> SEQ ID NO 30
<211> LENGTH: 76
<212> TYPE: DNA
<213> ORGANISM: Artificial sequence
<220> FEATURE:
<223> OTHER INFORMATION: Synthetic primer

<400> SEQUENCE: 30
ggacagaaga gactataaaa tttgctgcaa ctttctatga cattgaaaca ctaaaagtta    60
tagatgaaga atggca                                                    76

<210> SEQ ID NO 31
<211> LENGTH: 34
<212> TYPE: DNA
<213> ORGANISM: Artificial sequence
<220> FEATURE:
<223> OTHER INFORMATION: Synthetic primer

<400> SEQUENCE: 31
gcggatcctc aaggattctt tcggctgtgg ggcc                                34

<210> SEQ ID NO 32
<211> LENGTH: 44
<212> TYPE: DNA
<213> ORGANISM: Artificial sequence
<220> FEATURE:
<223> OTHER INFORMATION: Synthetic primer

<400> SEQUENCE: 32
gcggatccgt ccagtaatga acatggacca gtgaggcgat catc                     44

<210> SEQ ID NO 33
<211> LENGTH: 64
<212> TYPE: DNA
<213> ORGANISM: Artificial sequence
<220> FEATURE:
<223> OTHER INFORMATION: Synthetic primer

<400> SEQUENCE: 33
gcctgacact gtggtagtgt tgctggcagg gatcttctga taattgagta tggatggcgg    60
gggg                                                                 64

<210> SEQ ID NO 34
<211> LENGTH: 56
<212> TYPE: DNA
<213> ORGANISM: Artificial sequence
```

```
<220> FEATURE:
<223> OTHER INFORMATION: Synthetic primer

<400> SEQUENCE: 34
gccatccata ctcaattatc agaagatccc tgccagcaac actaccacag tgtcag      56

<210> SEQ ID NO 35
<211> LENGTH: 49
<212> TYPE: DNA
<213> ORGANISM: Artificial sequence
<220> FEATURE:
<223> OTHER INFORMATION: Synthetic primer

<400> SEQUENCE: 35
gcggatcctt agctcatttg tggtcttttc caatatgaag ggacacaac              49

<210> SEQ ID NO 36
<211> LENGTH: 1110
<212> TYPE: DNA
<213> ORGANISM: Homo sapiens
<220> FEATURE:
<221> NAME/KEY:
<223> OTHER INFORMATION: CDD construct

<400> SEQUENCE: 36
atggagacag acacactcct gctatgggta ctgctgctct gggttccagg ttccactggt    60
gacgcggccc aggatccgtt cgagtccgga ctcgacctct cggacgcgga gcccgacgcg   120
ggcgaggcca cggcttatgc aagcaaagat ctggaggagc agttacggtc tgtgtccagt   180
gtagatgaac tcatgactgt actctaccca gaatattgga aatgtacaa gtgtcagcta    240 aggaaaggag gctggcaaca taacagaaa caggccaacc tcaactcaag gacagaagag    300
actataaaat ttgctgcaac tttctatgac attgaaacac taaaagttat agatgaagaa   360
tggcaaagaa ctcagtgcag ccctagaaaa cgtgcgtgg aggtggccag tgagctgggg    420
aagagtacca acacattctt caagccccct tgtgtgaacg tgttccgatg tggtggctgt   480
tgcaatgaag agagccttat ctgtatgaac accagcacct cgtacatttc caaacagctc   540
tttgagatat cagtgccttt gacatcagta cctgaattag tgcctgttaa agttgccaat   600
catacaggtt gtaagtgctt gccaacagcc ccccgccatc catactcaat tatcagaaga   660
tccatccaga tccctgaaga gatcgctgt tcccattcca agaaactctg tcctattgac    720
atgctatggg atagcaacaa atgtaaatgt gttttgcagg aggaaaatcc acttgctgga   780
acagaagacc actctcatct ccaggaacca gctctctgtg gccacacat gatgtttgac    840 gaagatcgtt gcgagtgtgt ctgtaaaaca ccatgtccca agatctaat ccagcacccc   900 aaaaactgca gttgctttga gtgcaaagaa agtctggaga cctgctgcca gaagcacaag   960
ctatttcacc cagacacctg cagctgtgag gacagatgcc cctttcatac cagaccatgt  1020
gcaagtggca aaacagcatg tgcaaagcat tgccgctttc caaaggagaa aagggctgcc  1080
cagggggccc acagccgaaa gaatccttga                                   1110

<210> SEQ ID NO 37
<211> LENGTH: 369
<212> TYPE: PRT
<213> ORGANISM: Homo sapiens
<220> FEATURE:
<221> NAME/KEY:
<223> OTHER INFORMATION: CDD construct

<400> SEQUENCE: 37

Met Glu Thr Asp Thr Leu Leu Leu Trp Val Leu Leu Leu Trp Val Pro
```

```
                1               5              10               15
Gly Ser Thr Gly Asp Ala Ala Gln Asp Pro Phe Glu Ser Gly Leu Asp
                20                      25                  30

Leu Ser Asp Ala Glu Pro Asp Ala Gly Glu Ala Thr Ala Tyr Ala Ser
                35                      40                  45

Lys Asp Leu Glu Glu Gln Leu Arg Ser Val Ser Ser Val Asp Glu Leu
 50                      55                      60

Met Thr Val Leu Tyr Pro Glu Tyr Trp Lys Met Tyr Lys Cys Gln Leu
 65                      70                      75                      80

Arg Lys Gly Gly Trp Gln His Asn Arg Glu Gln Ala Asn Leu Asn Ser
                        85                      90                      95

Arg Thr Glu Glu Thr Ile Lys Phe Ala Ala Thr Phe Tyr Asp Ile Glu
                       100                     105                 110

Thr Leu Lys Val Ile Asp Glu Glu Trp Gln Arg Thr Gln Cys Ser Pro
                       115                     120                 125

Arg Glu Thr Cys Val Glu Val Ala Ser Glu Leu Gly Lys Ser Thr Asn
                       130                     135                 140

Thr Phe Phe Lys Pro Pro Cys Val Asn Val Phe Arg Cys Gly Gly Cys
145                    150                     155                     160

Cys Asn Glu Glu Ser Leu Ile Cys Met Asn Thr Ser Thr Ser Tyr Ile
                       165                     170                 175

Ser Lys Gln Leu Phe Glu Ile Ser Val Pro Leu Thr Ser Val Pro Glu
                       180                     185                 190

Leu Val Pro Val Lys Val Ala Asn His Thr Gly Cys Lys Cys Leu Pro
                       195                     200                 205

Thr Ala Pro Arg His Pro Tyr Ser Ile Ile Arg Arg Ser Ile Gln Ile
                       210                     215                 220

Pro Glu Glu Asp Arg Cys Ser His Ser Lys Lys Leu Cys Pro Ile Asp
225                    230                     235                     240

Met Leu Trp Asp Ser Asn Lys Cys Lys Cys Val Leu Gln Glu Glu Asn
                       245                     250                 255

Pro Leu Ala Gly Thr Glu Asp His Ser His Leu Gln Glu Pro Ala Leu
                       260                     265                 270

Cys Gly Pro His Met Met Phe Asp Glu Asp Arg Cys Glu Cys Val Cys
                       275                     280                 285

Lys Thr Pro Cys Pro Lys Asp Leu Ile Gln His Pro Lys Asn Cys Ser
                       290                     295                 300

Cys Phe Glu Cys Lys Glu Ser Leu Glu Thr Cys Cys Gln Lys His Lys
305                    310                     315                     320

Leu Phe His Pro Asp Thr Cys Ser Cys Glu Asp Arg Cys Pro Phe His
                       325                     330                 335

Thr Arg Pro Cys Ala Ser Gly Lys Thr Ala Cys Ala Lys His Cys Arg
                       340                     345                 350

Phe Pro Lys Glu Lys Arg Ala Ala Gln Gly Pro His Ser Arg Lys Asn
                       355                     360                 365

Pro

<210> SEQ ID NO 38
<211> LENGTH: 1239
<212> TYPE: DNA
<213> ORGANISM: Homo sapiens
<220> FEATURE:
<221> NAME/KEY:
<223> OTHER INFORMATION: CDC construct

<400> SEQUENCE: 38
```

-continued

```
atggagacag acacactcct gctatgggta ctgctgctct gggttccagg ttccactggt      60
gacgcggccc aggatccgtt cgagtccgga ctcgacctct cggacgcgga gcccgacgcg     120
ggcgaggcca cggcttatgc aagcaaagat ctggaggagc agttacggtc tgtgtccagt     180
gtagatgaac tcatgactgt actctaccca gaatattgga aaatgtacaa gtgtcagcta     240
aggaaaggag gctggcaaca taacagagaa caggccaacc tcaactcaag gacagaagag     300
actataaaat ttgctgcaac tttctatgac attgaaacac taaaagttat agatgaagaa     360
tggcaaagaa ctcagtgcag ccctagaaaa cgtgcgtgg aggtggccag tgagctgggg      420
aagagtacca acacattctt caagcccccct tgtgtgaacg tgttccgatg tggtggctgt    480
tgcaatgaag agagccttat ctgtatgaac accagcacct cgtacatttc caaacagctc     540
tttgagatat cagtgccttt gacatcagta cctgaattag tgcctgttaa agttgccaat     600
catacaggtt gtaagtgctt gccaacagcc ccccgccatc catactcaat tatcagaaga     660
tccctgccag caacactacc acagtgtcag gcagcgaaca agacctgccc caccaattac     720
atgtggaata atcacatctg cagatgcctg gctcaggaag atttttatgtt ttcctcggat    780
gctggagatg actcaacaga tggattccat gacatctgtg accaaacaa ggagctggat      840
gaagagacct gtcagtgtgt ctgcagagcg gggcttcggc ctgccagctg tggaccccac     900
aaagaactag acagaaactc atgccagtgt gtctgtaaaa acaaactctt ccccagccaa     960
tgtgggcca accgagaatt tgatgaaaac acatgccagt gtgtatgtaa agaacctgc      1020
cccagaaatc aaccccctaaa tcctggaaaa tgtgcctgtg aatgtacaga agtccacag   1080
aaatgcttgt taaaaggaaa gaagttccac caccaaacat gcagctgtta cagacggcca  1140
tgtacgaacc gccagaaggc ttgtgagcca ggattttcat atagtgaaga agtgtgtcgt  1200
tgtgtccctt catattggaa aagaccacaa atgagctaa                          1239
```

<210> SEQ ID NO 39  
<211> LENGTH: 412  
<212> TYPE: PRT  
<213> ORGANISM: Homo sapiens  
<220> FEATURE:  
<221> NAME/KEY:  
<223> OTHER INFORMATION: CDC construct

<400> SEQUENCE: 39

```
Met Glu Thr Asp Thr Leu Leu Trp Val Leu Leu Trp Val Pro
1               5                   10                  15
Gly Ser Thr Gly Asp Ala Ala Gln Asp Pro Phe Glu Ser Gly Leu Asp
                20                  25                  30
Leu Ser Asp Ala Glu Pro Asp Ala Gly Glu Ala Thr Ala Tyr Ala Ser
            35                  40                  45
Lys Asp Leu Glu Glu Gln Leu Arg Ser Val Ser Ser Val Asp Glu Leu
        50                  55                  60
Met Thr Val Leu Tyr Pro Glu Tyr Trp Lys Met Tyr Lys Cys Gln Leu
65                  70                  75                  80
Arg Lys Gly Gly Trp Gln His Asn Arg Glu Gln Ala Asn Leu Asn Ser
                85                  90                  95
Arg Thr Glu Glu Thr Ile Lys Phe Ala Ala Thr Phe Tyr Asp Ile Glu
            100                 105                 110
Thr Leu Lys Val Ile Asp Glu Glu Trp Gln Arg Thr Gln Cys Ser Pro
        115                 120                 125
Arg Glu Thr Cys Val Glu Val Ala Ser Glu Leu Gly Lys Ser Thr Asn
    130                 135                 140
```

```
Thr Phe Phe Lys Pro Pro Cys Val Asn Val Phe Arg Cys Gly Gly Cys
145                 150                 155                 160

Cys Asn Glu Glu Ser Leu Ile Cys Met Asn Thr Ser Thr Ser Tyr Ile
                165                 170                 175

Ser Lys Gln Leu Phe Glu Ile Ser Val Pro Leu Thr Ser Val Pro Glu
            180                 185                 190

Leu Val Pro Val Lys Val Ala Asn His Thr Gly Cys Lys Cys Leu Pro
        195                 200                 205

Thr Ala Pro Arg His Pro Tyr Ser Ile Ile Arg Arg Ser Leu Pro Ala
    210                 215                 220

Thr Leu Pro Gln Cys Gln Ala Ala Asn Lys Thr Cys Pro Thr Asn Tyr
225                 230                 235                 240

Met Trp Asn Asn His Ile Cys Arg Cys Leu Ala Gln Glu Asp Phe Met
                245                 250                 255

Phe Ser Ser Asp Ala Gly Asp Asp Ser Thr Asp Gly Phe His Asp Ile
                260                 265                 270

Cys Gly Pro Asn Lys Glu Leu Asp Glu Glu Thr Cys Gln Cys Val Cys
            275                 280                 285

Arg Ala Gly Leu Arg Pro Ala Ser Cys Gly Pro His Lys Glu Leu Asp
        290                 295                 300

Arg Asn Ser Cys Gln Cys Val Cys Lys Asn Lys Leu Phe Pro Ser Gln
305                 310                 315                 320

Cys Gly Ala Asn Arg Glu Phe Asp Glu Asn Thr Cys Gln Cys Val Cys
                325                 330                 335

Lys Arg Thr Cys Pro Arg Asn Gln Pro Leu Asn Pro Gly Lys Cys Ala
            340                 345                 350

Cys Glu Cys Thr Glu Ser Pro Gln Lys Cys Leu Leu Lys Gly Lys Lys
        355                 360                 365

Phe His His Gln Thr Cys Ser Cys Tyr Arg Arg Pro Cys Thr Asn Arg
    370                 375                 380

Gln Lys Ala Cys Glu Pro Gly Phe Ser Tyr Ser Glu Glu Val Cys Arg
385                 390                 395                 400

Cys Val Pro Ser Tyr Trp Lys Arg Pro Gln Met Ser
                405                 410

<210> SEQ ID NO 40
<211> LENGTH: 1209
<212> TYPE: DNA
<213> ORGANISM: Homo sapiens
<220> FEATURE:
<221> NAME/KEY:
<223> OTHER INFORMATION: DDC construct

<400> SEQUENCE: 40
atggagacag acacactcct gctatgggta ctgctgctct gggttccagg ttccactggt      60
gacgcggccc aggatccgtc cagtaatgaa catggaccag tgaagcgatc atctcagtcc     120
acattggaac gatctgaaca gcagatcagg gctgcttcta gtttggagga actacttcga     180
attactcact ctgaggactg gaagctgtgg agatgcaggc tgaggctcaa aagttttacc     240
agtatggact ctcgctcagc atcccatcgg tccactaggt tgcggcaac tttctatgac      300 attgaaacac taaagttat agatgaagaa tggcaaagac tcagtgcag ccctagaaa        360 acgtgcgtgg aggtggccag tgagctgggg aagagtacca acacattctt caagccccct    420
tgtgtgaacg tgttccgatg tggtggctgt tgcaatgaag agagcctat ctgtatgaac      480 accagcacct cgtacatttc caaacagctc tttgagatat cagtgccttt gacatcagta    540
```

```
cctgaattag tgcctgttaa agttgccaat catacaggtt gtaagtgctt gccaacagcc      600
ccccgccatc catactcaat tatcagaaga tccctgccag caacactacc acagtgtcag      660
gcagcgaaca agacctgccc caccaattac atgtggaata atcacatctg cagatgcctg      720
gctcaggaag attttatgtt ttcctcggat gctggagatg actcaacaga tggattccat      780
gacatctgtg gaccaaacaa ggagctggat gaagagacct gtcagtgtgt ctgcagagcg      840
gggcttcggc ctgccagctg tggacccac aaagaactag acagaaactc atgccagtgt      900
gtctgtaaaa acaaactctt ccccagccaa tgtggggcca accgagaatt tgatgaaaac      960
acatgccagt gtgtatgtaa agaacctgc cccagaaatc aacccctaaa tcctggaaaa     1020
tgtgcctgtg aatgtacaga aagtccacag aaatgcttgt taaaaggaaa gaagttccac     1080
caccaaacat gcagctgtta cagacggcca tgtacgaacc gccagaaggc ttgtgagcca     1140 ggatttcat atagtgaaga agtgtgtcgt tgtgtcccctt catattggaa aagaccacaa     1200
atgagctaa                                                             1209

<210> SEQ ID NO 41
<211> LENGTH: 402
<212> TYPE: PRT
<213> ORGANISM: Homo sapiens
<220> FEATURE:
<221> NAME/KEY:
<223> OTHER INFORMATION: DDC construct

<400> SEQUENCE: 41

Met Glu Thr Asp Thr Leu Leu Leu Trp Val Leu Leu Leu Trp Val Pro
1               5                   10                  15

Gly Ser Thr Gly Asp Ala Ala Gln Asp Pro Ser Ser Asn Glu His Gly
                20                  25                  30

Pro Val Lys Arg Ser Ser Gln Ser Thr Leu Glu Arg Ser Glu Gln Gln
            35                  40                  45

Ile Arg Ala Ala Ser Ser Leu Glu Glu Leu Leu Arg Ile Thr His Ser
        50                  55                  60

Glu Asp Trp Lys Leu Trp Arg Cys Arg Leu Arg Leu Lys Ser Phe Thr
65                  70                  75                  80

Ser Met Asp Ser Arg Ser Ala Ser His Arg Ser Thr Arg Phe Ala Ala
                85                  90                  95

Thr Phe Tyr Asp Ile Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Ser Thr Asn Thr Phe Phe Lys Pro Pro Cys Val Asn Val
    130                 135                 140

Phe Arg Cys Gly Gly Cys Cys Asn Glu Glu Ser Leu Ile Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Val Ala Asn His Thr
            180                 185                 190

Gly Cys Lys Cys Leu Pro Thr Ala Pro Arg His Pro Tyr Ser Ile Ile
        195                 200                 205

Arg Arg Ser Leu Pro Ala Thr Leu Pro Gln Cys Gln Ala Ala Asn Lys
    210                 215                 220

Thr Cys Pro Thr Asn Tyr Met Trp Asn Asn His Ile Cys Arg Cys Leu
225                 230                 235                 240
```

```
Ala Gln Glu Asp Phe Met Phe Ser Ser Asp Ala Gly Asp Ser Thr
                245                 250                 255

Asp Gly Phe His Asp Ile Cys Gly Pro Asn Lys Glu Leu Asp Glu Glu
            260                 265                 270

Thr Cys Gln Cys Val Cys Arg Ala Gly Leu Arg Pro Ala Ser Cys Gly
        275                 280                 285

Pro His Lys Glu Leu Asp Arg Asn Ser Cys Gln Cys Val Cys Lys Asn
    290                 295                 300

Lys Leu Phe Pro Ser Gln Cys Gly Ala Asn Arg Glu Phe Asp Glu Asn
305                 310                 315                 320

Thr Cys Gln Cys Val Cys Lys Arg Thr Cys Pro Arg Asn Gln Pro Leu
                325                 330                 335

Asn Pro Gly Lys Cys Ala Cys Glu Cys Thr Glu Ser Pro Gln Lys Cys
            340                 345                 350

Leu Leu Lys Gly Lys Lys Phe His His Gln Thr Cys Ser Cys Tyr Arg
        355                 360                 365

Arg Pro Cys Thr Asn Arg Gln Lys Ala Cys Glu Pro Gly Phe Ser Tyr
    370                 375                 380

Ser Glu Glu Val Cys Arg Cys Val Pro Ser Tyr Trp Lys Arg Pro Gln
385                 390                 395                 400

Met Ser

<210> SEQ ID NO 42
<211> LENGTH: 170
<212> TYPE: PRT
<213> ORGANISM: Homo sapiens
<220> FEATURE:
<221> NAME/KEY:
<223> OTHER INFORMATION: PlGF-2

<400> SEQUENCE: 42

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asp Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Arg Arg Pro
    130                 135                 140

Lys Gly Arg Gly Lys Arg Arg Arg Glu Asn Gln Arg Pro Thr Asp Cys
145                 150                 155                 160

His Leu Cys Gly Asp Ala Val Pro Arg Arg
                165                 170

<210> SEQ ID NO 43
<211> LENGTH: 221
```

```
<212> TYPE: PRT
<213> ORGANISM: Homo sapiens
<220> FEATURE:
<221> NAME/KEY:
<223> OTHER INFORMATION: PlGF-3

<400> SEQUENCE: 43

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Arg Met Glu Trp Gly Cys Ala Leu Thr Gly Ser Gln Ser
                165                 170                 175

Ala Val Trp Pro Ser Ser Pro Val Pro Glu Glu Ile Pro Arg Met His
            180                 185                 190

Pro Gly Arg Asn Gly Lys Lys Gln Gln Arg Lys Pro Leu Arg Glu Lys
        195                 200                 205

Met Lys Pro Glu Arg Cys Gly Asp Ala Val Pro Arg Arg
    210                 215                 220

<210> SEQ ID NO 44
<211> LENGTH: 188
<212> TYPE: PRT
<213> ORGANISM: Homo sapiens
<220> FEATURE:
<221> NAME/KEY:
<223> OTHER INFORMATION: VEGF-B167

<400> SEQUENCE: 44

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
```

```
                        100                 105                 110
Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
            130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185

<210> SEQ ID NO 45
<211> LENGTH: 207
<212> TYPE: PRT
<213> ORGANISM: Homo sapiens
<220> FEATURE:
<221> NAME/KEY:
<223> OTHER INFORMATION: VEGF-B186

<400> SEQUENCE: 45

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 46
<211> LENGTH: 71
<212> TYPE: PRT
<213> ORGANISM: Homo sapiens
<220> FEATURE:
<221> NAME/KEY:
<223> OTHER INFORMATION: N-terminal propeptide of VEGF-C

<400> SEQUENCE: 46

Phe Glu Ser Gly Leu Asp Leu Ser Asp Ala Glu Pro Asp Ala Gly Glu
1               5                   10                  15
```

```
Ala Thr Ala Tyr Ala Ser Lys Asp Leu Glu Glu Gln Leu Arg Ser Val
            20                  25                  30

Ser Ser Val Asp Glu Leu Met Thr Val Leu Tyr Pro Glu Tyr Trp Lys
        35                  40                  45

Met Tyr Lys Cys Gln Leu Arg Lys Gly Gly Trp Gln His Asn Arg Glu
    50                  55                  60

Gln Ala Asn Leu Asn Ser Arg
65                  70

<210> SEQ ID NO 47
<211> LENGTH: 192
<212> TYPE: PRT
<213> ORGANISM: Homo sapiens
<220> FEATURE:
<221> NAME/KEY:
<223> OTHER INFORMATION: C-terminal propeptide of VEGF-C

<400> SEQUENCE: 47

Ser Leu Pro Ala Thr Leu Pro Gln Cys Gln Ala Ala Asn Lys Thr Cys
1               5                   10                  15

Pro Thr Asn Tyr Met Trp Asn Asn His Ile Cys Arg Cys Leu Ala Gln
            20                  25                  30

Glu Asp Phe Met Phe Ser Ser Asp Ala Gly Asp Asp Ser Thr Asp Gly
        35                  40                  45

Phe His Asp Ile Cys Gly Pro Asn Lys Glu Leu Asp Glu Glu Thr Cys
    50                  55                  60

Gln Cys Val Cys Arg Ala Gly Leu Arg Pro Ala Ser Cys Gly Pro His
65                  70                  75                  80

Lys Glu Leu Asp Arg Asn Ser Cys Gln Cys Val Cys Lys Asn Lys Leu
                85                  90                  95

Phe Pro Ser Gln Cys Gly Ala Asn Arg Glu Phe Asp Glu Asn Thr Cys
            100                 105                 110

Gln Cys Val Cys Lys Arg Thr Cys Pro Arg Asn Gln Pro Leu Asn Pro
        115                 120                 125

Gly Lys Cys Ala Cys Glu Cys Thr Glu Ser Pro Gln Lys Cys Leu Leu
    130                 135                 140

Lys Gly Lys Lys Phe His His Gln Thr Cys Ser Cys Tyr Arg Arg Pro
145                 150                 155                 160

Cys Thr Asn Arg Gln Lys Ala Cys Glu Pro Gly Phe Ser Tyr Ser Glu
                165                 170                 175

Glu Val Cys Arg Cys Val Pro Ser Tyr Trp Lys Arg Pro Gln Met Ser
            180                 185                 190

<210> SEQ ID NO 48
<211> LENGTH: 71
<212> TYPE: PRT
<213> ORGANISM: Homo sapiens
<220> FEATURE:
<221> NAME/KEY:
<223> OTHER INFORMATION: N-terminal propeptide of VEGF-D

<400> SEQUENCE: 48

Ser Ser Asn Glu His Gly Pro Val Lys Arg Ser Ser Gln Ser Thr Leu
1               5                   10                  15

Glu Arg Ser Glu Gln Gln Ile Arg Ala Ala Ser Ser Leu Glu Glu Leu
            20                  25                  30

Leu Arg Ile Thr His Ser Glu Asp Trp Lys Leu Trp Arg Cys Arg Leu
        35                  40                  45
```

```
Arg Leu Lys Ser Phe Thr Ser Met Asp Ser Arg Ser Ala Ser His Arg
     50                  55                  60

Ser Thr Arg Phe Ala Ala Thr
 65                  70

<210> SEQ ID NO 49
<211> LENGTH: 153
<212> TYPE: PRT
<213> ORGANISM: Homo sapiens
<220> FEATURE:
<221> NAME/KEY:
<223> OTHER INFORMATION: C-terminal propeptide of VEGF-C

<400> SEQUENCE: 49

Ile Ile Arg Arg Ser Ile Gln Ile Pro Glu Glu Asp Arg Cys Ser His
 1               5                  10                  15

Ser Lys Lys Leu Cys Pro Ile Asp Met Leu Trp Asp Ser Asn Lys Cys
                20                  25                  30

Lys Cys Val Leu Gln Glu Glu Asn Pro Leu Ala Gly Thr Glu Asp His
             35                  40                  45

Ser His Leu Gln Glu Pro Ala Leu Cys Gly Pro His Met Met Phe Asp
         50                  55                  60

Glu Asp Arg Cys Glu Cys Val Cys Lys Thr Pro Cys Pro Lys Asp Leu
 65                  70                  75                  80

Ile Gln His Pro Lys Asn Cys Ser Cys Phe Glu Cys Lys Glu Ser Leu
                 85                  90                  95

Glu Thr Cys Cys Gln Lys His Lys Leu Phe His Pro Asp Thr Cys Ser
            100                 105                 110

Cys Glu Asp Arg Cys Pro Phe His Thr Arg Pro Cys Ala Ser Gly Lys
        115                 120                 125

Thr Ala Cys Ala Lys His Cys Arg Phe Pro Lys Glu Lys Arg Ala Ala
130                 135                 140

Gln Gly Pro His Ser Arg Lys Asn Pro
145                 150

<210> SEQ ID NO 50
<211> LENGTH: 258
<212> TYPE: PRT
<213> ORGANISM: Homo sapiens

<400> SEQUENCE: 50

Leu Ser Thr Cys Lys Thr Ile Asp Met Glu Leu Val Lys Arg Lys Arg
 1               5                  10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
             35                  40                  45

Leu Ala Leu Tyr Asn Ser Thr Arg Asp Arg Val Ala Gly Glu Ser Ala
         50                  55                  60

Glu Pro Glu Pro Glu Pro Glu Ala Asp Tyr Tyr Ala Lys Glu Val Thr
 65                  70                  75                  80

Arg Val Leu Met Val Glu Thr His Asn Glu Ile Tyr Asp Lys Phe Lys
                 85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
```

```
            130                 135                 140
Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser

<210> SEQ ID NO 51
<211> LENGTH: 459
<212> TYPE: DNA
<213> ORGANISM: Homo sapiens
<220> FEATURE:
<221> NAME/KEY:
<223> OTHER INFORMATION: VEGF109

<400> SEQUENCE: 51
atggagacag acacactcct gctatgggta ctgctgctct gggttccagg ttccactggt      60
gacgcggccc aggatcctgg cagaatcat cacgaagtgg tgaaattcat ggatgtctat     120
cagcgcagct actgccatcc gatcgagaca ctggtggaca tcttccagga ataccctgat     180
gagatcgagt acatcttcaa gccatcctgc gtgcccctga tgagatgtgg gggttgctgc     240
aatgacgaag gctggagtg cgttcccacc gaggagtcca acatcaccat gcagattatg     300
agaattaaac ctcaccaagg gcagcacatc ggagagatga gctttctcca gcataacaaa     360
tgtgaatgta gaccaaagaa agatttggtc ttcgaacaaa aactcatctc agaagaggat     420
ctgaatagcg ccgtcgacca tcatcatcat catcattga                            459

<210> SEQ ID NO 52
<211> LENGTH: 152
<212> TYPE: PRT
<213> ORGANISM: Homo sapiens
<220> FEATURE:
<221> NAME/KEY:
<223> OTHER INFORMATION: VEGF109

<400> SEQUENCE: 52

Met Glu Thr Asp Thr Leu Leu Leu Trp Val Leu Leu Leu Trp Val Pro
1               5                   10                  15

Gly Ser Thr Gly Asp Ala Ala Gln Asp Pro Gly Gln Asn His His Glu
                20                  25                  30

Val Val Lys Phe Met Asp Val Tyr Gln Arg Ser Tyr Cys His Pro Ile
            35                  40                  45

Glu Thr Leu Val Asp Ile Phe Gln Glu Tyr Pro Asp Glu Ile Glu Tyr
50                  55                  60

Ile Phe Lys Pro Ser Cys Val Pro Leu Met Arg Cys Gly Gly Cys Cys
65                  70                  75                  80

Asn Asp Glu Gly Leu Glu Cys Val Pro Thr Glu Glu Ser Asn Ile Thr
                85                  90                  95
```

Met Gln Ile Met Arg Ile Lys Pro His Gln Gly Gln His Ile Gly Glu
            100                 105                 110

Met Ser Phe Leu Gln His Asn Lys Cys Glu Cys Arg Pro Lys Lys Asp
        115                 120                 125

Leu Val Phe Glu Gln Lys Leu Ile Ser Glu Glu Asp Leu Asn Ser Ala
    130                 135                 140

Val Asp His His His His His His
145                 150

<210> SEQ ID NO 53
<211> LENGTH: 137
<212> TYPE: PRT
<213> ORGANISM: Homo sapiens
<220> FEATURE:
<221> NAME/KEY:
<223> OTHER INFORMATION: CUB domain of PDGF-C

<400> SEQUENCE: 53

Glu Ser Asn Leu Ser Ser Lys Phe Gln Phe Ser Ser Asn Lys Glu Gln
1               5                   10                  15

Asn Gly Val Gln Asp Pro Gln His Glu Arg Ile Ile Thr Val Ser Thr
            20                  25                  30

Asn Gly Ser Ile His Ser Pro Arg Phe Pro His Thr Tyr Pro Arg Asn
        35                  40                  45

Thr Val Leu Val Trp Arg Leu Val Ala Val Glu Glu Asn Val Trp Ile
    50                  55                  60

Gln Leu Thr Phe Asp Glu Arg Phe Gly Leu Glu Asp Pro Glu Asp Asp
65                  70                  75                  80

Ile Cys Lys Tyr Asp Phe Val Glu Val Glu Glu Pro Ser Asp Gly Thr
                85                  90                  95

Ile Leu Gly Arg Trp Cys Gly Ser Gly Thr Val Pro Gly Lys Gln Ile
            100                 105                 110

Ser Lys Gly Asn Gln Ile Arg Ile Arg Phe Val Ser Asp Glu Tyr Phe
        115                 120                 125

Pro Ser Glu Pro Gly Phe Cys Ile His
    130                 135

<210> SEQ ID NO 54
<211> LENGTH: 819
<212> TYPE: DNA
<213> ORGANISM: Homo sapiens
<220> FEATURE:
<221> NAME/KEY:
<223> OTHER INFORMATION: CUB domain PDGF-D

<400> SEQUENCE: 54
atgcaccggc tcatctttgt ctacactcta atctgcgcaa acttttgcag ctgtcgggac    60
acttctgcaa ccccgcagag cgcatccatc aaagctttgc gcaacgccaa cctcaggcga   120
gatgagagca atcacctcac agacttgtac cgaagagatg agaccatcca ggtgaaagga   180
aacggctacg tgcagagtcc tagattcccg aacagctacc caggaacct gctcctgaca   240 tggcggcttc actctcagga gaatacacgg atacagctag tgtttgacaa tcagtttgga   300
ttagaggaag cagaaaatga tatctgtagg tatgattttg tggaagttga agatatatcc   360
gaaaccagta ccattattag aggacgatgg tgtggacaca aggaagttcc tccaaggata   420
aaatcaagaa cgaaccaaat taaaatcaca ttcaagtccg atgactactt tgtggctaaa   480
cctggattca agatttatta ttctttgctg gaagatttcc aacccgcagc agcttcagag   540

-continued

```
accaactggg aatctgtcac aagctctatt tcaggggtat cctataactc tccatcagta    600
acggatccca ctctgattgc ggatgctctg gacaaaaaaa ttgcagaatt tgatacagtg    660
gaagatctgc tcaagtactt caatccagag tcatggcaag aagatcttga aatatgtat     720 ctggacaccc ctcggtatcg aggcaggtca taccatgacc ggaagtcaaa agttgacctg    780
gataggctca atgatgatgc caagcgttac agtgatcct                           819
```

<210> SEQ ID NO 55
<211> LENGTH: 273
<212> TYPE: PRT
<213> ORGANISM: Homo sapiens
<220> FEATURE:
<221> NAME/KEY:
<223> OTHER INFORMATION: CUB domain PDGF-D
<400> SEQUENCE: 55

```
Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Asp
            260                 265                 270

Pro
```

<210> SEQ ID NO 56
<211> LENGTH: 1209
<212> TYPE: DNA
<213> ORGANISM: Homo sapiens
<220> FEATURE:

<221> NAME/KEY:
<223> OTHER INFORMATION: CUB271VEGF109

<400> SEQUENCE: 56

```
atggagacag acacactcct gctatgggta ctgctgctct gggttccagg ttccactggt      60
gacgcggccc aaggatcaac cccgcagagc gcatccatca aagctttgcg caacgccaac     120
ctcaggcgag atgagagcaa tcacctcaca gacttgtacc gaagagatga gaccatccag     180
gtgaaaggaa acggctacgt gcagagtcct agattcccga cagctaccc caggaacctg     240
ctcctgacat ggcggcttca ctctcaggag aatacacgga tacagctagt gtttgacaat     300
cagtttggat tagaggaagc agaaaatgat atctgtaggt atgattttgt ggaagttgaa     360
gatatatccg aaaccagtac cattattaga ggacgatggt gtggacacaa ggaagttcct     420
ccaaggataa aatcaagaac gaaccaaatt aaaatcacat tcaagtccga tgactacttt     480
gtggctaaac ctggattcaa gatttattat tctttgctgg aagatttcca acccgcagca     540
gcttcagaga ccaactggga atctgtcaca agctctattt caggggtatc ctataactct     600
ccatcagtaa cggatcccac tctgattgcg gatgctctgg acaaaaaat tgcagaattt     660
gatacagtgg aagatctgct caagtacttc aatccagagt catggcaaga agatcttgag     720
aatatgtatc tggacacccc tcggtatcga ggcaggtcat accatgaccg gaagtcaaaa     780
gttgacctgg ataggctcaa tgatgatgcc aagcgttaca gtgatcctgg cagaatcat     840
cacgaagtgg tgaaattcat ggatgtctat cagcgcagct actgccatcc gatcgagaca     900
ctggtggaca tcttccagga ataccctgat gagatcgagt catcttcaa gccatcctgc     960
gtgcccctga tgagatgtgg gggttgctgc aatgacgaag gctggagtg cgttcccacc    1020
gaggagtcca acatcaccat gcagattatg agaattaaac ctcaccaagg gcagcacatc    1080
ggagagatga gctttctcca gcataacaaa tgtgaatgta gaccaaagaa agatttggtc    1140
ttcgaacaaa aactcatctc agaagaggat ctgaatagcg ccgtcgacca tcatcatcat    1200
catcattga                                                            1209
```

<210> SEQ ID NO 57
<211> LENGTH: 402
<212> TYPE: PRT
<213> ORGANISM: Homo sapiens
<220> FEATURE:
<221> NAME/KEY:
<223> OTHER INFORMATION: CUB271VEGF109

<400> SEQUENCE: 57

```
Met Glu Thr Asp Thr Leu Leu Leu Trp Val Leu Leu Leu Trp Val Pro
1               5                  10                  15

Gly Ser Thr Gly Asp Ala Ala Gln Gly Ser Thr Pro Gln Ser Ala Ser
            20                  25                  30

Ile Lys Ala Leu Arg Asn Ala Asn Leu Arg Arg Asp Glu Ser Asn His
        35                  40                  45

Leu Thr Asp Leu Tyr Arg Arg Asp Glu Thr Ile Gln Val Lys Gly Asn
    50                  55                  60

Gly Tyr Val Gln Ser Pro Arg Phe Pro Asn Ser Tyr Pro Arg Asn Leu
65                  70                  75                  80

Leu Leu Thr Trp Arg Leu His Ser Gln Glu Asn Thr Arg Ile Gln Leu
                85                  90                  95

Val Phe Asp Asn Gln Phe Gly Leu Glu Glu Ala Glu Asn Asp Ile Cys
            100                 105                 110

Arg Tyr Asp Phe Val Glu Val Glu Asp Ile Ser Glu Thr Ser Thr Ile
```

|     |     |     |     |     | 115 |     |     |     | 120 |     |     |     |     | 125 |
| --- | --- | --- | --- | --- | --- | --- | --- | --- | --- | --- | --- | --- | --- | --- |

Ile Arg Gly Arg Trp Cys Gly His Lys Glu Val Pro Pro Arg Ile Lys
130                     135                     140

Ser Arg Thr Asn Gln Ile Lys Ile Thr Phe Lys Ser Asp Asp Tyr Phe
145                     150                     155                 160

Val Ala Lys Pro Gly Phe Lys Ile Tyr Tyr Ser Leu Leu Glu Asp Phe
                165                     170                     175

Gln Pro Ala Ala Ala Ser Glu Thr Asn Trp Glu Ser Val Thr Ser Ser
            180                     185                     190

Ile Ser Gly Val Ser Tyr Asn Ser Pro Ser Val Thr Asp Pro Thr Leu
        195                     200                     205

Ile Ala Asp Ala Leu Asp Lys Lys Ile Ala Glu Phe Asp Thr Val Glu
    210                     215                     220

Asp Leu Leu Lys Tyr Phe Asn Pro Glu Ser Trp Gln Glu Asp Leu Glu
225                     230                     235                     240

Asn Met Tyr Leu Asp Thr Pro Arg Tyr Arg Gly Arg Ser Tyr His Asp
                245                     250                     255

Arg Lys Ser Lys Val Asp Leu Asp Arg Leu Asn Asp Asp Ala Lys Arg
            260                     265                     270

Tyr Ser Asp Pro Gly Gln Asn His His Glu Val Val Lys Phe Met Asp
        275                     280                     285

Val Tyr Gln Arg Ser Tyr Cys His Pro Ile Glu Thr Leu Val Asp Ile
    290                     295                     300

Phe Gln Glu Tyr Pro Asp Glu Ile Glu Tyr Ile Phe Lys Pro Ser Cys
305                     310                     315                     320

Val Pro Leu Met Arg Cys Gly Gly Cys Cys Asn Asp Glu Gly Leu Glu
                325                     330                     335

Cys Val Pro Thr Glu Glu Ser Asn Ile Thr Met Gln Ile Met Arg Ile
            340                     345                     350

Lys Pro His Gln Gly Gln His Ile Gly Glu Met Ser Phe Leu Gln His
        355                     360                     365

Asn Lys Cys Glu Cys Arg Pro Lys Lys Asp Leu Val Phe Glu Gln Lys
    370                     375                     380

Leu Ile Ser Glu Glu Asp Leu Asn Ser Ala Val Asp His His His His
385                     390                     395                     400

His His

<210> SEQ ID NO 58
<211> LENGTH: 1161
<212> TYPE: DNA
<213> ORGANISM: Homo sapiens
<220> FEATURE:
<221> NAME/KEY:
<223> OTHER INFORMATION: CUB254VEGF109

<400> SEQUENCE: 58

| atggagacag | acacactcct | gctatgggta | ctgctgctct | gggttccagg | ttccactggt | 60 |
| gacgcggccc | aaggatcaac | cccgcagagc | gcatccatca | agctttgcg | caacgccaac | 120 |
| ctcaggcgag | atgagagcaa | tcacctcaca | gacttgtacc | gaagagatga | gaccatccag | 180 |
| gtgaaaggaa | acggctacgt | gcagagtcct | agattcccga | acagctaccc | caggaacctg | 240 |
| ctcctgacat | ggcggcttca | ctctcaggag | aatacacgga | tacagctagt | gtttgacaat | 300 |
| cagtttggat | tagaggaagc | agaaaatgat | atctgtaggt | atgattttgt | ggaagttgaa | 360 |
| gatatatccg | aaaccagtac | cattattaga | ggacgatggt | gtggacacaa | ggaagttcct | 420 |

-continued

```
ccaaggataa aatcaagaac gaaccaaatt aaaatcacat tcaagtccga tgactacttt      480
gtggctaaac ctggattcaa gatttattat tctttgctgg aagatttcca acccgcagca      540
gcttcagaga ccaactggga atctgtcaca agctctattt caggggtatc ctataactct      600
ccatcagtaa cggatcccac tctgattgcg gatgctctgg acaaaaaaat tgcagaattt      660
gatacagtgg aagatctgct caagtacttc aatccagagt catggcaaga agatcttgag      720
aatatgtatc tggacacccc tcggtatcga ggcaggtcat accatgaccg gaatgatcct      780
gggcagaatc atcacgaagt ggtgaaattc atggatgtct atcagcgcag ctactgccat      840
ccgatcgaga cactggtgga catcttccag gaatacctg atgagatcga gtacatcttc      900
aagccatcct gcgtgcccct gatgagatgt gggggttgct gcaatgacga agggctggag      960
tgcgttccca ccgaggagtc caacatcacc atgcagatta tgagaattaa acctcaccaa     1020
gggcagcaca tcggagagat gagctttctc cagcataaca aatgtgaatg tagaccaaag     1080
aaagatttgg tcttcgaaca aaaactcatc tcagaagagg atctgaatag cgccgtcgac     1140
catcatcatc atcatcattg a                                                1161
```

<210> SEQ ID NO 59
<211> LENGTH: 386
<212> TYPE: PRT
<213> ORGANISM: Homo sapiens
<220> FEATURE:
<221> NAME/KEY:
<223> OTHER INFORMATION: CUB254VEGF109

<400> SEQUENCE: 59

```
Met Glu Thr Asp Thr Leu Leu Leu Trp Val Leu Leu Leu Trp Val Pro
1               5                   10                  15

Gly Ser Thr Gly Asp Ala Ala Gln Gly Ser Thr Pro Gln Ser Ala Ser
            20                  25                  30

Ile Lys Ala Leu Arg Asn Ala Asn Leu Arg Arg Asp Glu Ser Asn His
        35                  40                  45

Leu Thr Asp Leu Tyr Arg Arg Asp Glu Thr Ile Gln Val Lys Gly Asn
    50                  55                  60

Gly Tyr Val Gln Ser Pro Arg Phe Pro Asn Ser Tyr Pro Arg Asn Leu
65                  70                  75                  80

Leu Leu Thr Trp Arg Leu His Ser Gln Glu Asn Thr Arg Ile Gln Leu
                85                  90                  95

Val Phe Asp Asn Gln Phe Gly Leu Glu Glu Ala Glu Asn Asp Ile Cys
            100                 105                 110

Arg Tyr Asp Phe Val Glu Val Glu Asp Ile Ser Glu Thr Ser Thr Ile
        115                 120                 125

Ile Arg Gly Arg Trp Cys Gly His Lys Glu Val Pro Pro Arg Ile Lys
    130                 135                 140

Ser Arg Thr Asn Gln Ile Lys Ile Thr Phe Lys Ser Asp Asp Tyr Phe
145                 150                 155                 160

Val Ala Lys Pro Gly Phe Lys Ile Tyr Tyr Ser Leu Leu Glu Asp Phe
                165                 170                 175

Gln Pro Ala Ala Ala Ser Glu Thr Asn Trp Glu Ser Val Thr Ser Ser
            180                 185                 190

Ile Ser Gly Val Ser Tyr Asn Ser Pro Ser Val Thr Asp Pro Thr Leu
        195                 200                 205

Ile Ala Asp Ala Leu Asp Lys Lys Ile Ala Glu Phe Asp Thr Val Glu
    210                 215                 220

Asp Leu Leu Lys Tyr Phe Asn Pro Glu Ser Trp Gln Glu Asp Leu Glu
```

```
                225                 230                 235                 240
Asn Met Tyr Leu Asp Thr Pro Arg Tyr Arg Gly Arg Ser Tyr His Asp
                        245                 250                 255
Arg Asn Asp Pro Gly Gln Asn His His Glu Val Val Lys Phe Met Asp
                260                 265                 270
Val Tyr Gln Arg Ser Tyr Cys His Pro Ile Glu Thr Leu Val Asp Ile
            275                 280                 285
Phe Gln Glu Tyr Pro Asp Glu Ile Glu Tyr Ile Phe Lys Pro Ser Cys
        290                 295                 300
Val Pro Leu Met Arg Cys Gly Gly Cys Cys Asn Asp Glu Gly Leu Glu
305                 310                 315                 320
Cys Val Pro Thr Glu Glu Ser Asn Ile Thr Met Gln Ile Met Arg Ile
                    325                 330                 335
Lys Pro His Gln Gly Gln His Ile Gly Glu Met Ser Phe Leu Gln His
                340                 345                 350
Asn Lys Cys Glu Cys Arg Pro Lys Lys Asp Leu Val Phe Glu Gln Lys
            355                 360                 365
Leu Ile Ser Glu Glu Asp Leu Asn Ser Ala Val Asp His His His His
        370                 375                 380
His His
385

<210> SEQ ID NO 60
<211> LENGTH: 1167
<212> TYPE: DNA
<213> ORGANISM: Homo sapiens
<220> FEATURE:
<221> NAME/KEY:
<223> OTHER INFORMATION: CUB256VEGF109

<400> SEQUENCE: 60
atggagacag acacactcct gctatgggta ctgctgctct ggttccagg ttccactggt      60
gacgcggccc aaggatcaac cccgcagagc gcatccatca aagctttgcg caacgccaac     120
ctcaggcgag atgagagcaa tcacctcaca gacttgtacc gaagagatga gaccatccag     180
gtgaaaggaa acggctacgt gcagagtcct agattcccga cagctaccc caggaacctg      240
ctcctgacat ggcggcttca ctctcaggag aatacgga tacagctagt gtttgacaat       300
cagtttggat tagaggaagc agaaaatgat atctgtaggt atgattttgt ggaagttgaa     360
gatatatccg aaaccagtac cattattaga ggacgatggt gtggacacaa ggaagttcct     420
ccaaggataa atcaagaac gaaccaaatt aaaatcacat tcaagtccga tgactacttt      480
gtggctaaac ctggattcaa gatttattat tctttgctgg aagatttcca acccgcagca     540
gcttcagaga ccaactggga atctgtcaca agctctattt caggggtatc ctataactct     600
ccatcagtaa cggatcccac tctgattgcg atgctctgg acaaaaaaat tgcagaattt     660
gatacagtgg aagatctgct caagtacttc aatccagagt catggcaaga agatcttgag    720
aatatgtatc tggacacccc tcggtatcga ggcaggtcat accatgaccg gaagtcaaat    780
gatcctgggc agaatcatca cgaagtggtg aaattcatgg atgtctatca gcgcagctac    840
tgccatccga tcgagacact ggtggacatc ttccaggaat accctgatga gatcgagtac    900
atcttcaagc catcctgcgt gccctgatg agatgtgggg gttgctgcaa tgacgaaggg    960
ctggagtgcg ttcccaccga ggagtccaac atcaccatgc agattatgag aattaaacct   1020
caccaagggc agcacatcgg agagatgagc tttctccagc ataacaaatg tgaatgtaga   1080
ccaaagaaag atttggtctt cgaacaaaaa ctcatctcag aagaggatct gaatagcgcc   1140
```
gtcgaccatc atcatcatca tcattga                                              1167

<210> SEQ ID NO 61
<211> LENGTH: 388
<212> TYPE: PRT
<213> ORGANISM: Homo sapiens
<220> FEATURE:
<221> NAME/KEY:
<223> OTHER INFORMATION: CUB256VEGF109

<400> SEQUENCE: 61

Met Glu Thr Asp Thr Leu Leu Leu Trp Val Leu Leu Leu Trp Val Pro
1               5                   10                  15

Gly Ser Thr Gly Asp Ala Ala Gln Gly Ser Thr Pro Gln Ser Ala Ser
            20                  25                  30

Ile Lys Ala Leu Arg Asn Ala Asn Leu Arg Arg Asp Glu Ser Asn His
        35                  40                  45

Leu Thr Asp Leu Tyr Arg Arg Asp Glu Thr Ile Gln Val Lys Gly Asn
    50                  55                  60

Gly Tyr Val Gln Ser Pro Arg Phe Pro Asn Ser Tyr Pro Arg Asn Leu
65                  70                  75                  80

Leu Leu Thr Trp Arg Leu His Ser Gln Glu Asn Thr Arg Ile Gln Leu
                85                  90                  95

Val Phe Asp Asn Gln Phe Gly Leu Glu Glu Ala Glu Asn Asp Ile Cys
            100                 105                 110

Arg Tyr Asp Phe Val Glu Val Glu Asp Ile Ser Glu Thr Ser Thr Ile
        115                 120                 125

Ile Arg Gly Arg Trp Cys Gly His Lys Glu Val Pro Pro Arg Ile Lys
    130                 135                 140

Ser Arg Thr Asn Gln Ile Lys Ile Thr Phe Lys Ser Asp Asp Tyr Phe
145                 150                 155                 160

Val Ala Lys Pro Gly Phe Lys Ile Tyr Tyr Ser Leu Leu Glu Asp Phe
                165                 170                 175

Gln Pro Ala Ala Ala Ser Glu Thr Asn Trp Glu Ser Val Thr Ser Ser
            180                 185                 190

Ile Ser Gly Val Ser Tyr Asn Ser Pro Ser Val Thr Asp Pro Thr Leu
        195                 200                 205

Ile Ala Asp Ala Leu Asp Lys Lys Ile Ala Glu Phe Asp Thr Val Glu
    210                 215                 220

Asp Leu Leu Lys Tyr Phe Asn Pro Glu Ser Trp Gln Glu Asp Leu Glu
225                 230                 235                 240

Asn Met Tyr Leu Asp Thr Pro Arg Tyr Arg Gly Arg Ser Tyr His Asp
                245                 250                 255

Arg Lys Ser Asn Asp Pro Gly Gln Asn His His Glu Val Val Lys Phe
            260                 265                 270

Met Asp Val Tyr Gln Arg Ser Tyr Cys His Pro Ile Glu Thr Leu Val
        275                 280                 285

Asp Ile Phe Gln Glu Tyr Pro Asp Glu Ile Glu Tyr Ile Phe Lys Pro
    290                 295                 300

Ser Cys Val Pro Leu Met Arg Cys Gly Gly Cys Cys Asn Asp Glu Gly
305                 310                 315                 320

Leu Glu Cys Val Pro Thr Glu Glu Ser Asn Ile Thr Met Gln Ile Met
                325                 330                 335

Arg Ile Lys Pro His Gln Gly Gln His Ile Gly Glu Met Ser Phe Leu
            340                 345                 350

```
Gln His Asn Lys Cys Glu Cys Arg Pro Lys Lys Asp Leu Val Phe Glu
        355                 360                 365

Gln Lys Leu Ile Ser Glu Glu Asp Leu Asn Ser Ala Val Asp His His
    370                 375                 380

His His His His
385

<210> SEQ ID NO 62
<211> LENGTH: 515
<212> TYPE: DNA
<213> ORGANISM: Homo sapiens
<220> FEATURE:
<221> NAME/KEY:
<223> OTHER INFORMATION: CUB+V5+His

<400> SEQUENCE: 62
ggtacccggc caccatgcac cggctcatct ttgtctacac tctaatctgc gcaaactttt      60
gcagctgtcg ggacacttct gcaaccccgc agagcgcatc catcaaagct ttgcgcaacg     120
ccaacctcag gcgagatgag agcaatcacc tcacagactt gtaccgaaga gatgagacca     180
tccaggtgaa aggaaacggc tacgtgcaga gtcctagatt cccgaacagc taccccagga     240
acctgctcct gacatggcgg cttcactctc aggagaatac acggatacag ctagtgtttg     300
acaatcagtt tggattagag gaagcagaaa atgatatctg taggtatgat tttgtggaag     360
ttgaagatat atccgaaacc agtaccatta ttagaggacg atggtgtgga cacaaggaag     420
ttcctccaag gataaaatca agaacgaacc aaattaaaat cacattcaag tccgatgact     480
actttgtggc taaacctgga ttcaagattt attat                                515

<210> SEQ ID NO 63
<211> LENGTH: 196
<212> TYPE: PRT
<213> ORGANISM: Homo sapiens
<220> FEATURE:
<221> NAME/KEY:
<223> OTHER INFORMATION: CUB+V5+His

<400> SEQUENCE: 63

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Arg Gly Pro Phe Glu Gly Lys Pro
```

```
                    165                 170                 175
Ile Pro Asn Pro Leu Leu Gly Leu Asp Ser Thr Arg Thr Gly His His
                180                 185                 190

His His His His
        195

<210> SEQ ID NO 64
<211> LENGTH: 33
<212> TYPE: DNA
<213> ORGANISM: Artificial sequence
<220> FEATURE:
<223> OTHER INFORMATION: Synthetic primer

<400> SEQUENCE: 64
gcggatccgg ggcagaatca tcacgaagtg gtg                              33

<210> SEQ ID NO 65
<211> LENGTH: 36
<212> TYPE: DNA
<213> ORGANISM: Artificial sequence
<220> FEATURE:
<223> OTHER INFORMATION: Synthetic primer

<400> SEQUENCE: 65
gcggatccct aatctttctt tggtctacat tcacat                           36
```

US 8,025,886 B2

MODIFIED VEGF-A WITH IMPROVED ANGIOGENIC PROPERTIES

This application claims priority to U.S. Provisional Application No. 60/708,226, filed Aug. 15, 2005, the disclosure of which is incorporated herein by reference in its entirety.

The file copy of the sequence listing is submitted on a Compact-Disc-Read Only Memory (CD-ROM). The sequence listing is saved as an ASCII DOS text file named 41018A.txt (118 KB), which was created on Aug. 15, 2006. The contents of the CD-ROM are incorporated herein by reference in its entirety.

FIELD OF THE INVENTION

The present application is directed to materials and methods for promoting angiogenesis.

BACKGROUND

Angiogenesis is a fundamental process required for normal growth and development of tissues, and involves the proliferation of new capillaries from pre-existing blood vessels. Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the healthy individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor α (TGFα), and hepatocyte growth factor (HGF). See for example Folkman et al, "Angiogenesis", J. Biol. Chem., 1992 267 10931-10934 for a review.

It has been suggested that a particular family of endothelial cell-specific growth factors and their corresponding receptors is primarily responsible for stimulation of endothelial cell growth and differentiation, and for certain functions of the differentiated cells. These factors are members of the PDGF/VEGF family, and appear to act via receptor tyrosine kinases (RTKs).

To date a number of PDGF/VEGF family members have been identified. These include PDGF-A (see e.g., GenBank Acc. No. X06374), PDGF-B (see e.g., GenBank Acc. No. M12783), PDGF-C (Intl. Publ. No. WO 00/18212), PDGF-D (Intl. Publ. No. WO 00/027879), VEGF (also known as VEGF-A or by particular isoform), Placenta growth factor, PlGF (U.S. Pat. No. 5,919,899), VEGF-B (also known as VEGF-related factor (VRF) Intl. Publ. No. PCT/US96/02597 and WO 96/26736), VEGF-C, (U.S. Pat. No. 6,221,839 and WO 98/33917), VEGF-D (also known as c-fos-induced growth factor (FIGF) (U.S. Pat. No. 6,235,713, Intl. Publ. No. WO98/07832), VEGF-E (also known as NZ7 VEGF or OV NZ7; Intl. Publ. No. WO00/025805 and U.S. Patent Publ. No. 2003/0113870), NZ2 VEGF (also known as OV NZ2; see e.g., GenBank Acc. No. S67520), D1701 VEGF-like protein (see e.g., GenBank Acc. No. AF106020; Meyer et al., EMBO J. 18:363-374), and NZ10 VEGF-like protein (described in Intl. Patent Application PCT/US99/25869) [Stacker and AChen, Growth Factors 17:1-11 (1999); Neufeld et al., FASEB J 13:9-22 (1999); Ferrara, J Mol Med 77:527-543 (1999)].

Vascular endothelial growth factors act by binding to receptor tyrosine kinases. Seven receptor tyrosine kinases have been identified, namely Flt-1 (VEGFR-1), KDR/Flk-1 (VEGFR-2), Flt4 (VEGFR-3), PDGFR-α, PDGFR-β, Tie and Tek/Tie-2. All of these have the intrinsic tyrosine kinase activity which is necessary for signal transduction. The essential, specific role in vasculogenesis and angiogenesis of Flt-1, Flk-1, Tie and Tek/Tie-2 has been demonstrated by targeted mutations inactivating these receptors in mouse embryos. Overexpression of either the VEGF/PDGF family of growth factors or VEGF/PDGF receptors can lead to aberrant development of the vasculature system (Saaristo et al., *FASEB J.* 16:1041-9, 2002; Kubo et al., *Proc Natl Acad Sci USA.* 99:8868-73, 2002.). The activity of VEGF/VEGFR also promotes angiogenesis of new cells and developing tissue, thereby facilitating the angiogenesis and vascularization of tumor cells.

While the aforementioned VEGF molecules have shown some promise with respect to the development of new blood vessels and other growth factor properties, there remains a need for the development of improved therapeutic approaches for promoting angiogenesis.

SUMMARY OF THE INVENTION

The present invention is directed recombinant polynucleotides and polypeptides of the VEGF PDGF family of growth factors that are modified with flanking sequences to impart improved properties. Polypeptide and polynucleotide materials and methods for stimulation of angiogenesis are among the preferred embodiments of the invention.

The invention addresses existing needs by providing new compounds, compositions of matter, materials, devices, and methods for modulating processes such as angiogenesis, lymphangiogenesis, and wound healing, which have numerous therapeutic and prophylactic applications.

One aspect of the invention is novel compounds, especially proteinaceous compounds, with angiogenic properties. One aspect of the invention is a chimeric construct comprising: an RTK binding domain; at least one heterologous flanking domain or CUB domain; and at least one linkage that connects the RTK binding domain to the at least one flanking domain or CUB domain; wherein the construct and the RTK binding domain bind to the extracellular domain of at least one receptor tyrosine kinase selected from the group consisting of: VEGFR-1, VEGFR-2, VEGFR-3, PDGFR-alpha, and PDGFR-beta. Those constructs that bind and stimulate the receptor are useful as receptor agonists. Those constructs that bind, but fail to stimulate the receptor, are useful as receptor antagonists. As described in greater detail below, some embodiments of the invention behave as pro-agonists, insofar as a cleavable CUB domain prevents receptor activation, but under appropriate conditions (e.g., administration or stimulation of a protease to cleave the CUB domain), the CUB domain is cleaved, creating a receptor agonist. The term "heterologous" in the context used above, refers to the flanking/CUB domain being from a different protein than the RTK binding domain. For example, if the at least one flanking domain comprises a VEGF-C pro-peptide, then exemplary heterologous RTK domains include any VEGF/PDGF family member other than VEGF-C (e.g., VEGF-A, -B, or -D; PDGF-A, -B, -C, or -D; or PlGF, but not VEGF-C).

In certain exemplary embodiments, the present invention is a construct comprising a receptor tyrosine kinase RTK binding domain, at least one flanking domain, and at least one linkage that connects the RTK binding domain to the at least one flanking domain. The term "construct" generally refers to a molecule, compound, or composition of matter and is not intended to be limiting as to structure or function. The term "domain" as used herein is descriptive of the fact that a portion of a molecule (that may be less than the whole molecule) may be used, and also is descriptive of the fact that the construct itself has discrete portions that contribute to the overall functionality (biological activity) of the construct. In some embodiments, the RTK binding domain comprises an amino acid sequence that is at least 90% identical to an RTK binding domain amino acid sequence selected from the group consisting of: mammalian VEGF-A, mammalian VEGF-B, mammalian VEGF-C, mammalian VEGF-D, mammalian VEGF-E, PlGF, PDGF-A, PDGF-B, PDGF-C and PDGF-D RTK binding domain amino acid sequences. The construct and the RTK binding domain bind to at least one receptor tyrosine kinase selected from the group consisting of: VEGFR-1, VEGFR-2, VEGFR-3, PDGFR-alpha, and PDGFR-beta. In preferred embodiments, the flanking domain comprises an amino acid sequence that is at least 90% identical to an amino acid sequence selected from the group consisting of: a mammalian VEGF-C amino-terminal propeptide; a mammalian VEGF-C carboxy-terminal propeptide; a mammalian VEGF-D amino-terminal propeptide; a mammalian VEGF-D carboxy-terminal propeptide; a mammalian TGF-β1 LAP peptide; and fragments thereof that are effective to bind extracellular matrix proteins or neuropilin proteins, with the proviso that when the RTK binding domain is at least 90% identical to a VEGF-C RTK binding domain amino acid sequence, the construct contains at least one flanking domain that is not at least 90% identical to a VEGF-C pro-peptide; and when the RTK binding domain is at least 90% identical to a VEGF-D RTK binding domain amino acid sequence, the construct contains at least one flanking domain that is not at least 90% identical to a VEGF-D pro-peptide. In other words, constructs of the invention are heterologous compounds, the domains of which do not come exclusively from VEGF-C or exclusively from VEGF-D.

In the constructs described herein, a linker (or linkers) is used to attach the RTK binding domain(s) to one or more flanking domains (or to further attach flanking domains to each other or to attach optional additional domains such as a heparin binding domain or a CUB domain). In some embodiments, the linker comprises a covalent bond. In related embodiments, the linker comprises a peptide bond.

In some variations, the domains constitute separate and distinct peptides attached by the linker. In other variations, domains are joined by peptide bonds to form a continuous polypeptide chain.

For example, in some embodiments, the construct is a chimeric polypeptide comprising a structure that satisfies the formula Fn-L-RTK-L-Fc, wherein Fn comprises a flanking domain that comprises an amino acid sequence that is at least 90% identical to an amino acid sequence selected from the group consisting of: a mammalian VEGF-C amino-pro-peptide and a mammalian VEGF-D amino-pro-peptide; wherein Fc comprises a flanking domain that comprises an amino acid sequence that is at least 90% identical to an amino acid sequence selected from a mammalian VEGF-C carboxy-pro-peptide and a mammalian VEGF-D carboxy-pro-peptide; wherein RTK comprises the RTK binding domain; and wherein L comprises the linkage between the flanking domain and the RTK binding domain.

In some particular embodiments, the at least one flanking domain of the polypeptide comprises an amino acid sequence that is at least 90% identical to an amino acid sequence selected from the group consisting of: the VEGF-C amino-pro-peptide sequence of SEQ ID NO: 46; the VEGF-C carboxy-pro-peptide sequence of SEQ ID NO: 47; the VEGF-D amino-pro-peptide sequence of SEQ ID NO: 48; and the VEGF-D carboxy-pro-peptide sequence of SEQ ID NO: 49.

In some particular embodiments, the chimeric polypeptide that comprises the formula Fn-L-RTK-L-Fc binds VEGFR-1 or VEGFR-2; wherein the RTK binding domain comprises an amino acid sequence that is at least 90% identical to a sequence selected from the group consisting of: amino acids 27 to 147 of the VEGF121 amino acid sequence of SEQ ID NO: 4 or fragment thereof; amino acids 27 to 171 of the VEGF145 amino acid sequence of SEQ ID NO: 5 or fragment thereof; amino acids 27 to 191 of the VEGF165 amino acid sequence of SEQ ID NO: 6 or fragment thereof; amino acids 27 to 215 of the VEGF189 amino acid sequence of SEQ ID NO: 7 or fragment thereof; amino acids 27-232 of the VEGF206 amino acid sequence of SEQ ID NO: 3 or fragment thereof.

In a particularly preferred embodiment the chimeric polypeptide comprises an amino acid sequence that is at least 90% identical to the CAC construct amino acid sequence of SEQ ID NO 27.

In other particular embodiments, the chimeric polypeptide that comprises the formula Fn-L-RTK-L-Fc binds VEGFR-1 or VEGFR-2; wherein the RTK binding domain comprises an amino acid sequence that is at least 90% identical to a sequence selected from the group consisting of: amino acids 22 to 188 of the VEGF-B167 amino acid sequence of SEQ ID NO: 44 or fragment thereof, amino acids 22 to 207 of the VEGF-B186 amino acid sequence of SEQ ID NO: 45 or fragment thereof; amino acids 19 to 149 of the PlGF-1 amino acid sequence of SEQ ID NO: 9 or fragment thereof; amino acids 19 to 170 of the PlGF-2 amino acid sequence of SEQ ID NO: 42 or fragment thereof; and amino acids 19 to 221 of the PlGF-3 amino acid sequence of SEQ ID NO: 43 or fragment thereof.

In alternative embodiments, the chimeric polypeptide that comprises the formula Fn-L-RTK-L-Fc binds PDGFR-alpha or PDGFR-beta; wherein the RTK binding domain comprises an amino acid sequence that is at least 90% identical to a sequence selected from the group consisting of: amino acids 87 to 211 of the PDGF-A amino acid sequence of SEQ ID NO: 17 or fragment thereof; amino acids 82 to 190 of the PDGF-B amino acid sequence of SEQ ID NO: 19 or fragment thereof; amino acids 230 to 345 of the PDGF-C amino acid sequence of SEQ ID NO: 21 or fragment thereof; and amino acids 255 to 370 of the PDGF-D amino acid sequence of SEQ ID NO: 24 or fragment thereof.

In still other embodiments, the chimeric polypeptide comprising the formula Fn-L-RTK-L-Fc binds VEGFR-3 or VEGFR-2; wherein the RTK binding domain comprises an amino acid sequence that is at least 90% identical to a sequence selected from the group consisting of: amino acids 103 to 227 of the VEGF-C amino acid sequence of SEQ ID NO: 13 or fragment thereof; and amino acids 93 to 201 of the VEGF-D amino acid sequence of SEQ ID NO: 15 or fragment thereof.

In some embodiments, the chimeric polypeptide comprises an amino acid sequence that is at least 90% identical to a sequence selected from the group consisting of: the CAC construct amino acid sequence of SEQ ID NO 27; the CDD construct amino acid sequence of SEQ ID NO: 37; the CDC construct amino acid sequence of SEQ ID NO: 39; and; the DDC construct amino acid sequence of SEQ ID NO: 41.

In yet another embodiment, another chimeric construct is provided (designated "CUB-VEGF") which comprises an RTK binding domain, a CUB domain, and at least one linkage that connects the RTK binding domain to the CUB domain, wherein the RTK binding domain comprises an amino acid sequence that is at least 90% identical to an amino acid sequence selected from the group consisting of: mammalian VEGF-A RTK binding domain amino acid sequences; mammalian VEGF-B RTK binding domain amino acid sequences; mammalian VEGF-C RTK binding domain amino acid sequences; mammalian VEGF-D RTK binding domain amino acid sequences; mammalian VEGF-E RTK binding domain amino acid sequences; mammalian PlGF RTK binding domain amino acid sequences; mammalian PDGF-A RTK binding domain amino acid sequences; and mammalian PDGF-B RTK binding domain amino acid sequences, wherein the CUB domain comprises an amino acid sequence at least 90% identical to an amino acid sequence selected from the group consisting of PDGF-C CUB domain amino acid sequences and PDGF-D CUB domain amino acid sequences; and wherein the construct and the RTK binding domain bind to the extracellular domain of at least one receptor tyrosine kinase selected from the group consisting of: VEGFR-1, VEGFR-2, VEGFR-3, PDGFR-alpha, and PDGFR-beta. It will be apparent that the construct of this embodiment is not required to have a flanking domain (although constructs of this embodiment optionally further comprise a flanking domain).

In some embodiments, the CUB domain is connected to the N-terminus of the RTK binding domain, while in other embodiments the CUB domain is connected to the C-terminus of the RTK binding domain. In one embodiment, the CUB domain comprises an amino acid sequence that is at least 90% identical to the amino acid sequence set forth in either SEQ ID NO: 54 or SEQ ID NO: 56.

In particular embodiments, RTK binding domain comprises an amino acid sequence that is at least 90% identical to amino acids 27 to 127 of the VEGF109 amino acid sequence of SEQ ID NO: 52.

In other particular embodiments, the chimeri construct polypeptide comprises an amino acid sequence at least 90% identical to an amino acid sequence selected from the group consisting of SEQ ID NOS: 57, 59 and 61.

In some embodiments, the CUB domain is attached to the RTK binding domain via a recognition sequence specifically recognized by a proteolytic enzyme such that the proteolytic enzyme if present cleaves at the recognition sequence to remove the CUB domain and produce an activated growth factor.

It is particularly contemplated that any of the constructs and polypeptides of the inventions may be prepared to further include a peptide tag, e.g., a polyhistidine tag. Inclusion of such a tag facilitates purification. In additional embodiments, the constructs or polypeptides may be PEGylated with one or more polyethylene glycol (PEG) moieties.

The constructs and polypeptides of the present invention may advantageously be formulated into compositions wherein such compositions comprise a construct of polypeptide of the invention in a pharmaceutically acceptable carrier, excipient or diluent.

Constructs of the invention comprise polypeptide domains, and are optionally made by recombinant techniques in vitro and/or expressed in vivo. Polynucleotides that comprise nucleotide sequences that encode all (or a portion of) a construct are an additional aspect of the invention. Vectors including expression vectors for in vitro production and gene therapy vectors for in vivo production/expression of constructs, are also an aspect of the invention.

For example, the invention includes polynucleotides comprising a nucleotide sequence that encodes any chimeric polypeptide of the invention, including a chimeric polypeptide of the formula Fn-L-RTK-L-Fc, or a chimeric polypeptide designated "CUB-VEGF," as discussed above and described in further detail in the description below. In specific embodiments, the polynucleotide further comprises a nucleotide sequence that encodes a signal peptide fused in-frame with the polypeptides described above. The signal peptide facilitates extracellular secretion of the encoded construct when expressed in a suitable host cell.

The invention also includes an expression vector comprising a nucleotide sequence that encodes any chimeric polypeptide of the invention, including a chimeric polypeptide of the formula Fn-L-RTK-L-Fc, or a chimeric polypeptide designated "CUB-VEGF," operably linked to an expression control sequence or promoter sequence. In some variations, a tissue-specific promoter is used to make a polynucleotide that encodes a construct and that is preferentially expressed in one or a few tissues of an organism; such as skin (for wound healing), muscle (for ischemia), endothelial cells, neurons, or other tissues. In certain embodiments, the promoter sequence is a skin-specific promoter selected from the group consisting of K14, K5, K6, K16 and alpha 1(I) collagen promoter. In other embodiments the promoter is an endothelial cell specific promoter. The expression vector may be any vector used for the expression of a nucleic acid and may for example, be selected from the group consisting of replication deficient adenoviral vectors, adeno-associated viral vectors, and lentivirus vectors. The polynucleotides and vectors of the invention may be formulated as compositions in which the polynucleotides or the vector is presented in a pharmaceutically acceptable carrier, excipient or diluent.

Other aspects of the invention include host cells that have been transformed or transfected with a polynucleotide or vector of the invention. In some variations, the cells are any prokaryotic or eukaryotic cell that can be manipulated (e.g., through transformation or transfection) to express polypeptide constructs of the invention. In some variations, the cells are suitable for ex vivo transfection/transformation and reinplantation into a host organism. For example, in one variation, the host cells are mammalian endothelial cells or mammalian endothelial precursor cells. In another variation, the cells are muscle or neuronal cells or precursors.

Other aspects of the invention are directed to methods of modulating the growth of mammalian endothelial cells or mammalian endothelial precursor cells, using constructs of the invention or using polynucleotides/vectors that encode the constructs. An exemplary method comprises contacting the cells with a composition comprising one or more of the following: a polypeptide construct comprising an RTK binding domain, at least one flanking domain, and at least one linkage that connects the RTK binding domain to the at least one flanking domain; a chimeric polypeptide comprising the formula Fn-L-RTK-L-Fc; a polynucleotide that encodes such a chimeric polypeptide; an expression vector containing such a polynucleotide operatively linked to an expression control sequence; and a cell transformed or transfected with such a polynucleotide or such a vector that expresses the polypeptide construct. In certain embodiments, the contacting comprises administering the composition to a mammalian subject in an amount effective to modulate endothelial cell growth in vivo. In particular embodiments, the mammalian subject is human.

Also contemplated as part of the invention is a method of modulating angiogenesis in a mammalian subject comprising administering to a mammalian subject in need of modulation of angiogenesis a composition, in an amount effective to modulate angiogenesis, comprising one or more of the following: any construct of the invention; a polynucleotide that encodes such a construct; an expression vector containing such a polynucleotide operatively linked to an expression control sequence; and a cell transformed or transfected with such a polynucleotide or such a vector that expresses the polypeptide construct.

Other embodiments of the invention are directed to methods of modulating lymphangiogenesis in a mammalian subject comprising administering to a mammalian subject in need of modulation of lymphangiogenesis a composition in an amount effective to modulate lymphangiogenesis, comprising one or more of the following: any construct of the invention; a polynucleotide that encodes such a construct; an expression vector containing such a polynucleotide operatively linked to an expression control sequence; and a cell transformed or transfected with such a polynucleotide or such a vector that expresses the polypeptide construct.

Also contemplated herein is a method of improving the healing of a skin graft or skin flap to underlying tissue of a mammalian subject, comprising contacting skin graft or skin flap tissue or underlying tissue with a composition comprising a healing agent that is present in said composition in an amount effective to reduce edema or increase perfusion at the skin graft or skin flap, thereby improving the healing of the skin graft or skin flap; wherein the healing agent comprises one or more of the following: any construct of the invention; a polynucleotide that encodes such a construct; an expression vector containing such a polynucleotide operatively linked to an expression control sequence; and a cell transformed or transfected with such a polynucleotide or such a vector that expresses the polypeptide construct.

Also contemplated is an improvement in a medical device for improving circulation, wound healing, or blood flow, comprising coating or impregnating the device with a composition comprising one or more of the following: any construct of the invention; a polynucleotide that encodes such a construct; an expression vector containing such a polynucleotide operatively linked to an expression control sequence; and a cell transformed or transfected with such a polynucleotide or such a vector that expresses the polypeptide construct.

Other aspects of the invention include a patch comprising a pad material having an upper surface and lower surface, an adhesive on the lower surface, and a therapeutic composition, wherein the composition comprises one or more of the following: any construct of the invention; a polynucleotide that encodes such a construct; an expression vector containing such a polynucleotide operatively linked to an expression control sequence; and a cell transformed or transfected with such a polynucleotide or such a vector that expresses the polypeptide construct.

Yet another aspect of the invention is a surgical suturing thread impregnated with a composition, wherein the composition comprises one or more of the following: any construct of the invention; a polynucleotide that encodes such a construct; an expression vector containing such a polynucleotide operatively linked to an expression control sequence; and a cell transformed or transfected with such a polynucleotide or such a vector that expresses the polypeptide construct.

Another aspect of the invention includes methods and compositions for antagonizing a receptor for a PDGF/VEGF family growth factor, the method comprising providing a construct of the invention which inhibits the binding of a growth factor to its respective receptor. In some embodiments, the invention includes methods for antagonizing in a cell at least one receptor selected from the group consisting of VEGFR-1, VEGFR-2, VEGFR-3, PDGFR-α and PDGFR-β, wherein the method comprises administering to the cell an agent selected from the group consisting of a CUB-VEGF construct; a dimer comprising two, chimeric polypeptides of the invention, a polynucleotide that encodes such a construct; an expression vector containing such a polynucleotide operatively linked to an expression control sequence; and a cell transformed or transfected with such a polynucleotide or such a vector that expresses the polypeptide construct.

In other embodiments, the invention includes a method for blocking PDGF-D binding to PDGFR-α, but not to PDGFR-β in a cell where both PDGFR-α and PDGFR-β are present; the method comprising administering to the cell an agent selected from the group selected from the group consisting of a CUB-VEGF construct; a dimer comprising two chimeric polypeptides of the invention, a polynucleotide that encodes such a construct; an expression vector containing such a polynucleotide operatively linked to an expression control sequence; and a cell transformed or transfected with such a polynucleotide or such a vector that expresses the polypeptide construct.

Yet another aspect of the invention includes a method for modulating activities of a receptor of a cell which receptor specifically binds to and is activated by a growth factor selected from the group consisting PDGF-A, PDGF-B, the VEGF-homology domain of PDGF-C, VEGF, VEGF-B, VEGF-C and PlGF, the method comprising administering to the cell an agent selected from the group consisting of a CUB-VEGF construct; a dimer comprising two chimeric polypeptides of the invention, a polynucleotide that encodes such a construct; an expression vector containing such a polynucleotide operatively linked to an expression control sequence; and a cell transformed or transfected with such a polynucleotide or such a vector that expresses the polypeptide construct; and providing the cell with a proteolytic enzyme, whereby the growth factor is activated.

Yet another aspect of the invention includes the discovery that fully-processed PDGF-D binds to and activates both PDGFR-α and PDGFR-β. Accordingly, in one embodiment, the present invention provides fully-processed PDGF-D molecules, pharmaceutical compositions comprising the same, and the use thereof for regulating PDGFR-α.

Additional aspects of the invention are defined or summarized in the following numbered paragraphs:

1. A construct comprising:
an RTK binding domain, at least one flanking domain, and at least one linkage that connects the RTK binding domain to the at least one flanking domain;
wherein the RTK binding domain comprises an amino acid sequence that is at least 90% identical to an amino acid sequence selected from the group consisting of: mammalian VEGF-A RTK binding domain amino acid sequences; mammalian VEGF-B RTK binding domain amino acid sequences; mammalian VEGF-C RTK binding domain amino acid sequences; mammalian VEGF-D RTK binding domain amino acid sequences; mammalian VEGF-E RTK binding domain amino acid sequences; mammalian PlGF RTK binding domain amino acid sequences; mammalian PDGF-A RTK binding domain amino acid sequences; mammalian PDGF-B RTK binding domain amino acid sequences; mammalian PDGF-C RTK binding domain amino acid sequences; and mammalian PDGF-D RTK binding domain amino acid sequences;

wherein the construct and the RTK binding domain bind to the extracellular domain of at least one receptor tyrosine kinase selected from the group consisting of: VEGFR-1, VEGFR-2, VEGFR-3, PDGFR-alpha, and PDGFR-beta; and wherein the at least one flanking domain comprises an amino acid sequence that is at least 90% identical to an amino acid sequence selected from the group consisting of: a mammalian VEGF-C amino-terminal propeptide; a mammalian VEGF-C carboxy-terminal propeptide; a mammalian VEGF-D amino-terminal propeptide; a mammalian VEGF-D carboxy-terminal propeptide; a mammalian TGF-β1 LAP peptide; and fragments thereof that are effective to bind extracellular matrix proteins or neuropilin proteins;

with the proviso that when the RTK binding domain is at least 90% identical to a VEGF-C RTK binding domain amino acid sequence, the at least one flanking domain is not at least 90% identical to a VEGF-C pro-peptide; and when the RTK binding domain is at least 90% identical to a VEGF-D RTK binding domain amino acid sequence, the at least one flanking domain is not at least 90% identical to a VEGF-D pro-peptide.

2. A construct according to paragraph 1, wherein at least one flanking domain comprises an amino acid sequence that is at least 90% identical to an amino acid sequence selected from the group consisting of: a mammalian VEGF-C amino-pro-peptide; a mammalian VEGF-C carboxy-pro-peptide; a mammalian VEGF-D amino-pro-peptide; and a mammalian VEGF-D carboxy-pro-peptide.

3. A construct according to paragraph 1 or paragraph 2, further comprising a heparin binding domain connected to the construct by a linkage.

4. A construct according to any one of paragraphs 1-3, further comprising a CUB domain connected to the construct by a linkage.

5. A construct according to any one of paragraphs 1-4, wherein each of the at least one linkage comprises a peptide bond, whereby the RTK binding domain and the at least one flanking domain comprises a chimeric polypeptide.

6. A construct according to paragraph 5, wherein the chimeric polypeptide further comprises a signal peptide.

7. The construct of paragraph 5 or 6, wherein the chimeric polypeptide further comprises a peptide tag.

8. A construct according to any one of paragraphs 5-7, wherein the chimeric polypeptide comprises at least two flanking domains.

9. A construct according to any one of paragraphs 5-8, wherein the chimeric polypeptide satisfies the formula:

Fn-L-RTK-L-Fc, wherein Fn comprises a flanking domain that comprises an amino acid sequence that is at least 90% identical to an amino acid sequence selected from the group consisting of: a mammalian VEGF-C amino-pro-peptide and a mammalian VEGF-D amino-pro-peptide;

wherein Fc comprises a flanking domain that comprises an amino acid sequence that is at least 90% identical to an amino acid sequence selected from a mammalian VEGF-C carboxy-pro-peptide and a mammalian VEGF-D carboxy-pro-peptide;

wherein RTK comprises the RTK binding domain; and wherein L comprises the linkage between the flanking domain and the RTK binding domain.

10. A construct according to any one of paragraphs 5-9, wherein the at least one flanking domain comprises an amino acid sequence that is at least 90% identical to an amino acid sequence selected from the group consisting of:

the VEGF-C amino-pro-peptide sequence of SEQ ID NO: 46;

the VEGF-C carboxy-pro-peptide sequence of SEQ ID NO: 47;

the VEGF-D amino-pro-peptide sequence of SEQ ID NO: 48; and the VEGF-D carboxy-pro-peptide sequence of SEQ ID NO: 49.

11. A construct according to any one of paragraphs 5-10, wherein the chimeric polypeptide binds VEGFR-1 or VEGFR-2;

wherein the RTK binding domain comprises an amino acid sequence that is at least 90% identical to a sequence selected from the group consisting of:

(a) amino acids 27 to 147 of the VEGF121 amino acid sequence of SEQ ID NO: 4;

(b) amino acids 27 to 171 of the VEGF145 amino acid sequence of SEQ ID NO: 5;

(c) amino acids 27 to 191 of the VEGF165 amino acid sequence of SEQ ID NO: 6;

(d) amino acids 27 to 215 of the VEGF189 amino acid sequence of SEQ ID NO: 7;

(e) amino acids 27-232 of the VEGF206 amino acid sequence of SEQ ID NO: 3; and (f) fragments of (a)-(e) that bind to VEGFR-1 or VEGFR-2.

12. A construct according to any one of paragraphs 1-11, comprising an amino acid sequence that is at least 90% identical to the amino acid sequence of SEQ ID NO 27.

13. A construct according to any one of paragraphs 5-10, wherein the chimeric polypeptide binds VEGFR-1 or VEGFR-2; and wherein the RTK binding domain comprises an amino acid sequence that is at least 90% identical to a sequence selected from the group consisting of:

(a) amino acids 22 to 188 of the VEGF-B167 amino acid sequence of SEQ ID NO: 44;

(b) amino acids 22 to 207 of the VEGF-B186 amino acid sequence of SEQ ID NO: 45;

(c) amino acids 19 to 149 of the PlGF-1 amino acid sequence of SEQ ID NO: 9;

(d) amino acids 19 to 170 of the PlGF-2 amino acid sequence of SEQ ID NO: 42;

(e) amino acids 19 to 221 of the PlGF-3 amino acid sequence of SEQ ID NO: 43; and (f) fragments of (a)-(e) that bind to VEGFR-1 or VEGFR-2.

14. A construct according to any one of paragraphs 5-10, wherein the chimeric polypeptide binds PDGFR-alpha or PDGFR-beta; and wherein the RTK binding domain comprises an amino acid sequence that is at least 90% identical to a sequence selected from the group consisting of:

(a) amino acids 87 to 211 of the PDGF-A amino acid sequence of SEQ ID NO: 17;

(b) amino acids 82 to 190 of the PDGF-B amino acid sequence of SEQ ID NO: 19;

(c) amino acids 230 to 345 of the PDGF-C amino acid sequence of SEQ ID NO: 21;

(d) amino acids 255 to 370 of the PDGF-D amino acid sequence of SEQ ID NO: 24; and (e) fragments of (a)-(d) that bind to PDGFR-alpha or PDGFR-beta.

15. A construct according to any one of paragraphs 5-10, wherein the chimeric polypeptide binds VEGFR-3 or VEGFR-2; and wherein the RTK binding domain comprises an amino acid sequence that is at least 90% identical to a sequence selected from the group consisting of:
  (a) amino acids 103 to 227 of the VEGF-C amino acid sequence of SEQ ID NO: 13;
  (b) amino acids 93 to 201 of the VEGF-D amino acid sequence of SEQ ID NO: 15; and
  (c) fragments of (a)-(b) that bind to VEGFR-3 or VEGFR-2.

16. A construct according to paragraph 15, comprising an amino acid sequence that is at least 90% identical to a sequence selected from the group consisting of:
  (a) the CDD construct amino acid sequence of SEQ ID NO 37;
  (b) the CDC construct amino acid sequence of SEQ ID NO: 39; and,
  (c) the DDC construct amino acid sequence of SEQ ID NO: 41.

17. A composition comprising the construct of any one of paragraphs 1-16 in a pharmaceutically acceptable carrier.

18. A polynucleotide comprising a nucleotide sequence that encodes the construct of any one of paragraphs 1-16, wherein the construct comprises a polypeptide.

19. A polynucleotide according to paragraph 18, wherein the polynucleotide further comprises a nucleotide sequence that encodes a signal peptide fused in-frame with the polypeptide.

20. A polynucleotide according to paragraph 18 or 19, further comprising a promoter sequence that promotes expression of the polynucleotide in a mammalian cell.

21. A polynucleotide according to paragraph 20, wherein the promoter sequence comprises a skin-specific promoter.

22. A polynucleotide according to paragraph 21 wherein the promoter is selected from the group consisting of K14, K5, K6, K16 and alpha 1(I) collagen promoter.

23. A polynucleotide according to paragraph 20, wherein the promoter is an endothelial cell specific promoter.

24. A vector comprising the polynucleotide of any one of paragraphs 18-23.

25. An expression vector comprising the polynucleotide of any one of paragraphs 18-23 operably linked to an expression control sequence.

26. An expression vector of paragraph 25, wherein the expression control sequence comprises an endothelial cell specific promoter.

27. A vector of any one of paragraphs 24-26, selected from the group consisting of replication deficient adenoviral vectors, adeno-associated viral vectors, and lentivirus vectors.

28. A composition comprising the polynucleotide of any one of paragraphs 18-23 and a pharmaceutically acceptable carrier, diluent or excipient.

29. A composition comprising the vector of any one of paragraphs 24-27 and a pharmaceutically acceptable carrier, diluent or excipient.

30. A host cell transformed or transfected with the polynucleotide of any one of paragraphs 18-23.

31. A host cell transformed or transfected with the vector of any one of paragraphs 24-27.

32. A host cell according to paragraph 31 that expresses the polypeptide encoded by the polynucleotide.

33. A host cell according to any one of paragraphs 30-32 that comprises a mammalian endothelial cell or endothelial precursor cell.

34. A method of modulating the growth of mammalian endothelial cells or mammalian endothelial precursor cells, comprising contacting the cells with a composition comprising a member selected from the group consisting of:
  (a) the construct of any one of paragraphs 1-16 and 44-54;
  (b) a polynucleotide that encodes (a);
  (c) an expression vector containing (b) operatively linked to an expression control sequence; and
  (d) a cell transformed or transfected with (b) or (c) and that expresses the polypeptide of (a).

35. A method of paragraph 34, wherein the contacting comprises administering the composition to a mammalian subject in an amount effective to modulate endothelial cell growth in vivo.

36. A method of paragraph 35, wherein the mammalian subject is a human.

37. A method of modulating angiogenesis in a mammalian subject comprising administering to a mammalian subject in need of modulation of angiogenesis a composition comprising a member selected from the group consisting of:
  (a) the construct of any one of paragraphs 1-16 and 43-54;
  (b) a polynucleotide that encodes (a);
  (c) an expression vector containing (b) operatively linked to an expression control sequence; and
  (d) a cell transformed or transfected with (b) or (c) and that expresses the polypeptide of (a);
  wherein the composition is administered in an amount effective to modulate angiogenesis.

38. A method of modulating lymphangiogenesis in a mammalian subject comprising administering to a mammalian subject in need of modulation of lymphangiogenesis a composition comprising a member selected from the group consisting of:
  (a) the construct of any one of paragraphs 1-16 and 43-54;
  (b) a polynucleotide that encodes (a);
  (c) an expression vector containing (b) operatively linked to an expression control sequence; and
  (d) a cell transformed or transfected with (b) or (c) and that expresses the polypeptide of (a);
  wherein the composition is administered in an amount effective to modulate lymphangiogenesis.

39. A method of improving the healing of a skin graft or skin flap to underlying tissue of a mammalian subject, comprising:
  contacting skin graft or skin flap tissue or underlying tissue with a composition comprising a healing agent that is present in said composition in an amount effective to reduce edema or increase perfusion at the skin graft or skin flap, thereby improving the healing of the skin graft or skin flap;
  wherein the healing agent is selected from the group consisting of:
  (a) the construct of any one of paragraphs 1-16 and 43-54;
  (b) a polynucleotide that encodes (a);
  (c) an expression vector containing (b) operatively linked to an expression control sequence; and
  (d) a cell transformed or transfected with (b) or (c) and that expresses the polypeptide of (a).

40. An improvement in a medical device for improving circulation, wound healing, or blood flow, comprising coating or impregnating the device with a composition comprising an angiogenic agent selected from the group consisting of:
  (a) the construct of any one of paragraphs 1-16 and 43-54;
  (b) a polynucleotide that encodes (a);
  (c) an expression vector containing (b) operatively linked to an expression control sequence; and
  (d) a cell transformed or transfected with (b) or (c) and that expresses the polypeptide of (a).

41. A patch comprising a pad material having an upper surface and lower surface, an adhesive on the lower surface, and a therapeutic composition, wherein the composition comprises a healing agent selected from the group consisting of
  (a) the construct of any one of paragraphs 1-16 and 43-54;
  (b) a polynucleotide that encodes (a);
  (c) an expression vector containing (b) operatively linked to an expression control sequence; and
  (d) a cell transformed or transfected with (b) or (c) and that expresses the polypeptide of (a).

42. A surgical suturing thread coated or impregnated with a composition,
wherein the composition comprises a healing agent selected from the group consisting of:
  (a) the construct of any one of paragraphs 1-16 and 43-54;
  (b) a polynucleotide that encodes (a);
  (c) an expression vector containing (b) operatively linked to an expression control sequence; and
  (d) a cell transformed or transfected with (b) or (c) and that expresses the polypeptide of (a).

43. A construct comprising:
an RTK binding domain, a CUB domain, and at least one linkage that connects the RTK binding domain to the CUB domain;
wherein the RTK binding domain comprises an amino acid sequence that is at least 90% identical to an amino acid sequence selected from the group consisting of: mammalian VEGF-A RTK binding domain amino acid sequences; mammalian VEGF-B RTK binding domain amino acid sequences; mammalian VEGF-C RTK binding domain amino acid sequences; mammalian VEGF-D RTK binding domain amino acid sequences; mammalian VEGF-E RTK binding domain amino acid sequences; mammalian PlGF RTK binding domain amino acid sequences; mammalian PDGF-A RTK binding domain amino acid sequences; and mammalian PDGF-B RTK binding domain amino acid sequences;
wherein the CUB domain comprises an amino acid sequence at least 90% identical to an amino acid sequence selected from the group consisting of PDGF-C CUB domain amino acid sequences and PDGF-D CUB domain amino acid sequences; and
wherein the construct and the RTK binding domain bind to the extracellular domain of at least one receptor tyrosine kinase selected from the group consisting of: VEGFR-1, VEGFR-2, VEGFR-3, PDGFR-alpha, and PDGFR-beta.

44. The construct according to paragraph 43, wherein the CUB domain is connected to the N-terminus of the RTK binding domain.

45. The construct according to paragraph 43, wherein the CUB domain is connected to the C-terminus of the RTK binding domain.

46. The construct according to any one of paragraphs 43-45, wherein the CUB domain comprises an amino acid sequence set forth in SEQ ID NO: 53.

47. The construct according to any one of paragraphs 43-45, wherein the CUB domain comprises an amino acid sequence set forth in SEQ ID NO: 55.

48. The construct according to any one of paragraphs 1-11 and 43-47, wherein the RTK binding domain comprises an amino acid sequence that is at least 90% identical to amino acids 27 to 127 of the VEGF109 amino acid sequence of SEQ ID NO: 52:

49. The construct according to any one of paragraphs 43-48, further comprising a heparin binding domain connected to the construct by a linkage.

50. A construct according to any one of paragraphs 43-49, wherein the linkage comprises a peptide bond, whereby the RTK binding domain and the CUB domain comprise a chimeric polypeptide.

51. The construct according to paragraph 50, wherein the chimeric polypeptide further comprises a signal peptide.

52. The construct of paragraph 51, wherein the chimeric polypeptide further comprises a peptide tag.

53. The construct according to paragraph 48, wherein the construct comprises an amino acid sequence selected from the group consisting of SEQ ID NOS: 57, 59, and 61.

54. The construct according to paragraphs 43-53, wherein the CUB domain is connected to the growth factor via a recognition sequence specifically recognized by a proteolytic enzyme such that the proteolytic enzyme if present cleaves at the recognition sequence to remove the CUB domain and produce an activated growth factor.

55. A dimer comprising two construct polypeptides of paragraphs 5-15 and 49-54.

56. The dimer of paragraph 54, which is a homodimer.

57. The dimer of paragraph 54, which is a heterodimer.

58. A method for antagonizing in a cell at least one receptor selected from the group consisting of VEGFR-1, VEGFR-2, VEGFR-3, PDGFR-α and PDGFR-β, wherein the method comprises administering to the cell an agent selected from the group consisting of:
  (a) the construct of any one of paragraphs 43-54;
  (b) the dimer of any one of claims 55-57;
  (c) a polynucleotide that encodes (a);
  (d) an expression vector containing (b) operatively linked to an expression control sequence; and
  (e) a cell transformed or transfected with (b) or (c) and that expresses the polypeptide of (a).

59. A method for blocking PDGF-D binding to PDGFR-α, but not to PDGFR-β in a cell where both PDGFR-α and PDGFR-β are present, the method comprising administering to the cell an agent selected from the group consisting of:
  (a) the construct of any one of paragraphs 43-54;
  (b) the dimer of any one of claims 55-57;
  (c) a polynucleotide that encodes (a);
  (d) an expression vector containing (b) operatively linked to an expression control sequence; and
  (e) a cell transformed or transfected with (b) or (c) and that expresses the polypeptide of (a).

60. A method for modulating activities of a receptor of a cell which receptor specifically binds to and is activated by a growth factor selected from the group consisting PDGF-A, PDGF-B, the VEGF-homology domain of PDGF-C, VEGF, VEGF-B, VEGF-C and PlGF, the method comprising administering to the cell an agent selected from the group consisting of:
  (a) the construct of any one of claims 43-54;
  (b) the dimer of any one of claims 55-57;
  (c) a polynucleotide that encodes (a);
  (b) an expression vector containing (c) operatively linked to an expression control sequence; and
  (e) a cell transformed or transfected with (c) or (d) and that expresses the polypeptide of (a); and
  providing the cell with a proteolytic enzyme, whereby the growth factor is activated.

61. An isolated and fully-processed PDGF-D polypeptide comprising an amino acid sequence at least 95% identical to SEQ ID NO: 22.

62. The isolated polypeptide of paragraph 61, consisting of the amino acid sequence set forth SEQ ID NO: 22.

63. A pharmaceutical composition comprising the polypeptide of paragraph 61 and a pharmaceutically acceptable excipient.

64. An isolated polynucleotide that encodes the polypeptide of paragraph 61.

65. An expression vector comprising the polynucleotide of paragraph 64 operably linked to a promoter.

66. The expression vector of paragraph 65, wherein the promoter is a tissue- or cell type-specific promoter.

67. A cell comprising the expression vector of paragraph 65 or paragraph 66.

68. A method for stimulating phosphorylation of PDGFR-α of a cell, the method comprising administering to the cell the isolated PDGF-D polypeptide of paragraph 61, wherein the polypeptide binds to PDGFR-α.

69. The method of paragraph 68, wherein the PDGFR-α of the cell is activated.

70. The method of c paragraph 68, wherein the phosphorylation of both PDGFR-α and PDGFR-β of the cell are stimulated.

71. The method of paragraph 70, wherein both PDGFR-α and PDGFR-β of the cell are activated.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

The following drawings from part of the present specification and are included to further illustrate aspects of the present invention. The invention may be better understood by reference to the drawings in combination with the detailed description of the specific embodiments presented herein.

DETAILED DESCRIPTION OF THE PREFERRED EMBODIMENTS

Figure 1A:
FIG. 1A: Schematic depiction of a chimeric polypeptide wherein one flanking domain (F) is positioned amino-terminal to the receptor tyrosine kinase (RTK) binding domain.
Figure 1B:
FIG. 1B: Schematic depiction of a chimeric polypeptide wherein one flanking domain is positioned carboxy-terminal to the RTK binding domain.
Figure 1C:
FIG. 1C: Schematic depiction of a chimeric polypeptide wherein two flanking domains ($F_1$, $F_2$) are positioned with a central RTK binding domain.
Figure 1D:
FIG. 1D: Schematic depiction of a chimeric polypeptide wherein two flanking domains are both positioned amino-terminal to the RTK binding domain.
Figure 1E:
FIG. 1E: Schematic depiction of a chimeric polypeptide wherein two flanking domains are both positioned carboxy-terminal to the RTK binding domain.
Figure 1F:
FIG. 1F: Schematic depiction of a chimeric polypeptide wherein two RTK binding domains are positioned with a central flanking domain.
Figure 1G:
FIG. 1G: Schematic depiction of a chimeric polypeptide wherein three flanking domains are alternating with two RTK binding domains.

The invention includes new materials (e.g., biomolecules, compositions, medical devices) and methods and medical uses for modulating angiogenic processes as well as modulating the growth and maturation of progenitor cells.

A. Chimeric Molecules of the Present Invention

One aspect of the invention are constructs (e.g., molecules or compounds) comprised of a receptor tyrosine kinase receptor (RTK) binding domain attached to at least one flanking (F) domain that confer novel biological properties to the constructs, compared to the properties of the RTK domain alone. The attachment is generically referred to as a linkage (L) and can be as simple as a peptide bond or oligopeptide that link the domains to form a single, chimeric polypeptide chain, or can be more complex structures described herein. Because the constructs comprise at least one RTK and one flanking sequence that do not originate from the same gene but have been recombined, the constructs are referred to herein as "chimeric" constructs or "chimeric" polypeptides. Chimeric polypeptide constructs of the invention can have a variety of structures, as depicted by the following schematic formulae:

F-L-RTK (one flanking domain positioned amino terminal to the RTK binding domain)

RTK-L-F (one flanking domain positioned carboxy-terminal to the RTK binding domain)

$F_1$-$L_1$-RTK-$L_2$-$F_2$ (two flanking domains with a central RTK binding domain)

$F_1$-$L_1$-$F_2$-$L_2$-RTK or RTK-$L_1$-$F_1$-$L_2$-$F_2$ (two flanking domains, both amino-terminal or both carboxy-terminal to the RTK binding domain).

$RTK_1$-$L_1$-$F_1$-$L_2$-$RTK_2$ (two RTK binding domains with a central flanking domain)

$F_1$-$L_1$-$RTK_1$-$L_2$-$F_2$-$L_3$-$RTK_2$-$L_4$-$F_3$ (two RTK binding domains, three flanking domains, alternating)

Other structures that vary from the foregoing examples will be readily apparent.

1. Receptor Tyrosine Kinase (RTK) binding domain.

All naturally occurring VEGF and PDGF polypeptides can be used to manufacture constructs of the invention, and numerous such sequences are known through Genbank, scientific literature, and patent literature, for example. Preferred VEGF/PDGF family members include those of avian and mammalian species and of viral species that infect avian and mammalian species. Exemplary mammalian species are primates, rodents, bovine, equine, canine, porcine and feline species. Exemplary sequences include (1) all such VEGF and PDGF family member sequences listed in GENBANK's publicly accessible database as of the priority date of this application; (2) all VEGF and PDGF sequences that hybridize to specific human sequences identified herein under moderate or high stringency conditions; and (3) all VEGF and PDGF sequences that can be amplified from a genomic or CDNA library using PCR and related techniques and using primers designed from highly conserved regions of the sequences provided herein. Highly preferred embodiments are manufactured using human VEGF/PDGF sequences and viral sequences, such as those described in the following paragraphs.

VEGF-A (or VEGF) was originally purified from several sources on the basis of its mitogenic activity toward endothelial cells, and also by its ability to induce microvascular permeability, hence it is also called vascular permeability factor (VPF). VEGF-A has subsequently been shown to induce a number of biological processes including the mobilization of intracellular calcium, the induction of plasminogen activator and plasminogen activator inhibitor-1 synthesis, promotion of monocyte migration in vitro, induction of anti-apoptotic protein expression in human endothelial cells, induction of fenestrations in endothelial cells, promotion of cell adhesion molecule expression in endothelial cells and induction of nitric oxide mediated vasodilation and hypotension [Ferrara, J. Mol. Med. 77: 527-543 (1999); Neufeld, et al., FASEB. J. 13:9-22 (1999); Zachary, Intl. J. Biochem. Cell. Bio. 30:1169-74 (1998)].

VEGF-A (SEQ ID NOs: 1 and 2) is a secreted, disulfide-linked homodimeric glycoprotein composed of 23 kD subunits. Five human VEGF-A isoforms of 121 (SEQ ID NO: 4), 145 (SEQ ID NO: 5), 165 (SEQ ID NO: 6), 189 (SEQ ID NO: 7) or 206 (SEQ ID NO: 3) amino acids in length ($VEGF_{121-206}$), encoded by distinct mRNA splice variants, have been described, all of which are capable of stimulating mitogenesis in endothelial cells. However, each isoform differs in biological activity, receptor specificity, and affinity for cell surface- and extracellular matrix-associated heparan-sulfate proteoglycans, which behave as low affinity receptors for VEGF-A. $VEGF_{121}$ does not bind to either heparin or heparan-sulfate; $VEGF_{145}$ and $VEGF_{165}$ (GenBank Acc. No. M32977) are both capable of binding to heparin; and $VEGF_{189}$ and $VEGF_{206}$ show the strongest affinity for heparin and heparan-sulfates. $VEGF_{121}$, $VEGF_{145}$, and $VEGF_{165}$ are secreted in a soluble form, although most of $VEGF_{165}$ is confined to cell surface and extracellular matrix proteoglycans, whereas $VEGF_{189}$ and $VEGF_{206}$ remain associated with extracellular matrix. Both $VEGF_{189}$ and $VEGF_{206}$ can be released by treatment with heparin or heparinase, indicating that these isoforms are bound to extracellular matrix via proteoglycans. Cell-bound $VEGF_{189}$ can also be cleaved by proteases such as plasmin, resulting in release of an active soluble $VEGF_{110}$. Most tissues that express VEGF are observed to express several VEGF isoforms simultaneously, although $VEGF_{121}$ and $VEGF_{165}$ are the predominant forms, whereas $VEGF_{206}$ is rarely detected (Ferrara, J Mol Med 77:527-543, 1999). $VEGF_{145}$ differs in that it is primarily expressed in cells derived from reproductive organs (Neufeld et al., FASEB J 13:9-22, 1999).

As noted above, the human VEGF-A gene is expressed as numerous isoforms, including $VEGF_{145}$, $VEGF_{165}$, $VEGF_{189}$, and $VEGF_{206}$. A human $VEGF_{206}$ sequence obtained from the Swiss Prot database (accession no. P15692) is set forth below and in SEQ ID NO: 3:

```
  1 mnfllswvhw slalllylhh akwsqaapma egggqnhhev vkfmdvyqrs ychpietlvd
 61 ifqeypdeie yifkpscvpl mrcggccnde glecvptees nitmqimrik phqgqhigem
121 sflqhnkcec rpkkdrarqe kksvrgkgkg qkrkrkksry kswsvyvgar cclmpwslpg
181 phpcgpcser rkhlfvqdpq tckcsckntd srckarqlel nertcrcdkp rr
```

Amino acids 1-26 of this sequence represent the signal peptide and mature $VEGF_{206}$ comprises amino acids 27-232. Referring to the same sequence, the signal peptide and amino acids 142-226 are absent in mature isoform $VEGF_{121}$ (SEQ ID NO: 4). The signal peptide and amino acids 166-226 are absent in mature isoform $VEGF_{145}$ (SEQ ID NO: 5). The signal peptide and amino acids 142-182 are absent in mature isoform $VEGF_{165}$ (SEQ ID NOs: 6). The signal peptide and amino acids 166-182 are absent in mature isofrom $VEGF_{189}$ (SEQ ID NO.: 7).

$VEGF_{109}$, which comprises only the VEGF homology domain (i.e., the minimal receptor binding domain), has been tested for angiogenic activity in a chick CAM assay but results indicated that it was less angiogenic than $VEGF_{165}$ (Jeltsch et al., J. Biol. Chem., 281, 12187-95, 2006).

VEGF-A is a ligand for VEGFR-1/Flt-1 (fms-like tyrosine kinase-1) and VEGFR-2/Kdr/Flk-1 (kinase insert domain containing receptor/fetal liver kinase-1). The expression of VEGF receptors occurs mainly in vascular endothelial cells, although some may be present on monocytes and melanoma cells. Only endothelial cells have been reported to proliferate in response to VEGF, and endothelial cells from different sources show different responses. Thus, the signals mediated through VEGFR-1 and VEGFR-2 appear to be cell type specific.

PlGF (SEQ ID NOs: 8 and 9), a second member of the VEGF subfamily, is generally a poor stimulator of angiogenesis and endothelial cell proliferation in comparison to VEGF-A, and the in vivo role of PlGF is not well understood. Its isolation and characteristics are described in detail in Maglione et al., Proc. Natl. Acad. Sci. USA, 88: -9267-9271, 1991. PlGF-2 (SEQ ID NO: 42) and PlGF-3 (SEQ ID NO: 43) are produced by alternative mRNA splicing (Hauser et al., Growth Factors 9:259-268, 1993; Maglione et al., Oncogene 8:925-931, 1993). PlGF forms both disulfide-linked homodimers and heterodimers with VEGF-A. The PlGF-VEGF-A heterodimers are more effective at inducing endothelial cell proliferation and angiogenesis than PlGF homodimers. PlGF is primarily expressed in the placenta, and is also co-expressed with VEGF-A during early embryogenesis in the trophoblastic giant cells of the parietal yolk sac (Stacker and Achen, Growth Factors 17:1-11, 1999).

VEGF-B (SEQ ID NOs: 10 and 11), described in detail in International Patent Publication No. WO 96/26736 and U.S. Pat. Nos. 5,840,693 and 5,607,918, incorporated herein by reference, shares approximately 44% amino acid identity with VEGF-A. Although the biological functions of VEGF-B in vivo remain incompletely understood, it has been shown to have angiogenic properties, and may also be involved in cell adhesion and migration, and in regulating the degradation of the extracellular matrix. VEGF-B is expressed as two isoforms of 167 and 186 amino acid residues generated by alternative splicing. $VEGF-B_{167}$ (SEQ ID NO: 44) is associated with the cell surface or extracellular matrix via a heparin-binding domain, whereas VEGF-B$_{186}$ (SEQ ID NO: 45) is secreted. Both VEGF-B$_{167}$ and VEGF-B$_{186}$ can form disulfide-linked homodimers or heterodimers with VEGF-A. The association to the cell surface of VEGF$_{165}$-VEGF-B$_{167}$ heterodimers appears to be determined by the VEGF-B component, suggesting that heterodimerization may be important for sequestering VEGF-A. VEGF-B is expressed primarily in embryonic and adult cardiac and skeletal muscle tissues (Joukov et al., *J Cell Physiol* 173:211-215, 1997; Stacker and Achen, (supra). Mice lacking VEGF-B survive but have smaller hearts, dysfunctional coronary vasculature, and exhibit impaired recovery from cardiac ischemia (Bellomo et al., *Circ Res.*, E29-E35, 2000).

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-C (SEQ ID NOS: 12 and 13) was isolated from conditioned media of PC-3 prostate adenocarcinoma cell line (CRL1435) by selecting for a component of the medium that caused tyrosine phosphorylation of the endothelial cell-specific receptor tyrosine kinase Flt4 (VEGFR-3), using cells transfected to express Flt4. VEGF-C isolation and characteristics are described in detail in Joukov et al, *EMBO J.* 15 290-298, 1996 and U.S. Pat. Nos. 6,221,839; 6,235,713; 6,361,946; 6,403,088; and 6,645,933 and International Patent Publ. Nos. WO 97/05250, WO 98/07832, and WO 98/01973, incorporated herein by reference. In mouse embryos, VEGF-C mRNA is expressed primarily in the allantois, jugular area, and the metanephros. (Joukov et al., *J Cell Physiol* 173:211-215, 1997), and appears to be involved in the regulation of lymphatic angiogenesis (Jeltsch et al., *Science,* 276: 1423-1425, 1997). As described below in greater detail, the RTK binding domain of mature VEGF-C corresponds to residues 103-227 of SEQ ID NO: 14.

VEGF-D (SEQ ID NOs: 14 and 15) is initially expressed as a prepro-peptide that undergoes removal of a signal peptide (residues 1-21 of SEQ ID NO: 15) N-terminal (residues 22-92 of SEQ ID NO: 15) and C-terminal (residues 202-354 of SEQ ID NO: 15) proteolytic processing, and forms non-covalently linked dimers. VEGF-D stimulates mitogenic responses in endothelial cells in vitro. During embryogenesis, VEGF-D is expressed in a complex temporal and spatial pattern, and its expression persists in the heart, lung, and skeletal muscles in adults. Isolation of a biologically active fragment of VEGF-D designated VEGF-DΔNΔC, is described in International Patent Publication No. WO 98/07832 (PCT/US97/14696), incorporated herein by reference. VEGF-DΔNΔC consists of amino acid residues 93 to 201 of VEGF-D (SEQ ID NO: 15) and binds VEGFR-2 and VEGFR-3. Partially processed forms of VEGF-D bind to VEGFR-3.

Preferred fragments of VEGF-C or -D for use in making the chimeric molecules of the invention are continuous fragments that bind one or more of the VEGF receptors. However, it has been demonstrated that VEGFR binding can be achieved with molecules that incorporate discrete, discontinuous fragments of VEGF-C, fused, e.g., to fragments of VEGF-A or other amino acid sequences. Such chimeric VEGFR ligands are described in U.S. patent application Ser. No. 09/795,006, filed Feb. 26, 2001, and International Patent Publication No. WO 01/62942, each of which is incorporated herein by reference in its entirety.

PDGF-A (SEQ ID NOs: 16 and 17) and PDGF-B (SEQ ID NOs: 19 and 20) can homodimerize or heterodimerize to produce three different isoforms: PDGF-AA, PDGF-AB, or PDGF-BB. PDGF-A is only able to bind the PDGF α-receptor (PDGFR-α including PDGFR-α/α homodimers). PDGF-B can bind both the PDGFR-α and a second PDGF receptor (PDGFR-β). More specifically, PDGF-B can bind to PDGFR-α/α and PDGFR-β/β homodimers, as well as PDGFR-α/β heterodimers.

PDGF-AA and -BB are the major mitogens and chemoattractants for cells of mesenchymal origin, but have no, or little effect on cells of endothelial lineage, although both PDGFR-α and -β are expressed on endothelial cells (EC). PDGF-BB and PDGF-AB have been shown to be involved in the stabilization/maturation of newly formed vessels (Isner et al., *Nature* 415:234-9, 2002; Vale et al., *J Interv Cardiol* 14:511-28, 2001); Heldin et al., *Physiol Rev* 79:1283-1316, 1999; Betsholtz et al., *Bioassays* 23:494-507, 2001). Other data however, showed that PDGF-BB and PDGF-AA inhibited bFGF-induced angiogenesis in vivo via PDGFR-α signaling. PDGF-AA is among the most potent stimuli of mesenchymal cell migration, but it either does not stimulate or it minimally stimulates EC migration. In certain conditions, PDGF-AA even inhibits EC migration (Thommen et al., *J. Cell Biochem.* 64:403-13, 1997; De Marchis et al., *Blood* 99:2045-53, 2002; Cao et al., *FASEB. J.* 16:1575-83, 2002). Moreover, PDGFR-α has been shown to antagonize the PDGFR-β-induced SMC migration Yu et al. (*Biochem. Biophys. Res. Commun.* 282:697-700, 2001) and neutralizing antibodies against PDGF-AA enhance smooth muscle cell (SMC) migration (Palumbo, R., et al., *Arterioscler. Thromb. Vasc. Biol.* 22:405-11, 2002). Thus, the angiogenic/arteriogenic activity of PDGF-A and -B, especially when signaling through PDGFR-α, has been controversial and enigmatic.

PDGF-AA and -BB have been reported to play important roles in the proliferation and differentiation of both cardiovascular and neural stem/progenitor cells. PDGF-BB induced differentiation of Flkl+ embryonic stem cells into vascular mural cells (Carmeliet, P., *Nature* 408:43-45, 2000; Yamashita et al., *Nature* 408:92-6, 2000), and potently increased neurosphere derived neuron survival (Caldwell et al., *Nat. Biotechnol.* 19:475-479, 2001); while PDGF-AA stimulated oligodendrocyte precursor proliferation through $α_vβ_3$ integrins (Baron, et al., *Embo. J.* 21:1957-66, 2002).

The nucleotide and amino acid sequences for PDGF-C are set out in SEQ ID NOs: 20 and 21, respectively, and the nucleotide and amino acid for PDGF-D are set out in SEQ ID NOs: 22 and 23, respectively. PDGF-C binds PDGFR-α/α homodimers and PDGF-D binds PDGFR-β/β homodimers and both have been reported to bind PDGFR-α/β heterodimers. PDGF-C polypeptides and polynucleotides were characterized by Eriksson et al. in International Patent Publication No. WO 00/18212, U.S. Patent Application Publication No. 2002/0164687 A1, and U.S. patent application. Ser. No. 10/303,997 [published as U.S. Pat. Publ. No. 2003/0211994]. PDGF-D polynucleotides and polypeptides were characterized by Eriksson, et al. in International Patent Publication No. WO 00/27879 and U.S. Patent Application Publication No. 2002/0164710 A1. These documents are all incorporated by reference in their entirety. As described therein, PDGF-C and -D bind to PDGF receptors alpha and beta, respectively. However, a noteworthy distinction between these polypeptides and PDGF-A and -B is that PDGF-C and -D each possess an amino-terminal CUB domain that can be proteolytically cleaved to yield a biologically active (receptor binding) carboxy-terminal domain with sequence homology to other PDGF family members.

PDGF-C (SEQ ID NO: 21) requires proteolytic removal of the N-terminal CUB domain for receptor binding and activation of the receptor.

A preferred form of PDGF-C comprises the PDGF/VEGF homology domain (PVHD) of PDGF-C and retains receptor binding and activation functions. The minimal domain is approximately residues 230-345 of SEQ ID NO: 21. However, the domain can extend towards the N terminus up to residue 164. The PVHD of PDGF-C is also referred to as truncated PDGF-C. The truncated PDGF-C is an activated form of PDGF-C. A putative proteolytic site in PDGF-C is found in residues 231-234 of SEQ ID NO: 21, a dibasic motif. The putative proteolytic site is also found in PDGF-A, PDGF-B, VEGF-C and VEGF-D. In these four proteins, the putative proteolytic site is also found just before the minimal domain for the PDGF/VEGF homology domain. The CUB domain of PDGF-C represents approximately amino acid residues 23-159 of SEQ ID NO: 21. (U.S. Patent Application Publication No.: 2002/0164687).

Similar to PDGF-C, PDGF-D has a two domain structure with a N-terminal CUB domain (described as approximately residues 67-167 or 54-171 of SEQ ID NO: 23) and a C-terminal PDGF/VEGF homology domain (PVHD). A putative proteolytic site in PDGF-D is found in residues 255-258 of SEQ ID NO: 23. A preferred PDGF-D polypeptide comprises the PDGF/VEGF homology domain (PVHD) of PDGF-D and retains receptor binding and activation functions. The minimal domain of PDGF-D is approximately residues 272-362 or 255-370 of SEQ ID NO: 23. However, PDGF-D's PVHD extends toward the N terminus up to residue 235 of SEQ ID NO: 23. The truncated PDGF-D is the putative activated form of PDGF-D. (U.S. Patent Application Publication No. 2002/0164710.)

PDGF-C and PDGF-D also possess a three amino acid insert (NCA) between conserved cysteines 3 and 4 in the VEGF homology domain. The VHD of PDGF-C and PDGF-D most closely resemble that of VEGF-C and VEGF-D. PDGF-C requires proteolytic removal of the N-terminal CUB domain for receptor binding and activation of the receptor. This indicates that the CUB domains are likely to sterically block the receptor binding epitopes of the unprocessed dimer. The in vitro and in vivo proteolytically processed proteins are devoid of N-terminal portions corresponding to more than 14-16 kDa as determined from SDS-PAGE analysis which is consistent with a loss of the 110 amino acid long CUB domain and a part of the hinge region between the CUB and core domains that vary in length.

The "invariant" fifth cysteine found in the other members of the PDGF/VEGF family is not conserved in PDGF-D. This feature is unique to PDGF-D. The VHD of PDGF-D most closely resembles that of VEGF-C and VEGF-D. PDGF-D mRNA expression was highest in heart, ovary and pancreas, and expressed at lower levels in testis, kidney, liver, placenta, prostate and small intestine.

During development, PDGF-C is expressed in muscle progenitor cells and differentiated smooth muscle cells in most organs, including the heart, lung and kidney (Aase et al., *Mech. Dev.* 110:187-91, 2002). In adulthood, PDGF-C is widely expressed in most organs, with the highest expression level in the heart and kidney (Li et al., *Nat. Cell. Biol.* 2:302-09, 2000). PDGF-CC is secreted as an inactive homodimer of approximately 95 kD. Upon proteolytic removal of the CUB domain, PDGF-CC is capable of binding and activating its receptor, PDGFR-α (Li et al., *Cytokine & Growth Factor Reviews* 244:1-8, 2003). In cells co-expressing both PDGFR-α and -β, PDGF-CC may also activate the PDGFR-α/β heterodimer, but not the PDGFR-β/β homodimer (Cao et al., *FASEB. J.* 16:1575-83, 2002; Gilbertson et al., *J. Biol. Chem.* 276:27406-14, 2001).

Active PDGF-CC is a potent mitogen for fibroblast and vascular smooth muscle cells (Li et al., *Nat. Cell. Biol.* 2:302-09, 2000; Cao, et al., *FASEB. J.* 16:1575-83, 2002; Uutela et al., *Circulation* 103:2242-7, 2001). Both PDGF-AA and PDGF-CC bind PDGFR-α, but only PDGF-CC potently stimulates angiogenesis in mouse cornea pocket and chick chorioallanoic membrane (CAM) assays (Cao, et al., *FASEB. J.* 16:1575-83, 2002). PDGF-CC also promotes wound healing by stimulating tissue vascularization (Gilbertson et al., supra). However, these studies did not address whether PDGF-CC stimulated vessel growth by affecting endothelial or smooth muscle cells, nor did they examine whether PDGF-CC promoted the maturation of newly formed vessels (including vasculogenesis, angiogenesis, neoangiogenesis and arteriogenesis).

Four additional members of the VEGF subfamily collectively referred to as VEGF-E factors have been identified in poxviruses, which infect humans, sheep and goats. The orf virus-encoded VEGF-E (SEQ ID NOs: 24 and 25) and NZ2 VEGF are potent mitogens and permeability enhancing factors. Both show approximately 25% amino acid identity to mammalian VEGF-A, and are expressed as disulfide-linked homodimers. Another variant of orf virus VEGF-E like protein from strain NZ10 is described in WO 00/25805, incorporated here by reference. Infection by these viruses is characterized by pustular dermititis which may involve endothelial cell proliferation and vascular permeability induced by these viral VEGF proteins (Ferrara, *J Mol Med* 77:527-543, 1999; Stacker and Achen, *Growth Factors* 17:1-11, 1999). VEGF-like proteins have also been identified from two additional strains of the orf virus, D1701 (GenBank Acc. No. AF106020; described in Meyer et al., EMBO J. 18:363-374, 1999) and NZ10 [described in International Patent Application WO 00/25805 (incorporated herein by reference). These viral VEGF-like proteins have been shown to bind VEGFR-2 present on host endothelium, and this binding is important for development of infection and viral induction of angiogenesis (Meyer et al., *EMBO J* 18:363-374, 1999; International Patent Application WO 00/25805).

| Name | SEQ ID NO | Fully Processed Natural (RTK) Ligand | Heparin Binding Domain |
| --- | --- | --- | --- |
| VEGF-A | 2 | see isoforms | |
| VEGF109 | 52 | 27-127 | |
| VEGF206 | 3 | 27-232 | 142-226 |
| VEGF121 | 4 | 27-147 | N/A |
| VEGF145 | 5 | 27-171 | 142-165 |
| VEGF165 | 6 | 27-191 | 183-226 |
| VEGF189 | 7 | 27-215 | 142-215 |
| PlGF-1 | 9 | 19-149 | N/A |
| PlGF-2 | 42 | 19-170 | 142 to 162 |
| PlGF-3 | 43 | 19-221 | 193-213 |
| VEGF-B | 11 | see isoforms | |
| VEGF-B167 | 44 | 22-188 | 138 to 182 |
| VEGF-B186 | 45 | 22-207 | N/A |
| VEGF-C | 13 | 103-227 | N/A |
| VEGF-D | 15 | 93-201 | N/A |
| PDGF-A | 17 | 87-211 | N/A |
| PDGF-B | 19 | 82-190 | N/A |
| PDGF-C | 21 | 230-345 | N/A |
| PDGF-D | 23 | 272-362 or 255-370 | N/A |
| VEGF-E | 25 | | N/A |

Smaller fragments of most or all of the VEGF and PDGF family also may bind to their respective receptors and the identity of such smaller fragments is determined by RTK binding assays such as those described herein or in the literature.

2. Flanking Domain

A flanking domain used to make the constructs of the invention comprises a peptide or polypeptide sequence similar to or identical to a propeptide from a VEGF or PDGF family member. In native preproproteins the propeptides flank the VEGF homology domain (RTK binding domain), i.e., they are positioned adjacent to the VEGF homology domain (VHD). In a preferred embodiment described in the following paragraphs, the flanking domain comprises N-terminal ($F_N$) and C-terminal ($F_C$) propeptides of VEGF-C or VEGF-D (where "terminal" refers to the location of the propeptide relative to the VHD).

VEGF-C, comprises a VHD that is approximately 30% identical at the amino acid level to VEGF-A. Secreted VEGF-C protein consists of a non-covalently-linked homodimer, in which each monomer contains the VHD. The intermediate forms of VEGF-C produced by partial proteolytic processing show increasing affinity for the VEGFR-3 receptor, and the mature protein is also able to bind to the VEGFR-2 receptor. [See WO 97/05250; WO 98/33917; WO 00/24412, U.S. Pat. Nos. 6,221,839, 6,361,946, 6,645,933, 6,730,658 and 6,245,530; and Joukov, et al., EMBO J., 16(13):3898-3911 (1997), all of which are incorporated herein by reference.]. It has also been demonstrated that a mutant VEGF-C, in which a single cysteine at position 156 is either substituted by another amino acid or deleted, loses the ability to bind VEGFR-2 but remains capable of binding and activating VEGFR-3 [See International Patent Publication No. WO 98/33917 and U.S. Pat. Nos. 6,130,071, and 6,361, 946, each of which are incorporated herein by reference].

VEGF-C (SEQ ID NOs: 12 and 13) is originally expressed as a larger precursor protein, prepro-VEGF-C, having extensive amino- and carboxy-terminal peptide sequences flanking a VEGF homology domain (VHD), with the C-terminal peptide containing tandemly repeated cysteine residues in a motif typical of Balbiani ring 3 protein. The prepro-VEGF-C polypeptide is processed in multiple stages to produce a mature and most active VEGF-C polypeptide (ANAC VEGF-C) of about 21-23 kD (as assessed by SDS-PAGE under reducing conditions). Such processing includes cleavage of a signal peptide (SEQ ID NO: 13, residues 1-31); cleavage of a carboxyl-terminal peptide (SEQ ID NO: 47, which corresponds approximately to residues 228-419 of SEQ ID NO: 13) to produce a partially-processed form of about 29 kD; and cleavage (apparently extracellularly) of an amino-terminal peptide (SEQ ID NO: 46, which corresponds approximately to residues 32-102 of SEQ ID NO: 13) to produced a fully-processed mature form of about 21-23 kD. Experimental evidence demonstrates that partially-processed forms of VEGF-C (e.g., the 29 kD form) are able to bind the Flt4 (VEGFR-3) receptor, whereas high affinity binding to VEGFR-2 occurs only with the fully processed forms of VEGF-C. Moreover, it has been demonstrated that amino acids 103-227 of SEQ ID NO: 13 are not all critical for maintaining VEGF-C functions. A polypeptide consisting of amino acids 112-215 (and lacking residues. 103-111 and 216-227) of SEQ ID NO: 13 retains the ability to bind and stimulate VEGF-C receptors, and it is expected that a polypeptide spanning from about residue 131 to about residue 211 of SEQ ID NO: 13 will retain VEGF-C biological activity. The cysteine residue at position 156 has been shown to be important for VEGFR-2 binding ability. It appears that VEGF-C polypeptides naturally associate as non-disulfide linked dimers. The interaction of VEGF-C propeptides with neuropilin-1 (NP-1) and neuropilin-2 (NP-2) was recently studied and the N-terminal domain of the VEGF-C propeptides was found to be an important mediator in binding to NP-1 and NP-2 (Karpenen et al., FASEB J., 20:1462-1472, 2006).

VEGF-D is structurally and functionally most closely related to VEGF-C. [See International Patent Publ. No. WO 98/07832, incorporated herein by reference]. Like VEGF-C, VEGF-D (SEQ ID NOs: 14 and 15) is initially expressed as a prepro-peptide that undergoes removal of a signal peptide (residues 1-21 of SEQ ID NO: 10), amino-terminal propeptide (SEQ ID NO: 48, which corresponds to residues 22-92 of SEQ ID NO: 15) and Carboxy-terminal propeptide (SEQ ID NO: 49, which corresponds to residues 202-354 of SEQ ID NO: 15) proteolytic processing, and forms non-covalently linked dimers. VEGF-D stimulates mitogenic responses in endothelial cells in vitro. During embryogenesis, VEGF-D is expressed in a complex temporal and spatial pattern, and its expression persists in the heart, lung, and skeletal muscles in adults. Isolation of a biologically active fragment of VEGF-D designated VEGF-DΔNΔC, is described in International Patent Publication No. WO 98/07832, incorporated herein by reference. VEGF-DΔNΔC consists of amino acid residues 93 to 201 of VEGF-D (SEQ ID NO: 15) and binds VEGFR-2 and VEGFR-3. Partly processed forms of VEGF-D bind to VEGFR-3.

In addition, VEGF-D is described in greater detail in International Patent Publication No. WO 98/07832 and U.S. Pat. No. 6,235,713, each of which is incorporated herein by reference and describes VEGF-D polypeptides and variants thereof that are useful in producing the chimeras of the present invention. VEGF-D related molecules also are described in International Patent Publication Nos. WO 98/02543 and WO 97/12972, and U.S. Pat. No. 6,689,580, and U.S. patent application Ser. Nos. 09/219,345 and 09/847, 524, all of which are incorporated by reference.

The LAP (Latency-Associated Protein) domain of TGF-β1 also may serve as a flanking sequence (SEQ ID NO: 50). LAP has been shown to provide a disulphide-linked shell hindering interaction of the TGF-β1 cytokine with its cellular receptors, conferring a very long half-life of 55 hours iv vivo (Adams et al., Nature Biotechnol., 21, 1314-1320, 2003). Without being bound to any mechanisms of action, it is contemplated that the presence of a LAP domain in constructs of the invention increases the serum half-life of constructs in vivo, and/or assists in localizing the constructs to the extracellular matrix to increase the efficiency of binding of the constructs to their respective cell surface receptors, thereby increasing the bioavailability and potency as a therapeutic.

These and other molecules that may serve as flanking sequences are described in further detail herein.

3. Heparin Binding Domain

The chimeric molecules of the invention may additionally include a heparin binding domain. Without being bound to any mechanisms of action, it is contemplated that the presence of a heparin binding domain on the growth factors facilitates the binding of the growth factors to heparin and allows the concentration of the growth factors in the extracellular matrix to increase the efficiency of binding of the growth factors to their respective cell surface receptors, thereby increasing the bioavailability of the growth factors at a given site.

Mulloy et al., (*Curr Opin Struct Biol.* 11(5):623-8, 2001) describes properties from many heparin binding domain structures and identifies many heparin binding domain examples, and is incorporated herein by reference. Any such heparin binding domains may be used in the chimeric molecules of the present invention. In a further embodiment, the chimeric-molecules of the present invention may comprise the heparin binding domain of PlGF-2 (see Hauser and Weich, *Growth Factors*, 9 259-68, 1993). Heparin binding domains from other growth factors also may be used in the present chimeric polypeptides, such as for example the heparin binding domain from EGF-like growth factor (Shin et al., *J Pept Sci.* 9(4):244-50, 2003); the heparin binding domain from insulin-like growth factor-binding protein (Shand et al., *J Biol Chem.* 278(20):17859-66, 2003), and the like. Other heparin binding domains that may be used herein include, but are not limited to, the pleiotrophin and amphoterin heparin binding domains (*Matrix Biol.* 19(5):377-87, 2000); CAP37 (Heinzelmann et al., *Int J Surg Investig.* 2(6):457-66, 2001); and the heparin-binding fragment of fibronectin (Yasuda et al., *Arthritis Rheum.* 48(5):1271-80, 2003).

The inclusion of a heparin binding domain in a chimeric VEGF molecule has been previously described in commonly owned U.S. Patent Publication No. 2005/0032697 and PCT Publication No. WO 2005/016963, both of which are incorporated herein by reference. Preferred heparin binding domains are found in native VEGF/PDGF molecules. VEGF-C and VEGF-D, like $VEGF_{121}$, lack a heparin binding domain. However, it is known that $VEGF_{145}$, $VEGF_{165}$, $VEGF_{189}$ and $VEGF_{206}$, comprise heparin-binding domains (Keck et al., Arch. Bioch. Biophys., 344:103-113, 1997; Fairbrother et al., Structure 6:637-648, 1998). Exons 6 (21 amino acids) and 7 (44 amino acids) contain two independent heparin binding domains (Poltorak et al., Herz, 25:126-9, 2000). In a preferred embodiment, the heparin binding domain is encoded by exon 6, and/or exon 7 of VEGF. The heparin binding domain may further comprise the amino acids encoded by exon 8 of VEGF. The sequences of the various exons of VEGF are widely known and may be found at e.g., Genbank Accession numbers M63976-M63978, where M63976 is exon 6, M63977 is exon 7; and M63978 is exon 8.

In other embodiments, the heparin binding domain may be of other, VEGF growth factors, for example the heparin binding, domain of VEGF-B may be used. Makinen et al., (*J. Biol. Chem.*, 274:21217-22, 1999), have described various isoforms of VEGF-B and have shown that the exon 6B encoded sequence of $VEGF-B_{167}$ resembles the heparin and NRP1-binding domain encoded by exon 7 of $VEGF_{165}$. Thus exon-6B of $VEGF-B_{167}$ (or a heparin binding fragment thereof) may be used as the heparin binding domain of the chimeric molecules of the present invention. The publication of Makinen et al., *J. Biol. Chem.*, 274: 21217-22, 1999 provides a detailed description of the construction of the VEGF-B exon 6B-encoded sequence. Nucleotide and deduced amino acid sequences for VEGF-B are deposited in GenBank under Acc. No. U48801, incorporated herein by reference. Also incorporated herein by reference is Olofsson et al., *J. Biol. Chem.* 271 (32), 19310-19317 (1996), which describes the genomic organization of the mouse and human genes for VEGF-B, and its related Genbank entry at AF468110, which provides an exemplary genomic sequence of VEGF-B.

The heparin binding domain of VEGF/PDGF members can be attached to the polypeptide of the invention at either end of the RTK binding domain or to the flanking domain.

4. CUB Domain

The chimeric molecules of the invention may additionally include a CUB domain. Without being bound to any mechanisms of action, it is contemplated that the presence of a CUB domain on the growth factors provides an attachment site for proteolytic enzymes that process the factors in suitable biological conditions where they need to be activated.

The CUB domain of PDGF-C and/or PDGF-D can be attached to the chimeric polypeptide of the invention at either end of the RTK binding domain or to the flanking domain.

In still another embodiment, the chimeric molecules of the invention may comprise the CUB domain attached to the RTK binding domain of a member of the VEGF-PDGF family (either directly or through a linker), where the resulting construct does not necessarily additionally include a flanking domain as defined above. For example, the CUB domain of PDGF-C and/or PDGF-D can be attached to VEGF-A to result in a chimeric protein designated CUB-VEGF, and is also contemplated as an aspect of the invention. It is contemplated that the property of proteolytic activation of the latent forms of PDGF-C and PDGF-D containing CUB domains could be transferred to other factors of the VEGF/PDGF family by making chimeric proteins containing the CUB domain fused to the growth factor domains of another one of the VEGF/PDGF family ligands, wherein the CUB domain contains or is attached by a linkage that is proteolytically cleavable. CUB-VEGF (or CUB attached to any RTK binding domain of the VEGF/PDGF family) is contemplated for use in restricting the biological activity of these factors until they are activated in a desired manner in vivo. In some embodiments, the addition of the CUB domain to the RTK binding domain would introduce a protease cleavage site for potential activation of these factors. Additionally, the protease-sensitive site can been replaced by a cleavage site for a proteolytic enzyme not available in the biological system but which could be provided in trans as protein or gene expression vector for the activation of the latent ligand chimeras. In another variation, the linkage and construct is noncleavable and the resulting construct is a latent form that binds but does not activate receptors and is useful as an inhibitor.

5. Linkers

To make molecules of the invention, a linker, preferably a covalent linker, is used to attach the RTK binding domain to one or more flanking domains (or to further attach flanking domains to each other or to attach optional additional domains such as a heparin binding domain). In some embodiments, the linker is simply a covalent bond. For example, in a preferred embodiment, where $F_N$-L-RTK-L-$F_C$ ("L" denotes a linker), comprises a single continuous polypeptide, the linker can denote an amide (peptide) bond between the C-terminal amino acid of $F_N$ and the N-terminal amino acid of the RTK binding domain, or between the N-terminal amino acid of $F_C$ and the C-terminal amino acid of the RTK binding domain.

The linker may be an organic moiety constructed to contain an alkyl, aryl backbone and may contain an amide, ether, ester, hydrazone, disulphide linkage or any combination thereof. Linkages containing amino acid, ether and amide bound components will be stable under conditions of physiological pH, normally 7.4 in serum and 4-5 on uptake into cells (endosomes). Disulphide linkages are preferred because they are sensitive to reductive cleavage; amino acid linkers can be designed to be sensitive to cleavage by specific enzymes in the desired target organ. Exemplary linkers are set out in Blattler et al. Biochem. 24:1517-1524, 1985; King et al. Biochem. 25:5774-5779, 1986; Srinivasachar and Nevill, Biochem. 28:2501-2509, 1989.

In still other embodiments, entity L is a chemically, or otherwise, cleavable bond that, under appropriate conditions, allows the release of subunit $F_N$ from subunit F. For example, domains $F_N$ and the RTK binding domain can be covalently linked by one or more disulfide bridges linking cysteine residues of $F_N$ and the RTK binding domain; or by mutual attachment to a distinct chemical entity, such as a carbohydrate moiety.

The linker is optionally a heterologous protein polypeptide. In particular embodiments, the linker comprises a peptide linker comprising from 1 to about 500 amino acids in length. In some embodiments, the linker has from 1 to 10 residues. In some embodiments, the linker has from 1 to 50 residues. In some embodiments, the linker has from 1-100 residues. Linkers of 4-50 amino acids are preferred, and 4-15 are highly preferred. Preferred peptide linkers are linear peptides joined N-terminally and C-terminally to domains $F_N$ and the RTK binding domain so as to form a single continuous polypeptide. In certain embodiments, the peptide linker comprises a protease cleavage site such as a Factor Xa cleavage site, an enterokinase cleavage site (New England Biolabs), a thrombin cleavage site, a TEV protease cleavage site (Life Technologies), and a PreScission cleavage site (Amersham Pharmacia Biotech). Numerous other proteases and their cleavage sites are known. Preferably the protease and linker are selected so that the protease cleaves the linkage but not the RTK domain of the construct.

In other variations, the linker may comprise a hinge domain deriving from PDGF-C or PDGF-D. The hinge domain can separate the CUB domain from the RTK binding domain of the construct.

The linker may affect whether the polypeptide(s) to which it is fused to is able to dimerize to another identical polypeptide or to another polypeptide. When the linker comprises a peptide, the construct is expressible as a single recombinant polypeptide molecule. Linkers may be chosen such that they are less likely to induce an allergic or antigenic reaction.

More than one linker is used per construct molecule, when more than two distinct domains are joined, such as in constructs that satisfy the formula $F_N$-L-RTK-L-$F_C$, wherein in $F_N$ and $F_C$ denote an N-terminal and C-terminal flanking sequences, respectively. The linker may be selected for optimal conformational (steric) freedom between the growth factor (RTK binding domain) and flanking and optional heparin binding or CUB domains to allow them to interact with binding partners. The linker may be linear such that $F_N$ and RTK are linked in series, or the linker may serve as a scaffold to which two or more $F_N$ or RTK binding units are attached. A linker may also have multiple branches. For example, using linkers disclosed in Tam, J. Immunol. Methods 196:17 (1996). $F_N$ and RTK may be attached to each other or to the linker scaffold via N-terminal amino groups, C-terminal carboxyl groups, side chains, chemically modified groups, side chains, or other means.

When comprising peptides, the linker may be designed to have sequences that permit desired characteristics. For example, the use of glycyl residues allow for a relatively large degree of conformational freedom, whereas a proline would tend to have the opposite effect. Peptide linkers may be chosen so that they achieve particular secondary and tertiary structures, e.g., alpha helices, beta sheets and beta barrels. Quaternary structure can also be utilized to create linkers that join two binding units together non-covalently. For example, fusing a protein domain with a hydrophobic face to each binding unit may permit the joining of the two binding units via the interaction between the hydrophobic interaction of the two molecules. In some embodiments, the linker may provide for polar interactions. For example, a leucine zipper domain of the proto-oncoproteins Myc and Max, respectively may be used. Luscher and Larsson, Ongogene 18:2955-2966 (1999). In some embodiments, the linker allows for the formation of a salt bridge or disulfide bond. Linkers may comprise non-naturally occurring amino acids, as well as naturally occurring amino acids that are not naturally incorporated into a polypeptide. In some embodiments, the linker comprises a coordination complex between a metal or other ions and various residues from the multiple peptides joined thereby.

In some embodiments, the linear peptide linker comprises residues with relatively inert side chains. Peptide linker amino acid residues need not be linked entirely or at all via alpha-carboxy and alpha-amino groups. That is, peptides may be linked via side chain groups of various residues. In some embodiments, a linker is used as is described in Liu et al. U.S. Pat. Appl. Pub. No. 2003/0064053.

6. Variation from Natural (Wildtype) Sequences in Constructions of the Invention.

In one preferred embodiment, constructs of the invention are constructed with naturally occurring RTK and flanking domain sequences (and, when included, naturally occurring other sequence such as heparin binding domain sequences or CUB domain sequences). In other words, RTK or flanking sequences or other sequences are 100% identical to human or other mammalian or avian sequences. Especially for in vivo applications, 100% identity to a wildtype sequence minimizes immunoreactivity towards constructs of the invention.

The growth factor receptors include splice variants and naturally-occurring allelic variations. Allelic variants are well known in the art, and represent alternative forms or a nucleic acid sequence that comprise substitution, deletion or addition of one or more nucleotides, but which do not result in any substantial functional alteration of the encoded polypeptide.

In other embodiments, constructs of the invention are constructed with RTK or flanking sequences or other sequences similar to, but not identical to naturally occurring sequences. Amino acid sequences that are at least 70%, 75%, 80%, 85%, 90%, 91%, 92%, 93%, 94%, 95%, 96%, 97%, 98%, 99%, or 99.5% identical to a naturally occurring sequence are contemplated. Specifically contemplated are variants that retain a biological property/activity for which they were selected. For example, an RTK variant should retain receptor binding properties of the wildtype sequences.

For example, in one embodiment, a flanking domain comprises an amino acid sequence at least 90%, 92%, 94%, 95%, 96%, 97%, 98% or 99% identical to a N-terminal VEGF-C propeptide amino acid sequence, a N-terminal VEGF-D propeptide amino acid sequence, or a fragment of either of the foregoing. Exemplary fragments useful as flanking domains for practice of the invention are fragments of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or more amino acids, to as large as one residue smaller that the wildtype flanking sequence. Preferred fragments include fragments that retain one or more structural motifs of a wildtype sequence and/or that enhance the same activity of an RTK domain that is enhanced by the full length flanking sequence.

In another embodiment, a flanking domain comprises an amino acid sequence at least 90%, 92%, 94%, 95%, 96%, 97%, 98% or 99% identical to a C-terminal VEGF-C propeptide amino acid sequence, a C-terminal VEGF-D propeptide amino acid sequence, or a fragment of either of the foregoing. Exemplary fragments useful as flanking domains for practice of the invention are fragments of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75-80, 81-90, 91-100, 101-120, 121-140, 141-160, 161-180, 181-200, or more amino acids. Preferred fragments include fragments that retain a structural or functional motif characteristic of the flanking domain, such as fragments that include one or more BR3P homology domains. Referring to the VEGF-C C-terminal amino acid sequence of SEQ ID NO: 47, exemplary BR3P domains include approximately residues 16-29, residues 53-68, residues 77-92, residues 101-116, residues 120-135, residues 142-160 and residues 171-180. Referring to VEGF-D C-terminal amino acid sequence of SEQ ID NO: 49, exemplary BR3P domains include approximately residues 21-34, residues 76-92, residues 99-117, and residues 127-135.

In another embodiment, a CUB domain comprises an amino acid sequence at least 90%, 92%, 94%, 95%, 96%, 97%, 98% or 99% identical to a wild type PDGF-C or PDGF-D CUB domain sequence, or fragments thereof.

Amino acid differences resulting from insertions, deletions, and substitutions (relative to a wildtype sequence) are specifically contemplated.

Standard methods can readily be used to generate such polypeptides including site-directed mutagenesis of polynucleotides, or specific enzymatic cleavage and ligation. Similarly, use of peptidomimetic compounds or compounds in which one or more amino acid residues are replaced by a non-naturally-occurring amino acid or an amino acid analog that retain binding activity is contemplated. Preferably, where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one similarly charge or polar residue for another, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted amino acid.

Alternatively, conservative amino acids can be grouped as described in Lelminger, (*Biochemistry*, Second Edition; Worth Publishers, Inc. NY:NY, pp. 71-77 (1975)) as set out in the following:

Non-polar (hydrophobic)
  A. Aliphatic: A, L, I, V, P,
  B. Aromatic: F, W,
  C. Sulfur-containing: M,
  D. Borderline: G.
Uncharged-polar
  A. Hydroxyl: S, T, Y,
  B. Amides: N, Q,
  C. Sulfhydryl: C,
  D. Borderline: G.
Positively Charged (Basic): K, R, H.
Negatively Charged (Acidic): D, E.

Referring to the RTK binding domain, analogs that retain VEGF/PDGF receptor binding biological activity are contemplated for use in constructs of the present invention. In a preferred embodiment, analogs having 1, 2, 3, 4, 5, 6, 7, 8, 9, 10, 11, 12, 13, 14, 15, 16, 17, 18, 19, 20, 21, 22, 23, 24, or 25 such modifications and that retain VEGF/PDGF receptor binding activity are contemplated for inclusion in constructs of the present invention. Polynucleotides encoding such analogs are generated using conventional PCR, site-directed mutagenesis, and chemical synthesis techniques. Analogs that bind and stimulate phosphorylation of one or more receptors that w wildtype RTK polypeptide stimulates (e.g., VEGFR-1 and/or VEGFR-2, in the case of VEGF-A) are preferred.

B. Methods of Making Chimeric VEGF Polypeptides

Constructs of the invention or portions thereof can be synthesized in solution or on a solid support in accordance with conventional techniques. Such polypeptides may be synthesized as small fragments of the complete construct or as a complete full length sequence. Various automatic synthesizers are commercially available and can be used in accordance with known protocols. See, for example, Stewart and Young, Solid Phase Peptide Synthesis, 2d. ed., Pierce Chemical Co., (1984); Tam et al., J. Am. Chem. Soc., 105:6442, (1983); Merrifield, Science, 232: 341-347, (1986); and Barany and Merrifield, The Peptides, Gross and Meienhofer, eds, Academic Press, New York, 1-284, (1979), each incorporated herein by reference. The chimeric VEGF polypeptides of the invention can be readily synthesized and then screened using any of a number of assays that identify the polypeptides for VEGF-A-like, VEGF-C-like, VEGF-D-like or other PDGF-like or other VEGF-like activity, such as e.g., binding to VEGFR-1, VEGFR-2, or VEGFR-3, induction of vascular permeability, activity in an endothelial cell proliferation assay, induction of growth of lymphatic or blood vessels, promotion of growth and differentiation of CD34+ progenitor cells in vitro, activity in CAM assays, and the like. These and other assays for determining the activity of the vascular endothelial growth factor activity are described in commonly owned applications, U.S. Patent Publication No. 2002/0151680 and WO 01/62942, both of which are incorporated herein by reference.

Examples of solid-phase technology that may be used in the present invention include a Model 433A from Applied Biosystems Inc. peptide synthesizer. Methods of using such automated solid phase synthesizers to produce pure polypeptides are well known.

As an alternative to automated peptide synthesis, recombinant DNA technology may be employed wherein a nucleotide sequence that encodes a construct of the invention that is a chimeric polypeptide or that encodes a polypeptide portion of a construct is inserted into an expression vector, transformed or transfected into an appropriate host cell and cultivated under conditions suitable for expression. Recombinant methods are especially preferred for producing longer polypeptides of the invention. Constructs of the invention also may be produced by a combination of techniques whereby domains are synthesized recombinantly or synthetically in two or more steps and joined together with a linker.

A variety of expression vector/host systems may be utilized to contain and express the construct coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); ar animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the polypeptides in bacteria, yeast and other invertebrates are described herein below.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), pET vectors (Novagen) and pQE vectors (Qiagen). The DNA sequence encoding a peptide domain or chimeric polypeptide is cloned into such a vector, for example, pGEX 3x (Pharmacia, Piscataway, N.J.) designed to produce a fusion protein comprising glutathione S transferase (GST), encoded by the vector, and a protein encoded by a DNA fragment inserted into the vector's cloning site. Treatment of the recombinant fusion protein with thrombin or factor Xa (Pharmacia, Piscataway, N.J.) is expected to cleave the fusion protein, releasing the polypeptide of interest from the GST portion. The pGEX 3x/chimeric VEGF polypeptide construct is transformed into E. coli XL 1 Blue cells (Stratagene, La Jolla Calif.), and individual transformants were isolated and grown. Plasmid DNA from individual transformants is purified and partially sequenced using an automated sequencer to confirm the presence of the desired peptide or polypeptide encoding nucleic acid insert in the proper orientation.

Induction of the GST/substrate fusion protein is achieved by growing the transformed XL 1 Blue culture at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis Mo.).

The GST fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate is cleared by sonication, and cell debris is pelleted by centrifugation for 10 minutes at 12,000×g. The fusion protein containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{2+}$ and $Ca^{2+}$.

The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel running buffer lacking SDS. If the GST/chimeric VEGF polypeptide fusion protein is produced in bacteria as a soluble protein, it may be purified using the GST Purification Module (Pharmacia Biotech).

The fusion protein may be subjected to thrombin digestion to cleave the GST from the construct polypeptide. The digestion reaction (20-40 μg fusion protein, 20-30 units human thrombin (4000 U/mg (Sigma) in 0.5 ml PBS) is incubated 16-48 hrs. at room temperature and loaded on a denaturing SDS PAGE gel to fractionate the reaction products. The gel is soaked in 0.4 M KCl to visualize the protein bands. The identity of the protein band corresponding to the expected molecular weight of the construct polypeptide may be confirmed by partial amino acid sequence analysis using an automated sequencer (Applied Biosystems Model 473A, Foster City, Calif.).

Alternatively, the DNA sequence encoding the construct polypeptide or portion thereof may be cloned into a plasmid containing a desired promoter and, optionally, a leader sequence (see, e.g., Better et al., Science, 240: 104143, 1988). The sequence of this construct may be confirmed by automated sequencing. The plasmid is then transformed into E. coli using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, a leader sequence will effect secretion of the construct polypeptide and be cleaved during secretion. The secreted recombinant protein may then be purified using conventional protein purification techniques.

Similarly, yeast host cells from genera including *Saccharomyces, Pichia*, and *Kluveromyces* may be employed to generate the peptide recombinantly. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for, replication and selection in *E. coli*. Direct secretion of polypeptides expressed in yeast hosts may be accomplished by the inclusion of nucleotide sequence encoding the yeast I-factor leader sequence at the 5' end of the substrate-encoding nucleotide sequence.

Generally, a polypeptide is recombinantly expressed in yeast using a commercially available expression system, e.g., the *Pichia* Expression System (Invitrogen, San Diego, Calif.), following the manufacturer's instructions. This system also relies on the pre pro alpha sequence to direct secretion, but transcription of the insert is driven by the alcohol oxidase (AOX1) promoter upon induction by methanol.

The secreted recombinant polypeptide is purified from the yeast growth medium by, e.g., the methods used to purify polypeptides from bacterial and mammalian cell supernatants.

Alternatively, the chimeric polypeptides of the invention may be expressed in an insect system. Insect systems for protein expression are well known. In one such system, *Autographa californica* nuclear polyhedrosis virus (AcNPV) is used as a vector to express foreign genes in *Spodoptera frugiperda* cells or in *Trichoplusia larvae*. The polypeptide coding sequence is cloned into a nonessential region of the virus, such as the polyhedrin gene, and placed under control of the polyhedrin promoter. Successful insertion will render the polyhedrin gene inactive and produce recombinant virus lacking protein coat. The recombinant viruses are then used to infect *S. frugiperda* cells or *Trichoplusia larvae* in which the desired polypeptide is expressed (Smith et al., J Virol 46: 584, 1983; Engelhard E K et al., Proc. Nat. Acad. Sci. USA 91: 3224-7, 1994). For example, DNA encoding a polypeptide of the invention may be cloned into the baculovirus expression vector pVL1393 (PharMingen, San Diego, Calif.; Luckow and Summers, Bio/Technology 6:47 (1988)). This resulting vector is then used according to the manufacturer's directions (PharMingen) to infect *Spodoptera frugiperda* cells in SF9 protein free media and to produce recombinant protein. The protein or peptide is purified and concentrated from the media using a heparin Sepharose column (Pharmacia, Piscataway, N.J.) and sequential molecular sizing columns (Amicon, Beverly, Mass.), and resuspended in PBS. SDS PAGE analysis shows a single band and confirms the size of the protein, and Edman sequencing on a Porton 2090 Peptide Sequencer confirms its N-terminal sequence.

Mammalian host systems for the expression of recombinant proteins also are well known. Host cell strains may be chosen for a particular ability to process the expressed protein or produce certain post translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection and its presence allows growth and recovery of cells which successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; als which confers resistance to chlorsulfuron; and hygro, that confers resistance to hygromycin. Additional selectable genes that may be used include trpB, which allows cells to utilize indole in place of tryptophan, or hisD, which allows cells to utilize histinol in place of histidine. Markers that give a visual indication for identification of transformants include anthocyanins, b-glucuronidase and its substrate, GUS, and luciferase and its substrate, luciferin.

C. Protein Purification.

For many applications, it is desirable to purify the constructs, such as chimeric VEGF polypeptides, of the present invention. Protein purification techniques are well known. These techniques involve, at one level, the crude fractionation of the cellular milieu to polypeptide and non-polypeptide fractions. Having separated the peptide or polypeptides of the invention from other proteins, the polypeptides or peptides of interest may be further purified using chromatographic and electrophoretic techniques to achieve partial or complete purification (or purification to homogeneity).

Generally, "purified" will refer to a polypeptide, protein or peptide composition that has been subjected to fractionation to remove various other components, and which composition substantially retains its biological activity. Where the term "substantially purified" is used, this designation will refer to a composition in which the polypeptide, protein or peptide forms the major component of the composition, such as constituting about 50%, about 60%, about 70%, about 80%, about 90%, about 95% or more of the proteins in the composition.

Various methods for quantifying the degree of purification of the polypeptide, protein or peptide will be apparent. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed polypeptide, protein or peptide exhibits a detectable activity.

Various techniques known for use in protein purification are also suitable for molecules of the present invention. These include, for example, precipitation with ammonium sulphate, PEG, antibodies and the like or by heat denaturation, followed by centrifugation; chromatography steps such as ion exchange, gel filtration, reverse phase, hydroxylapatite, exclusion, and affinity chromatography; isoelectric focusing; gel electrophoresis (including polyacrylamide gel electrophoresis); and combinations of such and other techniques. The order of conducting the various purification steps may be varied, and certain steps may be omitted, and still result in a suitable method for the preparation of a substantially purified polypeptide, protein or peptide.

There is no general requirement that the polypeptide, protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., Biochem. Biophys. Res. Comm., 76:425, 1977). It will therefore be appreciated that under differing electrophoresis conditions, the apparent molecular weights of purified or partially purified expression products may vary.

In still another related embodiment, the invention provides a method for producing a protein construct, comprising the steps of growing a host cell of the invention in a nutrient medium and isolating the construct polypeptide from the cell or the medium. Isolation of the polypeptide from the cells or from the medium in which the cells are grown is accomplished by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein. Cleavage of the fusion component may produce a form of the desired protein having additional amino acid residues as a result of the cleavage process.

In preferred embodiments, purification of the chimeric polypeptides of the present invention may be achieved using affinity purification using an extracellular domain of one or more of the PDGF/VEGF family of receptors such as VEGFR-1 (Flt1) or VEGFR-2 (KDR/flk-1), or other portions of a receptor that the chimeric polypeptides of the invention may bind. Exemplary affinity purification of VEGF related compositions is described in e.g., U.S. Pat. No. 6,342,219, incorporated herein by, reference. In an exemplary affinity purification procedure using the VEGFR-2 extracellular domain, the chimeric polypeptide-containing composition to be purified are initially concentrated 30-50 fold using. Centriprep filter cartridges and loaded onto a column of immobilized VEGFR-extracellular domain (EC). Two affinity matrices are prepared. In the first case, the VEGFR-EC-6×His fusion protein is crosslinked to CNBr-activated Sepharose 4B (Pharmacia) and in the second case the VEGFR-EC-Ig fusion protein is coupled to protein A Sepharose using dimethylpimelidate (Schneider et al., J. Biol. Chem. 257: 10766-10769, 1982). The material eluted from the affinity column is subjected to further purification using ion exchange and reverse-phase high pressure chromatography and SDS-polyacrylamide gel electrophoresis. An affinity purification protocol using the VEGFR-3 EC domain is described in U.S. Pat. No. 5,776,755, incorporated herein by reference, Another affinity chromatography purification procedure that may be used to purify the chimeric polypeptides of the present invention employs immunoaffinity chromatography using antibodies specific for one or more of the RTK binding domains, a flanking domain, or additional domain if included, such as a heparin binding domain, epitope tag or linker sequence. Antibodies to various VEGF and PDGF growth factors are well known and also readily produced using conventional techniques. For example, antibodies specific for VEGF-A are useful for purification of constructs that include the RTK binding domain of VEGF-A. In addition, purification of the chimeric polypeptides of the present invention may be achieved using methods for the purification of VEGF-A or VEGF-A that are described in U.S. Pat. No. 5,332,671.

D. Nucleic Acids and Related Compositions.

The invention embraces polynucleotides that encode the polypeptides of the invention and also polynucleotides that hybridize under moderately stringent or high stringency conditions to the complete non-coding strand, or complement, of such polynucleotides. Complementary molecules are useful as templates for synthesizing coding molecules, and for making stable double-stranded polynucleotides. Due to the well-known degeneracy of the universal genetic code, one can synthesize numerous polynucleotide sequences that encode each chimeric polypeptide of the present invention. All such polynucleotides are contemplated as part of the invention. Such polynucleotides are useful for recombinant expression of polypeptides of the invention in vivo or in vitro (e.g., for gene therapy). The polynucleotides also are useful for manipulation to design constructs of the inventions with introduced functional domains or mutations or the like.

This genus of polynucleotides embraces polynucleotides that encode polypeptides with one or a few amino acid differences (additions, insertions, or deletions) relative to amino acid sequences specifically depicted herein. Such changes are easily introduced by performing site directed mutagenesis, for example.

Polynucleotides of the invention (and polypeptides encoded thereby) can be defined by molecules that hybridize under specified conditions to a polynucleotide sequence complementary to a sequence that encodes a construct of the invention.

Exemplary highly stringent hybridization conditions are as follows: hybridization at 65° C. for at least 12 hours in a hybridization solution comprising 5×SSPE, 5×Denhardt's, 0.5% SDS, and 2 mg sonicated non homologous DNA per 100 ml of hybridization solution; washing twice for 10 minutes at room temperature in a wash solution comprising 2×SSPE and 0.1% SDS; followed by washing once for 15 minutes at 65° C. with 2×SSPE and 0.1% SDS; followed by a final wash for 10 minutes at 65° C. with 0.1×SSPE and 0.1% SDS. Moderate stringency washes can be achieved by washing with 0.5×SSPE instead of 0.1×SSPE in the final 10 minute wash at 65° C. Low stringency washes can be achieved by using 1×SSPE for the 15 minute wash at 65° C., and omitting the final 10 minute wash. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook et al., (Eds.), Molecular Cloning: A Laboratory Manual, Cold Spring Harbor Laboratory Press: Cold Spring Harbor, N.Y. (1989), pp. 9.47 to 9.51.

For example, the invention provides a polynucleotide that comprises a nucleotide sequence that hybridizes under moderately stringent or high stringency hybridization conditions to the complement of any specific nucleotide sequence of the invention, and that encodes a chimeric polypeptide as described herein that binds at least one of the naturally occurring vascular endothelial growth factor or platelet derived growth factor receptors.

In a related embodiment, the invention provides a polynucleotide that comprises a nucleotide sequence that is at least 75%, 80%, 85%, 90%, 95%, 97%, 98%, or 99% identical to any specific nucleotide sequence of the invention, and that encodes a polypeptide that binds at least one of the naturally occurring vascular endothelial growth factor receptors or platelet derived growth factor receptors.

In a related embodiment, the invention provides vectors comprising a polynucleotide of the invention. Such vectors are useful, e.g., for amplifying the polynucleotides in host cells to create useful quantities thereof, and for expressing polypeptides of the invention using recombinant techniques. In preferred embodiments, the vector is an expression vector wherein the polynucleotide of the invention is operatively linked to a polynucleotide comprising an expression control sequence. Autonomously replicating recombinant expression constructs such as plasmid and viral DNA vectors incorporating polynucleotides of the invention are specifically contemplated. Expression control DNA sequences include promoters, enhancers, and operators, and are generally selected based on the expression systems in which the expression construct is to be utilized. Preferred promoter and enhancer sequences are generally selected for the ability to increase gene expression, while operator sequences are generally selected for the ability to regulate gene expression. Expression vectors are useful for recombinant production of polypeptides of the invention. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

In preferred embodiments, polynucleotides of the invention further comprise additional sequences to facilitate the gene therapy. In one embodiment, a "naked" transgene encoding a polypeptide of the invention (i.e., a transgene without a viral, liposomal, or other vector to facilitate transfection) is employed for gene therapy. In this embodiment, the polynucleotide of the invention preferably comprises a suitable promoter and/or enhancer sequence (e.g., cytomegalovirus promoter/enhancer [Lehner et al., J. Clin. Microbiol., 29:2494 2502 (1991); Boshart et al., Cell, 41:521 530 (1985)]; Rous sarcoma virus promoter [Davis et al., Hum. Gene Ther., 4:151 (1993)]; Tie promoter [Korhonen et al., Blood, 86(5): 1828 1835 (1995)]; or simian virus 40 promoter) for expression in the target mammalian cells, the promoter being operatively linked upstream (i.e., 5') of the polypeptide coding sequence. In a preferred embodiment, the promoter sequence comprises a skin specific promoter. Preferred promoter sequences include the K14, K5, K6, K16 promoters for the epidermis and alpha 1(I) collagen promoter for the dermis (Diamond, I., et al., J. Invest. Dermatol., 115 (5):788-794 (2000); Galera, P., et al., Proc. Natl. Acad. Sci. USA, 91(20):9372-9376 (1994); Wawersik, M. J., et al., Mol. Biol. Cell, 12(11):3439-3450 (2001)). All of the foregoing documents are incorporated herein by reference in the entirety. The polynucleotides of the invention also preferably further includes a suitable polyadenylation sequence (e.g., the SV40 or human growth hormone gene polyadenylation sequence) operably linked downstream (i.e., 3') of the polypeptide coding sequence. The polynucleotides of the invention also preferably comprise a nucleotide sequence encoding a secretory signal peptide fused in frame with the polypeptide sequence. The secretory signal peptide directs secretion of the polypeptide of the invention by the cells that express the polynucleotide, and is cleaved by the cell from the secreted polypeptide. The signal peptide sequence can be that of another secreted protein, or can be a completely synthetic signal sequence effective to direct secretion in cells of the mammalian subject.

The polynucleotide may further optionally comprise sequences whose only intended function is to facilitate large scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention. One can manufacture and administer such polynucleotides for gene therapy using procedures that have been described in the literature for other transgenes. See, e.g., Isner et al., Circulation, 91: 2687-2692 (1995); and Isner et al., Human Gene Therapy, 7: 989-1011 (1996); incorporated herein by reference in their entirety.

Vectors also are useful for "gene therapy" treatment regimens, wherein a polynucleotide that encodes a polypeptide of the invention is introduced into a subject in need of treatment involving the modulation (stimulation or blockage) of vascular endothelial growth factor receptors, in a form that causes cells in the subject to express the polypeptide of the invention in vivo. Gene therapy aspects that are described in commonly owned U.S. Patent Publication No. 2002/0151680 and WO 01/62942 both of which are incorporated herein by reference, also are applicable herein.

Any suitable vector may be used to introduce a polynucleotide that encodes a polypeptide of the invention encoding one of the polypeptides of the invention, into the host. Exemplary vectors that have been described in the literature include replication deficient retroviral vectors, including but not limited to lentivirus vectors [Kim et al., J. Virol., 72(1): 811-816 (1998); Kingsman & Johnson, Scrip Magazine, October, 1998, pp. 43 46.]; adeno-associated viral (AAV) vectors [U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479; Gnatenko et al., J. Invest. Med., 45: 87 98 (1997)]; adenoviral (AV) vectors [See, e.g., U.S. Pat. No. 5,792,453; U.S. Pat. No. 5,824,544; U.S. Pat. No. 5,707,618; U.S. Pat. No. 5,693,509; U.S. Pat. No. 5,670,488; U.S. Pat. No. 5,585,362; Quantin et al., Proc. Natl. Acad. Sci. USA, 89: 2581 2584 (1992); Stratford Perricadet et al., J. Clin. Invest., 90: 626 630 (1992); and Rosenfeld et al., Cell, 68: 143 155 (1992)]; an adenoviral adenoassociated viral chimeric (see for example, U.S. Pat. No. 5,856,152) or a vaccinia viral or a herpesviral (see for example, U.S. Pat. No. 5,879,934; U.S. Pat. No. 5,849,571; U.S. Pat. No. 5,830,727; U.S. Pat. No. 5,661,033; U.S. Pat. No. 5,328,688; Lipofectin mediated gene transfer (BRL); liposomal vectors [See, e.g., U.S. Pat. No. 5,631,237 (Liposomes comprising Sendai virus proteins)] and combinations thereof. All of the foregoing documents are incorporated herein by reference in their entirety. Replication deficient adenoviral vectors constitute a preferred embodiment.

Naked plasmid DNA gene therapy is another vehicle to administer the chimeric polypeptides of the invention. A current trial, GENASIS (Genetic Angiogenic Stimulation Investigational Study), is being performed by Corautus Genetics, Inc., to evaluate the safety and efficacy of a VEGF family member for the treatment of patients with severe angina. The trial reportedly employs defined doses of the transgene in the form of "naked" plasmid DNA, a non-viral delivery vector, delivered to diseased heartmuscle tissue via the Stiletto™ (Boston Scientific Corporation) endocardial direct injection catheter system. Once administered, the DNA plasmid appears to be taken up and expressed by myocardium near the injection site. The clinical trial expects to see the therapeutic growth of new blood vessels.

In another related embodiment, the invention provides host cells, including prokaryotic and eukaryotic cells, that are transformed or transfected (stably or transiently) with polynucleotides of the invention or vectors of the invention. Polynucleotides of the invention may be introduced into the host cell as part of a circular plasmid, or as linear DNA comprising an isolated protein coding region or a viral vector. Methods for introducing DNA into the host cell, which are well known and routinely practiced in the art include transformation, transfection, electroporation, nuclear injection, or fusion with carriers such as liposomes, micelles, ghost cells, and protoplasts. As stated above, such host cells are useful for amplifying the polynucleotides and also for expressing the polypeptides of the invention encoded by the polynucleotide. The host cell may be isolated and/or purified. The host cell also my be a cell transformed in vivo to cause transient or permanent expression of the polypeptide in vivo. The host cell may also be an isolated cell transformed ex vivo and introduced post-transformation, e.g., to produce the polypeptide in vivo for therapeutic purposes. The definition of host cell explicitly excludes a transgenic human being.

Such host cells are useful in assays as described herein. For expression of polypeptides of the invention, any host cell is acceptable, including but not limited to bacterial, yeast, plant, invertebrate (e.g., insect), vertebrate, and mammalian host cells. For developing therapeutic preparations, expression in mammalian cell lines, especially human cell lines, is preferred. Use of mammalian host cells is expected to provide for such post-translational modifications (e.g., glycosylation, truncation, lipidation, and phosphorylation) as may be desirable to confer optimal biological activity on recombinant expression products of the invention. Glycosylated and non-glycosylated forms of polypeptides are embraced by the present invention. Similarly, the invention further embraces polypeptides described above that have been covalently modified to include one or more water soluble polymer, attachments such as polyethylene glycol, polyoxyethylene glycol, or polypropylene glycol.

Similarly, the invention provides for the use of polypeptides or polynucleotides or host cells of the invention in the manufacture of a medicament for the treatment of disorders described herein, including but not limited to disorders characterized by insufficient or undesirable endothelial cell proliferation and/or disorders characterized by ischemia and/or vessel occlusion, wherein neovascularization is desirable.

In a related embodiment, the invention provides a kit comprising a polynucleotide, polypeptide, or composition of the invention packaged in a container, such as a vial or bottle, and further comprising a label attached to or packaged with the container, the label describing the contents of the container and providing indications and/or instructions regarding use of the contents of the container to treat one or more disease states as described herein.

In yet another aspect, the present invention provides methods of producing polypeptides having novel VEGF receptor binding and stimulation properties, and methods for producing polynucleotides that encode such polypeptides.

As used herein, "modulate the growth of mammalian endothelial cells" means stimulate such growth by inducing a mitogenic signal through binding cell surface receptors expressed on vascular endothelial cells, or inhibiting such growth. The inhibition may be due to blockage of vascular or lymphatic endothelial growth factor receptors, or the formation of heterodimers with endogenous growth factors that prevent stimulation of endogenous receptors by the endogenous growth factors. Inhibition also may be achieved by conjugating cytotoxic agents to polypeptides of the invention that bind VEGF receptors. Exemplary toxins are known in the art and described elsewhere herein. Polypeptides of the invention conjugated to cytotoxic agents or other agents that modulate cell growth are contemplated as another aspect of the invention. Agonist molecules of the invention that stimulate endothelial cell growth are a preferred class of agents. Antagonists that inhibit endothelial cell growth also are preferred.

E. Methods of Using Constructs Such As Chimeric VEGF Polypeptides

In yet another embodiment, the invention provides numerous in vitro and in vivo methods of using the chimeric polypeptides and polynucleotides of the invention. Generally speaking, the chimeric polypeptides of the invention are useful for modulating (stimulating or inhibiting) cellular processes that are mediated through any of the PDGF/VEGF family of receptors. These receptors may be involved singularly in certain processes and in combination, to varying extents, in other processes.

Thus, in one variation, the invention is a method of modulating the signaling of one or more of VEGF receptors. In one variation, modulation to activate signaling (stimulation) is contemplated, and the cell is contacted with a polypeptide of the invention that stimulates receptor signaling in an amount sufficient to bind to one or more receptors and induce receptor signaling. Preferably, an amount is employed that is effective to stimulate a cellular response such as an in vitro or in vivo endothelial cell proliferation and/or recruitment or angiogenesis or lymphangiogenesis. Desired therapeutic goals include wound healing and improved circulation in tissues suffering from ischemia or occlusive disease.

In another variation, modulation to inhibit signaling is contemplated. The cell is contacted with a polypeptide that inhibits ligand-induced receptor activation, in an amount sufficient to inhibit signaling that is induced by receptor ligand growth factor polypeptides that exist endogenously in the cell's environment. In a related embodiment, inhibition is achieved by administering a construct of the invention that is conjugated to a cytotoxin or cytotoxin precursor, in order to arrest the growth of (or kill) a cell expressing a target receptor.

Dose-response studies permit accurate determination of a proper quantity of chimeric polypeptide to employ. Effective quantities can be estimated from measurements of the binding affinity of a polypeptide for a target receptor, of the quantity of receptor present on target cells, of the expected dilution volume (e.g., patient weight and blood volume for in vivo embodiments), and of polypeptide clearance rates. Existing literature regarding dosing of known VEGFR ligands also provides guidance for dosing of molecules of the invention.

Generally speaking, embodiments described herein in the context of administering polypeptides can also be practiced by administering polynucleotides that encode the polypeptides. Polynucleotide therapy (e.g., using gene therapy vectors) may result in sustained production of a construct in vivo, reducing or eliminating the need for repeated dosing of polypeptides.

Without intending to be limited to any particular theory, an attribute of constructs of the invention relevant to therapeutic efficacy may be reduced clearance rates and better targeting compared to wildtype RTK ligand polypeptides (native VEGF/PDGF's).

Polypeptides of the invention that can activate VEGFR-1 and VEGFR-2 can be used to promote endothelial functions of the blood vasculature and tissues such as to treat loss of blood vessels, occlusion of blood vessels, and ischemic tissues. In a preferred embodiment, the chimeric polypeptides described herein are used to treat a human subject who has been diagnosed with a cardiovascular disease.

VEGF-A has played a therapeutic role in various cardiovascular disorders. It has been shown that intraarterial or intramuscular administration of VEGF-A significantly augments perfusion and development of collateral vessels in a rabbit model where chronic ischemia was created by surgical removal of the femoral artery (Takeshita et al., J. Clin. Invest., 93:662-670, 1994; Takeshita et al., Circulation, 90:228-234, 1994). These studies provided angiographic evidence of neovascularization in the ischemic limbs. Other studies have shown that VEGF-A administration also leads to a recovery of normal endothelial reactivity in dysfunctional endothelium (Sellke et al., Am. J. Physiol., 262:H1669-1675, 1992; Bauters et al., Circulation, 91:2793-2801, 1995). Isner et al., (Hum. Gene Ther., 7:859-888, 1996) tested the hypothesis that treatment with VEGF-A results in therapeutically significant angiogenesis in a gene therapy trial in patients with severe limb ischemia. Arterial gene transfer of naked plasmid DNA encoding VEGF-A applied to the hydrogel polymer coating of an angioplasty balloon resulted in angiographic and histological evidence in the knee, midtibial, and ankle. Bauters et al., (Am. J. Physiol., 267:H1263-1271, 1994) have shown that both maximal flow velocity and maximal blood flow are significantly increased in ischemic limbs after VEGF-A administration. It has also been demonstrated that after VEGF-A administration, increased blood flow occurred in a dog model of coronary insufficiency (Banai et al., Circulation, 89:2189-2189, 1994). These observations provide an indication that the polynucleotides or polypeptides according to the invention may be used to treat or prevent various cardiovascular disorders through therapeutic angiogenesis.

Polypeptides of the invention that can activate VEGFR-3 can be used to promote the endothelial functions of lymphatic vessels and tissues such as to treat loss of lymphatic vessels, occlusions of lymphatic vessels, lymphangiomas, and primary idiopathic lymphedemas, including Milroy's disease and lymphedema praecox, as well as secondary lymphedemas, including those resulting from removal of lymph nodes and vessels, radiotherapy and surgery in treatment of cancer, trauma and infection.

Polynucleotides or polypeptides of the invention can be administered purely as a prophylactic treatment to prevent lymphedema in subjects at risk for developing lymphedema, or as a therapeutic treatment to subjects afflicted with lymphedema, for the purpose of ameliorating its symptoms (e.g., swelling due to the accumulation of lymph).

The polynucleotides and polypeptides of the invention that activate VEGFR-3 can also be used to promote re-growth or permeability of lymphatic vessels in patients whose auxiliary lymphatic vessels were removed during surgical interventions in the treatment of cancer (e.g., breast cancer). Polynucleotides and polypeptides of the invention can be used to treat vascularization in, for example, organ transplant patients. A composition containing the polypeptide(s) or polynucleotide(s) of the invention may be directly applied to the isolated vessel segment prior to its being grafted in vivo to minimize rejection of the transplanted material and to stimulate vascularization of the transplanted materials.

Polypeptides of the invention that activate VEGF receptor activity may be used to treat wounds, surgical incisions, sores, and other indications where healing is reasonably expected to be promoted if the process of neovascularization can be induced and/or accelerated. In certain embodiments, such polypeptides can be used to improve healing of skin flaps or skin grafts following surgery as described in commonly owned, co-filed U.S. patent application Ser. No. 10/868,549, filed Jun. 14, 2004, and International Patent Application No. PCT/US2004/019197, filed Jun. 14, 2004, each incorporated herein by reference.

In addition, the expression of receptors for vascular endothelial growth factors have been observed in certain progenitor cells, such as hematopoietic and/or endothelial progenitor cells, and VEGF-C has been observed to have myelopoietic activity. These observations provide an indication that polynucleotides or polypeptides according to the invention may be used to treat or prevent inflammation, infection, or immune disorders by modulating the proliferation, differentiation and maturation, or migration of immune cells or hematopoietic cells. Polynucleotides or polypeptides according to the invention may also be useful to promote or inhibit trafficking of leukocytes between tissues and lymphatic vessels and migration in and out of the thymus. See International Patent Publication No. WO 98/33917, incorporated by reference.

Polynucleotides and polypeptides of the invention can be used for stimulating myelopoiesis (especially growth of neutrophilic granuloctyes) or inhibiting it. See International Patent Publication No. WO 98/33917, incorporated by reference. Thus, the invention includes a method for modulating myelopoiesis in a mammalian subject comprising administering to a mammalian subject in need of modulation of myelopoiesis an amount of a polypeptide of the invention that is effective to modulate myelopoiesis. In one embodiment, a mammalian subject suffering from granulocytopenia is selected, and the method comprises administering to the subject an amount of a polypeptide effective to stimulate myelopoiesis. In particular, a polypeptide of the invention is administered in an amount effective to increase the neutrophil count in blood of the subject.

In a related embodiment, the invention includes a method of increasing the number of neutrophils in the blood of a mammalian subject comprising the step of expressing in a cell in a subject in need of an increased number of blood neutrophils a DNA encoding a polynucleotide of the invention that is able to activate signaling through VEGF receptors, the DNA operatively linked to a promoter or other control sequence that promotes expression of the DNA in the cell. Similarly, the invention includes a method of modulating the growth of neutrophilic granulocytes in vitro or in vivo comprising the step of contacting mammalian stem cells with a polypeptide of the invention in an amount effective to modulate the growth of mammalian endothelial cells.

The invention also includes a method for modulating the growth of mammalian CD34+ progenitor cells (especially hematopoietic progenitor cells and endothelial progenitor cells, more preferably CD34+/VEGFR-2+ and CD34+ NEGFR-3+, still more preferably CD133+/VEGFR2+ and, CD133+/VEGFR3+ cells) in vitro or in vivo comprising the step of contacting mammalian CD34+ progenitor cells with a polypeptide of the invention in an amount effective to modulate the growth and/or differentiation of such cells (Peichev et al, Blood, 95:952-958, 2000; Salven et al., Blood, 168-172, 2003). For in vitro methods, CD34+ progenitor cells isolated from cord blood or bone marrow are specifically contemplated. Further isolation of the CD133+/VEGFR2+ and CD133+VEGFR-3+, subfractions are also contemplated. In vitro and in vivo methods of the invention for stimulating the growth of CD34+ precursor cells also include methods wherein polypeptides of the invention are employed together (simultaneously or sequentially) with other polypeptide factors for the purpose of modulating hematopoiesis/myelopoiesis or endothelial cell proliferation. Such other factors include, but are not limited to colony stimulating factors ("CSFs," e.g., granulocyte-CSF (G-CSF), macrophage-CSF (M-CSF), and granulocyte-macrophage-CSF (GM-CSF)), interleukin-3 (IL-3, also called multi-colony stimulating factor), other interleukins, stem cell factor (SCF), other polypeptide factors, and their analogs that have been described and are known in the art. See generally *The Cytokine Handbook, Second Ed.*, Angus Thomson (editor), Academic Press (1996); Callard and Gearing, *The Cytokine FactsBook*, Academic Press Inc. (1994); and Cowling and Dexter, *TIBTECH*, 10(10): 349-357 (1992). The use of a polypeptide of the invention as a progenitor cell or myelopoietic cell growth factor or co-factor with one or more of the foregoing factors may potentiate previously unattainable myelopoietic effects and/or potentiate previously attainable myelopoietic effects while using less of the foregoing factors than would be necessary in the absence of a polypeptide of the invention.

Polynucleotides and polypeptides of the invention may also be used in the treatment of lung disorders to improve blood circulation in the lung and/or gaseous exchange between the lungs and the blood stream; to improve blood circulation to the heart and $O_2$ gas permeability in cases of cardiac insufficiency; to improve blood flow and gaseous exchange in chronic obstructive airway disease; and to treat conditions such as congestive heart failure, involving accumulations of fluid in, for example, the lung resulting from increases in vascular permeability, by exerting an offsetting effect on vascular permeability in order to counteract the fluid accumulation.

Polypeptides of the invention that bind but do not stimulate signaling through one or more of the VEGF receptors may be used to treat chronic inflammation caused by increased vascular permeability, retinopathy associated with diabetes, rheumatoid arthritis and psoriasis. Polynucleotides or polypeptides according to the invention that are able to inhibit the function of one or more VEGF receptors can also be used to treat edema, peripheral arterial disease, Kaposi's sarcoma, or abnormal retinal development in premature newborns.

In another embodiment, the invention provides a method for modulating the growth of endothelial cells in a mammalian subject comprising the steps of exposing mammalian endothelial cells to a polypeptide according to the invention in an amount effective to modulate the growth of the mammalian endothelial cells. In one embodiment, the modulation of growth is affected by using a polypeptide capable of stimulating tyrosine phosphorylation of VEGF receptors in a host cell expressing the VEGF receptors. In modulating the growth of endothelial cells, the invention contemplates the modulation of endothelial cell-related disorders. In a preferred embodiment, the subject, and endothelial cells, are human. The endothelial cells may be provided in vitro or in vivo, and they may be contained in a tissue graft. An effective amount of a polypeptide is an amount necessary to achieve a reproducible change in cell growth rate (as determined by, microscopic or macroscopic visualization and estimation of cell doubling time, or nucleic acid synthesis assays).

Since angiogenesis and neovascularization are essential for tumor growth, inhibition of angiogenic activity can prevent further growth and even lead to regression of solid tumors. Likewise inhibition of lymphangiogenesis may be instrumental in preventing metastases. See e.g., International Publication Nos. WO 02/060950 and WO 00/21560, incorporated herein by reference. Polynucleotides and polypeptides of the invention, when conjugated to a cytotoxic agent may be used to treat neoplasias including sarcomas, melanomas, carcinomas, and gliomas by inhibiting tumor angiogenesis.

Thus, it is contemplated that a wide variety of cancers may be treated using the peptides of the present invention including cancers of the brain (glioblastoma, astrocytoma, oligodendroglioma, ependymomas), lung, liver, spleen, kidney, lymph node, pancreas, small intestine, blood cells, colon, stomach, breast, endometrium, prostate, testicle; ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree or localized to a specific area and inhibited from spread to disparate sites. It may be that the tumor growth is completely blocked, however, or that some tumor regression is achieved. Clinical terminology such as "remission" and "reduction of tumor" burden also are contemplated given their normal usage. In the context of the present invention, the therapeutic effect may result from an inhibition of angiogenesis and/or an inhibition of lymphangiogenesis.

VEGF-C and VEGF-D of the VEGF family of growth factors have utility for preventing stenosis or restenosis of blood vessels. See International Patent Application No. PCT/US99/24054 (WO 00/24412), "Use of VEGF-C or VEGF-D Gene or Protein to Prevent Restenosis," filed Oct. 26, 1999, incorporated herein by reference in its entirety. As discussed therein, VEGF-A also has been tested to inhibit restonisis. VEGF-A accelerates reendotheliazation and has been found to attenuate intimal hyperplasia in balloon-injured rat carotid artery or rabbit aorta (Asahara et al., Circulation, 92:2802-2809, 1995; Callow et al., Growth Factors, 10:223-228, 1994). The polypeptides and polynucleotides of the invention also will have utility for these indications and can substitute for (or be used together with) VEGF-C and VEGF-D with respect to the materials and methods described therein. Thus, in another aspect, the invention provides a method of treating a mammalian subject to prevent stenosis or restenosis of a blood vessel, comprising the step of administering to a mammalian subject in need of treatment to prevent stenosis or restenosis of a blood vessel a composition comprising one or more polypeptide(s) or polynucleotide(s) of the invention, in an amount effective to prevent stenosis or restenosis of the blood vessel. In a preferred embodiment, the administering comprises implanting an intravascular stent in the mammalian subject, where the stent is coated or impregnated with the composition. Exemplary materials for constructing a drug-coated or drug-impregnated stent are described in literature cited above and reviewed in Lincoff et al., *Circulation*, 90: 2070-2084 (1994). In another preferred embodiment, the composition comprises microparticles composed of biodegradable polymers such as PGLA, non-degradable polymers, or biological polymers (e.g., starch) which particles encapsulate or are impregnated by a polypeptide(s) of the invention. Such particles are delivered to the intravascular wall using, e.g., an infusion angioplasty catheter. Other techniques for achieving locally sustained drug delivery are reviewed in Wilensky et al., *Trends Caridovasc. Med.*, 3:163-170 (1993), incorporated herein by reference. Such materials and devices are themselves aspects of the invention.

Administration via one or more intravenous injections concurrent with or subsequent to the angioplasty or bypass procedure also is contemplated. Localization of the polypeptides of the invention to the site of the procedure occurs due to expression of VEGF receptors on proliferating endothelial cells. Localization is further facilitated by recombinantly expressing the polypeptides of the invention as a fusion polypeptide (e.g., fused to an apolipoprotein B-100 oligopeptide as described in Shih et al., *Proc. Nat'l. Acad. Sci. USA*, 87:1436-1440 (1990). Co-administration of polynucleotides and polypeptides of the invention is also contemplated.

Likewise, the invention also provides surgical devices that are used to treat circulatory disorders, such as intravascular or endovascular stents (U.S. Pat. Nos. 6,846,323 and 4,580, 568), balloon catheters (U.S. Pat. No. 6,238,401), infusion-perfusion catheters (U.S. Pat. No. 5,713,860), extravascular collars (International Patent Publications WO 98/20027 and WO 99/55315), elastomeric membranes, and the like, which have been improved by coating with, impregnating with, adhering to, or encapsulating within the device a composition comprising a polynucleotide of polypeptide of the invention.

Polynucleotides or polypeptides of the invention can be administered purely as a prophylactic treatment to prevent stenosis, or shortly before, and/or concurrently with, and/or shortly after a percutaneous transluminal coronary angioplasty procedure, for the purpose of preventing restenosis of the subject vessel. In another preferred embodiment, the polynucleotide or polypeptide is administered before, during, and/or shortly after a bypass procedure (e.g., a coronary bypass procedure), to prevent stenosis or restenosis in or near the transplanted (grafted) vessel, especially stenosis at the location of the graft itself. In yet another embodiment, the polynucleotide or polypeptide is administered before, during, or after a vascular transplantation in the vascular periphery that has been performed to treat peripheral ischemia or intermittent claudication. By prevention of stenosis or restenosis is meant prophylactic treatment to reduce the amount/severity of, and/or substantially eliminate, the stenosis or restenosis that frequently occurs in such surgical procedures. The polynucleotide or polypeptide is included in the composition in an amount and in a form effective to promote stimulation of VEGF receptors in a blood vessel of the mammalian subject, thereby preventing stenosis or restenosis of the blood vessel.

In a preferred embodiment, the mammalian subject is a human subject. For example, the subject is a person suffering from coronary artery disease that has been identified by a cardiologist as a candidate who could benefit from a therapeutic balloon angioplasty (with or without insertion of an intravascular stent) procedure or from a coronary bypass procedure. Practice of methods of the invention in other mammalian subjects, especially mammals that are conventionally used as models for demonstrating therapeutic efficacy in humans (e.g., primate, porcine, canine, or rabbit animals), also is contemplated.

The polypeptides of the invention may be used to modulate the growth of isolated cells or cell lines. For example, certain neoplastic disease states are characterized by the appearance of VEGF receptors on cell surfaces [Valtola et al., *Am J Path* 154:1381-90 (1999)]. Polypeptides of the invention may be screened to determine the ability of the polypeptide to modulate the growth of the neoplastic cells. Other disease states are likely characterized by mutations in VEGF receptors [Ferrell et al., *Hum Mol Genetics* 7:2073-78 (1998)]. Polypeptides of the invention that modulate the activity of the mutant forms of the VEGF receptor in a manner different than naturally-occurring vascular endothelial growth factors will be useful at modulating the symptoms and severity of such disease states.

Polypeptides of the invention may be used to modulate the growth of stem cells, progenitor cells for various tissues, and primary cell isolates that express receptor for the polypeptides.

As indicated herein above, and discussed further in U.S. patent application Ser. No. 10/669,176, filed Sep. 23, 2003, VEGF-C compositions are useful in the treatment of neurological disorders. The compositions of the invention are useful in the treatment of such disorders either alone or in conjunction with additional therapeutics, such as a neural growth factor. Exemplary neural growth factors include, but are not limited to, interferon gamma, nerve growth factor, epidermal growth factor (EGF), basic fibroblast growth factor (bFGF), neurogenin, brain derived neurotrophic factor (BDNF), thyroid hormone, bone morphogenic proteins (BMPs), leukemia inhibitory factor (LIF), sonic hedgehog, and glial cell line-derived neurotrophic factor (GDNF), vascular endothelial growth factor (VEGF), interleukins, interferons, stem cell factor (SCF), activins, inhibins, chemokines, retinoic acid and ciliary neurotrophic factor (CNTF). In one aspect, the invention contemplates a composition comprising a heparin binding VEGFR-3 ligand of the invention and a neural growth factor in a pharmaceutically acceptable diluent or carrier, or polynucleotides comprising the same.

Various neural cells express one or more of the VEGF receptors (e.g., VEGFR-1, VEGFR-2 and neuropilin-1) and can thus directly respond to VEGF-A released by neighboring neural cells (Oosthuyse et al., Nat. Genet., 28:131-138, 2001; Sondell et al., J. Neurosci., 19-5731-5740, 1999; Sondell et al., Neuroreport, 12:105-108, 2001). For instance, VEGF-A stimulates axonal outgrowth in explant cultures of retinal or superior cervical and dorsal root ganglia. Furthermore, under conditions of hypoxic, excitotoxic, or oxidative stress, VEGF-A increases the survival of hippocampal, cortical, cerebellar granule, dopaminergic, autonomic, and sensory neurons. VEGF-A also stimulates the growth and survival of Schwann cells in hypoxic conditions, and increases proliferation and migration of astrocytes and microglial cells (Silverman et al., Neuroscience, 90:1529-1541, 1999; Krum et al., Neuroscience, 110:589-604, 2002; and Forstreuter et al., J. Neuroimmunol., 132:93-98, 2002). These observations provide an indication for use of the polynucleotides or polypeptides according to the invention to treat or prevent or slow the progression of neurodegenerative disorders.

Methods of the invention preferably are performed wherein the subject has a disease or condition characterized by aberrant growth of neuronal cells, neuronal scarring and damage or neural degeneration. A disease or medical disorder is considered to be nerve damage if the survival or function of nerve cells and/or their axonal processes is compromised. Such nerve damage occurs as the result of conditions including: physical injury, which causes, the degeneration of the axonal processes and/or nerve cell bodies near the site of the injury; ischemia, as a stroke; exposure to neurotoxins, such as the cancer and AIDS chemotherapeutic agents such as cisplatin and dideoxycytidine (ddC), respectively; chronic metabolic diseases, such as diabetes or renal dysfunction; and neurodegenerative diseases such as Parkinson's disease, Alzheimer's disease, and Amyotrophic Lateral Sclerosis (ALS), which cause the degeneration of specific neuronal populations. Conditions involving nerve damage include Parkinson's disease, Alzheimer's disease, Amyotrophic Lateral Sclerosis, stroke, diabetic polyneuropathy, toxic neuropathy, glial scar, and physical damage to the nervous system such as that caused by physical injury of the brain and spinal cord or crush or cut injuries to the arm and hand or other parts of the body, including temporary or permanent cessation of blood flow to parts of the nervous system, as in stroke.

In one embodiment, the disease or condition being treated is a neurodegenerative disorder, wherein the neurodegenerative disorder is selected from the group consisting of Alzheimer's disease, Parkinson's disease, Huntington's disease, motor neuron disease, Amyotrophic Lateral Sclerosis (ALS), dementia and cerebral palsy. In another embodiment, the disease or condition is selected from the group consisting of neural trauma or neural, injury. Methods of the invention also can be performed to treat or ameliorate the effects of neural trauma or injury, such as injury related to stroke, spinal cord injury, post-operative injury, brain ischemia and other traumas.

The invention can be used to treat one or more adverse consequences of central nervous system injury that arise from a variety of conditions. Thrombus, embolus, and systemic hypotension are among the most common causes of stroke. Other injuries may be caused by hypertension, hypertensive cerebral vascular disease, rupture of an aneurysm, an angioma, blood dyscrasia, cardiac failure, cardiac arrest, cardiogenic shock, kidney failure, septic shock, head trauma, spinal cord trauma, seizure, bleeding from a tumor, or other loss of blood volume or pressure. These injuries lead to disruption of physiologic function, subsequent death of neurons, and necrosis (infarction) of the affected areas. The term "stroke" connotes the resulting sudden and dramatic neurologic deficits associated with any of the foregoing injuries.

The terms "ischemia" or "ischemic episode," as used herein, means any circumstance that results in a deficient supply of blood to a tissue. Thus, a central nervous system ischemic episode results from an insufficiency or interruption in the blood supply to any locus of the brain such as, but not limited to, a locus of the cerebrum, cerebellum or brain stem.

The spinal cord, which is also a part of the central nervous system, is equally susceptible to ischemia resulting from diminished-blood flow. An ischemic episode may be caused by a constriction or obstruction of a blood vessel, as occurs in the case of a thrombus or embolus. Alternatively, the ischemic episode may result from any form of compromised cardiac function, including cardiac arrest, as described above. Where the deficiency is sufficiently severe and prolonged, it can lead to disruption of physiologic function, subsequent death of neurons, and necrosis (infarction) of the affected areas. The extent and type of neurologic abnormality resulting from the injury depend on the location and size of the infarct or the focus of ischemia. Where the ischemia is associated with a stroke, it can be either global or focal in extent.

Polypeptides and polynucleotide compositions of the invention will also be useful for treating traumatic injuries to the central nervous system that are caused by mechanical forces, such as a blow to the head. Trauma can involve a tissue insult selected from abrasion, incision, contusion, puncture, compression, etc., such as can arise from traumatic contact of a foreign object with any locus of or appurtenant to the mammalian head, neck or vertebral column. Other forms of traumatic injury can arise from constriction or compression of mammalian CNS tissue by an inappropriate accumulation of fluid (e.g., a blockade or dysfunction of normal cerebrospinal fluid or vitreous humour fluid production, turnover or volume regulation, or a subdural or intracranial hematoma or edema). Similarly, traumatic constriction or compression can arise from the presence of a mass of abnormal tissue, such as a metastatic or primary tumor.

It is further contemplated that methods of the invention directed to neurological indications can be practiced by co-administering a chimeric polypeptide of the present invention with a neurotherapeutic agent. By "neurotherapeutic agent" is meant an agent used in the treatment of neurodegenerative diseases or to treat neural trauma and neural injury. Exemplary neurotherapeutic agents include tacrine (Cognex), donepezil (Aricept), rivastigmine (Exelon), galantamine (Reminyl), and cholinesterase inhibitors and anti-inflammatory drugs, which are useful in the treatment of Alzheimer's disease as well as other neurodegenerative diseases.

Additional neurotherapeutic agents include anti-cholinergics, dopamine agonists, catechol-0-methyl-transterases (COMTs), amantadine (Symmetrel), Sinemet®, Selegiline, carbidopa, ropinirole (Requip), coenzyme Q10, Pramipexole (Mirapex) and levodopa (L-dopa), which are useful in the treatment of Parkinson's disease as well as other neurodegenerative diseases. Other therapeutics agents for the treatment of neurological disorders will be known to those of skill in the art and may be useful in the combination therapies contemplated herein.

F. VEGF/PDGF Receptors and Receptor Binding Assays

Abundant evidence demonstrates that the VEGF/PDGF family of growth factors exert their growth factor, cell maturation, cell migration, and other activities by binding and stimulating phosphorylation of cell surface receptor tyrosine kinases (RTKs). (Evidence indicates that a growth factor polypeptide dimer binds and stimulates a receptor dimer). Constructs of the invention that bind and stimulate phosphorylation of RTKs are useful as agonists of the RTKs. On the other hand, constructs that bind but fail to stimulate are useful as agonists of endogenous VEGF/PDGF growth factor activity. RTK binding properties of native growth factors are described below.

At least seven cell surface receptors that interact with PDGF/VEGF family members described above have been identified. These include PDGFR-α [See e.g., GenBank Acc. No. NM006206; Swiss Prot No. P16234], PDGFR-β [See e.g., GenBank Acc. No. NM002609; Swiss Prot. No. P09619], VEGFR-1/Flt-1 (fms-like tyrosine kinase-1;) [GenBank Acc. No. X51602; DeVries, et al., Science 255:989-991 (1992)]; VEGFR-2/KDR/Flk-1 (kinase insert domain containing receptor/fetal liver kinase-1) [GenBank Acc. Nos. X59397 (Flk-1) and L04947 (KDR); Terman, et al., Biochem. Biophys. Res. Comm. 187:1579-1586 (1992); Matthews, et al., Proc. Natl. Acad. Sci. USA 88:9026-9030 (1991)]; VEGFR-3/Flt4 (fms-like tyrosine kinase 4; sometimes referred herein as "R-3") [U.S. Pat. No. 5,776,755 and GenBank Acc. No. X68203 and S66407; Pajusola et al., Oncogene 9:3545-3555 (1994)], neuropilin-1 [Gen Bank Acc. No. NM003873], and neuropilin-2 [Gen Bank Acc. No. NM003872; SwissProt O60462]. The PDGF receptors -alpha and -beta mediate signaling of PDGFs.

VEGF121, VEGF165, VEGF-B, PlGF-1 and PlGF-2 bind VEGF-R1; VEGF121, VEGF145, VEGF165, (fully processed mature) VEGF-C, (fully processed mature). VEGF-D, VEGF-E, and NZ2 VEGF bind VEGFR-2; VEGF-C and VEGF-D bind VEGFR-3; VEGF165, VEGF-C, PlGF-2, and NZ2 VEGF bind neuropilin-1; and VEGF165 and VEGF-C binds neuropilin-2. [Neufeld, et al., FASEB. J. 13:9-22 (1999); Stacker and Achen, Growth Factors 17:1-11 (1999); Ortega, et al., Fron. Biosci. 4:141-152 (1999); Zachary, Intl. J. Biochem. Cell. Bio. 30:1169-1174 (1998); Petrova, et al., Exp. Cell. Res. 253:117-130 (1999); U.S. Pat. Appl. Pub. No. 20030113324]. PDGF-A, PDGF-B, and PDGF-C bind PDGFR-α. PDGF-B and PDGF-D bind PDGFR-β.

The expression of VEGFR-1 occurs mainly in vascular endothelial cells, although some may be present on monocytes, trophoblast cells, and renal mesangial cells [Neufeld et al., FASEB. J. 13:9-22 (1999)]. High levels of VEGFR-1 mRNA are also detected in adult organs, suggesting that VEGFR-1 has a function in quiescent endothelium of mature vessels not related to cell growth. VEGFR-1−/− mice die in utero between day 8.5 and 9.5. Although endothelial cells developed in these animals, the formation of functional blood vessels was severely impaired, suggesting that VEGFR-1 may be involved in cell-cell or cell-matrix interactions associated with cell migration. It has been demonstrated that mice expressing a mutated VEGFR-1, in which only the tyrosine kinase domain was missing, show normal angiogenesis and survival suggesting that the signaling capability of VEGFR-1 is not essential. [Neufeld, et al., FASEB. J. 13:9-22 (1999); Ferrara, J. Mol. Med. 77:527-543 (1999)].

VEGFR-2 expression is similar to that of VEGFR-1 in that it is broadly expressed in the vascular endothelium, but it is also present in hematopoietic stem cells, megakaryocytes, and retinal progenitor cells [Neufeld, et al., FASEB. J. 13:9-22 (1999)]. Although the expression pattern of VEGFR-1 and VEGFR-2 overlap extensively, evidence suggests that, in most cell types, VEGFR-2 is the major receptor through which most of the VEGFs exert their biological activities. Examination of mouse embryos deficient in VEGFR-2 further indicate that this receptor is required for both endothelial cell differentiation and the development of hematopoietic cells [Joukov, et al., J. Cell. Physiol. 173:211-215 (1997)].

VEGFR-3 is expressed broadly in endothelial cells during early embryogenesis. During later stages of development, the expression of VEGFR-3 becomes restricted to developing lymphatic vessels [Kaipainen, A., et al., Proc. Natl. Acad. Sci. USA 92:3566-70 (1995)]. In adults, the lymphatic endothelia and some high endothelial venules express VEGFR-3, and increased expression occurs in lymphatic sinuses in metastatic lymph nodes and in lymphangioma. VEGFR-3 is also expressed in a subset of CD34$^+$ hematopoietic cells which may mediate the myelopoietic activity of VEGF-C demonstrated by overexpression studies [WO 98/33917]. Targeted disruption of the VEGFR-3 gene in mouse embryos leads to failure of the remodeling, of the primary vascular network, and death after embryonic day 9.5 [Dumont, et al., Science 282:946-49 (1998)]. These studies suggest an essential-role for VEGFR-3 in the development of the embryonic vasculature, and also during lymphangiogenesis.

Neuropilin-1 was originally cloned as a receptor for the collapsin/semaphorin family of proteins involved in axon guidance [Stacker and Achen, Growth Factors 17:1-11 (1999)]. It is expressed in both endothelia and specific subsets of neurons during embryogenesis, and it thought to be involved in coordinating the developing neuronal and vascular system. Although activation of neuropilin-1 does not appear to elicit biological responses in the absence of the VEGF family tyrosine-kinase receptors, their presence on cells leads to more efficient binding of VEGF165 and VEGFR-2 mediated responses. [Neufeld, et al., FASEB. J. 13:9-22 (1999)] Mice lacking neuropilin-1 show abnormalities in the developing embryonic cardiovascular system. [Neufeld, et al., FASEB. J. 13:9-22 (1999)]

Neuropilin-2 was identified by expression cloning and is a collapsin/semaphorin receptor closely related to neuropilin-1. Neuropilin-2 is an isoform-specific VEGF receptor in that it only binds VEGF165. Like neuropilin-1, neuropilin-2 is expressed in both endothelia and specific neurons, and is not predicted to function independently due to its relatively short intracellular domain. The function of neuropilin-2 in vascular development is unknown [Neufeld, et al., FASEB. J. 13:9-22 (1999); WO 99/30157]. NP-2 is mainly expressed in the lymphatic system and is also expressed at low levels in veins (Karpanen et al., FASEB J., 20:1462-1472 (2006).

PDGF-A, PDGF-B, PDGF-C, and PDGF-D bind and activate, with distinct selectivity, dimeric complexes of the receptor tyrosine kinases PDGFR-α and PDGFR-β. [Heldin, C. H. & Westermark, B. *Physiol Rev* 79, 1283-1316 (1999).] PDGFR-α expression on cardiac vascular endothelial cells has been reported to be involved in the local communication among distinct cells in the heart [Edelberg, et al., *J. Clinical Inves.* 102:837-43 (1998)]. The PDGFs regulate cell proliferation, cell survival and chemotaxis of many cell types in vitro (reviewed in [Heldin et al., Biochimica et Biophysica Acta 1378:F79-113 (1998); Carmeliet P et al. Nature 380, 435-9 (1996); Hellström, M. et al. *J Cell Biol* 153, 543-53. (2001).] PDGF-A and PDGF-B can homodimerize or heterodimerize to produce three different isoforms: PDGF-AA, PDGF-AB, or PDGF-BB. PDGF-A is only able to bind the PDGF α-receptor (PDGFR-α including PDGR-α/α homodimers). PDGF-B can bind both the PDGFR-α and PDGFR-β. More specifically, PDGF-B can bind to PDGFR-α/α and PDGFR-β/β homodimers, as well as PDGFR-α/β heterodimers. PDGF-C binds PDGR-α/α homodimers and PDGF-D binds PDGFR-β/β homodimers and both have been reported to bind PDGFR-α/β heterodimers.

Both the ligands and the receptors generally exist as dimers, including both homodimers and heterodimers. Such dimers can influence binding. For example, for the PDGFs, PDGF-AA binds PDGFR-α/α. PDGF-AB and PDGF-CC bind PDGFR-α/α and PDGFR-α/β. PDGFR-BB binds both of the homodimers and the heterodimeric PDGF receptor. PDGF-DD binds PDGF receptor heterodimers and beta receptor homodimers. [See, e.g., Pietras, et al., Cancer Cell, 3:439-443 (2003).] VEGF-A can heterodimerize with VEGF-B and PlGF. The VEGFs, PDGFs, and PlGFs, may exist as two or more isoforms, e.g., splice variants, and not all isoforms of a particular growth factor will share the same binding profile, or ability to dimerize with particular molecules. Certain isoforms of the same growth factor may also dimerize with each other. For example the 167 and 186 isoforms of VEGF-B can heterodimerize with each other.

Receptor binding assays for determining the binding of such chimeric molecules to one or more of VEGF/PDGF receptors are well-known in the art. Examples of such receptor binding assays are taught in e.g., U.S. patent application Ser. No. 09/795,006, WO 01/62942; Thuringer et al., J. Biol. Chem., 277:2028-2032 (2002) and Cao et al., FASEB J., 16:1575-1583 (2002) each incorporated herein by reference. (See, e.g., Example 3 of U.S. patent application Ser. No. 09/795,006, and WO 01/62942, which details binding assays of VEGF-C and related VEGF receptor ligands to soluble VEGF receptor Fc fusion proteins. Example 5 of those documents details analyses of receptor activation or inhibition by such ligands. Example 6 describes analyses of receptor binding affinities of such ligands. In addition, Achen et al., Proc Natl Acad Sci USA 95:548 53 (1998), incorporated by reference in its entirety, teaches exemplary binding assays. Thuringer et al., J. Biol. Chem., 277:2028-2032 (2002) details binding assays (activation and inhibition) for VEGF-A to VEGFR-2. Binding assays for PDGFR-α and PDGFR-β are described in Cao et al., FASEB J., 16:1575-1583 (2002). The binding of the chimeric VEGF polypeptides described above to VEGFR-1 and VEGFR-2 may be analyzed using such exemplary assays.

It will be appreciated that such binding assays can be performed with any form of naturally occurring VEGF/PDGF receptors that retain the ability to bind their respective ligands, including but not limited to whole cells that naturally express a receptor or that have been recombinantly modified to express the receptor; truncated, solubilized extracellular ligand binding domains of receptors; fusions comprising receptor extracellular domains fused to other proteins such as alkaline phosphatase (e.g., VEGF R-2 AP described in Cao et al., J. Biol. Chem. 271:3154-62, 1996) or immunoglobulin sequences; and fusions comprising receptor extracellular domains fused to tag sequences (e.g., a polyhistidine tag) useful for capturing the protein with an antibody or with a solid support; and receptor extracellular domains chemically attached to solid supports such as CNBr activated Sepharose beads. Exemplary receptor binding assays may be performed according to the method set forth in Example 3 of e.g., U.S. patent application Ser. No. 09/795,006, and WO 01/62942, each incorporated herein by reference.

a) Analysis of Receptor Activation or Inhibition by the Chimeric VEGF Proteins.

In another set of assays, the chimeric polypeptides of the present invention are evaluated for therapeutic applications where either activation or inhibition of one or more VEGF receptors is desired. For example, a candidate chimeric protein can be added to stable cell lines expressing a particular VEGF receptor whose activation is necessary for cell survival. Survival of the cell line indicates that the candidate chimeric polypeptide protein is able to bind and activate that particular VEGF receptor. On the other hand, death of the cell line indicates that the candidate chimeric polypeptide fails to activate the receptor. Exemplary examples of such cell survival assays have been described in International Patent Publication No. WO 98/07832 and in Achen et al., Proc Natl Acad Sci USA 95:548 553 (1998), incorporated herein by reference. This assay employs Ba/F3 NYK EpoR cells, which are Ba/F3 pre B cells that have been transfected with a plasmid encoding a chimeric receptor consisting of the extracellular domain of VEGFR-2 and the cytoplasmic domain of the erythropoietin receptor (EpoR). These cells are routinely passaged in interleukin-3 (IL-3) and will die in the absence of IL-3. However, if signaling is induced from the cytoplasmic domain of the chimeric receptor, these cells survive and proliferate in the absence of IL-3. Such signaling is induced by ligands which bind to the VEGFR-2 extracellular domain of the chimeric receptor. For example, binding of VEGF-A or VEGF-D to the VEGFR-2 extracellular domain causes the cells to survive and proliferate in the absence of IL-3. Parental Ba/F3 cells which lack the chimeric receptor are not induced by either VEGF-A or VEGF-D to proliferate in the absence of IL-3, indicating that the responses of the Ba/F3-NYK-EpoR cells to these ligands are totally dependent on the chimeric receptor.

Candidate chimeric polypeptides of the present invention can be tested for binding to the VEGFR-2 extracellular domain and subsequent activation of a chimeric receptor by assaying cell survival in the absence of IL-3. On the other hand, chimeric polypeptides that interfere with the binding of VEGFR-2 ligands, such as VEGF-A or VEGF-D, to the extracellular domain, or with the activation of the cytoplasmic domain, will cause cell death in the absence of IL-3.

b) VEGFR-1 (flt1), VEGFR-2 (KDR), VEGFR-3 (Flt4), PDGFR-α and PDGFR-β Autophosphorylation Assays.

As an alternative indicator of activity, the ability of a chimeric polypeptide of the invention to stimulate autophosphorylation of a particular VEGF or PDGF receptor can also be examined. A candidate chimeric polypeptide is added to cells expressing a particular VEGF or PDGF receptor. The cells are then lysed and immunoprecipitated with anti-VEGF or anti-PDGF receptor antiserum and analyzed by Western blotting using anti phosphotyrosine antibodies to determine chimeric polypeptide induced phosphorylation of the VEGF or PDGF receptor.

The ability of a chimeric polypeptide to stimulate autophosphorylation (detected using the anti phosphotyrosine antibodies) is scored as stimulating the receptor. The level of stimulation observed for various concentrations of chimeric polypeptide, relative to known concentrations of VEGF and PDGF molecules, provide an indication of the potency of receptor stimulation. Polypeptides that have been shown to bind the receptor, but are incapable of stimulating receptor phosphorylation, are scored as inhibitors. Inhibitory activity can be further assayed by mixing a known receptor agonist such as recombinant VEGF-A or VEGF-C with either media alone or with concentrated conditioned media, to determine if the concentrated conditioned media inhibits VEGF-A mediated or VEGF-C-mediated receptor phosphorylation.

c) Assays for Neuropilin Binding.

Results indicate that NRP-1 is a co-receptor for $VEGF_{165}$ binding, forming a complex with VEGFR-2, which results in enhanced $VEGF_{165}$ signaling through VEGFR-2, over $VEGF_{165}$ binding to VEGFR-2 alone, thereby enhancing the biological responses to this ligand (Soker et al., Cell 92: 735-45. 1998). A similar phenomenon may apply to VEGF-C signaling via possible VEGFR-3/NRP-2 receptor complexes. The compositions of the present invention are tested using neuropilin binding assays. Exemplary such assays are described in detail in e.g., U.S. patent application Ser. No. 10/669,176, filed Sep. 23, 2003, U.S. Pat. Nos. 6,428,965 and 6,515,105.

Such assays may employ cells transformed with expression constructs that encode neuropilins. Antibodies and reagents that can be used in neuropilin binding assays are well known to those of skill in the art. See for example, Sema3A-AP which recognizes neuropilin. Competitive binding assays using Sema3 AP and the compositions of the invention demonstrate whether the compositions described herein possess neuropilin binding activity.

d) Analysis of Receptor Binding Affinities of Chimeric Polypeptides.

The chimeric polypeptides of the present invention may bind more than one VEGFR. Assays may be performed to determine that receptor binding activity of these chimeric polypeptides. For such experiments, the chimeric polypeptide may be expressed in an insect cell system, e.g., SF9 cells, to eliminate contamination with endogenous VEGF-A found in mammalian cells. To measure the relative binding affinities of selected chimeric polypeptide, an ELISA type approach is used. For example, to examine binding affinity for VEGFR-2, serial dilutions of competing VEGFR-2 IgG fusion proteins and a subsaturating concentration of the candidate chimeric polypeptide tagged with the myc epitope is added to microtitre plates coated with VEGFR-2, and incubated until equilibrium is established. The plates are then washed to remove unbound proteins. Chimeric polypeptide molecules that remain bound to the VEGFR-2 coated plates are detected using an anti-myc antibody conjugated to a readily detectable label e.g., horseradish peroxidase. Binding affinities (EC50) can be calculated as the concentration of competing VEGFR IgG fusion protein that results in half maximal binding. These values can be compared with those obtained from analysis of VEGF-A or VEGF-C to determine changes in binding affinity of one or more of the VEGFRs. Similarly, binding to VEGFR-3 is accomplished by using a VEGFR-3 IgG fusion protein, and binding to VEGFR-1 is determined using a VEGFR-1 IgG fusion protein.

G. Pharmaceutical Formulations and Routes of Administration

Polypeptides and/or polynucleotides of the invention may be administered in any suitable manner using an appropriate pharmaceutically acceptable vehicle, e.g., a pharmaceutically acceptable diluent, adjuvant, excipient or carrier. Liquid, semisolid, or solid diluents that serve as pharmaceutical vehicles, excipients, or media are preferred. Any diluent known in the art may be used. Exemplary diluents include, but are not limited to, water, saline solutions, polyoxyethylene sorbitan monolaurate, magnesium stearate, methyl and propylhydroxybenzoate, talc, alginates, starches, lactose, sucrose, dextrose, sorbitol, mannitol, glycerol, calcium phosphate, mineral oil, and cocoa butter. Such formulations are useful, e.g., for administration of polypeptides or polynucleotides of the invention to mammalian (including human) subjects in therapeutic regimens.

The composition to be administered according to methods of the invention preferably comprises (in addition to the polynucleotide or vector) a pharmaceutically acceptable carrier solution such as water, saline, phosphate buffered saline, glucose, or other carriers conventionally used to deliver therapeutics intravascularly. Multi gene therapy is also contemplated, in which case the composition optionally comprises both the polynucleotide of the invention/vector and another polynucleotide/vector selected to prevent restenosis or other disorder mediated through the action of a VEGF receptor. Exemplary candidate genes/vectors for co-transfection with transgenes encoding polypeptides of the invention are described in the literature cited above, including genes encoding cytotoxic factors, cytostatic factors, endothelial growth factors, and smooth muscle cell growth/migration inhibitors.

The "administering" that is performed according to the present method may be performed using any medically-accepted means for introducing a therapeutic directly or indirectly into the vasculature of a mammalian subject, including but not limited to injections (e.g., intravenous, intramuscular, subcutaneous, or catheter); oral ingestion; intranasal or topical administration; and the like. In a preferred embodiment, administration of the composition comprising a polynucleotide of the invention is performed intravascularly, such as by intravenous, intra-arterial, or intracoronary arterial injection. The therapeutic composition may be delivered to the patient at multiple sites. The multiple administrations may be rendered simultaneously or may be administered over a period of several hours. In certain cases it may be beneficial to provide a continuous flow of the therapeutic composition. Additional therapy may be administered on a period basis, for example, daily, weekly or monthly. To minimize angiogenic side effects in non-target tissues, preferred methods of administration are methods of local administration, such as administration by intramuscular injection.

In general, peroral dosage forms for the therapeutic delivery of polypeptides is ineffective because in order for such a formulation to the efficacious, the peptide must be protected from the enzymatic environment of the gastrointestinal tract. Additionally, the polypeptide must be formulated such that it is readily absorbed by the epithelial cell barrier in sufficient concentrations to effect a therapeutic outcome. The chimeric polypeptides of the present invention may be formulated with uptake or absorption enhancers to increase their efficacy. Such enhancer include for example, salicylate, glycocholate/linoleate, glycholate, aprotinin, bacitracin, SDS caprate and the like. An additional detailed discussion of oral formulations of peptides for therapeutic delivery is found in Fix, J. Pharm. Sci., 85(12) 1282 1285, 1996, and Oliyai and Stella, Ann. Rev. Pharmacol. Toxicol., 32:521 544, 1993, both incorporated by reference.

The amounts of peptides in a given dosage will vary according to the size of the individual to whom the therapy is being administered as well as the characteristics of the disorder being treated. In exemplary treatments, it may be necessary to administer about 50 mg/day, 75 mg/day, 100 mg/day, 150 mg/day, 200 mg/day, 250 mg/day. These concentrations may be administered as a single dosage form or as multiple doses.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100 fold) due to the presence of infection-defective particles.

The polypeptides may also be employed in accordance with the present invention by expression of such polypeptide in vivo, which is often referred to as gene therapy. The present invention provides a recombinant DNA vector containing a heterologous segment encoding a chimeric polypeptide of the invention that is capable of being inserted into a microorganism or eukaryotic cell and that is capable of expressing the encoded chimeric protein.

In a preferred embodiment, the composition is administered locally. Thus, in the context of treating restenosis or stenosis, administration directly to the site of angioplasty or bypass is preferred. For example, the administering comprises a catheter mediated transfer of the transgene containing composition into a blood vessel of the mammalian subject, especially into a coronary artery of the mammalian subject. Exemplary materials and methods for local delivery are reviewed in Lincoff et al., Circulation, 90: 2070 2084 (1994); and Wilensky et al., Trends Cardiovasc. Med., 3:163.170 (1993), both incorporated herein by reference. For example, the composition is administered using infusion perfusion balloon catheters (preferably microporous balloon catheters) such as those that have been described in the literature for intracoronary drug infusions. See, e.g., U.S. Pat. No. 5,713,860 (Intravascular Catheter with Infusion Array); U.S. Pat. No. 5,087,244; U.S. Pat. No. 5,653,689; and Wolinsky et al., J. Am. Coll. Cardiol., 15: 475 481 (1990) (Wolinsky Infusion Catheter); and Lambert et al., Coron. Artery Dis., 4: 469 475 (1993), all of which are incorporated herein by reference in their entirety. Use of such catheters for site directed somatic cell gene therapy is described, e.g., in Mazur et al., Texas Heart Institute Journal, 21; 104 111 (1994), incorporated herein by reference. In an embodiment where the transgene encoding a chimeric polypeptide of the invention is administered in an adenovirus vector, the vector is preferably administered in a pharmaceutically acceptable carrier at a dose of $10^7$ to $10^{13}$ viral particles, and more preferably at a dose of $10^9$ to $10^{11}$ viral particles. The adenoviral vector composition preferably is infused over a period of 15 seconds to 30 minutes, more preferably 1 to 10 minutes.

For example, in patients with angina pectoris due to a single or multiple lesions in coronary arteries and for whom PTCA is prescribed on the basis of primary coronary angiogram findings, an exemplary protocol involves performing PTCA through a 7F guiding catheter according to standard clinical practice using the femoral approach. If an optimal result is not achieved with PTCA alone, then an endovascular stent also is implanted. (A nonoptimal result is defined as residual stenosis of >30% of the luminal diameter according to a visual estimate, and B or C type dissection.) Arterial gene transfer at the site of balloon dilatation is performed with a replication deficient adenoviral vector expressing a polypeptide of the invention immediately after the angioplasty, but before stent implantation, using an infusion perfusion balloon catheter. The size of the catheter will be selected to match the diameter of the artery as measured from the angiogram, varying, e.g., from 3.0 to 3.5F in diameter. The balloon is inflated to the optimal pressure and gene transfer is performed during a 10 minute infusion at the rate of 0.5 ml/min with virus titer of $1.15 \times 10^{10}$ pfu/ml.

In another embodiment, intravascular administration with a gel coated catheter is contemplated, as has been described in the literature to introduce other transgenes. See, e.g., U.S. Pat. No. 5,674,192 (Catheter coated with tenaciously adhered swellable hydrogel polymer); Riessen et al., Human Gene Therapy, 4: 749 758 (1993); and Steg et al., Circulation, 96: 408.411 (1997) and 90: 1648 1656 (1994); all incorporated herein by reference. Briefly, DNA in solution (e.g., a polynucleotide of the invention) is applied one or more times ex vivo to the surface of an inflated angioplasty catheter balloon coated with a hydrogel polymer (e.g., Slider with Hydroplus, Mansfield Boston Scientific Corp., Watertown, Mass.). The Hydroplus coating is a hydrophilic polyacrylic acid polymer that is cross linked to the balloon to form a high molecular weight hydrogel tightly adhered to the balloon. The DNA covered hydrogel is permitted to dry before deflating the balloon. Re-inflation of the balloon intravascularly, during an angioplasty procedure, causes the transfer of the DNA to the vessel wall.

In yet another embodiment, an expandable elastic membrane or similar structure mounted to or integral, with a balloon angioplasty catheter or stent is employed to deliver the transgene encoding a polypeptide of the invention. See, e.g., U.S. Pat. Nos. 5,707,385, 5,697,967, 5,700,286, 5,800,507, and 5,776,184, all incorporated by reference herein.

In yet another embodiment, the composition containing the polypeptides or polynucleotides of the invention are administered by intramuscular injection. See e.g., Shyu et al., Am. J. Med., 114:85-92 (2002); Freedman et al., Hum. Gene Ther., 13:1595-1603 (2002).

The polypeptides and polynucleotides of the invention can be administered by a transdermal patch. The thickness of the transdermal patch depends on the therapeutic requirements and may be adapted accordingly. Transdermal patches represent an alternative to the liquid forms of application. These devices can come in a variety of forms, all having the capability of adhering to the skin, and thereby permitting prolonged contact between the therapeutic composition and the target area. They also have the advantage of being relatively compact and portable, and permitting very precise delivery of a composition to the area to be treated. These patches come in a variety of forms, some containing fluid reservoirs for the active component, others containing dry ingredients that are released upon contact with moisture in the skin. Many require some form of adhesive to retain them in connection with the skin for an adequate period. A different type of patch is applied dry, with water applied to wet the patch to form a sticky film that is retained on the skin As used herein "patch" comprises at least a topical composition according to the invention and a covering layer, such that, the patch can be placed over a surgically closed wound, incision, skin flap, skin graft, or burn, thereby positioning the patch/composition adjacent to the compromised tissue surface. Preferably, the patch is designed to maximize composition delivery through the stratum corneum, upper epidermis, and into the dermis, and to minimize absorption into the circulatory system, reduce lag time, promote uniform absorption, and reduce mechanical rub-off.

Preferred patches include (1) the matrix type patch; (2) the reservoir type patch; (3) the multi-laminate drug-in-adhesive type patch; and (4) the monolithic drug-in-adhesive type patch; (Ghosh, T. K., et al., *Transdermal and Topical Drug Delivery Systems*, Interpharm Press, Inc. p. 249-297 (1997) incorporated herein by reference). These patches are well known in the art and generally available commercially.

In another embodiment, a dressing for the delivery of a composition comprising the polypeptides or polynucleotides of the invention is provided. The term "dressing", as used herein, means a covering designed to protect and or deliver a (previously applied) composition. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the pain site, which provides for greater comfort.

In another embodiment, a surgical suturing thread impregnated with the polypeptides or polynucleotides of the invention is provided.

In another variation, the composition containing the transgene encoding a polypeptide of the invention is administered extravascularly, e.g., using a device to surround or encapsulate a portion of vessel. See, e.g., International Patent Publication WO 98/20027, incorporated herein by reference, describing a collar that is placed around the outside of an artery. (e.g., during a bypass procedure) to deliver a transgene to the arterial wall via a plasmid or liposome vector.

In still another variation, endothelial cells or endothelial progenitor cells are transfected ex vivo with the transgene encoding a polypeptide of the invention, and the transfected cells as administered to the mammalian subject. Exemplary procedures for 10: seeding a vascular graft with genetically modified endothelial cells are described in U.S. Pat. No. 5,785,965, incorporated herein by reference.

Other non-viral delivery mechanisms contemplated include calcium phosphate precipitation (Graham and Van Der Eb, Virology, 52:456-467, 1973; Chen and Okayama, Mol. Cell. Biol., 7:2745-2752, 1987; Rippe et al., Mol. Cell. Biol., 10:689-695, 1990) DEAE-dextran (Gopal, Mol. Cell. Biol., 5:1188-1190, 1985), electroporation (Tur-Kaspa et al., Mol. Cell. Biol., 6:716-718, 1986; Potter et al., Proc. Nat. Acad. Sci. USA, 81:7161-7165, 1984), direct microinjection (Harland and Weintraub, J. Cell Biol., 101:1094-1099, 1985.), DNA-loaded liposomes (Nicolau and Sene, Biochim. Biophys. Acta, 721:185-190, 1982; Fraley et al., Proc. Natl. Acad. Sci. USA, 76:3348-3352, 1979; Feigner, Sci Am. 276 (6):102 6, 1997; Feigner, Hum Gene Ther. 7(15):17913, 1996), cell sonication (Fechheimer et al., Proc. Natl. Acad. Sci. USA, 84:8463-8467, 1987), gene bombardment using high velocity microprojectiles (Yang et al., Proc. Natl. Acad. Sci. USA, 87:9568-9572, 1990), and receptor-mediated transfection (Wu and Wu, J. Biol. Chem., 262:4429-4432, 1987; Wu and Wu, Biochemistry, 27:887-892, 1988; Wu and Wu, Adv. Drug Delivery Rev., 12:159-167, 1993).

The expression construct (or the polypeptide construct itself) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: Liver diseases, targeted diagnosis and therapy using specific receptors and ligands, Wu G, Wu C ed., New York: Marcel Dekker, pp. 87-104, 1991). The addition of DNA to cationic liposomes causes a topological transition from liposomes to optically birefringent liquid-crystalline condensed globules (Radler et al., Science, 275(5301):8104, 1997). These DNA-lipid complexes are potential non-viral vectors for use in gene therapy and delivery.

Liposome-mediated nucleic acid delivery and expression of foreign DNA in vitro has been successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda et al., Science, 243:375-378, 1989). In other embodiments, the liposome may be complexed or employed in conjunction with nuclear nonhistone chromosomal proteins (HMG-1) (Kato et al., J. Biol. Chem., 266:3361-3364, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, supra).

In other embodiments, the delivery vehicle may comprise a ligand and a liposome. For example, Nicolau et al. (Methods Enzymol., 149:157-176, 1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky et al. (Proc. Nat. Acad. Sci. USA, 81:7529-7533, 1984) successfully injected polyomavirus DNA in the form of CaPO4 precipitates into liver and spleen of adult and newborn mice demonstrating active viral replication and acute infection. Benvenisty and Neshif (Proc. Nat. Acad. Sci. USA, 83:9551-9555, 1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., Nature, 327:70-73, 1987). Several devices for accelerating small particles have been developed. One such device relies on a high voltage discharge to generate an electrical current, which in turn provides the motive force (Yang et al., Proc. Natl. Acad. Sci. USA, 87:9568-9572, 1990). The microprojectiles used have consisted of biologically inert substances such as tungsten or gold beads.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the invention.

Similarly, the invention includes kits which comprise compounds or compositions of the invention packaged in a manner which facilitates their use to practice methods of the invention. In a simplest embodiment, such a kit includes a compound or composition described herein as useful for practice of the invention (e.g., polynucleotides or polypeptides of the invention), packaged in a container such as a sealed bottle or vessel, with a label affixed to the container or included in the package that describes use of the compound or composition to practice the method of the invention. Preferably, the compound or composition is packaged in a unit dosage form. In another embodiment, a kit of the invention includes a composition of both a polynucleotide or polypeptide packaged together with a physical device useful for implementing methods of the invention, such as a stent, a catheter, an extravascular collar, a polymer film, a bandage, a suture or the like. In another embodiment, a kit of the invention includes compositions of both a polynucleotide or polypeptide of the invention packaged together with a hydrogel polymer, or microparticle polymers, or other carriers described herein as useful for delivery of the polynucleotides or polypeptides to the patient:

Example 1

VEGF-CAC Chimeric Construct

The present example describes the generation of a chimeric polypeptide molecule designated VEGF-CAC (or simply "CAC") comprising amino- and carboxy-terminal VEGF-C propeptides (flanking domains of the invention) fused to a VEGF-A receptor tyrosine kinase (RTK) binding domain. An encoding polynucleotide was generated to express the VEGF-CAC recombinantly.

Cloning: A polynucleotide encoding the CAC fusion protein was produced by PCR amplification and subcloning of the N-terminus and C-terminus from a human VEGF-C cDNA and the RTK binding domain of a human VEGF-A cDNA. A His-tag was added to the C-terminal end and an $IgG_K$ signal peptide was added to the N-terminal end. The resulting cDNA (SEQ ID NO. 26) was sequenced and encoded the amino acid sequence set forth in SEQ ID NO: 27. This cDNA was inserted into the pSecTagI-ACAswap vector as a BamHI-NotI fragment. For transient transfections and binding assays, the K14-promoter was removed from the construct. The VEGF-CAC polynucleotide was cut with restriction enzymes AgeI and ClaI, blunted and ligated into psub-CMV-WPRE plasmid.

Transfection and immunopreopitation. The secretion and processing of the recombinant protein was analyzed by transfection into 293T cells, which were then labeled with radioactive amino acids. 293T cells were transfected with psub-CMV/CAC or the pEBS7/psub:CMV vector using liposomes (FuGENE 6, Roche) or cationic polymers (jetPEI, Qbiogene). Transfected cells were cultured for 24 or 48 hours, and were then metabolically labeled in methionine-free and cysteine-free modified Eagle medium supplemented with [$^{35}$S] methionine/[$^{35}$S]cysteine (Promix, Amersham Pharmacia Biotech) at 100 µCi/mL for 8 h. Conditioned medium was then harvested, cleared of particulate material by centrifugation and incubated with soluble receptor extracellular domain-immunoglobulin fusions VEGFR1-Ig, VEGFR2-Ig, VEGFR3-Ig; anti-VEGF-A antibody (R&D); anti-VEGF-C antibody (R&D); and polyclonal antibodies against VEGF-C (Joukov et al., Embo J 16: 3898-911, 1997). The formed antigen-antibody and ligand-receptor-Ig complexes were bound to protein A-Sepharose and protein-G-Sepharose (Pharmacia Biotech) respectively, which were then washed twice with 0.5% bovine serum albumin/0.02% Tween 20 in phosphate-buffered saline (PBS) and once with PBS, and analyzed in sodium dodecyl sulfate-polyacrilamide gel electrophoresis (SDS-PAGE) under reducing conditions. Also unreduced samples were made from some bindings. It was determined that media from transfected cells expressing psub-CMV/CAC and psub-CMV/VEGF-A165 activated VEGFR-1 and VEGFR-2 in similar dilutions, but did not activate VEGFR-3.

Bioassay for growth factor-mediated cell survival: 293T cells expressing psub-CMV/CAC were seeded in 96-well plates at 15,000 cells/well in triplicates supplied with conditioned medium (0, 1, 5, 10 or 20 µl) as described in commonly, owned PCT Application No. PCT/US2004/019122 or the pREP7 vector. Cell viability was measured by a colorimetric assay. MTT (3-(4,5-dimethylthiazol-2-yl)-2,5-diphenyl tetrazolium bromide (Sigma), 0.5 mg/ml) was added into each well and incubated for 4 h at 37° C. The reaction was terminated by adding 100 µl of lysis buffer (10% SDS, 10 mM HCl), and the resulting formazan products were solubilized overnight at 37° C. in a humid atmosphere. The absorbance at 540 nm was measured with a Multiscan microtiter plate reader (Labsystems).

The chimeric VEGF-CAC polypeptide was produced as described, and the secretion and processing of the resulting protein was analyzed by transfection into 293T cells, which were then labeled with radioactive amino acids. The conditioned media were immunoprecipitated with anti-VEGF-C or anti-VEGF-A antibodies or soluble VEGFR-1. Under non-reducing conditions the VEGF-CAC polypeptides had apparent molecular weights of 94 kDa, 66 kDa, while VEGF-C migrated at 58 kDa. The VEGF growth factor domain migrated as a doublet at 56 kDa and 50 kDa.

For pulse chase analysis, VEGF-CAC and VEGF-C transfected 293T cells were labeled for 30 minutes with radioactive amino acids and then chased in non-radioactive growth medium for 30 minutes, 6 hours and 24 hours. Conditioned media were immunoprecipitated with anti-VEGF-C antibodies and analyzed in SDS-PAGE. Gel electrophoresis indicated secretion of a major 66 kDa form of VEGF-CAC and 68 kDa doublet for VEGF-C, as expected (Joukov et al., Embo J., 16:3898-3911, 1997). These were cleaved after a 30 minute chase period to doublets of about 30 kDa. The unprocessed 66 kDa form was no longer detected at 24 hours, whereas at this timepoint, small amounts of the 20 kD mature forms containing the growth factor domain were also generated from both polypeptides. To conclude, the processing of VEGF-CAC occurred similarly to the processing of wild-type VEGF-C, with each propeptide apparently being cleaved in the order C-terminal, then N-terminal.

Example 2

VEGF-CDD, VEGF-CDC and VEGF-DDC Chimeric Constructs

The present example describes the generation of chimeric polynucleotide and polypeptide molecules designated VEGF-CDD, VEGF-CDC and VEGF-DDC, comprising various combinations of amino- and carboxy-terminal of VEGF-C or VEGF-D propeptides fused to a VEGF-D receptor tyrosine kinase binding domain.

A polynucleotide encoding the CDD chimeric (SEQ ID NOs: 36 and 37) protein combining the N-terminal propeptide of human VEGF-C with the VEGF homology domain (VHD) of VEGF-D and the C-terminal propeptide of human VEGF-D was constructed via PCR using the primers 5'-GCGGATCCGTTCGAGTC CGGACTCGACCTCTCG-GAC-3' (SEQ ID NO: 28) (Primer I, containing Barn HI site) and 5'CTTTTAGTGTTTCAA TGTCATAGAAAGTTG-CAGCAAATTTTAT AGTCTCTTCTGTCCTTGAGTTG AGG-3' (SEQ ID NO: 29) to amplify the $F_N$ of human VEGF-C and the primers 5'-GGACAGAAGAGAC-TATAAAATTT GCTGCAACTTTCTATGACATTGA AACACTAAAAGTTATAGATGAAG AATGGCA-3' (SEQ ID NO: 30) and 5'-CGGATCCTCAAGGATTCTTTCGGCT GTGGGGCC-3' (SEQ ID NO: 31) (Primer II, containing a BamHI site) to amplify the VHD and CT of human VEGF-D. These PCR fragments were annealed and used as a template to amplify the CDD chimera with the primers I and II, the obtained PCR fragment was ligated into pCRII vector (Invitrogen), excised with BamHI and ligated into the BamHI site of the pSecTaqI vector in frame with the signal sequence.

A polynucleotide encoding the DDC chimeric (SEQ ID NOs: 40 and 41) protein containing the N-terminal propeptide and the VEGF homology domain of human VEGF-D combined to the C-terminal propeptide of human VEGF-C was constructed via PCR using the primers 5'-GCGGATC-CGTCCAGTAATGAACA TGGACCAGTGAGGCGA TCATC-3' (SEQ ID NO: 32) (Primer III, containing a Barn HI site) and 5'GCCTGACACTGTGGTAGTGTTGCTG-GCAGGGATCTT CTGATAATT GAGTATGGATG-GCGGGGGG-3' (SEQ ID NO: 33) to amplify the AT and the VHD of human VEGF-D and the primers 5'-GCCATCCAT-ACTCA ATTATCAGAAGATCCCTGCCAGCA ACAC-TACCACAGTGTCAG-3' (SEQ ID NO: 34) and 5'-GCG-GATCC TTAGCTCATTTGTGGTCTTTTCCAATATGA AGGGAC ACAAC-3' (SEQ ID NO: 35) (Primer IV, containing a BamHI site) to amplify the $F_N$ of human VEGF-C. These PCR fragments were annealed and used as a template to amplify the DDC chimera with the primers III and IV, the obtained PCR fragment was ligated into pCRII vector (Invitrogen), excised with BamHI and ligated into the BamHI site of the pSecTaqI vector in frame with the signal sequence.

The cDNA for the CDC chimeric (SEQ ID NOs: 38 and 39) protein was constructed by ligating the 954 bp NdeI-EcoRV fragment of the CDD/pSecTaqI to the NdeI (in the CMV promoter sequence) and EcoRV (in the VHD of VEGF-D) cut DDC/pSecTaqI plasmid.

Transfection and Metabolic Labeling 293T cells were transfected with DDC/pSecTaqI, CDC/pSecTaqI or CDD/pSecTaqI plasmids using the JetPEI transfection reagent. 48 hours after transfection the cells were washed twice with PBS and metabolically labeled in MEM medium containing 100 µCi/ml 35S-methionine and 35S-cysteine (Promix, Amersham) and 10 U/ml heparin overnight. Plasmids coding for neuropilin-1-Ig (Makinen et. al., J Biol Chem 274 (1999): 21217-21222) or neuropilin-2-Ig (Karkkainen et. al., PNAS 98 (2001): 12677-12682) were similarly transfected to 293T cells and 48 hours after transfection the cells were washed and the Ig-fusion proteins were produced into starvation medium. The conditioned media was harvested and cleared by centrifugation.

The conditioned media was supplemented with BSA and Tween 20 to final concentrations of 0.5% and 0.02%, respectively. The CDD, CDC and DDC chimeras were bound either with 200 ng of VEGFR-1-Ig (Mäkinen et. al., Nat Med 7 (2001): 199-205), VEGFR-2-Ig (Uutela et. al., Blood 104 (2004): 3198-3204) or VEGFR-3-Ig (Makinen et. al., Nat Med 7 (2001): 199-205) fusion proteins or with the NP-1-Ig or NP-2-Ig conditioned media. The complexes were then precipitated with protein A-Sepharose and washed three times with 1× binding buffer (0.5% BSA, 0.02% Tween20 in PBS) and once with PBS at 4° C. The proteins were analyzed by SDS-PAGE in a 12.5% gel under reducing conditions.

Results:

All the chimeric proteins CDD (SEQ ID NO: 37), CDC (SEQ ID NO: 39) and DDC (SEQ ID NO: 41) were expressed, although the CDD and CDC rather weakly, and processed to a similar manner as wild-type VEGF-C and VEGF-D. Like wild-type VEGF-C and VEGF-D, the CDD, CDC and DDC chimeras all bind to Neuropilin-1 and DDC binds also to neuropilin-2. The binding of CDD and CDC to neuropilin-2 could not be detected in these experiments, possibly because of the lower expression levels of these chimeras.

The activity of the chimeric polypeptides described in this example can be assessed by performing experiments as described in the following examples.

Example 3

VEGF-CAC Gene Therapy Materials and Methods

Materials and Methods: The methods described in Example 1 are incorporated into the present example by reference. The studies described in the present example also employed the following additional experimental protocols.

Production and in vivo delivery of VEGF-CAC by Viral Vectors: The AAV vector psub-CAG-WPRE was cloned by substituting the CMV promoter fragment of psub-CMV-WPRE (Paterna et al., Gene Ther., 7(15):1304-1311, 2000)

with the CMV-chicken beta-actin insert (Niwa et al., Gene, 108(2):193-199, 1991). The full-length CAC expression cassette was cloned into the NheI site of the psub-CMV-WPRE vector plasmid as an AgeI-ClaI fragment. The cDNA encoding VEGF-CAC was cloned into the pAdBglII vector (Ad-CAC), and recombinant adenoviruses were produced as described in Laitinen et al., Hum. Gene Ther., 9(10):1481-1486, 1998. Hela cells were used for expression analysis and infected with an adenovirus (MOI 100). Expression of the recombinant protein was examined by metabolic labeling, immunoprecipitation followed by SDS-PAGE.

Adenoviruses (AdVEGF-CAC or AdLacZ, approximately $3 \times 10^8$ pfu), were injected into the skins of NMRI nu/nu mice, while AAV were injected stereotaxically into the mouse cerebrum (volume 30. Tissues were collected for histological analysis two weeks after adenoviral or three weeks after AAV transduction.

Figure 2A:
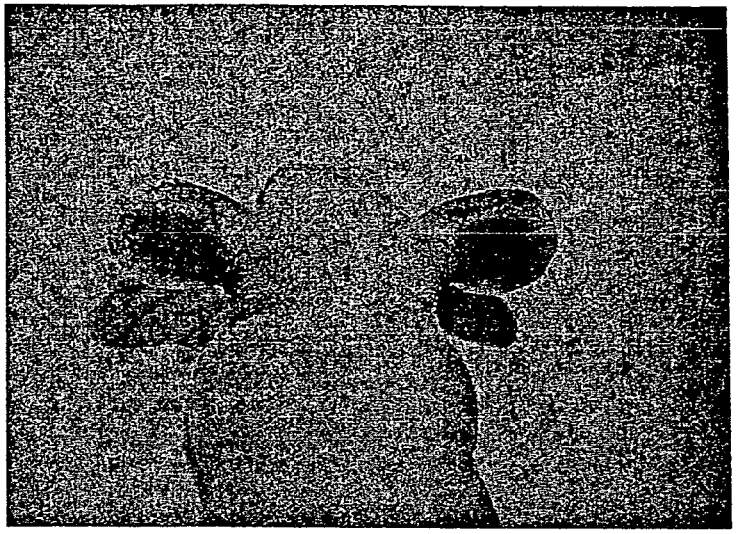
FIGS. 2A-2C: Photograph depicting the effects of adenoviral vectors that code for either VEGF-CAC (FIG. 2A), VEGF-A165 (FIG. 2B) or control (LacZ, FIG. 2C) on the blood vasculature of mouse skin.
Figure 2B:
Figure 2C:
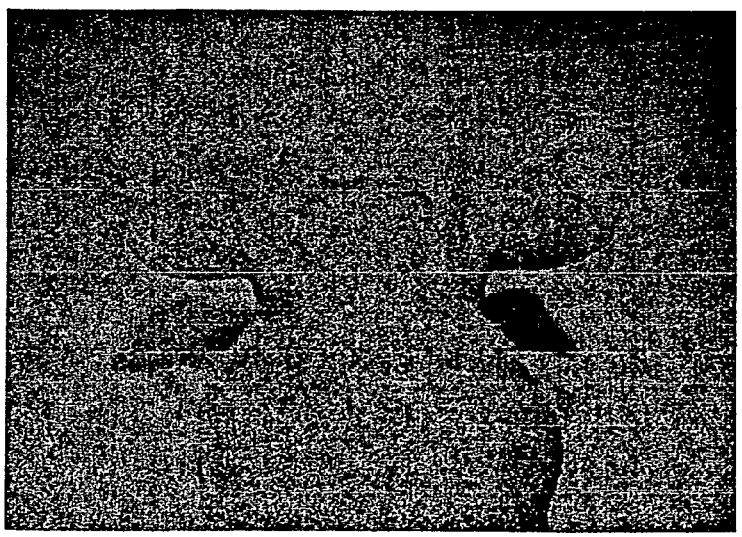

Immunohistochemistry. For whole mount staining, tissues were fixed in 4% paraformaldehyde (PFA), blocked with 5% goat serum in PBS-containing 0.3% Triton-X1000, and incubated with polyclonal antibodies for LYVE-1 (Karkkainen et al., Nat. Immunol., 5:74-80, 2004) and/or monoclonal antibodies against PECAM-1 (PharMingen), nidogen (Chemicon) and smooth muscle α-actin (SMA, Cy2-conjugate). For staining of tissue sections, tissues were fixed in 4% PFA overnight at 4° C. and paraffin or frozen sections (6-20 μm) were immunostained with anti-LYVE-1, monoclonal antibodies against PECAM-1 or PDGFR-β. Alexa594 and Alexa488 conjugated secondary antibodies (Molecular Probes) were used for staining, and samples were then mounted with Vectashield (Vector Laboratories) and analyzed with a Zeiss LSM510 confocal microscope. Part of the experimental mice were perfused with FITC-conjugated *Lycopersicon esculentum* lectin, followed by perfusion fixation with 1% PFA and PBS washes, Results. Adenoviral VEGF-CAC transduction of the mouse ear skin resulted in erythema, swelling and thickening of the ear, while such effects were mild in AdVEGF-A165 transduced ears and nonexistent in control LacZ ears (FIG. 2). AdVEGF-CAC transduction led to a massive angiogenic response characterized by blood endothelial sheets with partial lack of luminal structures. AdVEGFA165 induced a prominent angiogenic response that was however weaker when compared to AdVEGF-CAC. VEGF-A165 has been shown to induce angiogenesis by a gradient dependent mechanism, characterized by endothelial proliferation, sprouting and guided migration (Ruhrberg et al, Genes Dev., 16:2684-2698, 2002). This coordinated action is apparently due to the intermediate diffusion properties of VEGF165. The chimeric VEGF-CAC is a very potent inducer of angiogenesis. This suggests that the VEGF-C propeptides associate differentially with the extracellular environment when compared to the heparin binding domains of VEGF165 and result in increased bioavailability of the VEGF core domain. Lymphatic capillaries in the ears of mice treated with AdVEGF-CAC or AdVEGF-A165 were distended, and their lumina were enlarged compared to controls. Similar lymphatic vascular dilation has also previously been observed in response to adenoviral overexpression of VEGF-A165 in the mouse ear skin (Saaristo et al., FASEB J., 16:1041-1049, 2002).

Both the blood and lymphatic vasculatures were unaffected by treatment with the control adenovirus encoding LacZ. Marked circumferential hyperplasia of large blood vessels of the ear was also observed in AdVEGF-CAC transduced ears, while neither AdVEGF-A165 nor AdLacZ had similar effects. Staining for nidogen showed a massive increase in vessels that were surrounded by basement membrane in AdVEGF-CAC transduced ears when compared to the control, suggesting that the newly formed vessels were mature and stabile. Moreover, perfusion of the mice with FITC-conjugated *Lycopersicon esculentum* lectin, a marker for endothelial cells, showed that most of the newly formed vessels in AdVEGF-CAC transduced ears were perfused, and their number had increased when compared to the control ears. Interestingly, most of the medium and large caliber vessels formed in response to AdVEGF-CAC transduction were surrounded by smooth muscle actin positive pericytes, whereas only few nascent vessels in AdVEGF-A165 transduced ears were encircled by such cells. A normal hierarchy of blood vessels, characterized by SMA covered medium and large sized vessels, was found in AdLacZ ears. This suggests that the vessels formed in response to VEGF-CAC stimulation are more stable than those without pericyte coverage formed after VEGF-A165 stimulation. Sprouting of SMA positive pericytes was observed in both AdVEGF-CAC or AdVEGF165 transduced ears, suggesting that angiogenesis stimulated by these factors also leads to pericyte mobilization. Adenoviral or AAV-mediated gene transduction of VEGF-C has been shown to induce lymphangiogenesis in several tissues, whereas virally expressed VEGF-C is a weak stimulator of angiogenesis (Rissanen et al, Circ. Res. 30; 92(10):1098-106, 2003 and Saaristo et al. J. Exp. Med., 16; 196(6):719-30, 2002).

Example 4

Stimulation of Endothelial Cell Migration

Both VEGF-A and VEGF-C stimulate endothelial cell migration in collagen gel. The chimeric polypeptide constructs of the invention are examined to determine if they are also capable of stimulating endothelial cell migration in collagen gel, thus providing another indicia of biological activity. Exemplary experiments of such cell migration assays have been described in International Patent Publication No. WO 98/33917, incorporated herein by reference. Briefly, bovine capillary endothelial cells (BCE) are seeded on top of a collagen layer in tissue culture plates. Conditioned media from cells transfected with an expression vector producing the candidate chimeric polypeptide is placed in wells made in collagen gel approximately 4 mm away from the location of the attached BCE cells. The number of BCE cells that have migrated from the Original area of attachment in the collagen gel towards the wells containing the chimeric polypeptide is then counted to assess the ability of the chimeric polypeptide to induce cell migration.

BCE cells (Folkman et al., Proc. Natl. Acad. Sci. (USA), 76:5217 5221 (1979)) are cultured as described in Pertovaara et al., J. Biol. Chem., 269:6271 74 (1994). Collagen gels are prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. Tissue culture plates (5 cm diameter) are coated with about 1 mm thick layer of the solution, which is allowed to polymerize at 37° C. BCE cells are seeded atop this layer.

For the migration assays, the cells are allowed to attach inside a plastic ring (1 cm diameter) placed on top of the first collagen layer. After 30 minutes, the ring is removed and unattached cells are rinsed away. A second layer of collagen and a layer of growth medium (5% newborn calf serum (NCS), solidified by 0.75% low melting point agar (FMC BioProducts, Rockland, Me.), are added. A well (3 mm diameter) is punched through all the layers on both sides of the cell spot at a distance of 4 mm, and media containing a chimeric VEGF polypeptide such as VEGF-CAC (or media alone or media containing VEGF-A or VEGF-C to serve as controls) is pipetted daily into the wells. Photomicrographs of the cells migrating out from the spot edge are taken, e.g., after six days, through an Olympus CK 2 inverted microscope equipped with phase-contrast optics. The migrating cells are counted after nuclear staining with the fluorescent dye bisbenzimide (1 mg/ml, Hoechst 33258, Sigma).

The number of cells migrating at different distances from the original area of attachment towards wells containing media conditioned by the non-transfected (control) or transfected (mock; chimeric polypeptide; VEGF-C; or VEGF A) cells are determined 6 days after addition of the media. The number of cells migrating out from the original ring of attachment are counted in five adjacent 0.5 mm×0.5 mm squares using a microscope ocular lens grid and 10× magnification with a fluorescence microscope. Cells migrating further than 0.5 mm are counted in a similar way by moving the grid in 0.5 mm steps.

The ability of a chimeric polypeptide to induce migration of BCE cells is indicative of receptor agonist activity. The number of migrating cells in the presence of a chimeric polypeptide versus a similar concentration of VEGF-A or VEGF-C provides an indication of the potency of agonist activity. Polypeptides that have been shown to bind the receptors expressed on BCE cells, but are incapable of stimulating migration, are scored as potential inhibitors. Inhibitory activity can be further assayed by mixing a known receptor agonist such as recombinant VEGF-A or VEGF-C with either media alone or with concentrated conditioned media, to determine if the concentrated conditioned media inhibits VEGF-A mediated or VEGF-C mediated BCE migration.

Example 5

In Vivo Effects of Angiogenic Factors

The choroallantoic membrane (CAM) assay described in e.g., Oh et al., Dev Biol 188:96 109 (1997), incorporated herein in its entirety, is a commonly used method to examine the in vivo effects of angiogenic factors. Using this assay, VEGF growth factors including both VEGF-A and VEGF-C have been shown to induce the development of blood vessels [Oh et al., Dev Biol 188:96 109 (1997)]. Thus, this method can be used to study the angiogenic properties of the chimeric polypeptides of the invention.

Briefly, on day four of development, a window is cut out into the eggshell of chick or quail eggs. The embryos are checked for normal development, the window in the eggshell is sealed with cellotape, and the eggs are incubated until day 13 of development. Approximately 3.3 µg of chimeric polypeptide dissolved in 5 µl of distilled water is added to Thermanox coverslips (Nunc, Naperville, Ill.), which have been cut into disks with diameters of approximately 5 mm, and air dried. Disks without added protein are used as controls. The dried disks are then applied on the chorioallantoic membrane (CAM) of the eggs. After 3 days, the disks are removed and fixed in 3% glutaraldehyde and 2% formaldehyde and rinsed in 0.12 M sodium cacodylate buffer. The fixed specimens are photographed and embedded in Epon resin (Serva, Germany) for semi (0.75 µm) and ultrathin (70 nm) sectioning. Both semi and ultrathin sections are cut using an Ultracut S (Leika, Germany). Ultrathin sections are analyzed by an EM 10 (Zeiss, Germany). Specimens are then analyzed for evidence of growth of new capillaries, which would indicate that the chimeric polypeptide being examined is capable of stimulating angiogenesis. Natural VEGF polypeptides may be used as positive controls.

Example 6

Treatment of Ischemic Tissue

The use of chimeric polypeptides of the invention in treating ischemic tissue, such as limb ischemia due to insufficient circulation, is analyzed using recognized assays. The efficacy of the chimeric polypeptides in such indications may be determined using a model for ischemia. Such a rabbit model for ischemia has previously been described in Bauters et al., Am J. Physiol. 267:H1263-1271, 1996; and Pu et al., J. Invest. Surgery, 7:49-60, 1994. These animals are anesthetized and the femoral artery of the hind limb is excised from its proximal origin as a branch of the external iliac artery to the point where it bifurcates into the saphenous and popliteal arteries. As a result of this procedure, the blood flow to the ischemic limb is dependent on collateral vessels originating from the internal iliac artery (Takeshita et al., Circulation, 90:II-228-II-234, 1994). The animal is allowed a 10-day post-operative recovery period. During this period, endogenous collateral vessels develop. After the recovery period, the baseline physiological parameters, such as blood pressure, intravascular blood flow, iliac angiography and capillary vessel density is determined. Methods for determining these baseline physiological characteristics are detailed in Witzenbichler et al., (Am. J. Path. 153:381-394, 1998).

After obtaining the baseline physiological characteristics of the animal, the model animal is treated with an intra-arterial bolus of a chimeric polypeptide of the present invention. Preferably, the bolus comprises the equivalent of 500 µg of VEGF-A in an appropriate volume, e.g., 3 ml, of phosphate buffered saline (PBS) containing 0.1% rabbit serum albumin (RSA). The chimeric protein is administered over a period of 1 to 5 minutes through a catheter positioned in the internal iliac artery of the ischemic limb. The catheter is then washed with an equal volume of PBS containing RSA. The physiological parameters discussed above are then monitored at suitable intervals after administration of the chimeric polypeptides.

In an alternative embodiment, the ischemic model is treated using gene therapy with either naked DNA comprising polynucleotides that encode the chimeric polypeptides of the present invention or, preferably, gene therapy vectors described herein that encode a chimeric polypeptide of the present invention. Adenoviral gene therapy vectors are particularly preferred. In such gene therapy embodiments, the internal iliac artery of the ischemic limb of the animal is transfected with the naked DNA or the adenoviral or other gene therapy vector using e.g., a 2.0 mm balloon catheter (Slider with Hydroplus, Boston Scientific, MA). The angioplasty balloon is preferably prepared ex vivo by first advancing the deflated balloon through a Teflon sheath (Boston Scientific) and applying the gene therapy composition to the layer of hydrogel coating the external surface of the inflated balloon. The balloon is then retracted back into its protective sheath. The sheath and the angioplasty catheter are introduced via the right carotid artery and advanced to the lower abdominal aorta using an appropriate guide-wire. The balloon catheter is advanced to the internal iliac artery of the ischemic limb and inflated to administer the gene therapy composition locally at the ischemic limb. The balloon catheter is then deflated and withdrawn.

The above methods may be performed with controls that comprise no VEGF-related composition and positive controls that comprise VEGF-A, VEGF-C, or VEGF-D.

The above studies are described with respect to a rabbit model for ischemia. Similar studies may be conducted in models of ischemic heart disease, such as those described by Kastrup et al., (Curr. Gene Ther., 3(3):197-206, 2003), and Khan et al., (Gene Ther. 10(4):258-91, 2003).

Example 7

VEGF-CAC Gene Transfer to Prevent Restenosis

The following experiment is performed in vivo in a rabbit restenosis model to demonstrate the efficacy of the compositions for the prevention of post-angioplasty restenosis.

A first group of rabbits is fed a 0.25% cholesterol diet for two weeks, then subjected to balloon denudation of the aorta, then subjected three days later to the therapeutic compositions to be tested. Animals are sacrificed 2 or 4 weeks after the initiation of therapy. The compositions to be tested include VEGF-C, or VEGF-D or chimeric compositions of the invention such as VEGF-CAC either alone or in combination with a PDGF inhibitor (for example an α-PDGF-A antibody; α-PDGF-B antibody, α-PDGF-C antibody, α-PDGF-D antibody, a α-PDGFR-alpha antibody or a α-PDGFR-beta antibody or a short interfering RNA molecule directed to one or more of these targets) or with one or more other smooth muscle cell growth inhibitors. Polypeptide therapy or gene therapy is contemplated. As a gene therapy control, the vector of choice carries the LacZ gene.

In the first group of rabbits, the whole aorta, beginning from the tip of the arch, is denuded using a 4.0 F arterial embolectomy catheter (Sorin Biomedical, Irvine, Calif.). The catheter is introduced via the right iliac artery up to the aortic arch and inflated, and the aorta is denuded twice.

Three hours before sacrifice, the animals are injected intravenously with 50 mg of BrdU dissolved in 40% ethanol. After the sacrifice, the aortic segment where the gene transfer had been performed is removed, flushed gently with saline, and divided into five equal segments. The proximal segment is snap frozen in liquid nitrogen and stored at −70° C. The next segment is immersion-fixed in 4% paraformaldehyde/15% sucrose (pH 7.4) for 4 hours, rinsed in 15% sucrose (pH 7.4) overnight, and embedded in paraffin. The medial segment is immersion-fixed in 4% paraformaldehyde/phosphate buffered saline (PBS) (pH 7.4) for 10 minutes, rinsed 2 hours in PBS, embedded in OCT compound (Miles), and stored at −70° C. The fourth segment is immersion-fixed in 70% ethanol overnight and embedded in paraffin. The distal segment is directly stained for β-galactosidase activity in X-GAL staining solution at +37° C. for 16 hours, immersion-fixed in 4% paraformaldehyde/15% sucrose (pH 7.4) for 4 hours, rinsed in 15% sucrose overnight, and embedded in paraffin. Paraffin sections are used for immunocytochemical detection of smooth muscle cells (SMC), macrophages, and endothelium. BrdU-positive cells are detected according to manufacturer's instructions. Morphometric analysis performed using haematoxylin-eosin stained paraffin sections using image analysis software. Intima/media (I/M) ratio is used as a parameter for intimal thickening.

Histological analysis of the balloon-denuded mice is taken. Compositions that are effective at inhibiting restenosis will reveal that control groups (i.e., those groups without the compositions that comprise the VEGF-CAC related compositions) have an I/M ratio of that is higher than the ratio from those animals treated with the VEGF-CAC based therapeutic compositions.

The BrdU labeling will permit analysis of smooth muscle cell proliferation in treated versus control animals. SMC proliferation is expected to be reduced in the treated population. A more detailed description of assays and compositions for treating restenosisis is contained in international application no. PCT/US99/24054, published as WO 00/24412, the disclosure of which is incorporated herein by reference in its entirety.

Example 8

Effects of VEGF-CAC Gene Therapy on Motor Neurons

This example demonstrates that the administration of chimeric VEGF polypeptides such as VEGF-CAC to an amytrophic lateral sclerosis (ALS) mouse model.

VEGF 'knock-in' mice, in which the hypoxia-response element sequence in VEGF promoter is deleted, have an impaired potential to upregulate VEGF levels in conditions of stress. These mice develop ALS-like neuropathology (Oosthuyse et al., Nature Genet., 23:131-138 (2001), suggesting that motor neurons are particularly sensitive to reductions in the levels of VEGF. VEGF has also been reported to have favorable effects on ischemic neuropathy in mice (Schratzberger, P. Nat. Med., 6:405-413 (2000). The following example is performed to demonstrate the effects of VEGF-CAC gene transfer to motor neurons, which may slow down motor neuron degeneration in SOD1$^{G93A}$ mice. The protocol is performed as described in Azzouz et al., Nature, 429:413-417 (2004), incorporated herein by reference.

Animal Model. Transgenic mice overexpressing human SOD1 carrying a Gly93-Ala mutation are used (Gurney et al., Science, 264:1772-1775, 1994). This line of mice has the high-expressing form of mutant SOD1 and animals develop disease onset at about 90 days of age and die about 30 days later. Transgenic progeny are identified by PCR using primers specific for human SOD1 (Gurney et al., supra).

Viral Production. EIAV self-inactivating vector genomes are constructed from pONY8.0Z or pONY8.0G vectors as described previously (Mazarakis et al., Hum. Mol. Genet., 10:2109-2121, 2001; Azzouz et al., J. Neurosci., 22:10302-10312, 2002). The complementary DNA coding for the reporter gene LacZ or the VEGF-CAC is cloned in the EIAV transfer vector and EIAV-VEGFCAC-IRES-GFP are generated. Viral vector stocks pseudotyped with rabies-G glycoprotein were prepared using the HEK293T transient system as previously described (Mazarakis et al., Hum. Mol. Genet., 10:2109-2121, 2001; Mitrophanous et al., Gene Ther., 6:1808-1818, 1999). The titres (~1×10$^9$ TUml$^{-1}$) of concentrated EIAV-LacZ viral vectors are estimated by transduction of D17 cells. The titres (~7×10$^8$ to 3×10$^9$ TUml$^{-1}$) of the EIAV-VEGFCAC or EIAV-VEGFCAC-IRES-GFP vectors are estimated using real-time quantitative polymerase chain reaction with reverse transcription (RT-PCR) by comparison to EIAV-LacZ vectors and normalized for viral RNA (Rohll et al., Methods Enzymol., 346:466-500, 2002; Martin-Rendon et al., Mol. Ther., 566, 570, 2002).

VEGF ELISA. Dog osteosarcoma D17 cells are transduced in the presence of 8 mg/ml polybrene as described previously (Mitrophanous, supra). Cells are transduced with either EIAV-VEGFCAC or EIAV-LacZ vectors. Transduced cells are passed three times before analysis of transgene expression. One week post-transduction supernatants are collected and the VEGF-CAC levels are measured by enzyme-linked immunosorbent assay (ELISA) (R&D Systems). To determine plasma VEGF-CAC levels, blood is collected in 10-ml vacuum tubes containing 100 µl of a 4% tri-sodium citrate solution, quickly centrifuged and stored plasma fractions at −80° C. until analysis. VEGF-CAC ELISA assay measurements were also carried out using tissue samples from spinal cord and brain stem.

Viral vector delivery. Rabies-G pseudotyped lentiviral vectors carrying human VEGF-CAC or LacZ genes are injected bilaterally into the hindlimb gastrocnemius, facial, diaphragm, tongue and intercostal muscles of SOD1 transgenic mice before and at disease onset. The first group of SOD1 mice receive injections of EIAV-VEGFCAC-IRES-GFP (n=7) at 21 days of age. The control group is treated with EIAV-LacZ vector (n=6). The second set of animals is injected at the onset of disease (90-day-old mice) with EIAV-VEGFCAC (n=7) and the EIAV-LacZ control (n=7). Each mouse is injected with a total dosage of 90 µA of viral solution. Six sites per hindlimb muscle are injected with 5 µl per site.

Histology and immunohistochemistry. Animals are perfused transcardially with 0.9% NaCl solution followed by ice-cold 4% paraformaldehyde. Spinal cord, brain and muscle tissues are dissected out and post-fixed overnight in the same solution and then transferred to 30% sucrose. Tissues are analyzed by immunohistochemistry and X-gal (5-bromo-4-chloro-3-indolyl-b-D-galactoside) reaction.

Behavioral analysis. A rotarod task of the SOD1 mice by an Economex Rotarod instrument (Colombus Instruments) is analyzed every ten days during the light phase of the 12 h light/12 h dark cycle. Three trials are performed, and recorded the longest duration on the rod for every mouse. The timer is stopped when the mice fall from the rod or after an arbitrary limit of 180 seconds. Footprint analysis is also performed. Mouse hind paws are covered with ink to record walking patterns during continuous locomotion, and stride length is measured.

A therapeutic benefit is indicated by increased motor neuron survival in mice that receive the VEGF-CAC gene therapy, compared to controls.

Example 9

Induction of In Vivo Growth of Lymphatic and/or Blood Vessels in Skin of Transgenic Mice Experiments are conducted in transgenic mice to analyze the specific effects of overexpression of chimeric polypeptides in tissues. The physiological effects in vivo provide an indication of receptor activation/inhibition profile and an indication of the potential therapeutic action of a chimeric polypeptide. In one variation, the human K14 keratin promoter which is active in the basal cells of stratified squamous epithelia [Vassar et al., *Proc. Natl. Acad. Sci. (USA)*, 86:1563-1567 (1989)], is used as the expression control element in the recombinant chimeric polypeptide transgene. The vector containing the K14 keratin promoter is described in Vassar et al., *Genes Dev.*, 5:714-727 (1991) and Nelson et al., *J. Cell Biol.* 97:244-251 (1983).

A DNA fragment containing the K14 promoter, chimeric polypeptide encoding cDNA, and K14 polyadenylation signal is isolated, and injected into fertilized oocytes of the FVB-NIH mouse strain. The injected zygotes are transplanted to oviducts of pseudopregnant C57BL/6×DBA/2J hybrid mice. The resulting founder mice are then analyzed for the presence of the transgene by polymerase chain reaction of tail DNA using appropriate primers or by Southern analysis.

These transgenic mice are then examined for evidence of angiogenesis or lymphangiogenesis in the skin, such as the lymphangiogenesis seen in transgenic mice that overexpress VEGF-C [see International Publication WO98/33917]. Histological examination of K14-VEGF-C transgenic mice showed that in comparison to the skin of wildtype littermates, the dorsal dermis was atrophic and connective tissue was replaced by large lacunae devoid of red cells, but lined with a thin endothelial layer. These distended vessel-like structures resembled those seen in human lymphangiomas. The number of skin adnexal organs and hair follicles were reduced. In the snout region, an increased number of vessels was also seen.

Examination of the vessels in the skin of the transgenic mice using antibodies that recognize proteins specific for either blood or lymphatic vessels can further verify the identity of these vessels. Collagen types IV, XVIII [Muragaki et al., *Proc. Natl. Acad. Sci. USA*, 92: 8763-8776 (1995)] and laminin are expressed in vascular endothelial cells while desmoplakins I and II (Progen) are expressed in lymphatic endothelial cells. See Schmelz et al., *Differentiation*, 57: 97-117 (1994).

In addition, the chimeric molecules can be co-expressed with Ang-1 or other VEGF/PDGF family members to modulate the growth of new vessels.

Example 10

Assay for Determining Modulation of Myelopoiesis

Overexpression of VEGF-C in the skin of K14 VEGF-C transgenic mice correlates with a distinct alteration in leukocyte populations [see International Publication WO98/33917, incorporated herein by reference]. Notably, the measured populations of neutrophils were markedly increased in the transgenic mice. The effects of the chimeric polypeptides on hematopoiesis can be analyzed using fluorescence activated cell sorting analysis using antibodies that recognize proteins expressed on specific leukocyte cell populations. Leukocyte populations are analyzed in blood samples taken from the F1 transgenic mice described above, and from their non transgenic littermates. Alterations in leukocyte populations has numerous therapeutic indications, such as stimulating an immune response to pathogens, recovery of the immune system following chemotherapy or other suppressive therapy, or in the case of inhibitors, beneficial immunosuppression (e.g., to prevent graft-versus-host-disease or autoimmune disorders.) Use of molecules of the invention for these therapeutic indications is specifically contemplated. Use of antibodies that recognize various stem cell or progenitor cell populations permits evaluation of the effect of chimeric polypeptides of the invention on such cell types.

Example 11

Endothelial Cell Migration and Microvessel Sprouting

In this example, the effect of the PDGF chimeric constructs of the invention on endothelial cell (EC) migration and proliferation is compared to that of VEGF (which primarily affects endothelial cells [Senger, D. R., et al., Am. J. Pathol. 149:293-305. (1996)]), PDGF-AA, PDGF-BB, PDGF-CC (which primarily affect fibroblasts and smooth muscle cells [Heldin, C. H. & Westermark, B. Physiol. Rev. 79:1283-1316

(1999); Li et al., Nat. Cell. Biol., 2:302-309, 2000]) and PDGF-DD. Migration, proliferation and aortic ring assays are performed.

A. Cell Migration Assays

Cell migration assays are performed on growth-arrested confluent HMVEC or BAEC cells. Cell monolayers are wounded with a rubber policeman and are washed with serum-free medium. Dishes are then incubated for 20 hours in serum-free medium containing VEGF165, PDGF-AA, -BB, -CC or -DD or PDGF chimeric constructs. Each assay includes two dishes per condition and is repeated three times independently. Cells are photographed at 40× magnification, and migration percentage corresponding to the ratio between area of the cells and the total area of the wound (Biocom visiol@b 2000 version 4.52, San Diego). For the cell migration assay, ANOVA Dunett's test is used for data analyzing, with P<0.05 considered statistically significant. Data is presented as mean+/−SEM.

PDGFR-α expression on the human microvascular endothelial cells (HMVEC) is confirmed by Western blot. VEGF and the PDGF chimeric contsructs, but not PDGF-AA or PDGF-BB, stimulate migration of human microvascular endothelial cells (HMVEC) and bovine aorta endothelial cells (BAEC).

B. Proliferation Assay

For HMVEC proliferation assay, cells are seeded in 96-well plates (5 wells per condition), and incubated with PDGF-AA, PDGF-BB or PDGF chimeric construct (50 ng/ml) after serum starvation. After 7 days, viable cells are counted using cellTiter-glo luminescent cell viability assay (Promega). For NIH-3T3 and hSMC proliferation assay, cells cultured in 96-well plates are serum-starved overnight, followed by treatment with growth factors at different concentrations. Two days later, cell numbers are counted and proliferation percentage is calculated, using cells cultured in medium containing 10% serum as control.

C. Aortic Ring Assay

The aortic ring assay is a means of assessing outgrowth of microvessels from an intact vessel in vitro [Blacher, S., et al., Angiogenesis 4:133-42 (2001)]. The assay is performed as described in [Blacher, S., et al., Angiogenesis 4:133-42 (2001)]. Briefly, one-millimeter long aortic rings are embedded in gels of rat tail interstitial collagen and cultured at 37° C., supplemented with different wildtype of chimeric growth factors (50 ng/ml). Experiments include three explants per condition and are repeated at least twice. Aortic rings are photographed at 25× magnification.

At day 9 after culturing, microvessels and the distance of their outgrowth from the aortic ring are quantified and evaluated using Student's t-test. Specifically, two-tailed Student's t-test is used for data analysis, with P<0.05 considered statistically significant. For cell migration assay, ANOVA Dunett's test is used for data analyzing, with P<0.05 considered statistically significant. Quantification of the outgrowth of microvascular sprouts and perivascular fibroblast-like cells is performed using computer-assisted morphometry.

Example 12

Using VEGF-CAC Therapy in Reconstructive Surgery Following a Severe Burn or Other Skin Trauma The following example describes a procedure and delivery of a chimeric construct, such as VEGF-CAC, to tissue traumatized from a burn to improve healing following reconstructive surgery. Burn victims often require extensive surgical interventions that include substantial skin grafts to restore damaged tissue. The following example provides a method to improve tissue healing following reconstructive surgery for a burn or other skin trauma.

A. Animals and Skin Preparation

New Zealand white rabbits have been shown to be appropriate for burn studies (Bucky, et al., *Plast. Reconstr. Surg.*, 93(7):1473-1480 (1994)). Further, the structural characteristics of the skin layers in rabbits and humans are similar. Three days prior to the operation, the backs of 10 New Zealand White Rabbits are depilated with a depilatory cream. Since the thickness of the skin is dependent upon the stage of the hair growth cycle, estimation of the hair growth pattern is carefully assessed. Immediately prior to infliction of the burn injury, the operation area is depilated a second time to achieve a smooth and hairless skin surface.

B. Operative Technique

Rabbits are sedated by intramuscular administration of ketamine (25 mg/kg BM) as described in the art (Knabl et al., *Burns*, 25:229-235 (1999)). A soldering iron with an adjustable aluminum contact stamp is used for infliction of the burn. The temperature of the stamp is set to 80° C. and continuously monitored. Burns are inflicted on the dorsal skin of the rabbits for approximately. 14 seconds using only the weight of the stamp (approximately 85 g). The wounds are then immediately cooled with thermoelements which provide a consistent temperature of 10° C. for 30 minutes (Knabl, et al., supra).

To minimize the fact that different parts of the body with different skin thickness have different re-epithelialization and healing potentials, the same donor site on the animals is used. Therefore, any observed differences could be attributed to the treatment itself rather than to other variables. A Padget Electric Dermatome is used to harvest a 0.12 inch thick skin graft from the depilated thigh in all animals. The graft is carefully spread on the burn area. It is held in place either by gentle pressure from a well-padded dressing or by a few small stitches. The raw donor area is covered with a sterile nonadherent dressing for a 3-5 days to protect it from infection until full re-epithelialization is observed.

$1 \times 10^9$ pfu of AdVEGF, AdVEGF-CAC, AdVEGF-C, and AdLacZ are injected intradermally into the dorsal skin to the burn site of the rabbits. AdVEGF construction has been described previously (Makinen, et al., supra) and the AdVEGF-CAC, AdLacZ vectors are constructed as described herein. Reduction of edema and increase in skin perfusion at a burn wound site as a result of an increase in functional lymph nodes is assessed by following the accumulation of fluorescent dextran.

Additionally, healing is monitored by evaluating the cosmetic appearance of the skin graft. Normal graft color is similar to that of the recipient site. Surface temperature of the graft can be monitored using adhesive strips (for an accurate number) or the back of the hand (to provide a comparative assessment with the surrounding skin). Problems with arterial inflow are suggested when the graft is pale relative to the donor site and/or cool to the touch. Problems with venous outflow are suggested when the graft is congested and/or edematous. Color and appearance of congested grafts can vary depending on whether the congestion is mild or severe and ranges from a prominent pinkish hue to a dark bluish purple color.

C. Summary

The aforementioned model demonstrates the therapeutic potential of using VEGF-CAC to preserve function of the lymphatic vessels and to improve healing and reduce edema and concomitant post-surgical complications in burn victims. Thus, the procedures and compositions described herein provide an important need in the art. Specifically, the reduction of edema or increase in perfusion at a burn site is accomplished, for example, by delivery of AdVEGF-CAC to the site of the wound.

Example 13

Other Chimeric Construct Polynucleotide and Polypeptide Therapy

The procedures described in the preceding examples are repeated using a composition comprising other chimeric constructs that include RTK binding domains from other VEGF/PDGF family members and either VEGF-C or VEGF-D propeptides.

Example 14

Additional Experimental Data

This example provides additional experimental data for the CAC construct described in Example 1.

Cell culture. 293T and HeLa cells from ATCC (www.atcc.org) were maintained in DMEM (HaartBio, Helsinki, Finland) supplemented with 2 mM L-glutamine (HaartBio), 0.2% penicillin/streptomycin sulfate, and 10% fetal bovine serum (PromoCell, Heidelberg, Germany). Ba/F3 cells (Achen et al., Eur. J. Biochem/. 267:2505-2515, 2000) were grown in DMEM supplemented with 200 µg/ml Zeocine (Invitrogen, Carlsbad, Calif., USA) and recombinant mouse interleukin-3 (Calbiochem, San Diego, Calif., USA).

Constructs. A polynucleotide encoding the CAC fusion protein was produced by PCR amplification and subcloning of the N-terminus and C-terminus from a human VEGF-C cDNA and the RTK binding domain of a human VEGF-A cDNA. A 6×His-tag was added to the C-terminal end, and an IgG-signal peptide was added to the N-terminal end. The resulting cDNA sequence was verified. This cDNA was inserted into the pMosaic vector (Jeltsch et al., J. Biol. Chem., 281, 12187-95, 2006) as a BamHI-NotI fragment. The VEGF-CAC was cut with AgeI and ClaI, blunted and ligated into psub-CMV-WPRE AAV2 plasmid (Witzenbichler et al., Am. J. Pathol., 153:384-394, 1998; Marconcini et al., Proc. Natl. Acad. Sci. USA, 96:9671-9676, 1999).

The cDNA for VEGF-$A_{109}$, comprising 109 amino acids of the RTK binding domain of VEGF-A, was amplified with the primers 5'-GCGGATCCGGGGCAGAATCATC ACGAAGTGGTG-3' (SEQ ID NO: 64) and 5'-GCGGATC-CCTAATCTTTC TTTGGTCTACATTCACAT-3' (SEQ ID NO: 65) using the CAC/psub-CMV-WPRE AAV2 plasmid as a template. The obtained cDNA fragment was digested with BamHI and cloned into the BamHI site of the pMosaic vector.

Transfections and immunoprecipitations. 293T cells were transfected with psub-CMV/CAC, psub-CMV/VEGF-$A_{165}$, psub-CMV/VEGF-$A_{109}$, pEBS7/VEGF-C(fl) or the pEBS7/CMV vector using JetPEI (Qbiogene, Irvine, Calif., USA). Transfected cells were cultured for 48 hours and metabolically labeled in methionine-free and cysteine-free modified Eagle medium (HaartBio) supplemented with [$^{35}$S]methionine and [$^{35}$S]cysteine (Redivue ProMix, Amersham Biosciences, Uppsala, Sweden) at 100 µCi/mL for 16 hours. Conditioned medium was then collected, cleared of particulate material by centrifugation, supplemented with 5% BSA and 0.02% Tween 20, and incubated with anti-hVEGF-A antibodies (R&D Systems, Minneapolis, Minn., USA) or anti-hVEGF-C antibodies (R&D Systems) or 200 ng soluble VEGFR-1-Ig (Mäkinen et al., EMBO J., 20:4762-4773, 2001) or 200 ng soluble VEGFR-2-Ig (Uutela, Blood, 104: 3198-3204, 2004) or with soluble neuropilin-Ig fusion proteins with or without addition of 10 µg/ml heparin (Gibco BRL/Invitrogen). Neuropilin-Ig fusion proteins were produced in transiently transfected 293T cells using NP1-Ig (Karpanen et al., FASEB J., 20:1462-1472, 2006) and NP2-Ig (Karkkainen Proc. Natl. Acad. Sci. USA, 98:12677-12682, 2001) as described previously. The formed antigen-antibody complexes were then bound to protein-A-Sepharose or protein-G-Sepharose (Amersham Biosciences), followed by washing three times with 0.5% bovine serum albumin and 0.02% Tween 20 in phosphate-buffered saline (PBS) and once with PBS. Proteins were separated by 12% SDS-PAGE under reducing or unreducing conditions and visualized by autoradiography.

Pulse-chase analysis. Transiently transfected 293T cells were metabolically labeled in methionine-free and cysteine-free modified Eagle medium supplemented with [$^{35}$S]methionine and [$^{35}$S]cysteine (Redivue ProMix) at 100 µCi/mL for 30 min and then chased in non-radioactive DMEM for different time periods. The conditioned media were supplemented with 5% BSA and 0.02% Tween 20, and immunoprecipitated using anti-human VEGF-C antibodies (R&D Systems). Antigen-antibody complexes were analyzed as above under reducing conditions. Mock-transfected culture was analyzed only after 24 hours chase period.

Bioassay for growth factor-mediated cell survival. For Ba/F3-bioassay HeLa cells were transduced (MOI100) with Ad-CAC, Ad-VEGF$_{109}$, Ad-VEGF$_{165}$ and Ad-LacZ. 24 hours after transduction cells were serum starved for 16 hours, after which medium was collected, centrifuged at 2500 rpm for 5 minutes and stored at 4° C. To compare expression levels in different constructs, 100 µl conditioned medium was mixed with 25 µl 5×LSB, heated for 5 minutes at 95° C. and separated in 12% SDS-PAGE gels (Ready-Gel, Bio-Rad). Proteins were transferred to a nitrocellulose membrane, blocked with 5% BSA and incubated with a primary antibody (AF293NA). Rabbit anti-goat biotin and streptavidin-biotinylated HRP were used as secondary antibodies. Proteins were visualized using Femto ECL reagent (Amersham).

Ba/F3 cells expressing VEGFR-1/EpoR or VEGFR-2/EpoR chimeric receptor (Achen et al., Eur. J. Biochem., 267: 2505-2515, 2000) were seeded to 96-well plates at 20,000 cells/well in triplicates, supplied with conditioned medium from HeLa cells at different dilutions. Cell viability was quantified by a colorimetric assay after 48 hours. Briefly, 0.5 mg/ml of MTT (3-(4,5-dimethylthiazol-2-yl)-2,5-diphenyl tetrazolium bromide (Sigma-Aldrich, St. Louis, Mo.) was added into each well and incubated for 2 hours at 37° C. The reaction was terminated by adding 100 µl lysis buffer (10% SDS, 10 mM HCl), and the resulting formazan products were solubilized overnight at 37° C. in a humid atmosphere. The absorbance at 540 nm was measured using a Multiscan microtiter plate reader (Thermo Labsystems, Milford, Mass.).

Production and analysis of adenoviral vectors. The cDNAs encoding VEGF-CAC and VEGF-$A_{109}$ were cloned into the pAdBglII vector, and recombinant adenoviruses were produced as described previously (Laitinen et al., Hum. Gene Ther., 9:1481-1486, 1998). For analysis of protein production, HeLa cells were transduced with the adenoviruses (Ad-CAC, Ad VEGF-$A_{165}$, AdVEGF-$A_{109}$ or AdLacZ with MOI100). Expression of the recombinant proteins was examined by metabolic labeling and immunoprecipitation followed by 12% SDS-PAGE analysis as described above. After SDS-PAGE bands were visualized by autoradiography.

In vivo analysis of adenoviral vectors. Approximately 2×10$^8$ pfu of AdVEGF-CAC, AdVEGF-$A_{165}$, AdVEGF-$A_{109}$ or AdLacZ, were injected subcutaneously into the ears of NMRI nu/nu mice (Taconic Europe, Mollegaard, Denmark). Two weeks after adenoviral gene transduction, the mice were anesthetized and then perfused with 1% PFA for 2-3 minutes. The ears were collected, immersed in 4% paraformaldehyde for 2 hours, and dissected for whole mount staining.

Alternatively, the ears were embedded in OCT medium (TissueTek, Sakura Finetek, Zoeterwoude, the Netherlands), frozen and cut to 20 µm sections. The tissues were blocked with 5% normal goat or donkey serum in 0.3% Triton-X100 (Fluka Biochemika, Steinheim, Switzerland) in PBS. For staining of blood vessels in the ear, tissues were incubated overnight with hamster monoclonal anti-mouse PECAM-1 (CD31) antibodies (clone 2H8, MAB-13982Z, Chemicon, Temecula, Calif.).

Perfused blood vessels were visualized by injecting mice with 1 mg of FITC-conjugated *Lycopersicon esculentum* lectin (VectorLabs, Burlingame, Calif.), followed by perfusion fixation with 1% PFA. Basement membranes of blood vessels were stained with rat monoclonal antibodies against nidogen/entactin (Chemicon), while lymphatic vessels were visualized with a rabbit antiserum against LYVE-1 (Karkkainen et al., Nat. Immunol., 5:74-80, 2004). Antibodies to F4/80 (Serotec, Oxfordshire, UK) and CD45 (BD Pharmingen) were used to detect macrophages and hematopoietic cells, respectively, in frozen sections. Incubation with the primary antibody was followed by overnight incubation with appropriate fluorophore-conjugated secondary antibodies (Alexa 488, Alexa594 or Alexa633, Molecular Probes, Eugene, Oreg.; or FITC, Jackson ImmunoResearch, Bar Harbor, Me.). Fluorescently labeled samples were mounted with Vectashield (VectorLabs), and analyzed with a compound fluorescent microscope (Zeiss 2, Carl Zeiss, Göttingen, Germany; objective 10× with numerical aperture 0.30) or a confocal microscope (Zeiss LSM 510, objectives 40× with NA 1.3 and 63× with NA 1.4) by using multichannel scanning in frame mode. Three-dimensional projections were digitally constructed from confocal z-stacks.

To study collateral artery growth, semimembraneous rabbit hind-limb muscles were adenovirally gene transferred with AdCAC, AdA165 and AdLacZ as described previously (Rissanen et al., Circ. Res., 92:1098-1106, 2003). Evans blue injection and histological staining with CD31 were also carried out as in Rissanen et al (supra).

Results. The VEGF-CAC constructs comprising of the RTK binding domain of VEGF-A and the amino- and carboxyl terminal propeptides of VEGF-C were constructed in order to demonstrate the effects of the VEGF-C propeptides on the properties of VEGF. As expected, VEGF-CAC protein produced by transiently transfected 293T cells was found to bind to VEGFR-1 and -2, as well as to neuropilin-1 and -2. Heparin affected the binding greatly, and the interaction especially with neuropilin-2 was almost non-existent in the absence of heparin. The VEGF-A109 protein, consisting of the minimal receptor binding domain, was able to bind to VEGFR-1 and VEGFR-2, but its binding to neuropilin receptors was weak. Heparin somewhat enhanced the binding to neuropilin-1, leaving the interaction still extremely faint. VEGF-A165 bound to both VEGF receptors and neuropilins as expected. In non-reducing SDS-PAGE, the full-length VEGF-CAC polypeptide migrated as a 94 kD, indicating that the factor formed disulfide-linked dimers.

The activity of the produced VEGF-CAC was tested in Ba/F3-VEGFR-1 and Ba/F3-VEGFR-2 bioassays. VEGF-A165 and VEGF-A109 were used as controls and their activity was compared to that of VEGF-CAC. Expression levels of these growth factors in conditioned medium were equal. Medium from AdVEGF-CAC and AdVEGF-A165 transduced HeLa cells activated VEGFR-1 and VEGFR-2 in similar dilutions, but did not activate VEGFR-3. VEGF-A109 appeared to be a better inducer of VEGFR-1/EpoR or VEGFR-2/EpoR cell growth than VEGF-CAC or VEGF-A165.

In order to assay the biological activity of VEGF-CAC in vivo, AdCAC was injected into the ears of nude mice and into rabbit hind limb skeletal muscle. Two weeks after gene transduction, pronounced swelling and erythema was observed in ears transduced with AdVEGF-CAC, while no such effects were seen in AdLacZ treated ears. Whole mount immunofluorescent staining of AdVEGF-CAC transduced ears revealed extensive hyperplasia of PECAM-1 positive endothelium, while lymphatic capillaries were distended and their lumina were enlarged when compared to controls. Circumferential hyperplasia of larger arteries and veins of the ear was also observed. Similar effects were not seen in ears treated with the control virus. AdVEGF-CAC caused also enlargement of capillaries in rabbit skeletal muscle. Evans Blue injections into transduced hind limbs revealed that AdVEGF-CAC induced less permeable vessels than AdVEGF-A165.

As AdVEGF-CAC induced a prominent increase in PECAM-1 positive vessel-like structures, the potential increase in the number of functional blood vessels was also studied. Whole mount preparations of AdVEGF-CAC transduced ears stained with antibodies to nidogen (also known as entactin) and PECAM-1 showed a massive increase in the basement membrane tubes that contained endothelial cells, when compared to controls, indicating organization of endothelial cells into vessels.

The functionality of the new vessels formed after AdVEGF-CAC was also studied. Mice were injected intravenously with fluorescent *Lycopersicon esculentum* (tomato) lectin that binds to N-acetyl-D-glycosaminoglycan, a specific marker for blood vessel endothelial cells (BECs), in order to visualize perfused blood vessels. Ears transduced with AdVEGF-CAC showed a marked increase in the number of lectin positive vessels when compared to control, although some of the PECAM-1 positive endothelium remained lectin negative. Area density quantification (Baffert et al., Circ. Res. 94:984-992; Tammela et al., Blood, 105:4642-4648, 2005) of lectin positive vessels from whole mount preparations showed a 2.8 fold increase in perfused vessels in AdVEGF-CAC transduced ears compared to control, while the area of PECAM-1 positive vessels was increased 2.0 fold. AdVEGF-CAC induced angiogenesis was accompanied by pericyte hyperplasia.

Discussion. Example 1 discloses the generation and biological characterization of a chimeric VEGF, VEGF-CAC, comprised of the receptor activating domain of VEGF-A and the propeptides of VEGF-C. VEGF-CAC was secreted and processed identically when compared with VEGF-C, suggesting that the amino- and carboxyterminal cleavage sites are subject to proteolysis also in the chimera. VEGF-C does not bind to heparin, which is known to interact with the basic regions of the long VEGF-A splice isoforms. However, it is contemplated that immature VEGF-C or VEGF-CAC will associate with the extracellular environment via interactions with the C-terminal propeptide that contains EGF-like domains of other secreted proteins which are known to be involved with protein-protein and protein-cell surface interactions (Appella et al., FEBS Lett, 231:1-4, 1988).

VEGF-A165 has been shown to induce angiogenesis by a gradient dependent mechanism, characterized by endothelial proliferation, sprouting and guided migration (Ruhrberg et al., Gene Dev., 16:2684-2698; Gerhardt et al., J. Cell. Biol., 161:1163-1177, 2003). This coordinated action is apparently due to the intermediate diffusion properties of VEGF-A165 (Tammela et al., Cardiovasc. Res., 65:550-563, 2005). As indicated above, the chimeric VEGF-CAC was a potent inducer of proliferation BaF3-chimeric cells in vitro, while in vivo overexpression of the factor led to robust angiogenesis that was shown to exceed even the angiogenic activity of VEGF-A165. It is contemplated that this increase in biological activity is due to the greater solubility of the immature VEGF-CAC when compared to VEGF-A165. It is also contemplated that VEGF-CAC is more susceptible to proteolysis by extracellular proteases, such as plasmin, leading to an increased rate of release of the VEGF core domain (McColl et al., J. Exp. Med., 198:863-868, 2003). Concurrently, the architecture of the vessels formed in response to adenoviral overexpression of VEGF-CAC was chaotic and resembled hemangiomas at some locations, suggesting that, after proteolytic processing of VEGF-CAC, the released VEGF core domain induces endothelial proliferation without guidance cues, in a manner comparable to mice expressing only the VEGF-A120 isoform (homologue to the human VEGF-A121 isoform) (Ruhrberg et al., supra). In comparison with VEGF-A109, however, VEGF-CAC induced hyperplasia was more chaotic and wide spread.

In addition to its angiogenic activity, VEGF-CAC was shown to induce circumferential dilation of cutaneous lymphatic vessels. In line with the results, overexpression of VEGF-A has been shown to induce large, hyperplastic lymphatic vessels Saaristo et al., FASEB J., 16:1041-1049, 2002; Nagy et al., J. Exp. Med., 196:1497-1506, 2002 and Hon et al., FASEB J., 10:1111-1113, 2004). These signals may be mediated via VEGFR-2 that is also expressed by lymphatic vessels Jeltsch et al., Science, 276:1423-1425, 1997 and Veikkola et al., EMBO J., 6:1223-1231, 2001). It is possible that the effects of VEGF-CAC on lymphatic vessels could be due to increased drainage as a result of vascular hyperpermeability, and to the VEGFR-1 mediated recruitment of inflammatory cells that produce VEGF-C and VEGF-D (Schoppmann et al., Am. J. Pathol., 161:947-956, 2002; Cursiefen et al., Invest. Ophthalmol. Vis. Sci., 45:2666-2673, 2004; Baluk et al., J. Clin. Invest., 115:247-257, 2005; Veikkola et al., EMBO J., 6:1223-1231, 2001).

Example 15

CUB-VEGF Chimeric Constructs

The present example describes the generation of a chimeric polypeptide molecule designated CUB-VEGF comprising the CUB domain of PDGF-C or PDGF-D fused to a VEGF-A receptor tyrosine kinase (RTK) binding domain. The CUB domain was attached to the N-terminus of VEGF. An encoding polynucleotide was generated to express the CUB-VEGF recombinantly.

Expression Vectors. Human cDNAs for expression of full length PDGF-D (PDGF-DFL) (bp 176-1285 of SEQ ID NO: 22, Genbank seq. number: AF336376) was cloned into mammalian expression vector pcDNA 3.1/V5-His A (Invitrogen) as was CUB-domain with the hinge region from PDGF-D (bp 176-988 of SEQ ID NO: 22, Genbank seq. number: AF336376). The different CUB-VEGFs (CUB271; by 244-988 of SEQ ID NO: 22, CUB256 bp 244-943 of SEQ ID NO: 22; CUB254 bp 244-937 of SEQ ID NO: 22, all from Genbank seq. number: AF336376, fused to VEGF by 100-402, Genbank NM003376) were cloned into mammalian expression vector pSecTagB (Invitrogen).

Cell Culture, Transfection, and Metabolic Labeling. 293T-cells were cultured in Dulbecco's modified Eagle's medium (DMEM)-10% fetal calf serum (FCS). Cell transfections were performed using the JetPei-transfectionkit (Polyplus) according manufacturer's instructions. Equivalent amounts of expression plasmids without the inserts were used in mock transfections. Metabolic labeling of cells transfected with expression constructs were carried out by addition of 200 mCi/ml of Pro-Mix L-[35S] in vitro cell labeling mix (Amersham) to the culture medium devoid of cysteine and methionine, but with 3% FCS. After 6 hours the medium was collected, cleared by centrifugation and used for immunoprecipitation.

Immunoprecipitation. Immunoprecipitations of metabolically 35S-labelled PDGF-D and CUB271-VEGF were carried out by using PDGF receptor α-Ig and PDGF receptor β-Ig fusion proteins (R&D), anti-PDGF-D (R&D) and anti-myc (Invitrogen). Produced proteins bound to fusion proteins or antibodies were precipitated using protein A-sepharose (Pharmacia). Precipitated proteins were analyzed using SDS-page in reducing conditions.

Results. Precipitation of myc-tagged CUB271-VEGF with anti-myc demonstrated that it is produced and secreted. The medium containing CUB271-VEGF was mixed 1:1 with medium containing secreted full length PDGF-D (residues 1-370) and after 3 hours the media were precipitated with PDGFR-α or PDGFR-β. Results indicated that the presence of the chimeric protein blocked the binding of the mature form of PDGF-D to PDGFR-α but not to PDGFR-β. The experiment was repeated with co-transfection of PDGF-DFL and CUB271-VEGF chimera and the results were similar.

Example 16

Proteolytic Processing of the CUB-VEGF Chimeric Protein

To determine if the CUB domain can be cleaved when linked to another homologous protein, a PDGF-D-VEGF chimeric protein was made by fusing the growth factor domain of VEGF to the N-terminal part of the PDGF-D polypeptide containing the CUB domain so that the cleavage site at the C-terminus of the CUB domain of wildtype PDGF-D was preserved. Results indicated that the chimeric protein was cleaved in between the CUB domain and VEGF domain.

Detailed analysis of the various fusions showed that the cleavage was strongly inhibited when the N-terminal PDGF-D sequence was further truncated so that the tri-basic sequence RKSK was partly deleted. This suggested that the major cleavage site in the chimeric protein was located in this sequence.

Example 17

A Latent CUB-VEGF Fusion Polypeptide and Homodimers Thereof

The CUB domain from full length PDGF-D cDNA was cloned into a vector containing the VEGF growth factor domain. This form of VEGF, called VEGF109, was cloned into the modified vector pSecTag (Invitrogen) and produced a biologically active form of VEGF capable of binding to and activating VEGFR-1 and VEGFR-2. This VEGF has also a myc-tag attached at its C-terminus. Three different clones were made, one containing the CUB domain and the whole hinge region between it and the PDGF-homology domain, the second containing a CUB domain that ends at the presumed processing site and third one that ends just before this site.

The clones were prepared and transfected into 293T cells, using the FuGene6 transfection reagent (Roche). Two days after transfection the culture medium was replaced with methionine and cysteine-free medium including radioactively ($^{35}$S) labeled methionine and cysteine (Promix, Amersham). This medium was collected and 1 ml of it was used to extract proteins produced by the transfected constructs. Extraction was performed using the anti-myc antibodies (Babco) in immunoprecipitation. The extracted protein products were separated in 12% PAGE-gels. All three constructs produced protein products of approximately the size predicted from the previous immunoprecipitations of the component polypeptides.

The polypeptides seen in the gels are full-length CUB-VEGF109 and processed VEGF109 from which the CUB domain has been cleaved. This result also validated the processing site, since the product of the clone including the whole hinge area is slightly larger than the others and larger than the control VEGF109 protein. Electrophoresis in 7% PAGE in non-reducing conditions showed that these proteins also form dimers and that unprocessed CUB-VEGF109 proteins seem to form dimers not only with themselves, but also with the processed form of VEGF109. Use of such dimerizing forms as inhibitors is specifically contemplated as an aspect of the invention.

Example 18

Receptor Binding Activity of CUB-VEGF

Results indicated that all three CUB-VEGF109 chimeric protein products bound to both VEGFR-1 and VEGFR-2. The ability of these chimeric proteins to activate the receptors by stimulating the growth of Human Dermal Microvascular Endothelial Cells (HDMECs) was tested. Conditioned medium containing CUB(248)-VEGF109 was obtained for testing, while medium containing VEGF109, endothelial cell growth medium or starvation medium were used as controls. The cell proliferation test was carried out simultaneously in 10 wells each containing 10,000 cells; 100 µl of conditioned medium was administered per well. After 72 hours of incubation at 37° C., 10 µl of a 5 mg/ml solution of MTT was added and the wells were incubated for additional 4 hours after which the cells were lysed in 100 µl of 10% SDS/10 mmol/L HCl overnight. Absorbance was measured at 540 nm.

Results demonstrated that although CUB(248)-VEGF109 bound to the VEGFR-1 and VEGFR-2, it did not induce cell proliferation via these receptors when compared to full growth medium or VEGF109. One possible explanation could be that CUB(248)-VEGF109 cannot dimerize the receptors despite binding them. Accordingly, they may serve as inhibitors for VEGF-mediated receptor activation.

Example 19

CUB-VEGF Chimeric Protein Promoted Heterodimerization with PDGF-D

Co-transfection of the PDGF-D and CUB-VEGF vectors led to heterodimerization of the polypeptides. Myc- and V5-epitope-tagged CUB-VEGF and PDGF-D polypeptides, respectively, were expressed separately or in the same cells and precipitated with antibodies directed against the epitope tags. No processed VEGF-dimers were produced. The polypeptides migrating at about 105 kD represented a heterodimeric protein, as can be deduced from its precipitation with both antisera. Interestingly, at about 68 kD there were polypeptides that precipitated with both anti-V5 and anti-myc. This is believed to be a dimer where one chain of the CUB-VEGF is processed and the other chain is not. The bands were also visible when precipitated with both anti-V5 and anti-myc.

Example 20

Cleavage of the Cub Domain of the Cub-VEGF/PDGF-D Heterodimer

Surprisingly, when the chimeric proteins from Example 16 were analyzed in non-reducing conditions, very little of the homodimeric cleaved VEGF protein could be detected in the gels. Instead, the major species of the CUB-VEGF protein were the full-length dimer and a heterodimer between the full-length and cleaved CUB-VEGF chimera. This suggests that the first cleavage separating the N-terminal CUB domain of PDGF-D and the VEGF domain is efficient, but the second cleavage is much more inefficient after the loss of the first CUB domain. All forms retained VEGFR-1 and VEGFR-2 binding activity.

Example 21

CUB271-VEGF Chimera Blocks PDGF-D Binding to PDGFR-Alpha but Not to PDGFR-BETA

Co-transfection of PDGF-DFL and CUB-VEGF chimeras demonstrated that the presence of the chimeric protein blocked the binding of the mature form of PDGF-D to PDGFR-α but not to PDGFR-β. Results indicated that the co-expression of native VEGF with PDGF-D did not affect the binding of the mature form to either PDGFR-α 0or -β. This result was confirmed by producing CUB271-VEGF and PDGF-D separately and mixing the media to determine if CUB-VEGF would block the binding of PDGF-D to PDGFR-α. After 3 hours of mixing the precipitation with PDGFR-α and PDGFR-β was performed. Results confirmed the conclusion obtained from co-transfection: the presence of CUB271-VEGF blocks the PDGFR-α but not PDGFR-β binding of PDGF-D.

Thus, it is contemplated that the CUB-VEGF constructs of the invention will act as PDGFR-α antagonists and would be useful to treat subjects suffering from edema ascites, hydrothorax, hydropericardium, cerebral edema, hydrocephalus, glaucoma, and acute pulmonary edema and other diseases where edema is a significant clinical problem.

Example 22

Processing of Full-Length and Receptor Binding Activity of PDGF-D

This example provides data which indicates that fully-processed PDGF-D binds to and activates both PDGFR-α and PDGFR-β.

Expression vectors. Human cDNAs for expression of full length PDGF-D (bp 176-1285 of SEQ ID NO: 22, Genbank sequence AF336376) and CUB-domain from PDGF-D (bp 176-677 of SEQ ID NO: 22, Genbank sequence AF336376, and SEQ ID NO: 55) were cloned to the mammalian expression vector pcDNA 3.1/V5-His A (Invitrogen), cDNAs for PDGF-DAN (bp 917-1285 of SEQ ID NO: 22), all different CUB-VEGFs (CUB271; by 244-988 of SEQ ID NO: 22;

CUB256 bp 244-943 of SEQ ID NO: 22; CUB254 bp 244-937 of SEQ ID NO: 22 fused to VEGF by 100-402, Genbank NM_003376), PDGF-CAN (bp 912-1223 os SEQ ID NO: 20, GenBank AF244813) and full length PDGF-B (bp 1023-2368 of SEQ ID NO: 18, GenBank NM_002608) were cloned into mammalian expression vector pSecTagB (Invitrogen).

Cell culture, transfections and metabolical labeling. 293T-cells were cultured in Dulbecco's modified Eagle's medium (DMEM)-10% fetal calf serum (FCS). Cell transfections were carried out using the JetPei-transfection kit (Polyplus) according to the manufacturer's instructions. Equivalent amounts of expression plasmids without the inserts were used in the mock transfections. Metabolic labeling of cells transfected with the expression constructs was done by addition of 200 mCi/ml of Pro-Mix L-[$^{35}$S] in vitro cell labeling mix (Amersham) to the culture medium devoid of cysteine and methionine, but containing 3% FCS. After 6 hours the medium was collected, cleared by centrifugation and used for immunoprecipitation.

Immunoprecipitation. Immunoprecipitations and receptor precipitations of the metabolically $^{35}$S-labeled PDGF-D, PDGF-DAN, all different CUB-VEGFs, CUB, PDGF-CAN and PDGF-B were carried out by using PDGF receptor α-Ig and PDGF receptor β-Ig fusion proteins (R&D), anti-PDGF-D (R&D), anti-myc (Invitrogen) and anti-V5 (Invitrogen). The produced proteins bound to fusion proteins or antibodies were precipitated using protein A-sepharose (Pharmacia). Precipitated proteins were analyzed using SDS-page, in both reducing and non-reducing conditions.

Results. It has been previously shown that PDGF-D is secreted as a dimer of full-length polypeptides of about 60 kD, and in the presence of serum, PDGF-D undergoes proteolytic processing to generate the active growth factor dimer of the 23 kD PDGF homology domains, but lacking the N-terminal CUB domains (Bergsten, Nat. Cell. Biol., 3:512-516, 2001; LaRochelle, Nat. Cell. Biol., 3:517-521, 2001). An alternatively spliced PDGF-D RNA species was found in mouse heart that encodes only the CUB domain, with a stop codon at position 256 of the reading frame. Plasmid vectors were constructed for the expression of the CUB domain as well as full-length and activated forms of PDGF-D to test if this truncated protein and the CUB domain has a function in PDGF-D processing.

The processed growth factor domain cleaved from the full-length PDGF-D bound to PDGFR-α and -β, while the isolated CUB domain did not bind to either receptor. This was detected by precipitating metabolically labelled full length PDGF-D with PDGF receptor α-Ig fusion proteins. Interestingly, the PDGF-DAN polypeptide lacking the CUB domain, but containing part of the intervening sequences, also bound to PDGFR-β but only very weakly to the PDGFR-α. However, the PDGF-DAN polypeptide did not undergo proteolytic processing to the active form corresponding to the one cleaved from the full-length protein, suggesting that the presence of the intact CUB domain is necessary for the correct proteolytic cleavage. Control experiments showed that PDGF-CAN binds only to PDGFR-β and PDGF-B bound to both receptors, as has been previously reported.

Furthermore, pulse-chase labeling experiments demonstrated that the proteolytic processing occurs in the PDGF-D producing cells, but not in the growth medium after secretion. Also, the ability of the fully-processed PDGF-D to bind to both PDGFR-α and -β was further confirmed by pulse-chase labeling experiments. The expression plasmids encoding the PDGF forms discussed above were transfected into 293T cells, using the JetPei transfection reagent (Polyplus). Two days after transfection the culture medium was replaced with methionine and cysteine-free medium including radioactively ($^{35}$S) labeled methionine and cysteine (Promix, Amersham) and 5% fetal calf serum. This medium was collected after 24 hours and 1 ml was used to precipitate proteins produced by the transfected constructs. The precipitation was done by using PDGF receptor fusion proteins (R&D) and protein A-sephrarose. The precipitated proteins were separated in a 12% PAGE gel. All constructs produced polypeptides of the size predicted from the previous immunoprecipitations of the polypeptides in question.

Contrary to earlier reports, the naturally processed form of PDGF-D is also capable of binding to PDGFR-α. Precipitation with the PDGF receptor α-Ig fusion protein revealed binding of the processed form of PDGF-D. As a negative control the empty vector was used. PDGF-CAN and PDGF-B were used as positive controls. The short, recombinantly "activated" form, PDGF-DAN, seemed to bind to the α-receptor very weakly. Results indicated that PDGF-DAN as well as PDGF-B and PDGF-D bind to the PDGFR-β, whereas PDGF-CAN does not.

These results reveal that the endogenous cleavage site of PDGF-D is located more C-terminally as previously thought and that the correct cleavage of the CUB domain is essential to reveal the PDGFR-α binding activity of PDGF-D. It was also determined that fully-processed PDGF-D was capable of stimulating phosphorylation of both PDGFR-α and PDGFR-β receptors.

It should be understood that the foregoing description relates to preferred embodiments of the invention and equivalents and variations that will be apparent to the reader are also intended as aspects of the invention. The references cited herein throughout are all specifically incorporated herein by reference.

| SEQUENCE LISTING INDEX | | |
| --- | --- | --- |
| Sequence No. | Name | Sequence Type |
| 1. | VEGF-A | DNA |
| 2. | VEGF-A | AA |
| 3. | VEGF 206 | AA |
| 4. | VEGF 121 | AA |
| 5. | VEGF 145 | AA |
| 6. | VEGF 165 | AA |
| 7. | VEGF 189 | AA |
| 8. | PlGF | DNA |
| 9. | PlGF | AA |
| 10. | VEGF-B | DNA |
| 11. | VEGF-B | AA |
| 12. | VEGF-C | DNA |
| 13. | VEGF-C | AA |
| 14. | VEGF-D | DNA |
| 15. | VEGF-D | AA |
| 16. | PDGF-A | DNA |
| 17. | PDGF-A | AA |
| 18. | PDGF-B | DNA |
| 19. | PDGF-B | AA |
| 20. | PDGF-C | DNA |
| 21. | PDGF-C | AA |
| 22. | PDGF-D | DNA |
| 23. | PDGF-D | AA |
| 24. | VEGF-E | DNA |
| 25. | VEGF-E | AA |
| 26. | CAC | DNA |
| 27. | CAC | AA |
| 28. | PRIMER | DNA |
| 29. | PRIMER | DNA |
| 30. | PRIMER | DNA |
| 31. | PRIMER | DNA |
| 32. | PRIMER | DNA |

SEQUENCE LISTING INDEX

| Sequence No. | Name | Sequence Type |
|---|---|---|
| 33. | PRIMER | DNA |
| 34. | PRIMER | DNA |
| 35. | PRIMER | DNA |
| 36. | CDD | DNA |
| 37. | CDD | AA |
| 38. | CDC | DNA |
| 39. | CDC | AA |
| 40. | DDC | DNA |
| 41. | DDC | AA |
| 42. | PlGF-2 | AA |
| 43. | PlGF-3 | AA |
| 44. | VEGFB-167 | AA |
| 45. | VEGFB-186 | AA |
| 46. | N-terminal propeptide VEGF-C | AA |
| 47. | C-terminal propeptide VEGF-C | AA |
| 48. | N-terminal propeptide VEGF-D | AA |
| 49. | C-terminal propeptide VEGF-D | AA |
| 50. | LAP-1 | AA |
| 51. | VEGF109 | DNA |
| 52. | VEGF109 | AA |
| 53. | CUB domain PDGF-C | AA |
| 54. | CUB domain PDGF-D | DNA |
| 55. | CUB domain PDGF-D | AA |
| 56. | CUB271-VEGF | DNA |
| 57. | CUB271-VEGF | AA |
| 58. | CUB254-VEGF | DNA |
| 59. | CUB254-VEGF | AA |
| 60. | CUB256-VEGF | DNA |
| 61. | CUB256-VEGF | AA |
| 62. | CUB + V5 + His | DNA |
| 63. | CUB + V5 + His | DNA |
| 64. | primer | DNA |
| 65. | primer | DNA |

What is claimed is:

1. A construct comprising:
a receptor tyrosine kinase (RTK) binding domain, at least one flanking domain, and at least one linkage that connects the RTK binding domain to the at least one flanking domain;
wherein the RTK binding domain comprises an amino acid sequence that is identical to a mammalian VEGF-A RTK binding domain amino acid sequence;
wherein the construct and the RTK binding domain bind to the extracellular domain of at least one receptor tyrosine kinase selected from the group consisting of: human VEGFR-1 and human VEGFR-2; and wherein the at least one flanking domain comprises an amino acid sequence that is identical to an amino acid sequence selected from the group consisting of: a mammalian VEGF-C amino-terminal propeptide; a mammalian VEGF-C carboxy-terminal propeptide, and fragments of the mammalian VEGF-C carboxy-terminal mammalian propeptide that retain one or more BR3P homology domains of the full-length mammalian VEGF-C carboxy-terminal propeptide.

2. The construct according to claim 1, further comprising a heparin binding domain connected to the construct by a linkage.

3. The construct according to claim 1, further comprising a CUB domain connected to the construct by a linkage.

4. The construct according to claim 1, wherein each of the at least one linkage comprises a peptide bond, whereby the RTK binding domain and the at least one flanking domain comprises a chimeric polypeptide.

5. The construct according to claim 4, wherein the chimeric polypeptide further comprises a signal peptide.

6. The construct of claim 4, wherein the chimeric polypeptide further comprises a peptide tag.

7. The construct according to claim 4, wherein the chimeric polypeptide comprises at least two flanking domains.

8. A construct comprising:

a receptor tyrosine kinase (RTK) binding domain, at least one flanking domain, and at least one linkage that connects the RTK binding domain to the at least one flanking domain;

wherein the RTK binding domain comprises an amino acid sequence that is identical to a mammalian VEGF-A RTK binding domain amino acid sequence;

wherein the construct and the RTK binding domain bind to the extracellular domain of at least one receptor tyrosine kinase selected from the group consisting of: human VEGFR-1 and human VEGFR-2 and wherein the at least one flanking domain comprises an amino acid sequence at least 90% identical to an amino acid sequence selected from the group consisting of the VEGF-C amino-terminal propeptide amino acid sequence of SEQ ID NO: 46 and the VEGF-C carboxy-terminal propeptide amino acid sequence of SEQ ID NO: 47, wherein the flanking domain is capable of binding to neuropilins or extracellular matrix proteins.

9. The construct according to claim 8, wherein the chimeric polypeptide satisfies the formula:

Fn-L-RTK-L-Fc, wherein Fn comprises a flanking domain that comprises an amino acid sequence that is at least 95% identical to a the human VEGF-C amino-terminal propeptide of SEQ ID NO: 46;

wherein Fc comprises a flanking domain that comprises an amino acid sequence that is at least 95% identical to the human VEGF-C carboxy-terminal propeptide of SEQ ID NO: 47;

wherein RTK comprises the RTK binding domain; and wherein L comprises the linkage between the flanking domain and the RTK binding domain.

10. The construct of claim 8, wherein the at least one flanking domain comprises an amino acid sequence at least 95% identical to an amino acid sequence selected from the group consisting of the VEGF-C amino-terminal propeptide amino acid sequence of SEQ ID NO: 46 and the VEGF-C carboxy-terminal propeptide amino acid sequence of SEQ ID NO: 47.

11. The construct of claim 8, wherein the at least one flanking domain comprises an amino acid sequence selected from the group consisting of the VEGF-C amino-terminal propeptide amino acid sequence of SEQ ID NO: 46 and the VEGF-C carboxy-terminal propeptide amino acid sequence of SEQ ID NO: 47.

12. The construct of claim 1, wherein the fragment of the carboxy-terminal VEGF-C propeptide comprises one or more BR3P domains selected from the group consisting of amino acids 16-29 of SEQ ID NO: 47, amino acids 53-68 of SEQ ID NO: 47, amino acids 77-92 of SEQ ID NO: 47, amino acids 101-116 of SEQ ID NO: 47, amino acids 120-135 of SEQ ID NO: 47, amino acids 142-160 of SEQ ID NO: 47 and amino acids 171-180 of SEQ ID NO: 47.

13. The construct according to claim 4,
wherein the RTK binding domain comprises an amino acid sequence selected from the group consisting of:
(a) amino acids 27 to 147 of the VEGF121 amino acid sequence of SEQ ID NO: 4;
(b) amino acids 27 to 171 of the VEGF145 amino acid sequence of SEQ ID NO: 5;
(c) amino acids 27 to 191 of the VEGF165 amino acid sequence of SEQ ID NO: 6;
(d) amino acids 27 to 215 of the VEGF189 amino acid sequence of SEQ ID NO: 7;
(e) amino acids 27 to 232 of the VEGF206 amino acid sequence of SEQ ID NO: 3; and
(f) fragments of (a)-(e) that bind to VEGFR-1 or VEGFR-2.

14. The construct according to claim 4,
wherein the RTK binding domain comprises an amino acid sequence that is identical to amino acids 27 to 127 of the VEGF109 amino acid sequence of SEQ ID NO: 52.

15. The construct according to claim 1, comprising the amino acid sequence of SEQ ID NO 27.

16. The construct according to claim 4, wherein said construct further comprises a CUB domain amino acid sequence attached by a linkage.

17. A dimer comprising two chimeric polypeptides of claim 4.

18. The dimer of claim 17, which is a homodimer.

19. The dimer of claim 18, which is a heterodimer.

20. A composition comprising the construct of claim 1 or 8 in a pharmaceutically acceptable carrier.

21. A polynucleotide that comprises a nucleotide sequence that encodes a construct, said construct comprising:
a receptor tyrosine kinase (RTK) binding domain, at least one flanking domain, and at least one linkage that connects the RTK binding domain to the at least one flanking domain, wherein the at least one linkage comprises a peptide bond, whereby the construct comprises a chimeric polypeptide;
wherein the RTK binding domain comprises an amino acid sequence that is identical to a mammalian VEGF-A RTK binding domain amino acid sequence;
wherein the construct and the RTK binding domain bind to the extracellular domain of at least one receptor tyrosine kinase selected from the group consisting of: human VEGFR-1 and human VEGFR-2 and
wherein the at least one flanking domain comprises an amino acid sequence that is identical to an amino acid sequence selected from the group consisting of: a mammalian VEGF-C amino-terminal propeptide, a mammalian VEGF-C carboxy-terminal propeptide, and fragments of the mammalian VEGF-C carboxy-terminal propeptide that retain one or more BR3P homology domains of the mammalian VEGF-C carboxy-terminal propeptide.

22. A polynucleotide that comprises a nucleotide sequence that encodes a construct, said construct comprising:
a receptor tyrosine kinase (RTK) binding domain, at least one flanking domain, and at least one linkage that connects the RTK binding domain to the at least one flanking domain, wherein the at least one linkage comprises a peptide bond, whereby the construct comprises a chimeric polypeptide;
wherein the RTK binding domain comprises an amino acid sequence that is identical to a mammalian VEGF-A RTK binding domain amino acid sequence;
wherein the construct and the RTK binding domain bind to the extracellular domain of at least one receptor tyrosine kinase selected from the group consisting of: human VEGFR-1 and human VEGFR-2 and
wherein the at least one flanking domain comprises an amino acid sequence that is at least 90% identical to an amino acid sequence selected from the group consisting of the VEGF-C amino-terminal propeptide amino acid sequence of SEQ ID NO: 46 and the VEGF-C carboxy-terminal propeptide amino acid sequence of SEQ ID NO: 47, wherein the flanking domain is capable of binding to neuropilins or extracellular matrix proteins.

23. The polynucleotide of claim 22, wherein the at least one flanking domain comprises an amino acid sequence at least 95% identical to an amino acid sequence selected from the group consisting of the VEGF-C amino-terminal propeptide amino acid sequence of SEQ ID NO: 46 and the VEGF-C carboxy-terminal propeptide amino acid sequence of SEQ ID NO: 47.

24. The polynucleotide according to claim 21 or 22, wherein the polynucleotide further comprises a nucleotide sequence that encodes a signal peptide fused in-frame with the polypeptide.

25. The polynucleotide according to claim 21 or 22, further comprising a promoter sequence that promotes expression of the polynucleotide in a mammalian cell.

26. The polynucleotide according to claim 25, wherein the promoter sequence comprises a skin-specific promoter.

27. The polynucleotide according to claim 26, wherein the promoter is selected from the group consisting of K14, K5, K6, K16 and alpha 1(I) collagen promoter.

28. The polynucleotide according to claim 25, wherein the promoter is an endothelial cell specific promoter.

29. A vector comprising the polynucleotide of claim 21 or 22.

30. An expression vector comprising the polynucleotide of claim 21 or 22 operably linked to an expression control sequence.

31. The expression vector of claim 30, wherein the expression control sequence comprises an endothelial cell specific promoter.

32. The vector of claim 29, selected from the group consisting of replication deficient adenoviral vectors, adeno-associated viral vectors, and lentivirus vectors.

33. A composition comprising the polynucleotide of claim 21 or 22 and a pharmaceutically acceptable carrier, diluent or excipient.

34. The composition comprising the vector of claim 29 and a pharmaceutically acceptable carrier, diluent or excipient.

35. An isolated host cell transformed or transfected with the polynucleotide of claim 21 or 22.

36. An isolated host cell transformed or transfected with the vector of claim 29.

37. The isolated host cell according to claim 36 that expresses the polypeptide encoded by the polynucleotide.

38. The isolated host cell according to claim 35 that comprises a mammalian endothelial cell or endothelial precursor cell.

39. A method of stimulating the growth of mammalian endothelial cells or mammalian endothelial precursor cells, comprising contacting the cells with a composition comprising an effective amount of
the construct of claim 1 or 8.

40. The method of claim 39, wherein the contacting comprises administering the composition to a mammalian subject in an amount effective to stimulate endothelial cell growth in vivo.

41. The method of claim 39, wherein the mammalian subject is a human.

42. A method of stimulating angiogenesis in a mammalian subject comprising administering to a mammalian subject in need of stimulating of angiogenesis a composition comprising the
construct of claim 1 or 8
wherein the composition is administered an amount effective to stimulate angiogeneis.

43. A method of stimulating lymphangiogenesis in a mammalian subject comprising administering to a mammalian subject in need of stimulation of lymphangiogenesis the composition comprising the construct of claim 1 or 8, wherein the composition is administered in an amount effective to stimulate lymphangiogenesis.

44. A method of improving the healing of a skin graft or skin flap to underlying tissue of a mammalian subject, comprising:
contacting skin graft or skin flap tissue or underlying tissue with a composition comprising a healing agent that is present in said composition in an amount effective to reduce edema or increase perfusion at the skin graft or skin flap, thereby improving the healing of the skin graft or skin flap;
wherein the healing agent is the
construct of claim 1 or 8.

45. An improvement in a medical device for improving circulation, wound healing, or blood flow, comprising coating or impregnating the device with a composition comprising the construct of claim 1 or 8.

46. A patch comprising a pad material having an upper surface and lower surface, an adhesive on the lower surface, and a therapeutic composition, wherein the composition comprises the construct of claim 1 or 8.

47. A surgical suturing thread coated or impregnated with a composition, wherein the composition comprises the construct of claim 1 or 9.

48. A method for stimulating activities of a receptor of a cell which receptor specifically binds to and is activated by the VEGF-homology domain of VEGF-A, the method comprising administering to the cell an effective amount of an agent selected from the group consisting of:
(a) the construct of claim 1 or 8 and
(b) a dimer comprising the construct of (a); and
providing the cell with a proteolytic enzyme, whereby the growth factor is activated.

* * * * *